(12) United States Patent
Xiao et al.

(10) Patent No.: US 9,708,295 B2
(45) Date of Patent: Jul. 18, 2017

(54) SUBSTITUTED 2-AMINOPYRIDINE PROTEIN KINASE INHIBITOR

(71) Applicants: CHIA TAI TIANQING PHARMACEUTICAL GROUP CO., LTD, Lianyungang (CN); CENTAURUS BIOPHARMA CO., LTD., Beijing (CN); Lianyungang Runzhong Pharmaceutical Co., Ltd., Lianyungang (CN)

(72) Inventors: Dengming Xiao, Beijing (CN); Xinhe Xu, Beijing (CN); Xijie Liu, Beijing (CN); Yuandong Hu, Beijing (CN); Honghao Yu, Beijing (CN); Zhihua Liu, Beijing (CN); Yong Peng, Beijing (CN); Yinghui Sun, Beijing (CN); Hong Luo, Beijing (CN); Fansheng Kong, Beijing (CN); Yongxin Han, Beijing (CN); Jian Sun, Lianyugang (CN)

(73) Assignees: CHIA TAI TIANQING PHARMACEUTICAL GROUP CO., LTD., Lianyungang (CN); Centaurus Biopharma Co., Ltd., Beijing (CN); LIANYUNGANG RUNZHONG PHARMACEUTICAL CO., LTD., Lianyungang (CN)

(*) Notice: Subject to any disclaimer, the term of this patent is extended or adjusted under 35 U.S.C. 154(b) by 0 days.

(21) Appl. No.: 14/765,313

(22) PCT Filed: Jan. 27, 2014

(86) PCT No.: PCT/CN2014/071595
§ 371 (c)(1),
(2) Date: Jul. 31, 2015

(87) PCT Pub. No.: WO2014/117718
PCT Pub. Date: Aug. 7, 2014

(65) Prior Publication Data
US 2016/0002205 A1    Jan. 7, 2016

(30) Foreign Application Priority Data

Feb. 2, 2013   (CN) .......................... 2013 1 0051822
Feb. 2, 2013   (CN) .......................... 2013 1 0051825

(51) Int. Cl.
| | | |
|---|---|---|
| C07D 401/04 | (2006.01) |
| C07D 401/06 | (2006.01) |
| C07D 401/14 | (2006.01) |
| C07D 213/73 | (2006.01) |
| C07D 213/74 | (2006.01) |
| A61K 31/5377 | (2006.01) |
| A61K 31/444 | (2006.01) |
| A61K 31/4545 | (2006.01) |
| A61K 31/506 | (2006.01) |
| A61K 31/675 | (2006.01) |
| C07F 9/6558 | (2006.01) |

(52) U.S. Cl.
CPC .......... *C07D 401/14* (2013.01); *A61K 31/444* (2013.01); *A61K 31/4545* (2013.01); *A61K 31/506* (2013.01); *A61K 31/5377* (2013.01); *A61K 31/675* (2013.01); *C07D 213/73* (2013.01); *C07D 213/74* (2013.01); *C07D 401/04* (2013.01); *C07D 401/06* (2013.01); *C07F 9/65583* (2013.01)

(58) Field of Classification Search
CPC .. C07D 401/04; C07D 401/06; C07D 401/14; C07D 213/73; C07D 213/74
See application file for complete search history.

(56) References Cited

FOREIGN PATENT DOCUMENTS

| | | |
|---|---|---|
| CN | 102718745 A | 10/2012 |
| JP | 2008510790 A | 4/2008 |
| JP | 2008510792 A | 4/2008 |
| JP | 2011511005 A | 4/2011 |
| KR | 10-2007-0038562 A | 4/2007 |
| WO | 2006/021886 A1 | 3/2006 |
| WO | 2006/021884 A2 | 6/2006 |
| WO | 2009/099982 A1 | 8/2009 |
| WO | 2011/138751 A2 | 11/2011 |
| WO | 2012/116050 A2 | 8/2012 |

OTHER PUBLICATIONS

Cancer and Metastasis Reviews (1998), 17(1), 91-106.*
Science (1999), vol. 286, 531-537.*
Voskoglou-Nomikos et al., Clinical Cancer Research, vol. 9, 4227-4239.*
ptcl.chem.ox.ac.uk/MSDS structure activity relationship; Jaworska, 1-8, 2004.*
Rodig, et al., "'Crizotinib, a small-molecule dual inhibitor of the c-Met and ALK receptor tyrosine kinases," Curr Opin Investig Drugs., vol. 11, No. 12, pp. 1477-1490 (2010).
International Search Report for International Application No. PCT/CN2014/071595 dated May 19, 2014.
Kruczynski et al., "Anaplastic Lymphoma Kinase as a Therapeutic Target," Expert Opin. Ther. Targets (2012) 16(11); 1127-1138.
Cui et al., "Structure Based Drug Design of Crizotinib (PF-02341066), a Potent and Selective Dual Inhibitor of MesenchymalEpithelial Transition Factor (c-MET) Kinase and Anaplastic Lymphoma Kinase (ALK)," J. Med. Chem. 2011, 54, 6342-6363.

(Continued)

*Primary Examiner* — Rebecca Anderson
(74) *Attorney, Agent, or Firm* — Kilpatrick Townsend & Stockton LLP

(57) ABSTRACT

The present invention discloses substituted 2-aminopyridine derivatives as protein kinase inhibitors; specifically, the invention relates to 2-aminopyridine derivatives having protein kinase inhibitory properties, their manufacture, pharmaceutical compositions containing them, and use of the compounds and the pharmaceutical compositions thereof for the treatment of diseases associated with protein kinase.

17 Claims, No Drawings

(56) References Cited

OTHER PUBLICATIONS

Huang, et al., "Design of Potent and Selective Inhibitors to Overcome Clinical Anaplastic Lymphoma Kinase Mutations Resistant to Crizotinib," J. Med. Chem. 2014, 57, 1170-1187.

Milkiewicz, et al., "Inhibitors of Anaplastic Lymphoma Kinase: a Patent Review," Expert Opin. Ther. Patents (2010) 20(12) 1653-1681.

* cited by examiner

SUBSTITUTED 2-AMINOPYRIDINE PROTEIN KINASE INHIBITOR

CROSS REFERENCE TO RELATED APPLICATIONS

This application claims the benefit of Chinese Patent Application Nos. 201310051822.8 and 201310051825.1 both filed on Feb. 2, 2013.

TECHNICAL FIELD

The present invention relates to novel 2-aminopyridine derivatives having protein kinase inhibitory activities, their manufacture, and pharmaceutical compositions thereof, as well as use of the compounds and the pharmaceutical compositions for the treatment of diseases associated with protein kinase.

BACKGROUND

Proliferation, apoptosis, metastasis, and the like of tumors are closely related to the abnormal activity of protein kinases in a series of intracellular and extracellular signal transduction pathways. The abnormal activity of protein kinases not only directly associates with a tumor, but also leads to a series of human diseases associated with inflammation or proliferative responses, such as rheumatoid arthritis, cardiovascular diseases, nervous system diseases, asthma, psoriasis, and the like. At present, more than four hundred kinds of human diseases are known as being directly or indirectly associated with protein kinases, such that protein kinase has become an important medicine target.

Anaplastic lymphoma kinase (ALK), as a receptor tyrosine kinase, is a member of the insulin receptor superfamily and plays an important role in tumor cell growth and development. ALK gene can fuse with a variety of protein genes, be expressed to produce ALK protein, and can also generate variations such as mutation, amplification, and the like. In 1997, the oncogenic ALK gene rearrangement on the short arm of chromosome 2 of allobiosis large cell lymphoma was originally described, whereafter it was also found in other malignancies including diffuse large B-cell lymphoma and malignant tissues ball histiocytosis, as well as a variety of solid tumors including inflammatory myofibroblastic tumor, esophageal squamous cell carcinoma, neuroblastoma along with non-small cell lung carcinoma (NSCLC) recently reported.

In 2007, it was originally reported that ALK gene may encode and produce ALK by fusing with EML4 gene to form fusion gene, and thereby promote the growth of lung cancer cells. EML4-ALK fusion is caused by the insertion of the short arm of chromosome 2, and many types of variations have been found to date. Test shows that all of the fusion genes have biological functions, and the product they express is a chimeric tyrosine kinase, which began to be reported gradually in the study associated with NSCLC since 2007.

Because of the discovery of EML4-ALK fusion gene and the unique effect of the ALK inhibitor in the subgroup population thereof, NSCLC can be divided into different subtypes such as EGFR mutation, KRAS mutation, EML4-ALK gene fusion type, and the like, according to different molecular pathogenesis. In general NSCLC patients, the positive rate of EML4-ALK fusion gene is low in a range of between about 3% to 7%. EML4-ALK fusion gene mainly presents in non-smoking lung adenocarcinoma patients, and is mutually repulsive with both EGFR mutation and KRAS mutation. A study in 2010 showed that EML4-ALK fusion gene positive rate was 16.13% in Chinese lung adenocarcinoma patients, significantly higher than that of European and American patients; the positive rate was 19.23% in non-smoking lung adenocarcinoma patients; the mutation rate thereof was up to 42.8% in lung adenocarcinoma patients without EGFR and KRAS mutations.

Although a large amount of compounds with protein kinase inhibitory activity have been studied, and some protein kinase inhibitors have been launched for the antitumor therapy, drug resistance may arise. Therefore, it is urgent to develop new protein kinase inhibitors, such as ALK kinase inhibitors, for the prevention, mitigation and/or treatment of cancers mediated by protein kinases (such as ALK), such as ALK-positive non-small cell lung carcinoma (NSCLC) and the like.

DISCLOSURE OF INVENTION

The present invention provides a compound of Formula (I)

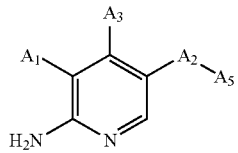

(I)

wherein:
$A_1$ is selected from the group consisting of hydrogen, —O—(CHR$^1$)-A$_4$, —CH$_2$OR$^2$, and aryl substituted by one or more R$^3$(s);

$R^1$ is selected from the group consisting of methyl and methyl substituted by one to three halogen(s);

$A_4$ is selected from the group consisting of aryl optionally substituted by one or more R$^4$(s);

$R^2$ is selected from the group consisting of aryl optionally substituted by one or more R$^3$(s);

$R^3$ is selected from the group consisting of halogen, —SO$_2$(C$_{1-6}$ alkyl), —SO$_2$NR$^6$R$^7$, —NR$^6$R$^7$, —NHSO$_2$(C$_{1-6}$ alkyl), and —P(O)R$^6$R$^7$;

$R^4$ is selected from the group consisting of halogen, C$_{1-6}$ alkyl, —NR$^6$R$^7$, and —P(O)R$^6$R$^7$;

$R^6$ and $R^7$ are each independently selected from the group consisting of hydrogen and C$_{1-6}$ alkyl, or $R^6$ and $R^7$ link to form a 3-12 membered heteroalicyclyl with the atom to which they are attached to;

$A_2$ is selected from the group consisting of phenyl, pyridinyl, pyrimidinyl, and pyrazolyl, all of which are optionally substituted by one or more substituent(s) selected from the group consisting of halogen and —OC$_{1-6}$ alkyl in which each hydrogen of the C$_{1-6}$ alkyl moiety is optionally substituted by hydroxy, carboxyl, or 3-12 membered heteroalicyclyl;

$A_5$ is a 3-12 membered heteroalicyclyl, which is optionally substituted by one or more substituent(s) selected from the group consisting of:
=O,
unsubstituted C$_{1-6}$ alkyl, and
C$_{1-6}$ alkyl substituted by one or more substituent(s) independently selected from the group consisting of hydroxy, carboxyl, and 3-12 membered heteroalicyclyl, and
3-12 membered heteroalicyclyl;

$A_3$ is selected from the group consisting of hydrogen, —NH-aryl, heteroaryl substituted by aryl, heteroaryl substituted by heteroaryl, heteroaryl substituted by arylalkyl, heteroaryl substituted by heteroarylalkyl, heteroarylethynyl substituted by arylalkyl, and heteroarylethynyl substituted by heteroarylalkyl, wherein each of the aryl and heteroaryl is optionally substituted by one or more substituent(s) selected from the group consisting of:

halogen, $C_{1-6}$ alkyl optionally substituted by halogen, hydroxy, or 3-12 membered heteroalicyclyl, and —OH, —OC$_{1-6}$ alkyl, —CN, —COOH, —C$_{1-6}$-alkyl-NH$_2$, —C$_{1-6}$-alkyl-NH(C$_{1-6}$ alkyl), —C$_{1-6}$-alkyl-N(C$_{1-6}$ alkyl)$_2$, —COO—C$_{1-6}$ alkyl, —SO$_2$(C$_{1-6}$ alkyl), —SO$_2$N(C$_{1-6}$ alkyl)$_2$, —SO$_2$NH(C$_{1-6}$ alkyl), —NR$^6$R$^7$, —NHSO$_2$(C$_{1-6}$ alkyl), and —P(O)R$^6$R$^7$; and with the proviso that $A_1$ and $A_3$ are not both hydrogen, and one of $A_1$ and $A_3$ must be hydrogen, and pharmaceutically acceptable salts, stereoisomers, and enantiomers thereof, and mixtures thereof.

In some embodiments of the compound of Formula (I), when $A_1$ is —O—(CHR$^1$)-$A_4$ and R$^1$ is methyl, $A_2$ is substituted by at least one —OC$_{1-6}$ alkyl; when $A_1$ is aryl substituted by one or more R$^3$(s) and R$^3$ is —NR$^6$R$^7$, R$^6$ and R$^7$ are each independently selected from the group consisting of C$_{1-6}$ alkyl, or R$^6$ and R$^7$ link to form a 3-12 membered heteroalicyclyl with the atom to which they are attached to.

In some embodiments, $A_3$ is selected from the group consisting of —NH-phenyl, heteroaryl substituted by phenyl, heteroaryl substituted by heteroaryl, heteroaryl substituted by phenylmethyl, heteroaryl substituted by heteroarylmethyl, heteroaryl ethynyl substituted by phenylmethyl, and heteroaryl ethynyl substituted by heteroaryl methyl, wherein each of the phenyl and heteroaryl is optionally substituted by one or more substituent(s) selected from the group consisting of halogen, $C_{1-6}$ alkyl optionally substituted by halogen, hydroxy, or 3-12 membered heteroalicyclyl, and —OH, —OC$_{1-6}$ alkyl, —CN, —COOH, —C$_{1-6}$ alkyl-NH$_2$, —C$_{1-6}$alkyl-NH(C$_{1-6}$ alkyl), —C$_{1-6}$ alkyl-N(C$_{1-6}$ alkyl)$_2$, —COOC$_{1-6}$ alkyl, —SO$_2$(C$_{1-6}$ alkyl), —SO$_2$N(C$_{1-6}$ alkyl)$_2$, —SO$_2$NH(C$_{1-6}$ alkyl), —NR$^6$R$^7$, —NHSO$_2$(C$_{1-6}$ alkyl), and —P(O)R$^6$R$^7$.

In some preferred embodiments, $A_3$ is selected from the group consisting of —NH-phenyl, heteroaryl substituted by phenyl, heteroaryl substituted by heteroaryl, heteroaryl substituted by phenylmethyl, heteroaryl substituted by heteroarylmethyl, heteroarylethynyl substituted by phenylmethyl, and heteroarylethynyl substituted by heteroarylmethyl, wherein each of the phenyl and heteroaryl is optionally substituted by one or more substituent(s) selected from the group consisting of halogen, $C_{1-4}$ alkyl optionally substituted by halogen, hydroxy, or 5 or 6 membered heteroalicyclyl, and —OH, —OC$_{1-4}$ alkyl, —CN, —COOH, —C$_{1-4}$ alkyl-NH$_2$, —C$_{1-4}$ alkyl-NH(C$_{1-4}$ alkyl), —C$_{1-4}$ alkyl-N(C$_{1-4}$ alkyl)$_2$, —COOC$_{1-4}$ alkyl, —SO$_2$(C$_{1-4}$ alkyl), —SO$_2$N(C$_{1-4}$ alkyl)$_2$, —SO$_2$NH(C$_{1-4}$ alkyl), —NH$_2$, —NH(C$_{1-4}$ alkyl), —N(C$_{1-4}$ alkyl)$_2$, —NHSO$_2$(C$_{1-4}$ alkyl), and —P(O)(C$_{1-4}$ alkyl)$_2$.

In some more preferred embodiments, $A_3$ is selected from the group consisting of —NH-phenyl, pyrazolyl substituted by phenyl, pyrazolyl substituted by phenylmethyl, and pyrazolyl ethynyl substituted by phenylmethyl, wherein phenyl is optionally substituted by one or more substituent(s) selected from the group consisting of halogen, $C_{1-4}$ alkyl substituted by halogen or hydroxy, and —OH, —OC$_{1-4}$ alkyl, —CN, —COOH, —C$_{1-4}$ alkyl NH$_2$, —C$_{1-4}$ alkyl NH(C$_{1-4}$ alkyl), —C$_{1-4}$ alkyl N(C$_{1-4}$ alkyl)$_2$, —COOC$_{1-4}$ alkyl, —SO$_2$(C$_{1-4}$ alkyl), —NH$_2$, —NH(C$_{1-4}$ alkyl), —N(C$_{1-4}$ alkyl)$_2$, —NHSO$_2$(C$_{1-4}$ alkyl), —SO$_2$N(C$_{1-4}$ alkyl)$_2$, —SO$_2$NH(C$_{1-4}$ alkyl), and —P(O)(C$_{1-4}$ alkyl)$_2$.

In some of the most preferred embodiments, $A_3$ is selected from the group consisting of —NH-phenyl, pyrazolyl substituted by phenyl, pyrazolyl substituted by phenylmethyl, and pyrazolylethynyl substituted by phenylmethyl, wherein phenyl is optionally substituted by one or more substituent(s) selected from the group consisting of: F, Cl, trifluoromethyl, —COOH, —CH$_2$OH, —OCH$_3$, —OC$_2$H$_5$, —CN, —SO$_2$NHCH(CH$_3$)$_2$, —COOCH$_3$, —SO$_2$CH$_3$, —NH$_2$, and —P(O)(CH$_3$)$_2$.

In some embodiments of the present invention, $A_3$ is hydrogen.

In some embodiments of the present invention, when $A_3$ is hydrogen and $A_1$ is aryl substituted by one or more R$^3$(s) and R$^3$ is —NR$^6$R$^7$, R$^6$ and R$^7$ are each independently selected from the group consisting of C$_{1-6}$ alkyl, or R$^6$ and R$^7$ link to form a 3-12 membered heteroalicyclyl with the atom to which they are attached to.

In some embodiments, R$^2$ is selected from the group consisting of phenyl optionally substituted by one or more R$^3$(s). In some preferred embodiments, R$^2$ is selected from the group consisting of phenyl optionally substituted by one or more R$^3$(s) selected from the group consisting of halogen, —SO$_2$(C$_{1-6}$alkyl), —SO$_2$N(C$_{1-6}$alkyl)$_2$, —SO$_2$NH(C$_{1-6}$ alkyl), —NH(C$_{1-6}$alkyl), —N(C$_{1-6}$alkyl)$_2$, —NHSO$_2$ (C$_{1-6}$alkyl), and —P(O)(C$_{1-6}$alkyl)$_2$. In more preferred embodiments, R$^2$ is selected from the group consisting of phenyl substituted by one or more R$^3$(s) selected from the group consisting of F, Cl, —SO$_2$CH$_3$, —SO$_2$N(CH$_3$)C$_2$H$_5$, —SO$_2$NHCH(CH$_3$)$_2$, —NHCH$_3$, —N(CH$_3$)C$_2$H$_5$, —NHSO$_2$CH$_3$, and —P(O) (CH$_3$)$_2$.

In some embodiments, R$^1$ is selected from the group consisting of methyl and trifluoromethyl.

In some embodiments, $A_4$ is selected from the group consisting of phenyl substituted by one or more R$^4$(s). In some preferred embodiments, $A_4$ is selected from the group consisting of phenyl substituted by one or more R$^4$(s), wherein R$^4$ is selected from the group consisting of halogen, C$_{1-6}$ alkyl substituted by halogen, —NR$^6$R$^7$, and —P(O)R$^6$R$^7$, wherein R$^6$ and R$^7$ are each independently selected from the group consisting of C$_{1-6}$ alkyl. In some more preferred embodiments, $A_4$ is selected from the group consisting of phenyl substituted by one or more R$^4$(s), wherein R$^4$ is selected from the group consisting of F, Cl, methyl substituted by halogen, ethyl substituted by halogen, —N(CH$_3$)$_2$, and —P(O)(CH$_3$)$_2$. In some more preferred embodiments, $A_4$ is selected from the group consisting of phenyl substituted by one or more R$^4$(s), wherein R$^4$ is selected from the group consisting of F, Cl, —CHF$_2$, —CF$_3$, —CF$_2$CH$_3$, —N(CH$_3$)$_2$, and —P(O)(CH$_3$)$_2$, and $A_4$ is substituted by at least one F atom.

In some embodiments, $A_2$ is selected from the group consisting of phenyl, pyridinyl, pyrimidinyl, and pyrazolyl. In some preferred embodiments, $A_2$ is selected from the group consisting of

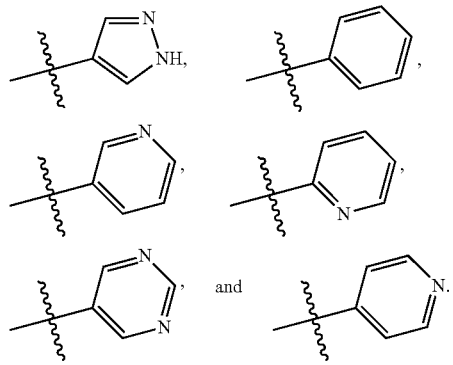

and

In some embodiments, $A_2$ is optionally substituted by one or more substituent(s) selected from the group consisting of halogen and —$OC_{1-6}$ alkyl in which each hydrogen of the $C_{1-6}$ alkyl moiety is optionally substituted by hydroxy, carboxyl, morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuranyl, or dihydrothienyl. In some preferred embodiments, $A_2$ is optionally substituted by one or more substituent(s) selected from the group consisting of halogen and —$OC_{1-6}$ alkyl in which each hydrogen of the $C_{1-6}$ alkyl moiety is optionally substituted by hydroxy, carboxyl, or morpholinyl. In some more preferred embodiments, $A_2$ is optionally substituted by one or more substituent(s) selected from the group consisting of F, Cl, methoxy, ethoxy, —$OCH_2CH_2OH$, and

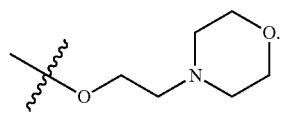 [SMILES: *OCCN1CCOCC1]

In some embodiments, $A_5$ is a 5 or 6 membered heteroalicyclyl. In more preferred embodiments, $A_5$ is morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, or dihydrothienyl. In some more preferred embodiments, $A_5$ is morpholinyl, 1,2,3,4-tetrahydropyridyl, 1,2,3,6-tetrahydropyridyl, 2,3,4,5-tetrahydropyridyl, piperazinyl, piperazin-2-one-yl, or piperidyl. In some more preferred embodiments, $A_5$ is piperazin-1-yl, piperazin-2-yl, piperazin-3-yl, piperidin-4-yl, piperidin-1-yl, piperidin-2-yl, piperidin-3-yl, morpholin-4-yl, morpholin-2-yl, morpholin-3-yl, 1,2,3,4-tetrahydropyridin-4-yl, 1,2,3,6-tetrahydropyridin-4-yl, 2,3,4,5-tetrahydropyridin-4-yl, or piperazin-2-one-yl. In some of the most preferred embodiments, $A_5$ is

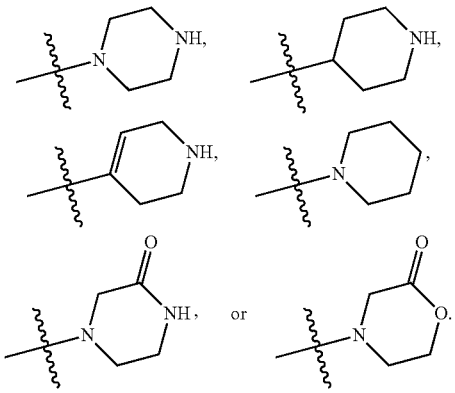

In some embodiments, $A_5$ is optionally substituted by one or more substituent(s) selected from the group consisting of
=O,
unsubstituted $C_{1-6}$ alkyl, and
$C_{1-6}$ alkyl substituted by one or more substituent(s) independently selected from the group consisting of hydroxy, carboxyl and 3-12 membered heteroalicyclyl, and 3-12 membered heteroalicyclyl, wherein the 3-12 membered heteroalicyclyl is further optionally substituted by substituents selected from the group consisting of $C_{1-6}$ alkyl, =O, —OH, —COOH, —CN, halogen, —NH($C_{1-6}$ alkyl), and —N($C_{1-6}$ alkyl)$_2$.

In some preferred embodiments, $A_5$ is optionally substituted by one or more the substitutents selected form the group consisting of: =O, methyl, ethyl, n-propyl, isopropyl, and 5 or 6 membered heteroalicyclyl, wherein each of methyl, ethyl, n-propyl, and isopropyl is optionally substituted by one or more substituent(s) independently selected from the group consisting of —OH, —COOH, and 5 or 6 membered heteroalicyclyl, wherein the 5 or 6 membered heteroalicyclyl is further optionally substituted by substituent(s) selected from the group consisting of: methyl, ethyl, n-propyl, isopropyl, =O, —OH, —COOH, —CN, halogen, —NH($C_{1-3}$ alkyl), and —N($C_{1-3}$ alkyl)$_2$. In some more preferred embodiments, $A_5$ is optionally substituted by one or more substituent(s) selected from the group consisting of methyl, ethyl, n-propyl, isopropyl, =O, piperidyl, and piperazinyl, wherein piperidyl or piperazinyl is optionally substituted by methyl.

In some embodiments, the structure of -$A_2$-$A_5$ is as follows:

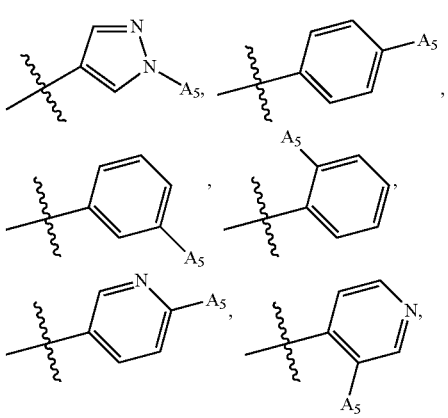

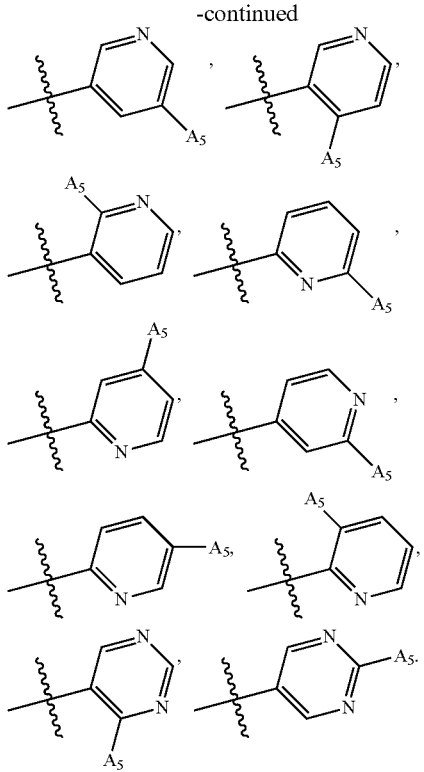

In some preferred embodiments, the structure of -A$_2$-A$_5$ is as follows:

In some preferred embodiments, when A$_3$ is hydrogen, A$_1$ is —O—(CHR$^1$)-A$_4$, and R$_1$ is methyl, A$_2$ is selected from the group consisting of phenyl, pyridyl, pyrimidinyl, and pyrazolyl, and A$_2$ is substituted by at least one —OC$_{1-6}$ alkyl in which each hydrogen of the C$_{1-6}$ alkyl moiety is optionally substituted by hydroxy, carboxyl, or 3-12 membered heteroalicyclyl.

Another aspect of the present invention provides a compound of Formula (II)

(II)

wherein:

A$_1$ is selected from the group consisting of —O—(CHR$^1$)-A$_4$, —CH$_2$OR$_2$, and aryl substituted by one or more R$^3$(s);

R$^1$ is selected from the group consisting of methyl and methyl substituted by one to three halogen(s);

A$_4$ is selected from the group consisting of aryl optionally substituted by one or more R$^4$(s);

R$^2$ is selected from the group consisting of aryl optionally substituted by one or more R$^3$(S);

R$^3$ is selected from the group consisting of halogen, —SO$_2$(C$_{1-6}$ alkyl), —SO$_2$NR$^6$R$^7$, —NR$^6$R$^7$, —NHSO$_2$(C$_{1-6}$ alkyl), and —P(O)R$^6$R$^7$;

R$^4$ is selected from the group consisting of halogen, C$_{1-6}$ alkyl, —NR$^6$R$^7$, and —P(O)R$^6$R$^7$;

R$^6$ and R$^7$ are independently selected from the group consisting of hydrogen and C$_{1-6}$ alkyl, or R$^6$ and R$^7$ link to form a 3-12 membered heteroalicyclyl with the atom to which they are attached to;

A$_2$ is selected from the group consisting of phenyl, pyridinyl, pyrimidinyl, and pyrazolyl, all of which are optionally substituted by one or more substituent(s) selected from the group consisting of halogen and —OC$_{1-6}$ alkyl in which each hydrogen of the C$_{1-6}$ alkyl moiety is optionally substituted by hydroxy, carboxyl, or 3-12 membered heteroalicyclyl;

A$_5$ is a 3-12 membered heteroalicyclyl, which is optionally substituted by one or more substituent(s) selected from the group consisting of:
=O,
unsubstituted C$_{1-6}$ alkyl, and
C$_{1-6}$ alkyl substituted by one or more substituent(s) independently selected from the group consisting of hydroxy, carboxyl, and 3-12 membered heteroalicyclyl, and
3-12 membered heteroalicyclyl, and pharmaceutically acceptable salts, stereoisomers, and enantiomers thereof, and mixtures thereof.

In some embodiments of the compound of Formula (II), when the A$_1$ is aryl substituted by one or more R$^3$(s) and R$^3$ is —NR$^6$R$^7$, R$^6$ and R$^7$ are each independently selected from the group consisting of C$_{1-6}$ alkyl, or R$^6$ and R$^7$ link to form a 3-12 membered heteroalicyclyl with the atom to which they are attached to.

In some embodiments, R$^2$ is selected from the group consisting of phenyl optionally substituted by one or more R$^3$(s). In some preferred embodiments, R$^2$ is selected from the group consisting of phenyl optionally substituted by one or more R$^3$(s) selected from the group consisting of halogen, —SO$_2$(C$_{1-6}$alkyl), —SO$_2$N(C$_{1-6}$alkyl)$_2$, —SO$_2$NH(C$_{1-6}$alkyl), —NH(C$_{1-6}$alkyl), —N(C$_{1-6}$alkyl)$_2$, —NHSO$_2$(C$_{1-6}$alkyl), and —P(O)(C$_{1-6}$alkyl)$_2$. In some more preferred embodiments, R$^2$ is selected from the group consisting of phenyl substituted by one or more R$^3$(s) selected from the group consisting of F, Cl, —SO$_2$CH$_3$, —SO$_2$N(CH$_3$)C$_2$H$_5$, —SO$_2$NHCH(CH$_3$)$_2$, —NHCH$_3$, —N(CH$_3$)C$_2$H$_5$, —NHSO$_2$CH$_3$, and —P(O)(CH$_3$)$_2$.

In some embodiments, R$^1$ is selected from the group consisting of methyl and trifluoromethyl.

In some embodiments, $A_4$ is selected from the group consisting of phenyl substituted by one or more $R^4$(s). In some preferred embodiments, $A_4$ is selected from the group consisting of phenyl substituted by one or more $R^4$(s) selected from the group consisting of halogen, $C_{1-6}$ alkyl substituted by halogen, —$NR^6R^7$, and —$P(O)R^6R^7$, wherein $R^6$ and $R^7$ are each independently selected from the group consisting of $C_{1-6}$ alkyl. In some preferred embodiments, $A_4$ is selected from the group consisting of phenyl substituted by one or more $R^4$(s) selected from the group consisting of F, Cl, methyl substituted by halogen, ethyl substituted by halogen, —$N(CH_3)_2$, and —$P(O)(CH_3)_2$. In some more preferred embodiments, $A_4$ is selected from the group consisting of phenyl substituted by one or more $R^4$(s) selected from the group consisting of F, Cl, —$CHF_2$, —$CF_3$, —$CF_2CH_3$, —$N(CH_3)_2$, and —$P(O)(CH_3)_2$, and $A_4$ is substituted by at least one F atom.

In some embodiments, $A_2$ is selected from the group consisting of phenyl, pyridinyl, pyrimidinyl, and pyrazolyl. In some preferred embodiments, $A_2$ is selected from the group consisting of

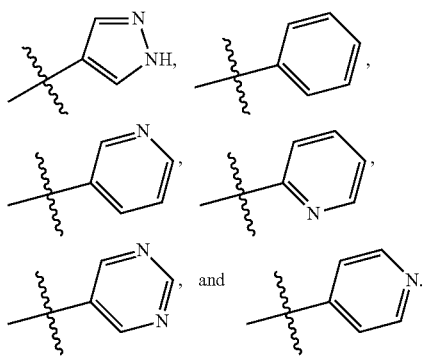

In some embodiments, $A_2$ is optionally substituted by one or more substituent(s) selected from the group consisting of halogen and —$OC_{1-6}$ alkyl in which each hydrogen of the $C_{1-6}$ alkyl moiety is optionally substituted by hydroxy, carboxyl, morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, or dihydrothienyl. In some preferred embodiments, $A_2$ is optionally substituted by one or more substituent(s) selected from the group consisting of halogen and —$OC_{1-6}$ alkyl in which each hydrogen of the $C_{1-6}$ alkyl moiety is optionally substituted by hydroxy, carboxyl, or morpholinyl. In some more preferred embodiments, $A_2$ is optionally substituted by one or more substituent(s) selected from the group consisting of F, Cl, methoxy, ethoxy, —$OCH_2CH_2OH$, and

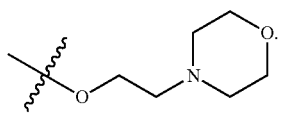 [SMILES: *OCCN1CCOCC1]

In some embodiments, $A_5$ is a 5 or 6 membered heteroalicyclyl. In more preferred embodiments, $A_5$ is morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, or dihydrothienyl. In some preferred embodiments, $A_5$ is morpholinyl, 1,2,3,4-tetrahydropyridyl, 1,2,3,6-tetrahydropyridyl, 2,3,4,5-tetrahydropyridyl, piperazinyl, piperazin-2-one-yl, or piperidyl. In some more preferred embodiments, $A_5$ is piperazin-1-yl, piperazin-2-yl, piperazin-3-yl, piperidin-4-yl, piperidin-1-yl, piperidin-2-yl, piperidin-3-yl, morpholin-4-yl, morpholin-2-yl, morpholin-3-yl, 1,2,3,4-tetrahydropyridin-4-yl, 1,2,3,6-tetrahydropyridin-4-yl, 2,3,4,5-tetrahydropyridin-4-yl, or piperazin-2-one-yl. In some of the most preferred embodiments, $A_5$ is

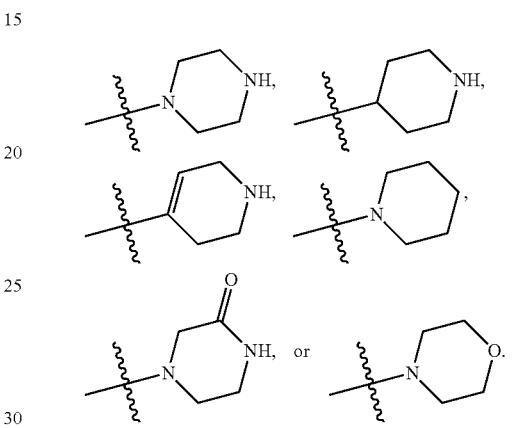

In some embodiments, $A_5$ is optionally substituted by one or more substituent(s) selected from the group consisting of

=O, unsubstituted $C_{1-6}$ alkyl, and $C_{1-6}$ alkyl substituted by one or more substituent(s) independently selected from the group consisting of hydroxy, carboxyl, and 3-12 membered heteroalicyclyl, and 3-12 membered heteroalicyclyl, wherein the 3-12 membered heteroalicyclyl is further optionally substituted by substituent(s) selected from the group consisting of $C_{1-6}$ alkyl, =O, —OH, —COOH, —CN, halogen, —NH($C_{1-6}$ alkyl), and —N($C_{1-6}$ alkyl)$_2$.

In some preferred embodiments, $A_5$ is optionally substituted by one or more substituent(s) selected from the group consisting of =O, methyl, ethyl, n-propyl, isopropyl, and 5 or 6 membered heteroalicyclyl, wherein each of methyl, ethyl, n-propyl and isopropyl is optionally substituted by one or more substituent(s) independently selected from the group consisting of —OH, —COOH, and 5 or 6 membered heteroalicyclyl, wherein the 5 or 6 membered heteroalicyclyl is further optionally substituted by substituent(s) selected from the group consisting of methyl, ethyl, n-propyl, isopropyl, =O, —OH, —COOH, —CN, halogen, —NH($C_{1-3}$ alkyl), and —N($C_{1-3}$ alkyl)$_2$. In some more preferred embodiments, $A_5$ is optionally substituted by one or more substituents selected from the group consisting of methyl, ethyl, n-propyl, isopropyl, =O, piperidyl, and piperazinyl, wherein each of piperidyl and piperazinyl is optionally substituted by methyl.

In some embodiments, the structure of -$A_2$-$A_5$ is as follows:

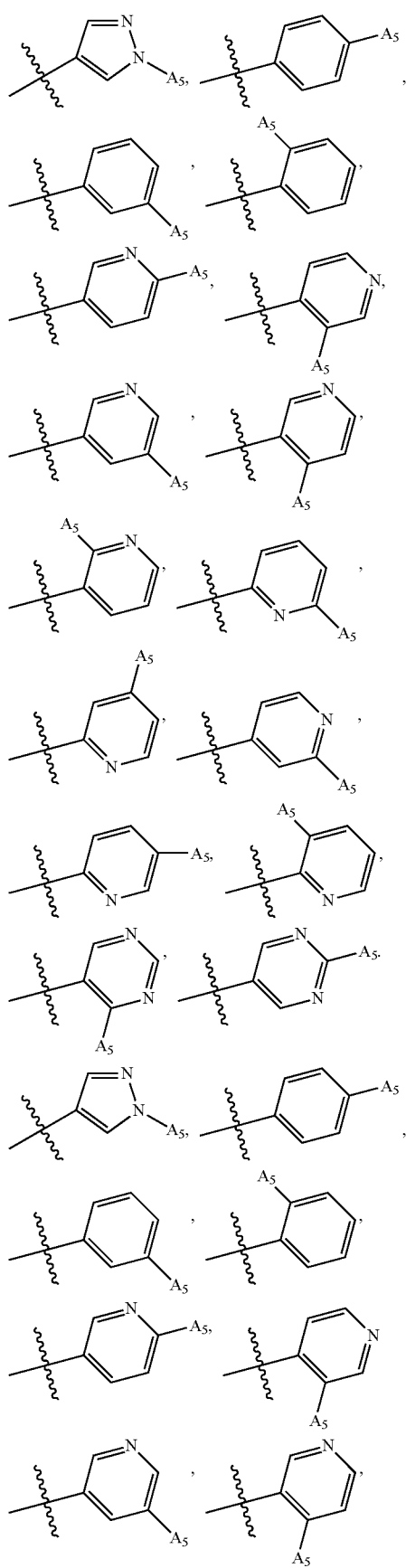

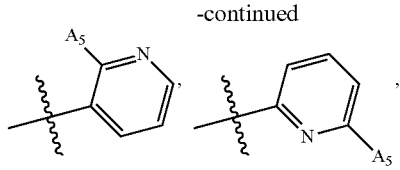
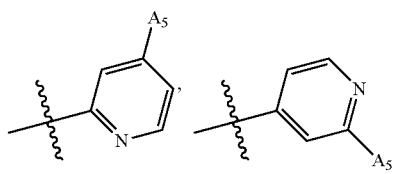
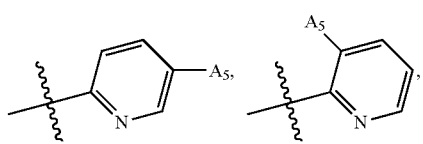
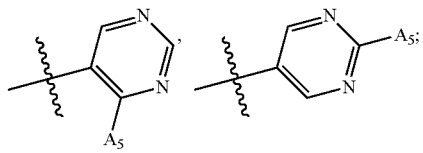

In some preferred embodiments, the structure of -A$_2$-A$_5$ is as follows:

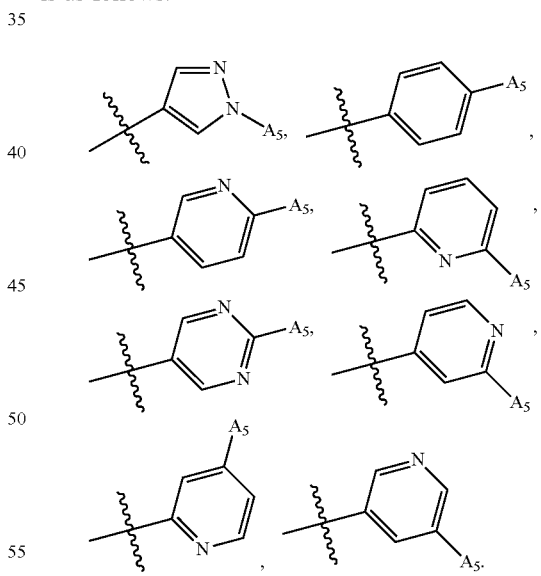

In some preferred embodiments, when A$_1$ is —O—(CHR$^1$)-A$_4$ and R$^1$ is methyl, A$_2$ is selected from the group consisting of phenyl, pyridyl, pyrimidinyl, and pyrazolyl, and A$_2$ is substituted by at least one —OC$_{1-6}$ alkyl in which each hydrogen of the C$_{1-6}$ alkyl moiety is optionally substituted by hydroxy, carboxyl, or 3-12 membered heteroalicyclyl.

Another aspect of the present invention provides a compound of Formula (III) or Formula (IV)

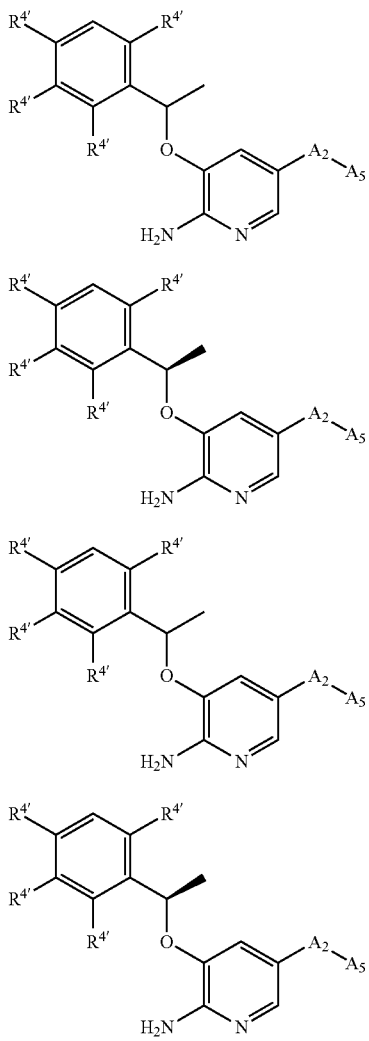

(III)

(IV)

(III)

(IV)

wherein:

$R^{4'}$ is independently selected from the group consisting of hydrogen, halogen, $C_{1-6}$ alkyl, —$NR^6R^7$, and —$P(O)R^6R^7$;

$R^6$ and $R^7$ are independently selected from the group consisting of hydrogen and $C_{1-6}$ alkyl, or $R^6$ and $R^7$ link to form a 3-12 membered heteroalicyclyl with the atom to which they are attached to;

$A_2$ is selected from the group consisting of phenyl, pyridinyl, and pyrimidinyl, all of which are optionally substituted by 1, 2, 3 or 4 substituent(s) independently selected from the group consisting of halogen and —$OC_{1-6}$ alkyl in which each hydrogen of the $C_{1-6}$ alkyl moiety is optionally substituted by hydroxy, carboxyl, or 3-12 membered heteroalicyclyl;

$A_5$ is a 3-12 membered heteroalicyclyl, which is optionally substituted by one or more substituent(s) selected from the group consisting of

=O, unsubstituted $C_{1-6}$ alkyl, and $C_{1-6}$ alkyl substituted by one or more substituent(s) independently selected from the group consisting of hydroxy, carboxyl, and 3-12 membered heteroalicyclyl, and 3-12 membered heteroalicyclyl, and pharmaceutically acceptable salts, stereoisomers, and enantiomers thereof, and mixtures thereof.

In some embodiments of the compound of Formula (III) or Formula (IV), each $R^{4'}$ is the same or different, with the proviso that at least one $R^{4'}$ is not hydrogen. In some preferred embodiments, the $R^{4'}$ substituent on 3-position is halogen. In some preferred embodiments, the $R^{4'}$ substituent on 3-position is F, and the other $R^{4'}$ substituents are each independently selected from the group consisting of hydrogen, halogen, $C_{1-6}$ alkyl substituted by halogen, —$NR^6R^7$, and —$P(O)R^6R^7$, wherein $R^6$ and $R^7$ are each independently selected from the group consisting of $C_{1-6}$ alkyl. In some preferred embodiments, the $R^{4'}$ substituent on 3-position is F, and the other $R^{4'}$ substituents are each independently selected from the group consisting of hydrogen, halogen, methyl substituted by halogen, ethyl substituted by halogen, —$N(CH_3)_2$, and —$P(O)(CH_3)_2$. In some preferred embodiments, the $R^{4'}$ substituent on 3-position is F, and the other $R^{4'}$ substituents are each independently selected from the group consisting of hydrogen, F, Cl, —$CHF_2$, —$CF_2CH_3$, —$N(CH_3)_2$, and —$P(O)(CH_3)_2$. In more preferred embodiments, the $R^{4'}$ substituent on 3-position is F, and the $R^{4'}$ substituents on 2-position and 6-position are Cl, the $R^{4'}$ substituent on 4-position is hydrogen.

In some embodiments, $A_2$ is selected from the group consisting of

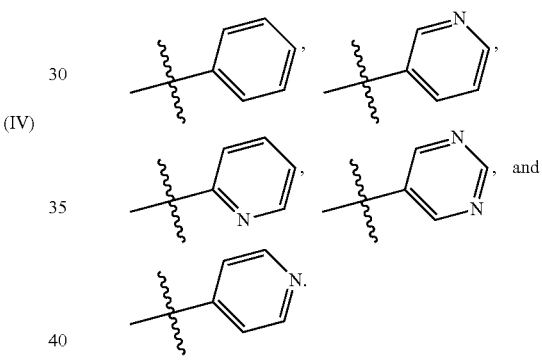

, and

In some embodiments, $A_2$ is optionally substituted by one or more substituent(s) selected from the group consisting of halogen and —$OC_{1-6}$ alkyl in which each hydrogen of the $C_{1-6}$ alkyl moiety is optionally substituted by hydroxy, carboxyl, morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, or dihydrothienyl. In some preferred embodiments, $A_2$ is optionally substituted by one or more substituent(s) selected from the group consisting of halogen and —$OC_{1-6}$ alkyl, wherein each hydrogen of the $C_{1-6}$ alkyl moiety is optionally substituted by hydroxy, carboxyl, or morpholinyl. In more preferred embodiments, $A_2$ is optionally substituted by one or more substituent(s) selected from the group consisting of F, Cl, methoxy, ethoxy, —$OCH_2CH_2OH$, and

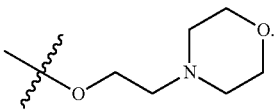

In some embodiments, $A_5$ is a 5 or 6 membered heteroalicyclyl. In more preferred embodiments, $A_5$ is morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, or dihydrothienyl. In some more preferred embodiments, $A_5$ is morpholinyl, 1,2,3,4-tetrahydropyridyl, 1,2,3,6-tetrahydropyridyl, 2,3,4,5-tetrahydropyridyl, piperazinyl, piperazin-2-one-yl, or piperidinyl. In some more preferred embodiments, $A_5$ is piperazin-1-yl, piperazin-2-yl, piperazin-3-yl, piperidin-4-yl, piperidin-1-yl, piperidin-2-yl, piperidin-3-yl, morpholin-4-yl, morpholin-2-yl, morpholin-3-yl, 1,2,3,4-tetrahydropyridin-4-yl, 1,2,3,6-tetrahydropyridin-4-yl, 2,3,4,5-tetrahydropyridin-4-yl, or piperazin-2-one-yl. In some of the most preferred embodiments, $A_5$ is

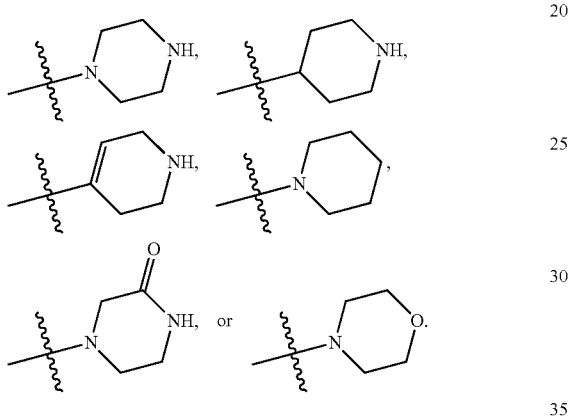

In some embodiments, $A_5$ is optionally substituted by one or more substituent(s) selected from the group consisting of
=O,
unsubstituted $C_{1-6}$ alkyl, and
$C_{1-6}$ alkyl substituted by one or more substituent(s) independently selected from the group consisting of hydroxy, carboxyl, and 3-12 membered heteroalicyclyl, and
3-12 membered heteroalicyclyl; wherein the 3-12 membered heteroalicyclyl is further optionally substituted by $C_{1-6}$ alkyl, =O, —OH, —COOH, —CN, halogen, —NH($C_{1-6}$ alkyl), or —N($C_{1-6}$ alkyl)$_2$.

In some preferred embodiments, $A_5$ is optionally substituted by one or more substituent(s) selected from the group consisting of =O, methyl, ethyl, n-propyl, isopropyl, and 5 or 6 membered heteroalicyclyl, wherein each of methyl, ethyl, n-propyl, and isopropyl is optionally substituted by one or more substituent(s) independently selected from the group consisting of —OH, —COOH, and 5 or 6 membered heteroalicyclyl, and the 5 or 6 membered heteroalicyclyl is further optionally substituted by substituent(s) selected from the group consisting of methyl, ethyl, n-propyl, isopropyl, =O, —OH, —COOH, —CN, halogen, —NH($C_{1-3}$ alkyl), and —N($C_{1-3}$ alkyl)$_2$. In some more preferred embodiments, $A_5$ is optionally substituted by one or more substituent(s) selected from the group consisting of methyl, ethyl, n-propyl, isopropyl, =O, piperidinyl, and piperazinyl, wherein each of piperidinyl and piperazinyl is optionally substituted by methyl.

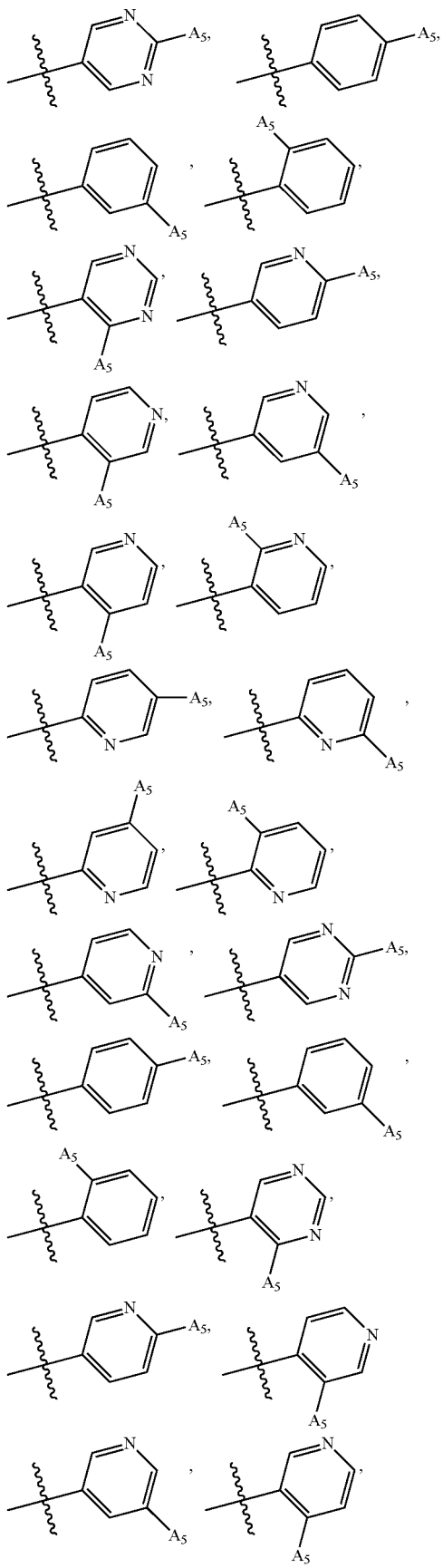

-continued

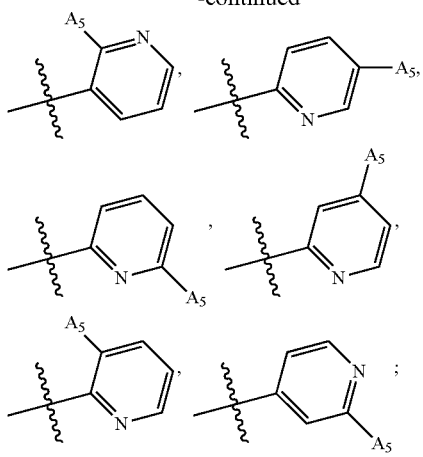

In some embodiments, the structure of -A$_2$-A$_5$ is as follows:

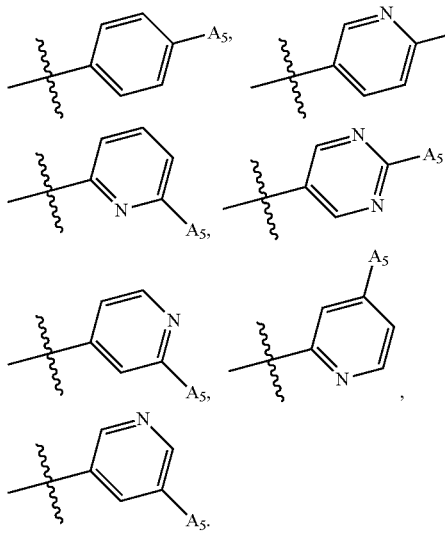

In some embodiments, A$_2$ is optionally substituted by 1 or 2 substituent(s) selected from the group consisting of halogen and —OC$_{1-6}$ alkyl. In some preferred embodiments, A$_2$ is substituted by at least one —OC$_{1-6}$ alkyl in which each hydrogen of the C$_{1-6}$ alkyl moiety is optionally substituted by hydroxy, carboxyl, or 3-12 membered heteroalicyclyl.

Specific examples of the compounds provided in the present invention include, but are not limited to, following compounds, and pharmaceutically acceptable salts, stereoisomers, and enantiomers thereof, and mixtures thereof:

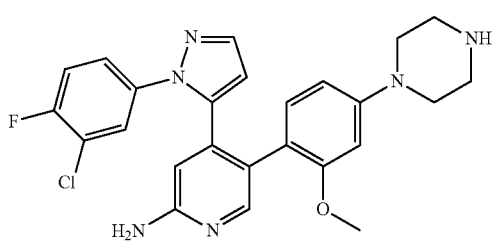

-continued

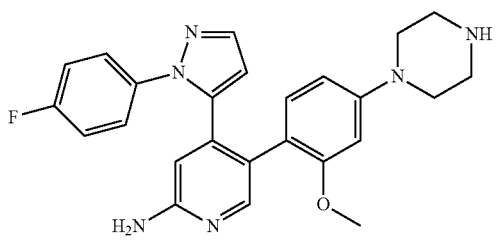

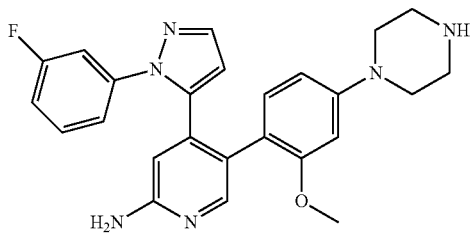

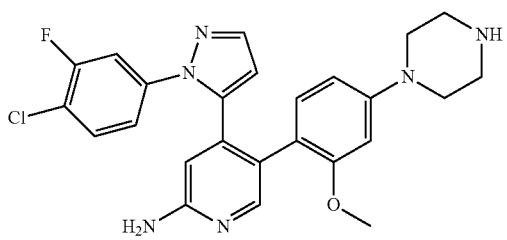

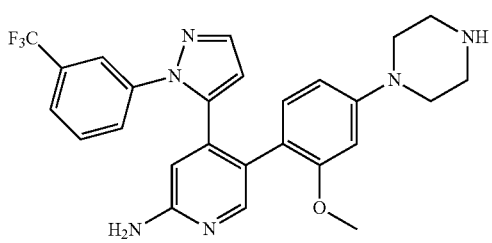

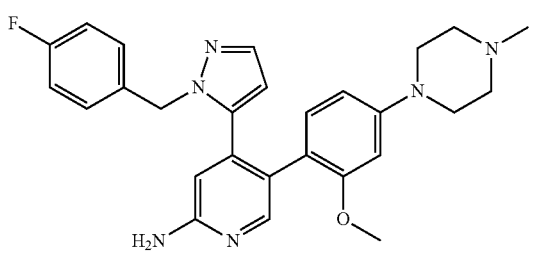

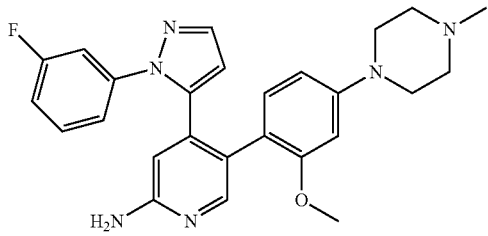

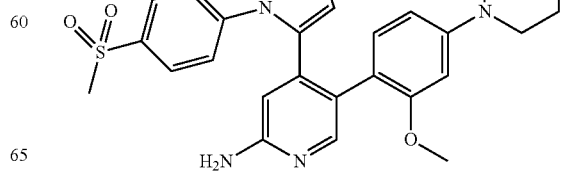

-continued
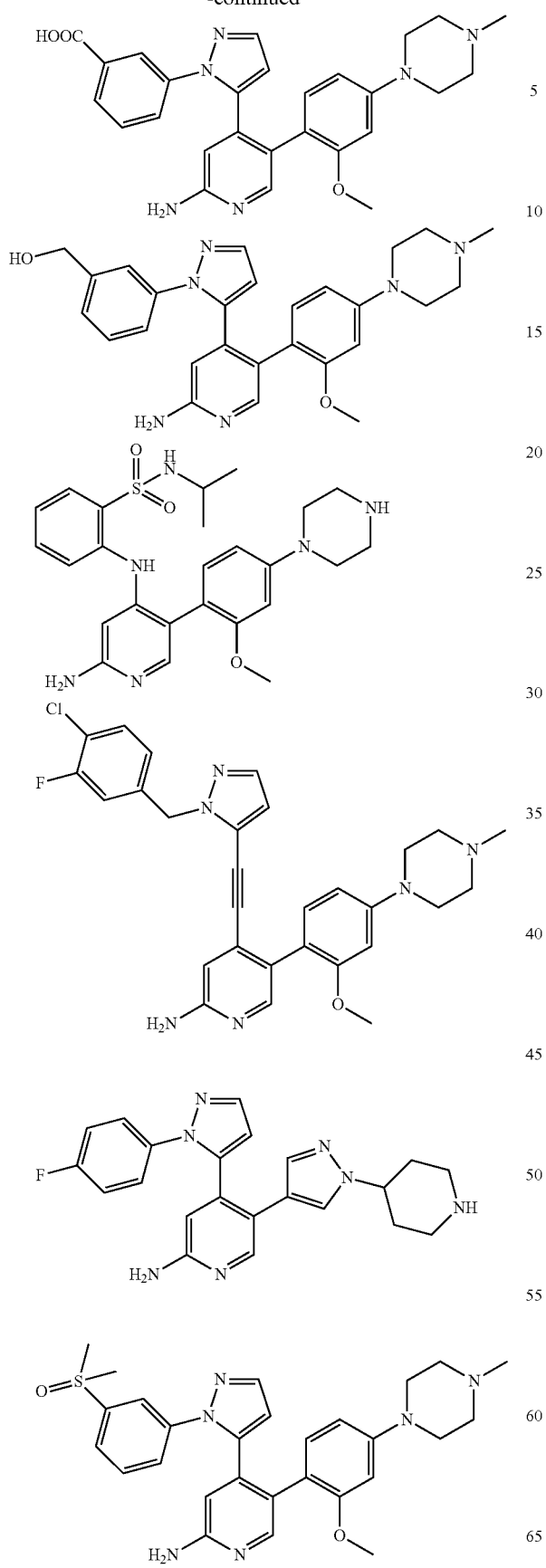
-continued
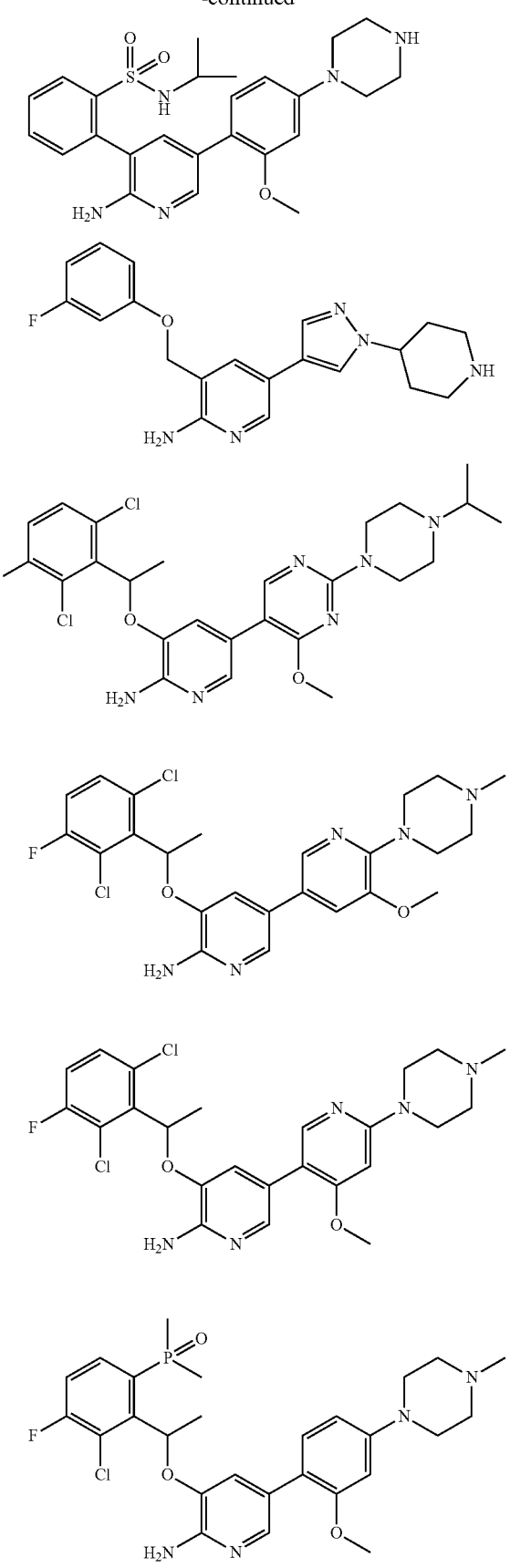

21
-continued
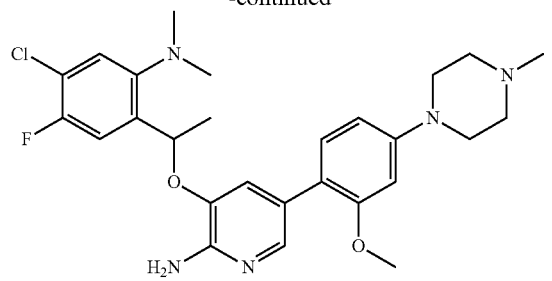
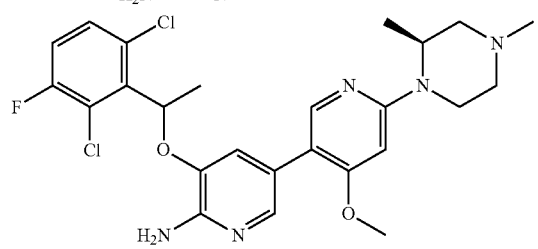
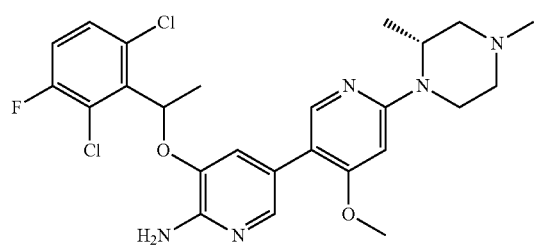
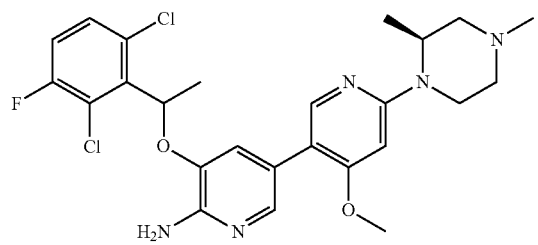
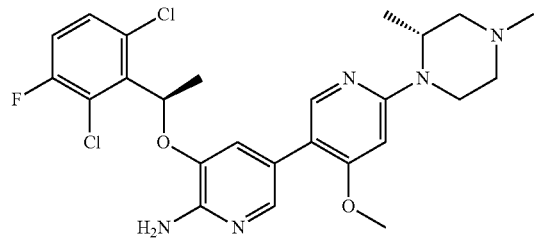
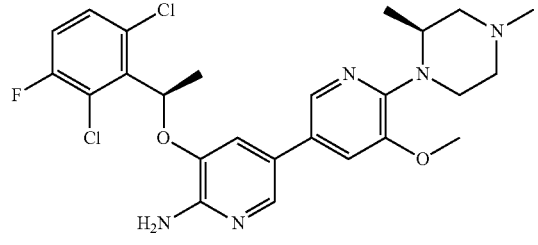
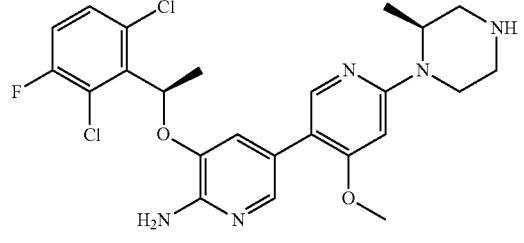
22
-continued
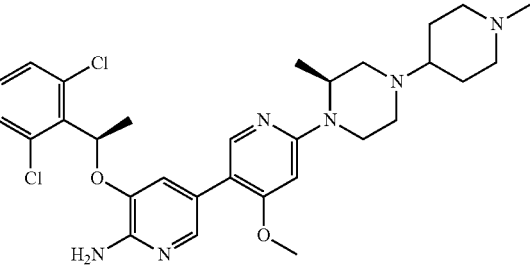
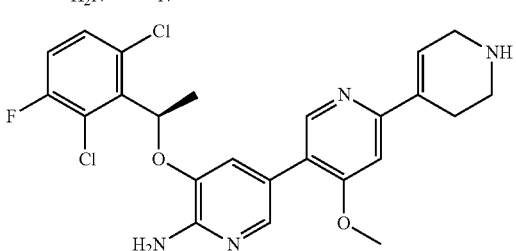
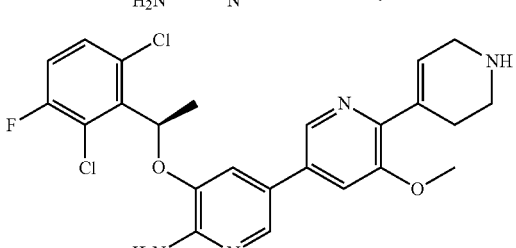
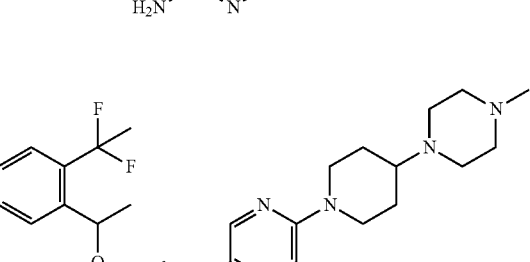
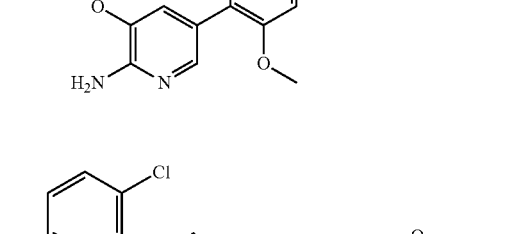
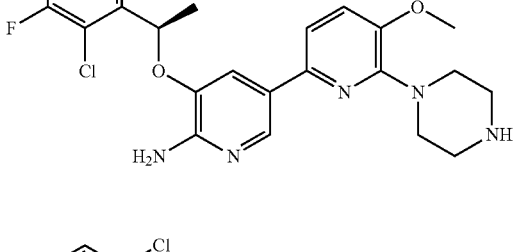
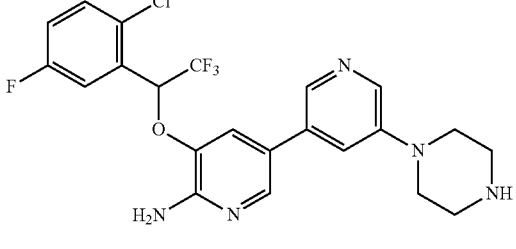

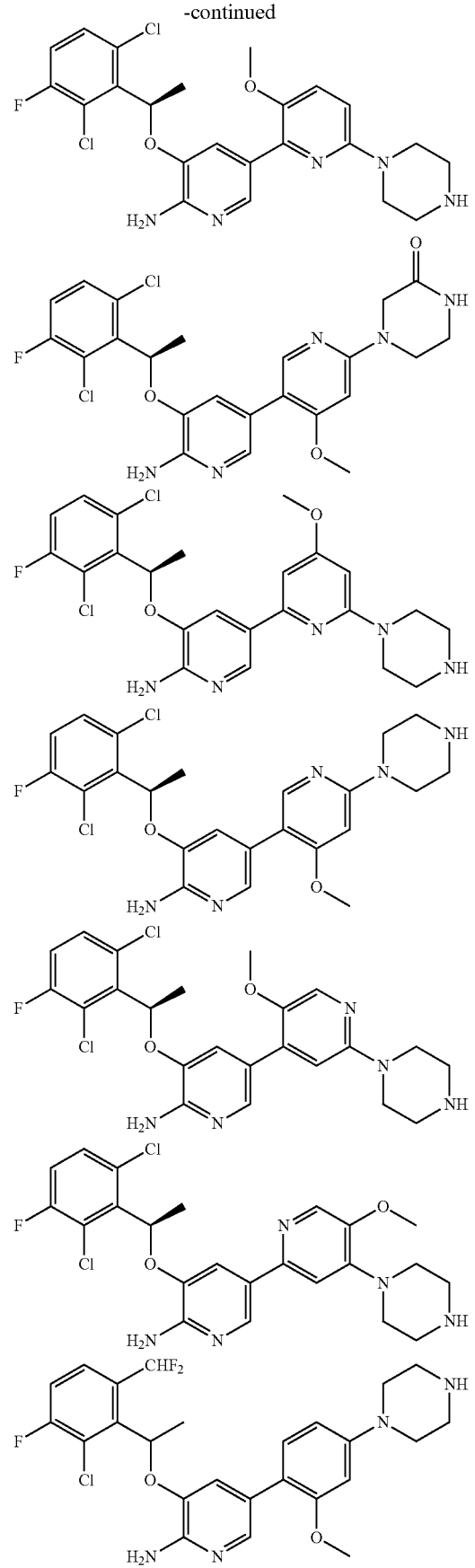
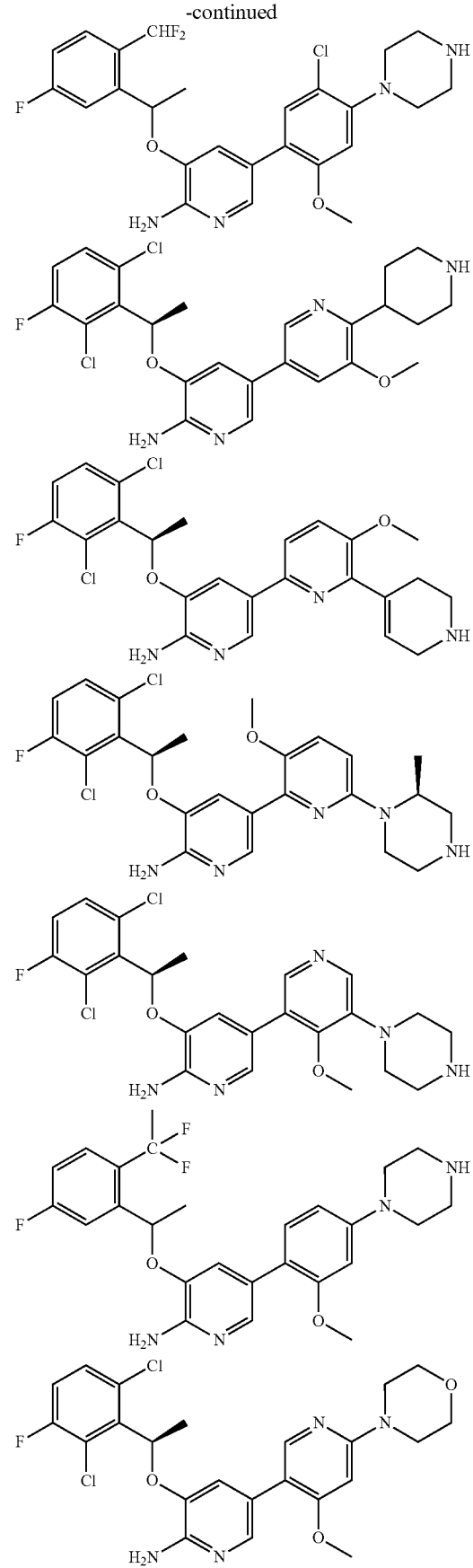

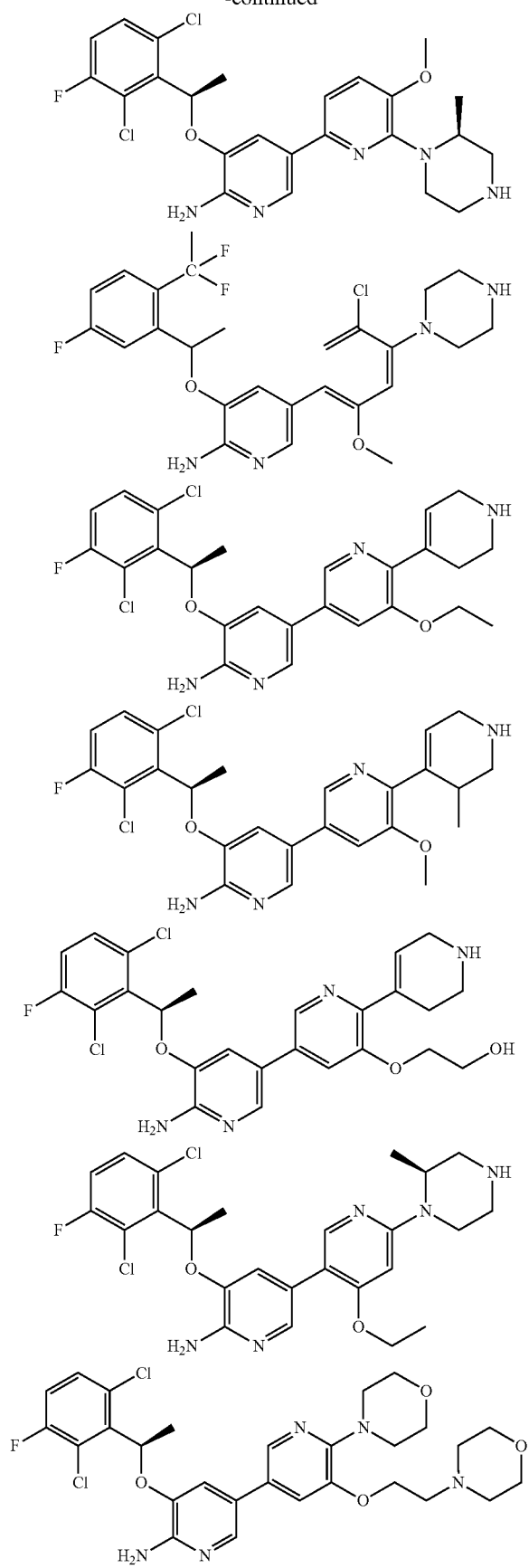

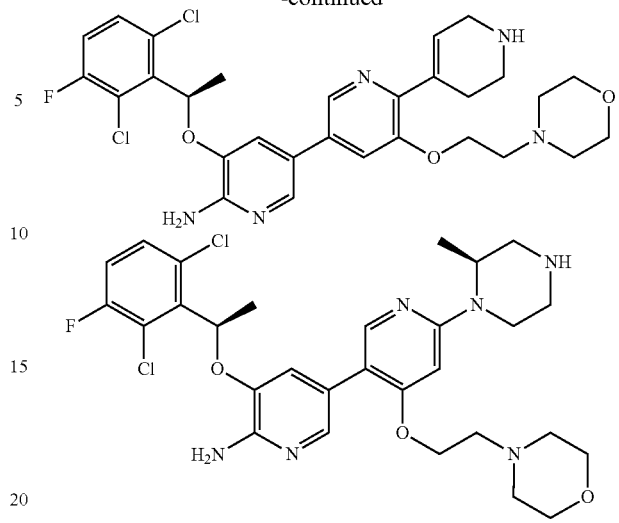

The present invention also provides a method for manufacturing compounds of the present invention, comprising the following Synthetic schemes:

Synthetic Scheme 1

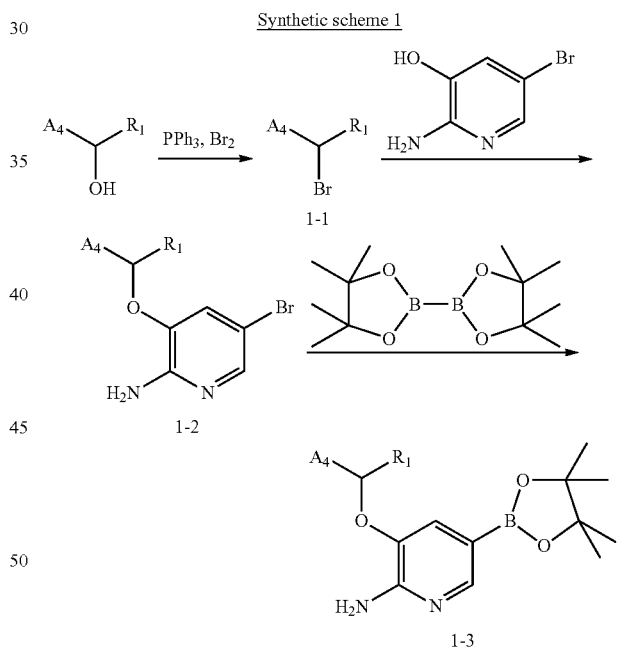

Compounds of Formula 1-3 can be synthesized following Synthetic scheme 1. Liquid bromine is added to a solution of triphenylphosphine in dichloromethane, and then alcohol is added to yield bromo-substituted Intermediate 1-1. Intermediate 1-1 reacts with 2-amino-3-hydroxy-5-bromopyridine in a solvent (such as N,N-dimethylformamide or other aprotic solvent) to yield Intermediate 1-2. Intermediate 1-2, bis(pinacolato)diboron, and a palladium-based catalyst (such as Pd(dppf)Cl$_2$) are reacted using a base (such as potassium carbonate, potassium acetate) in a solvent (such as dioxane, dimethyl sulfoxide) to yield the compound of Formula 1-3.

Synthetic scheme 2

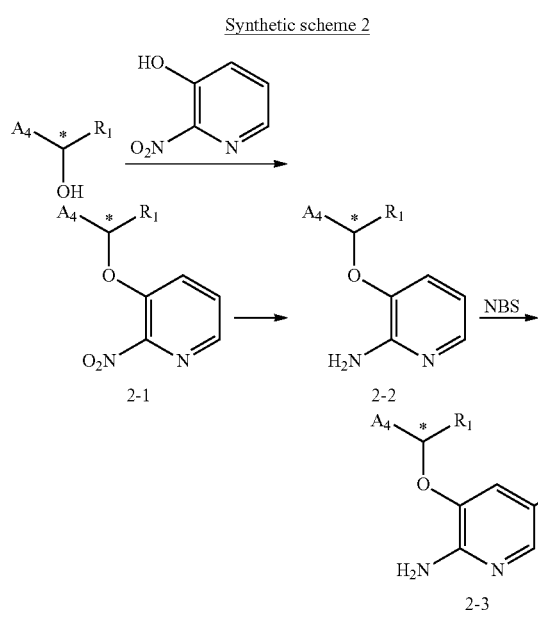

Compounds of Formula 2-3 can be synthesized following Synthetic scheme 2. Chiral alcohol and 3-hydroxy-2-nitropyridine, together with DIAD and triphenylphosphine are reacted in tetrahydrofuran to yield chirally inverted Intermediate 2-1. Under conventional reaction conditions, the nitro group of Intermediate 2-1 is reduced to yield Intermediate 2-2, and Intermediate 2-2 is reacted with bromosuccinimide in an organic solvent (such as acetonitrile, chloroform, carbon tetrachloride) to yield bromo-substituted Compound 2-3.

Synthetic scheme 3

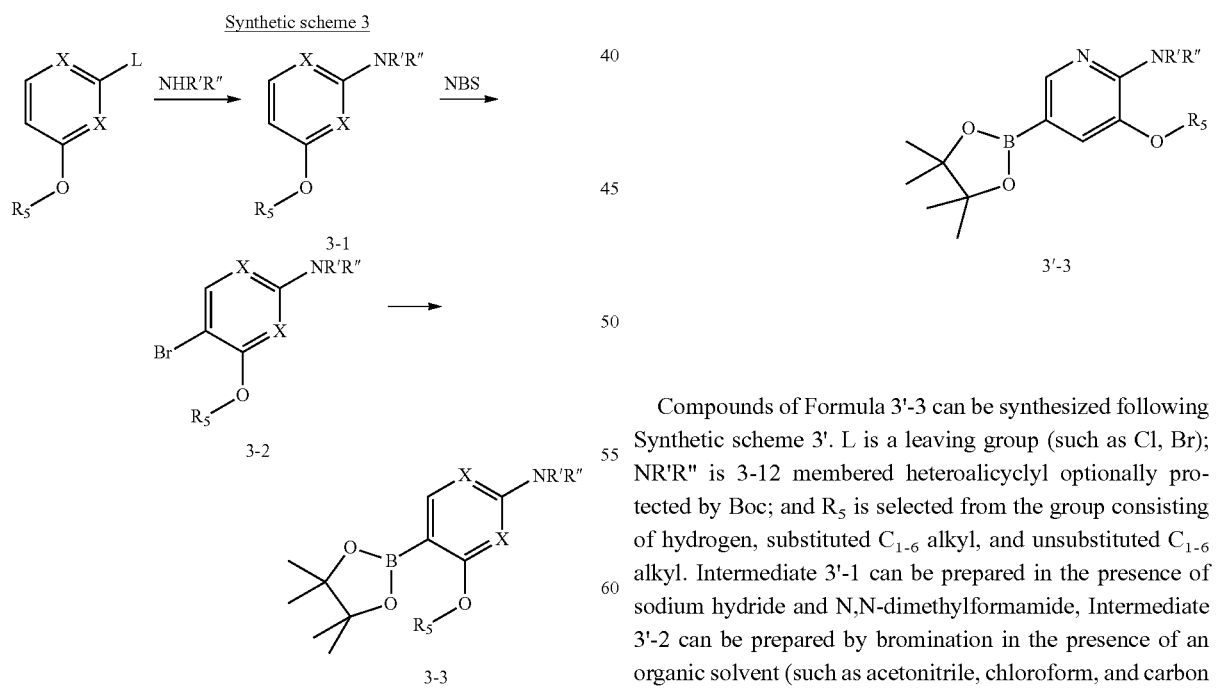

Compounds of Formula 3-3 can be synthesized following Synthetic scheme 3. L is a leaving group (such as Cl, Br); NR'R" is a 3-12 membered heteroalicyclyl optionally protected by Boc; X is independently selected from the group consisting of N and CH; and $R_5$ is selected from the group consisting of hydrogen substituted $C_{1-6}$ alkyl, and unsubstituted $C_{1-6}$ alkyl. Intermediate 3-1 can be prepared in the presence of sodium hydride and N,N-dimethylformamide, intermediate 3-2 can be prepared by bromination in the presence of an organic solvent (such as acetonitrile, chloroform, and carbon tetrachloride) and bromosuccinimide, and Intermediate 3-2 can be further reacted with bis(pinacolato)diboron to yield Intermediates 3-3.

Synthetic scheme 3'

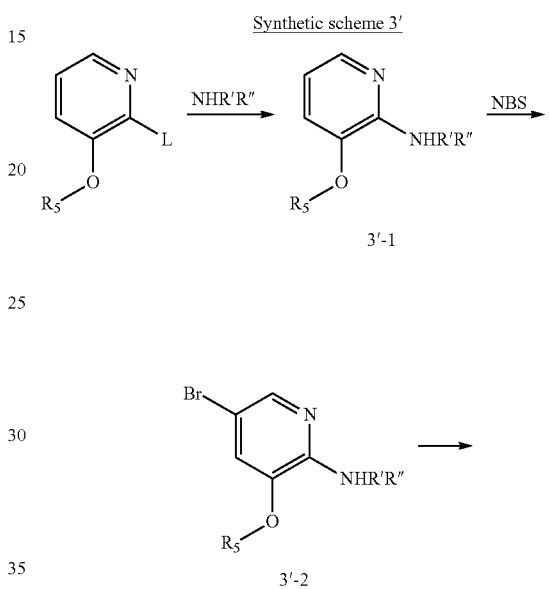

Compounds of Formula 3'-3 can be synthesized following Synthetic scheme 3'. L is a leaving group (such as Cl, Br); NR'R" is 3-12 membered heteroalicyclyl optionally protected by Boc; and $R_5$ is selected from the group consisting of hydrogen, substituted $C_{1-6}$ alkyl, and unsubstituted $C_{1-6}$ alkyl. Intermediate 3'-1 can be prepared in the presence of sodium hydride and N,N-dimethylformamide, Intermediate 3'-2 can be prepared by bromination in the presence of an organic solvent (such as acetonitrile, chloroform, and carbon tetrachloride) and bromosuccinimide, and Intermediate 3-2 can be further reacted with bis(pinacolato)diboron to yield Intermediate 3-3.

Synthetic scheme 4

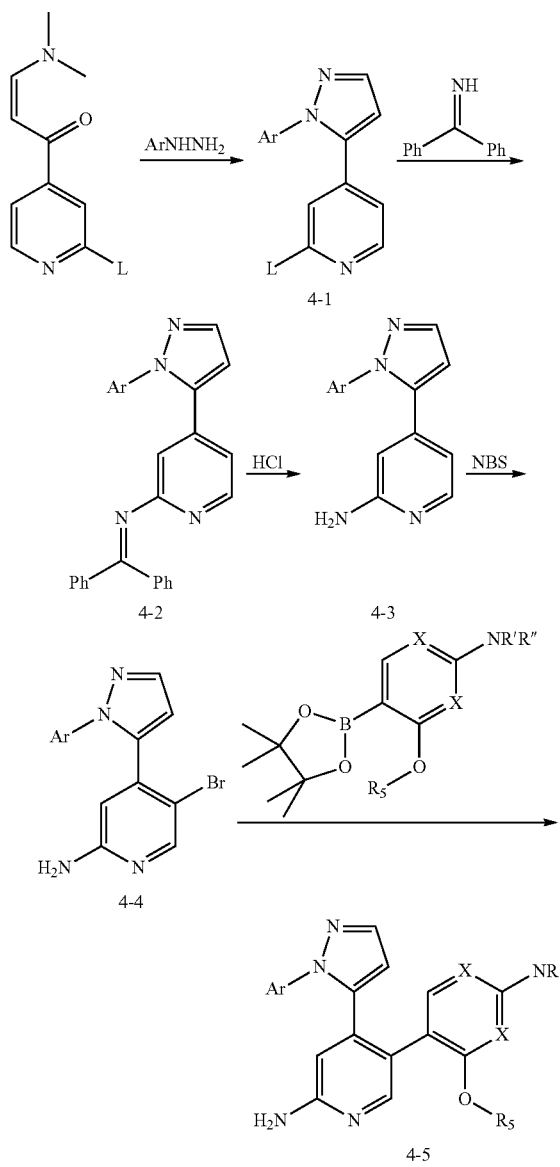

Synthetic scheme 5

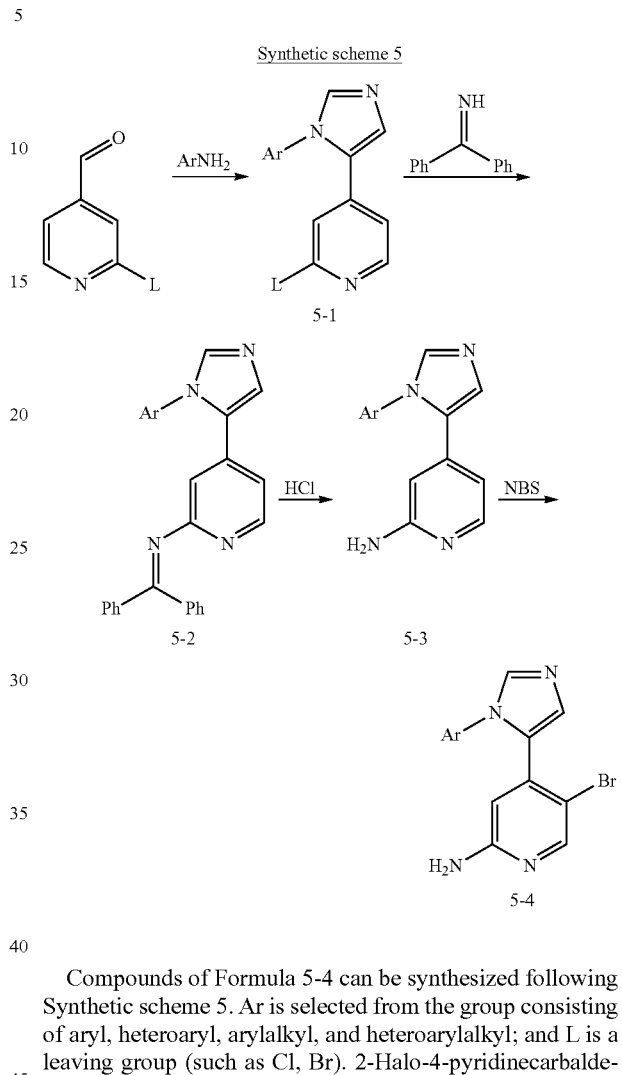

yield Compound 4-5. If Compound 4-5 has a protecting group (such as Boc), it can be further deprotected to yield the target compound.

Compounds of Formula 4-5 can be synthesized following Synthetic scheme 4. Ar is selected from the group consisting of aryl, heteroaryl, arylalkyl, and heteroarylalkyl; L is a leaving group (such as Cl, Br); NR'R" is a 3-12 membered heteroalicyclyl optionally protected by Boc; X is independently selected from the group consisting of N or CH; and $R_5$ is selected from the group consisting of hydrogen, substituted $C_{1-6}$ alkyl, and unsubstituted $C_{1-6}$ alkyl. Ring-closure reaction between 1-(2-halopyridin-4-yl)-3-(dimethylamino)prop-2-en-1-one and hydrazine in an organic solvent such as ethanol yields Intermediate 4-1. Intermediate 4-1 is coupled with benzophenone imine with palladium catalysis to yield Intermediate 4-2, and then the benzophenone protecting group is deproteced with acid (such as dilute hydrochloric acid) to yield Intermediate 4-3. Intermediate 4-3 is brominated with bromosuccinimide to yield Intermediate 4-4, which is then subject to coupling reaction with borate ester in the presence of a palladium catalysis to finally Compounds of Formula 5-4 can be synthesized following Synthetic scheme 5. Ar is selected from the group consisting of aryl, heteroaryl, arylalkyl, and heteroarylalkyl; and L is a leaving group (such as Cl, Br). 2-Halo-4-pyridinecarbaldehyde is first reacted with an amine in an organic solvent such as toluene, and then reacted with tosylmethyl isocyanide through ring closure under a basic condition to yield Intermediate 5-1. Intermediate 5-1 is coupled with benzophenone imine in the presence of a palladium catalysis to yield Intermediate 5-2, of which the benzophenone protecting group is then removed with acid (such as dilute hydrochloric acid) to yield Intermediate 5-3. Intermediate 5-3 is brominated with bromosuccinimide to yield Intermediate 5-4.

Synthetic scheme 6

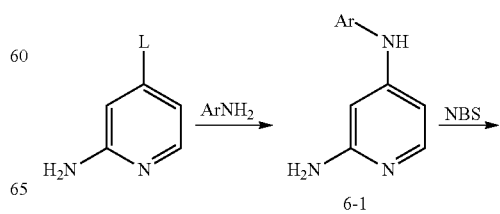

-continued

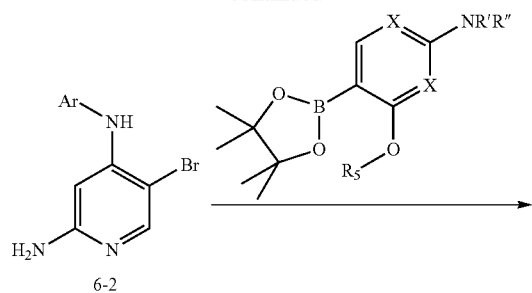

6-2

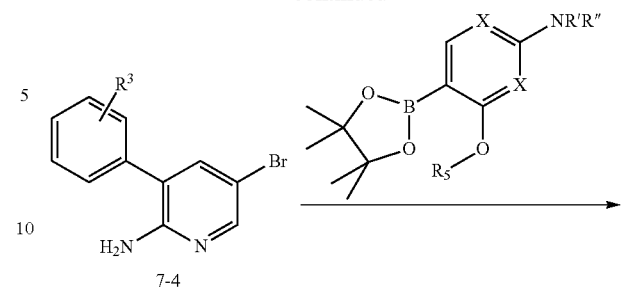

7-4

6-3

7-5

Compounds of Formula 6-3 can be synthesized following Synthetic scheme 6. Ar is selected from the group consisting of aryl and heteroaryl; L is a leaving group (such as Cl, Br); NR'R" is a 3-12 membered heteroalicyclyl optionally protected by Boc; X is independently selected from the group consisting of N and CH; and $R_5$ is selected from the group consisting of hydrogen, substituted $C_{1-6}$ alkyl, and unsubstituted $C_{1-6}$ alkyl. 4-Halo-2-aminopyridine is coupled with amine in the presence of a palladium catalysis to yield Intermediate 6-1, and Intermediate 6-1 is brominated with bromosuccinimide to yield Intermediate 6-2, which is then coupled with borate ester in the presence of a palladium catalysis to finally yield Compound 6-3. If Compound 6-3 has a protecting group, it can be further deprotected in an acidic condition to yield the target compound.

Compounds of Formula 7-5 can be synthesized following Synthetic scheme 7. NR'R" is a 3-12 membered heteroalicyclyl optionally protected by Boc; X is independently selected from the group consisting of N and CH, and $R_5$ is selected from the group consisting of hydrogen, substituted $C_{1-6}$ alkyl, and unsubstituted $C_{1-6}$ alkyl. Borate ester 7-1 is prepared in the presence of bis(pinacolato)diboron and palladium. Intermediate 7-1 is coupled in the presence of a palladium catalysis to yield Intermediate 7-2, which is then reduced with iron and dilute hydrochloric acid to yield Intermediate 7-3. Intermediate 7-3 is brominated with bromosuccinimide to yield Intermediate 7-4, which is then coupled with borate ester in the presence of a palladium catalysis to finally yield Compound 7-5. If Compound 7-5 has a protecting group, it can be further deprotected in an acidic condition to yield the target compound.

Synthetic scheme 7

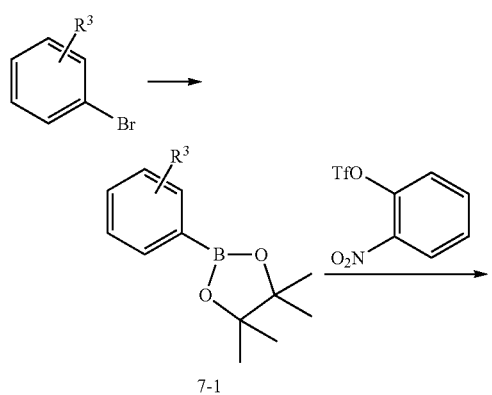

Synthetic scheme 8

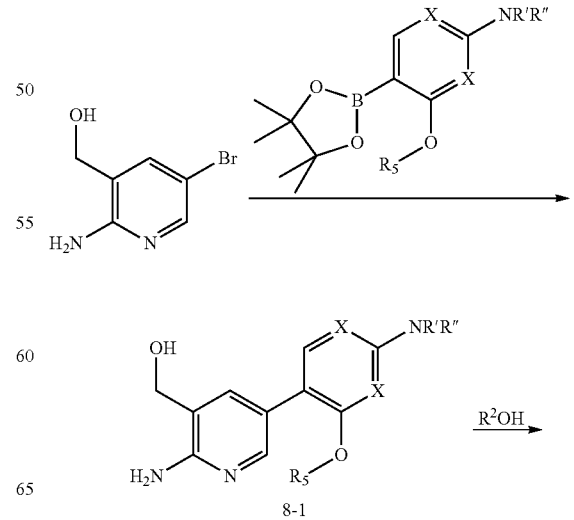

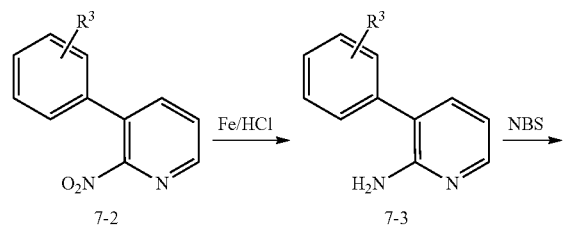

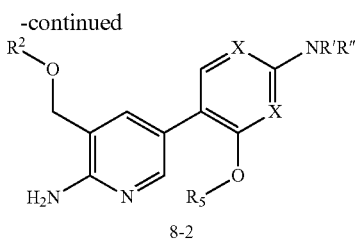

8-2

Compounds of Formula 8-2 can be synthesized following Synthetic scheme 8. NR'R" is a 3-12 membered heteroalicyclyl optionally protected by Boc; X is independently selected from the group consisting of N and CH; and R₅ is selected from the group consisting of hydrogen, substituted C₁₋₆ alkyl, and unsubstituted C₁₋₆ alkyl. 3-Hydroxymethyl-5-bromo-2-aminopyridine is coupled with borate ester in the presence of a palladium catalysis to yield Intermediate 8-1, which is then subject to Mitsunobu reaction to give compound of Formula 8-2. If Compound 8-2 has a protecting group, it can be further deprotected in an acidic condition to yield the title compound.

Synthetic scheme 9

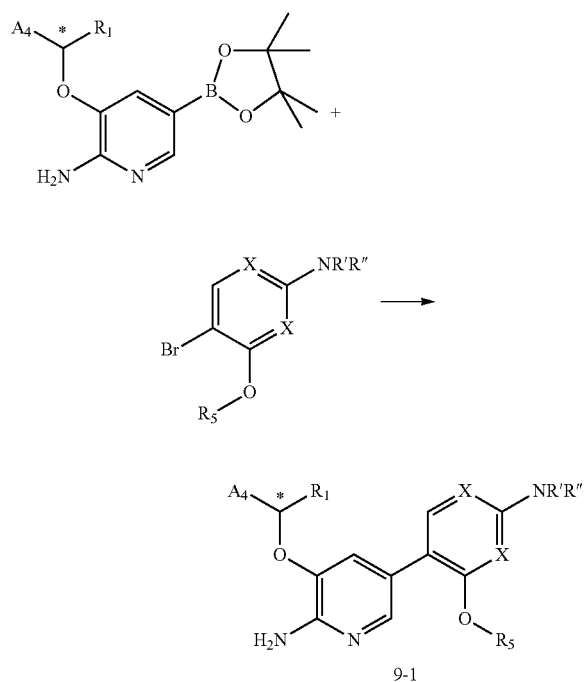

9-1

Compounds of Formula 9-1 can be synthesized following Synthetic scheme 9. NR'R" is a 3-12 membered heteroalicyclyl optionally protected by Boc; X is independently selected from the group consisting of N and CH; and R₅ is selected from the group consisting of hydrogen, substituted C₁₋₆ alkyl, and unsubstituted C₁₋₆ alkyl. Pyridine borate ester is coupled in the presence of a palladium catalysis to yield the target Compound 9-1. If Compound 9-1 has a protecting group, it can be further deprotected in an acidic condition to yield the target compound. When the compound of Formula 1-3 is used as the reactant, the corresponding target compound is obtained.

Synthetic scheme 10

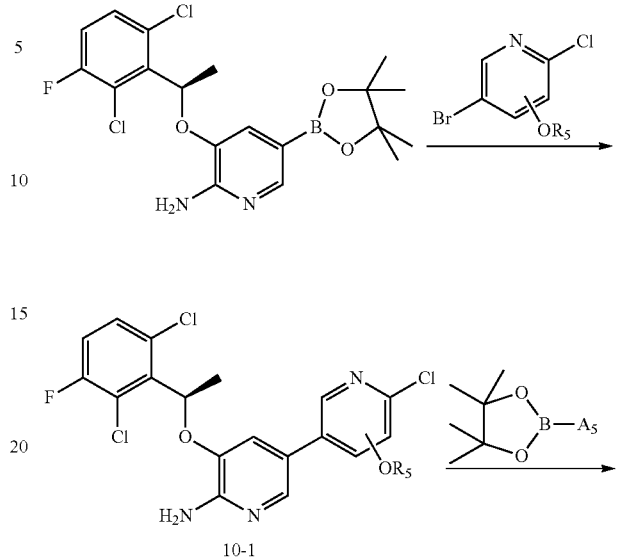

10-1

10-2

Compounds of Formula 10-2 can be synthesized following Synthetic scheme 10. A₅ is a 3-12 membered heteroalicyclyl optionally protected by Boc; the hetero atom of heteroalicyclyl may not be directly connected to the boron atom of borate ester; and R₅ is selected from the group consisting of C₁₋₆ alkyl. Borate ester is coupled in the presence of a palladium catalysis to yield Intermediate 10-1, which is then coupled with another borate ester in the presence of a palladium catalysis to finally yield Compound 10-2. If Compound 10-2 has a protecting group, it can be further deprotected in acidic conditions to yield the target compound.

Unless otherwise indicated, the meanings of groups and terms in the above Synthetic schemes are the same as those of compounds of Formula (I), (II), (III), and (IV).

The above Synthetic schemes only list the manufacture process of a part of compounds of the present invention; according to the general knowledge in the art and on the basis of the above Synthetic schemes, a person skilled in the art may also use similar methods to manufacture other compounds of the present invention.

When the present invention refers to compounds of Formula (III) or Formula (IV), the phenyl is numbered as follows:

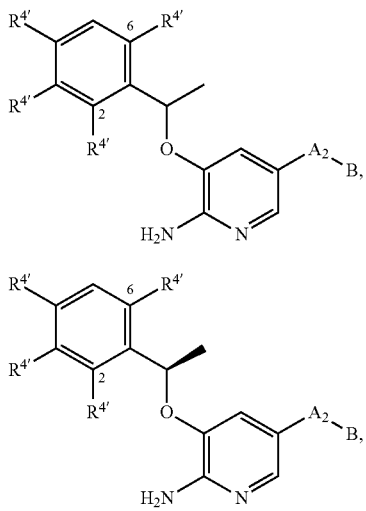

The term "Compound" of the present invention comprises all stereoisomers, geometric isomers, and tautomers.

Compounds of the present invention may be asymmetrical, for example, having one or more stereoisomer(s). Unless otherwise indicated, all stereoisomers are included, such as enantiomers and diastereomers thereof. Compounds containing asymmetric carbon atom(s) of the present invention can be isolated as a racemic form or an optically active pure form. The optically active pure form can be obtained from the resolution of racemic mixtures, or synthesized from chiral raw material(s) or chiral reagent(s).

Compounds of the invention also include tautomeric forms. Tautomeric forms derive from switching of a single bond and an adjacent double bond associated with the migration of a proton.

In the definition of compounds of Formulae (I)-(IV), terms as used herein have following meanings:

The term "halogen" refers to fluorine, chlorine, bromine, or iodine, preferably fluorine, chlorine, or bromine.

The term "hydroxy" refers to —OH.

The term "carboxyl" refers to —COOH.

The term "amino" refers to —NH$_2$, —NH(alkyl), or —N(alkyl)$_2$. Specific examples of "amino" include, but are not limited to, —NH$_2$, —NHCH$_3$, —NHCH(CH$_3$)$_2$, —N(CH$_3$)$_2$, —NHC$_2$H$_5$, —N(CH$_3$)C$_2$H$_5$, and the like.

The term "alkyl" refers to a linear or branched saturated hydrocarbon group consisting of carbon atom(s) and hydrogen atoms, such as C$_{1-20}$ alkyl, preferably C$_{1-6}$ alkyl, such as methyl, ethyl, propyl (such as n-propyl and isopropyl), butyl (such as n-butyl, isobutyl, sec-butyl or tert-butyl), pentyl (such as n-pentyl, isopentyl, neopentyl), n-hexyl, 2-methylhexyl, and the like. The "alkyl" group may be unsubstituted or substituted with substituent(s) including, but being not limited to, alkoxy, cyano, carboxyl, aryl, heteroaryl, amino, halogen, sulfonyl, sulfinyl, phosphoryl, and hydroxy.

The term "aryl" refers to an all-carbon monocyclic or fused ring having a completely conjugated π-electron system with 6-14 carbon atoms, preferably 6 to 12 carbon atoms, most preferably 6 carbon atoms. The aryl can be unsubstituted or substituted by one or more substituent(s). Examples of substituents include, but are not limited to, alkyl, alkoxy, aryl, arylalkyl, amino, halogen, hydroxy, sulfonyl, sulfinyl, phosphoryl, and heteroalicyclyl. Non-limiting examples of unsubstituted aryl include, but are not limited to, phenyl, naphthyl, and anthracenyl.

The term "arylalkyl" refers to alkyl substituted by aryl as hereinbefore defined, preferably C$_{1-6}$ alkyl substituted by aryl. Non-limiting examples of arylalkyl include, but are not limited to, —CH$_2$-phenyl, —(CH$_2$)$_2$-phenyl, —(CH$_2$)$_3$-phenyl, —CH(CH$_3$)-phenyl, —CH$_2$—CH(CH$_3$)-phenyl, —(CH$_2$)$_4$-phenyl, —CH$_2$—CH(CH$_3$)—CH$_2$-phenyl, —CH$_2$—CH$_2$—CH(CH$_3$)-phenyl, and the like.

The term "heteroaryl" refers to a 5-12 membered monocyclic or fused ring having a completely conjugated π-electron system with 5, 6, 7, 8, 9, 10, 11, or 12 ring atoms, among which 1, 2, 3, or 4 ring atom(s) is(are) selected from the group consisting of N, O, and S, and the other ring atom(s) is(are) C. The "heteroaryl" can be unsubstituted or substituted by substituent(s) including, but being not limited to, alkyl, alkoxy, aryl, arylalkyl, amino, halogen, hydroxy, cyano, nitro, carbonyl, and heteroalicyclyl. Non-limiting examples of unsubstituted heteroaryl groups include, but are not limited to, pyrrolyl, furyl, thienyl, imidazolyl, oxazolyl, pyrazolyl, pyridinyl, pyrimidinyl, pyrazinyl, quinolyl, isoquinolinyl, tetrazolyl, and triazinyl.

The term "heteroarylalkyl" refers to alkyl substituted by heteroaryl as hereinbefore defined, preferably C$_{1-6}$ alkyl substituted by heteroaryl. Non-limiting examples of heteroarylalkyl groups include, but are not limited to, —CH$_2$-pyrazolyl, —(CH$_2$)$_2$-pyridinyl, —(CH$_2$)$_3$-thienyl, —CH(CH$_3$)-pyrazinyl, —CH$_2$—CH(CH$_3$)-furyl, and the like.

The term "heteroalicyclyl" refers to a 3-12 membered monocyclic or fused ring having 3, 4, 5, 6, 7, 8, 9, 10, 11, or 12 ring atoms, among which 1 or 2 ring atom(s) is(are) heteroatom(s) selected from the group consisting of N, O, and S(O)$_n$ (wherein n is 0, 1, or 2), and the other ring atom(s) is(are) C. Such a ring may be saturated or unsaturated (e.g., having one or more double bond(s)), but it does not have a completely conjugated π-electron system. 3-Membered saturated heteroalicyclyl groups include, but are not limited to, oxiranyl, thiiranyl, and aziranyl; 4-membered saturated heteroalicyclyl groups include, but are not limited to, azetidinyl, dioxetanyl, and thietanyl; 5-membered saturated heteroalicyclyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl; 6-membered saturated heteroalicyclyl groups include, but are not limited to, piperidinyl, tetrahydropyranyl, tetrahydrothiopyranyl, morpholinyl, piperazinyl, 1,4-thioxanyl, 1,4-dioxanyl, thiomorpholinyl, and 1,4-dithianyl; 7-membered saturated heteroalicyclyl groups include, but are not limited to, azepanyl, oxepanyl, and thiepanyl; 5-membered unsaturated heteroalicyclyl groups include, but are not limited to, pyrrolinyl, dihydrofuryl, and dihydrothienyl; and 6-membered unsaturated heteroalicyclyl groups include, but are not limited to, dihydropyridyl, tetrahydropyridyl, dihydropyranyl, tetrahydropyranyl, and dihydrothiopyranyl. Heteroalicyclyl may be unsubstituted or each hydrogen atom of the heteroalicyclyl may be substituted by substituent(s) including, but being not limited to, alkyl, alkoxy, =O, aryl, arylalkyl, —COOH, —CN, amino, halogen, and hydroxy.

The term "therapeutically effective amount" refers to an amount of a compound of the general formula which is effective for treatment when the compound is administered to a mammal in need. The therapeutically effective amount will vary depending on the specific potency of the therapeutic agent and the age, physiological condition, presence of other disease states, and nutritional status of the patient. In addition, the simultaneous use of the other medication for the treatment will affect the determination of the therapeutically effective amount of the therapeutic agents to be administered.

"Treatment" means any treatment of diseases in mammals, including:

(i) preventing disease, that is to cause the clinical symptoms of the disease not to develop;

(ii) inhibiting the disease, that is to prevent the development of clinical symptoms; and/or (iii) relieving the disease, that is to cause regression of clinical symptoms.

The compounds of the present invention, or salts, stereoisomers, or enantiomers thereof, or mixtures thereof may be administered alone as active substance, and are preferably administered in the form of pharmaceutical compositions.

Another aspect of the present invention provides a pharmaceutical composition comprising a compound of Formula (I), (II), (III), or (IV), or a pharmaceutically acceptable salt, a stereoisomer, or an enantiomer thereof, or a mixture thereof as active ingredients, and one or more pharmaceutically acceptable carrier(s).

"Pharmaceutical composition" refers to a formulation consisting of one or more compound(s) of the present invention, or salt(s), stereoisomer(s), or enantiomer(s) thereof, or mixture(s) thereof, and carrier(s) that is generally accepted in the art for the delivery of biologically active compounds to an organism (such as human).

The term "pharmaceutically acceptable carrier" refers to a carrier that doesn't cause significant stimulation to an organism, and will not abrogate the biological activity and properties of the active compound. The "Pharmaceutically acceptable carrier" refers to an inert substance administered together with the active ingredient and beneficial to the administration, including, but not limited to, any glidants, sweetening agents, diluents, preservatives, dyes/colorants, flavor enhancers, surfactants, wetting agents, dispersing agents, disintegrating agents, suspending agents, stabilizers, isotonic agents, solvents, and emulsifiers, which are licensed by the State Food and Drug Administration and acceptable for human or animal (such as livestock). Non-limiting examples of the carriers include calcium carbonate, calcium phosphate, various sugars and various types of starch, cellulose derivatives, gelatin, vegetable oil, and polyethylene glycol.

The pharmaceutical compositions of the present invention may be formulated into solid, semi-solid, liquid or gaseous formulations, such as tablets, pills, capsules, powders, granules, pastes, emulsions, suspensions, solutions, suppositories, injections, inhalants, gels, microspheres, and aerosols, and the like.

Typical routes of the administration of a compound of the present invention, or a pharmaceutically acceptable salt thereof, or a pharmaceutical composition thereof include, but are not limited to, oral, rectal, transmucosal, enteral administration, and topical, transdermal, inhalation, parenteral, sublingual, intravaginal, intranasal, intraocular, intraperitoneal, intramuscular, subcutaneous, and intravenous administration. The preferred route of the administration is oral.

The pharmaceutical compositions of the present invention may be manufactured using the method well known in the art, such as conventional mixing method, dissolution method, granulation method, dragee manufacture method, grinding method, emulsion method, freeze drying method, and the like.

In a preferred embodiment, the pharmaceutical compositions are in oral form. For oral administration, the active compounds may be mixed with pharmaceutically acceptable carrier(s) well-known in the art to formulate a pharmaceutical composition. Such carrier(s) enable the compounds of the present invention to be formulated as tablets, pills, lozenges, dragees, capsules, liquids, gels, syrup, suspending agents, or the like, for oral administration to a patient.

A solid oral pharmaceutical composition may be manufactured by a conventional mixing, filling, or tabletting method. For example, it can be obtained by mixing the active compound with a solid excipient, optionally grinding the resulting mixture, adding other suitable auxiliaries as required, and then processing the mixture into granules, giving tablets or cores of dragees. Suitable auxiliaries include, but are not limited to, binders, diluents, disintegrating agents, lubricants, glidants, sweetening agents, and flavoring agents, and the like. Exemplified are microcrystalline cellulose, glucose solution, acacia mucilage, gelatin solution, sucrose and starch paste; talc, starch, magnesium stearate, calcium stearate or stearic acid; lactose, sucrose, starch, mannitol, sorbitol or dicalcium phosphate; silica; cross-linked sodium carboxymethylcellulose, pregelatinized starch, sodium starch glycolate, alginic acid, corn starch, potato starch, methyl cellulose, agar, carboxymethyl cellulose, crosslinked polyvinylpyrrolidone, and the like. The cores of dragees may be optionally coated according to well known methods in pharmaceutical practice, especially using an enteric coating.

The pharmaceutical compositions may also be adapted for parenteral administration, such as sterile solutions, suspensions, or lyophilized products with suitable unit dosage form. Suitable excipients, such as fillers, buffering agents, or surfactants, can be used.

Another aspect of the present invention provides a method to regulate the protein kinase activity comprising contacting the protein kinase with the compound of Formula (I), (II), (III), or (IV), or a pharmaceutically acceptable salt, a stereoisomer, or an enantiomer thereof, or a mixture thereof. Preferably, the protein kinase is selected from ALK. In addition, the protein kinase comprises a mutated kinase, wherein the mutated kinase is selected from ALK kinase.

Furthermore, the present invention also provides use of a compound of Formula (I), (II), (III), or (IV), or a pharmaceutically acceptable salt, a stereoisomer, or an enantiomer thereof, or a mixture thereof, or a pharmaceutical composition thereof for the manufacture of a medicament for the therapeutic and/or prophylactic treatment of diseases, wherein the diseases are those related to protein kinase (such as ALK) activity, such as abnormal cell proliferation, wherein the abnormal cell proliferation includes cancer. The present invention also provides use of a compound of Formula (I), (II), (III), or (IV), or a pharmaceutically acceptable salt, a stereoisomer, or an enantiomer thereof, a mixture thereof, or a pharmaceutical composition thereof for the manufacture of a medicament for the therapeutic and/or prophylactic treatment of diseases mediated by ALK.

Diseases mediated by ALK include ALK-positive non-small cell lung carcinoma, anaplastic large cell lymphoma, inflammatory myofibroblastic tumor, nasopharyngeal carcinoma, breast cancer, colorectal cancer, diffuse large B-cell lymphoma, systemic histiocytosis, and neuroblastoma, and the like, preferably ALK-positive non-small cell lung carcinoma.

Furthermore, the present invention also provides a method for the therapeutic and/or prophylactic treatment of mammalian (such as human) diseases, wherein the diseases are those related to protein kinase (such as ALK) activity, comprising administering to a mammal (such as human) a therapeutically effective amount of a compound of Formula (I), (II), (III), or (IV), or a pharmaceutically acceptable salt, a stereoisomer, an enantiomer thereof, or a mixture thereof, or a pharmaceutical composition thereof.

Furthermore, the present invention also provides a compound of Formula (I), (II), (III), or (IV) or a pharmaceutically acceptable salt, a stereoisomer, or an enantiomer thereof, a mixture thereof, or a pharmaceutical composition thereof for modulating protein kinase activity or for the therapeutic and/or prophylactic treatment of mammalian (such as human) diseases associated with protein kinase activity. The preferred protein kinase is ALK. The protein kinase comprises a mutated kinase, wherein the mutated kinase is selected from ALK kinase.

EXAMPLES

The purpose of following specific examples is to facilitate those skilled in the art to more clearly understand and implement the invention. They should not be construed as limiting the scope of the invention, and they are merely exemplary illustrations and typical representatives of the invention. Those skilled in the art would understand that there are other synthetic routes involved for preparing the compounds of the invention, ones provided below are non-limiting examples.

All operations involving raw materials which are easily oxidized or easily hydrolyzed are carried out under a nitrogen protection atmosphere. Unless otherwise indicated, raw materials used in the invention are commercially available and used without further purification.

Column chromatography was performed using silica gel (200-300 mesh) produced by Qingdao Chemical Co., Ltd. Thin Layer Chromatography was performed using prefabricated panels (silica gel 60 $PF_{254}$, 0.25 mm) produced by E. Merck. Separation of chiral compounds and measure of enantiomeric excess(ee) were performed using the Agilent LC 1200 series (column: CHIRALPAK AD-H, Ø4.6×250 mm, 5 micron, 30° C.). NMR spectrum (NMR) was performed using Varian VNMRS-400 NMR spectrometer; LC/MS was performed using FINNIGAN Thermo LCQ Advantage MAX, Agilent LC 1200 series (column: Waters Symmetry C18, Ø4.6×50 mm, 5 microns, 35° C.), and ESI (+) ion mode.

EXAMPLES

Intermediate 1: tert-butyl 4-(3-methoxyl-4-(4,4,5,5-tetramethyl-1,3,2-dioxaborolan-2-yl)phenyl) piperazine-1-carboxylate Step 1: tert-butyl 4-(3-methoxylphenyl)piperazine-1-carboxylate 3-Bromoanisole (1.0 g, 5 mmol), tert-butyl piperazine-1-carboxylate (1.2 g, 6 mmol), $Pd_2(dba)_3$ (229 mg, 0.25 mmol), BINAP (328 mg, 0.5 mmol), and sodium tert-butoxide (0.72 g, 7.5 mmol) were added into dry toluene (20 mL). The resultant were purged with nitrogen and stirred at 80° C. overnight. After the solution was cooled, it was concentrated and isolated by silica gel column chromatography to give tert-butyl 4-(3-methoxylphenyl) piperazine-1-carboxylate (1.4 g, 96% yield). MS m/z [ESI]: 293.2 [M+1].

Step 2: tert-butyl 4-(3-methoxyl-4-bromophenyl) piperazine-1-carboxylate

To a stirred solution of tert-butyl 4-(3-methoxylphenyl) piperazine-1-carboxylate (1.6 g, 5 mmol) in $CH_2Cl_2$ (100 mL), a solution of liquid bromine (0.87 g, 5 mmoL) in $CH_2Cl_2$ (10 mL) was added dropwise at 0° C. Upon completion of the addition, the resultant was stirred at 0° C. for 1 hour. The resultant was washed with saturated sodium bicarbonate solution, dried, concentrated, and isolated by silica gel column chromatography to give tert-butyl 4-(3-methoxyl-4-bromophenyl)piperazine-1-carboxylate (756 mg, 40% yield). MS m/z [ESI]: 371.1 [M+1].

Step 3: tert-butyl 4-(3-methoxyl-4-(4,4,5,5-tetramethyl-1,3,2-dioxaborolan-2-yl)phenyl) piperazine-1-carboxylate tert-Butyl 4-(3-methoxyl-4-bromophenyl)piperazine-1-carboxylate (740 mg, 2 mmol), bis(pinacolato)diboron (1008 mg, 4 mmol), $Pd(dppf)Cl_2$ (73 mg, 0.1 mmol), and anhydrous potassium acetate (588 mg, 6 mmol) were added into dry 1,4-dioxane (20 mL). The resultant was purged with nitrogen and then stirred at 120° C. for 2 hours. After the solution was cooled, it was concentrated and isolated by silica gel column chromatography to give tert-butyl 4-(3-methoxyl-4-(4,4,5,5-tetramethyl-1,3,2-dioxaborolan-2-yl) phenyl) piperazine-1-carboxylate (640 mg, 76% yield). MS m/z[ESI]: 419.3[M+1]. $^1$H-NMR (400 MHz, $CDCl_3$): δ=7.212 (d, J=6.8 Hz, 1H), 6.58-6.40 (m, 2H), 3.861 (s, 3H), 3.593-3.555 (m, 4H), 3.125-3.110 (m, 4H), 1.483 (s, 9H), 1.240 (s, 12H).

Intermediate 2: 1-(3-methoxyl-4-(4,4,5,5-tetramethyl-1,3,2-dioxaborolan-2-yl)phenyl)-4-methylpiperazine Step 1:
1-(3-methoxyl-4-nitrophenyl)-4-methylpiperazine 5-Fluoro-2-nitroanisole (14.0 g, 83 mmol), N-methylpiperazine (9.1 g, 91 mmol), and potassium carbonate (34.5 g, 250 mmol) were added into DMSO (200 mL). The resultant was stirred at 90° C. overnight. After the resultant cooled, water (3 L) was added, and the precipitated solid was filtered and dried to give 1-(3-methoxyl-4-nitrophenyl)-4-methylpiperazine (20.9 g). MS m/z [ESI]: 252.1 [M+1].

Step 2:
1-(3-methoxyl-4-aminophenyl)-4-methylpiperazine 1-(3-Methoxyl-4-nitrophenyl)-4-methylpiperazine (20.8 g, 83 mmol) and raney nickel (4.0 g) were added into methanol (200 mL), and then air was replaced with hydrogen. The resultant was stirred overnight under the hydrogen atmosphere. The resultant was filtered and concentrated to give 1-(3-methoxyl-4-aminophenyl)-4-methylpiperazine (17.0 g, 93% yield). MS m/z [ESI]: 222.2 [M+1].

Step 3:
1-(3-methoxyl-4-bromophenyl)-4-methylpiperazine 1-(3-Methoxyl-4-aminophenyl)-4-methylpiperazine (16.6 g, 75 mmol) and CuBr (21.5 g, 0.15 mol) were added into tetrahydrofuran (200 mL), and then amyl nitrite (17.6 g, 0.15 mol) was added dropwise under stirring. The resultant was stirred at room temperature for 1 hour and refluxed for 3 hours. After the resultant was cooled, it was filtered, and the filtrate was concentrated and isolated by silica gel column chromatography (petroleum ether: ethyl acetate=1:1) to give 1-(3-methoxyl-4-bromophenyl)-4-methylpiperazine (5.98 g, 28% yield). MS m/z [ESI]: 285.1 [M+1].

Step 4: 1-(3-methoxyl-4-(4,4,5,5-tetramethyl-1,3,2-dioxaborolan-2-yl)phenyl)-4-methylpiperazine 1-(3-Methoxyl-4-bromophenyl)-4-methylpiperazine (2.85 g, 10 mmol), bis(pinacolato) diboron (3.78 g, 15 mmol), Pd(dppf)Cl$_2$ (366 mg, 0.5 mmol), and anhydrous potassium acetate (1.96 g, 20 mmol) were added to dry 1,4-dioxane (100 mL). The resultant was purged with nitrogen and stirred at 120° C. for 3 hours. After the resultant was cooled, it was concentrated and isolated by silica gel column chromatography to give 1-(3-methoxyl-4-(4,4,5,5-tetramethyl-1,3,2-dioxaborolan-2-yl)phenyl)-4-methylpiperazine (1.86 g, 56% yield). MS m/z [ESI]: 333.2 [M+1].

Intermediate 3: tert-butyl 4-(4-(4,4,5,5-tetramethyl-1,3,2-dioxaborolan-2-yl)-1H-pyrazol-1-yl) piperidine-1-carboxylate Intermediate 4: 1-(2-chloropyridin-4-yl)-3-(dimethylamino)prop-2-en-1-one Step 1: 2-chloro-N-methoxyl-N-methylisonicotinamide To a solution of 2-chloroisonicotinic acid (18.0 g, 0.115 mol) in CH$_2$Cl$_2$ (250 mL), N,N'-carbonyldiimidazole (17.0 g, 0.105 mol) was added in portions under stirring at room temperature. Upon completion of the addition, the resultant was stirred for 0.5 hour, then N,O-dimethylhydroxylamine (10.2 g, 0.167 mol) was added, and the resultant was stirred at room temperature overnight. Diethyl ether (200 mL) was added, and the resultant was washed with water, dried, and concentrated to give 2-chloro-N-methoxyl-N-methylisonicotinamide (18.0 g, 78% yield). MS m/z [ESI]: 201.0 [M+1].

Step 2: 1-(2-chloropyridin-4-yl)ethanone

To a solution of 2-chloro-N-methoxyl-N-methylisonicotinamide (10.0 g, 50 mmol) in dry tetrahydrofuran (50 mL), 3 M methylmagnesium bromide (50 mL, 150 mmol) was added under stirring at 0° C. Upon completion of the addition, the resultant was stirred at room temperature overnight. The reaction was quenched with saturated ammonium chloride solution, extracted by ethyl acetate, dried, concentrated, and purified by silica gel column chromatography to give 1-(2-chloropyridin-4-yl)ethanone (7.5 g, 96% yield). MS m/z [ESI]: 156.0 [M+1].

Step 3: 1-(2-chloropyridin-4-yl)-3-(dimethylamino)prop-2-en-1-one 1-(2-Chloropyridin-4-yl)ethanone (7.5 g, 48 mmol) was added into DMF/DMA (40 mL), and the resultant was stirred at 100° C. for 2 hours. After the resultant was cooled, it was poured into petroleum ether (500 mL). The solid was filtered, washed by diethyl ether, and dried to give 1-(2-chloropyridin-4-yl)-3-(dimethylamino)prop-2-en-1-one (7.4 g, 74% yield). MS m/z [ESI]: 211.1 [M+1].

Intermediate 5: 3-(1-(2,6-dichloro-3-fluorophenyl)ethyoxyl)-5-(4,4,5,5-tetramethyl-1,3,2-dioxaborolan-2-yl)-2-aminopyridine

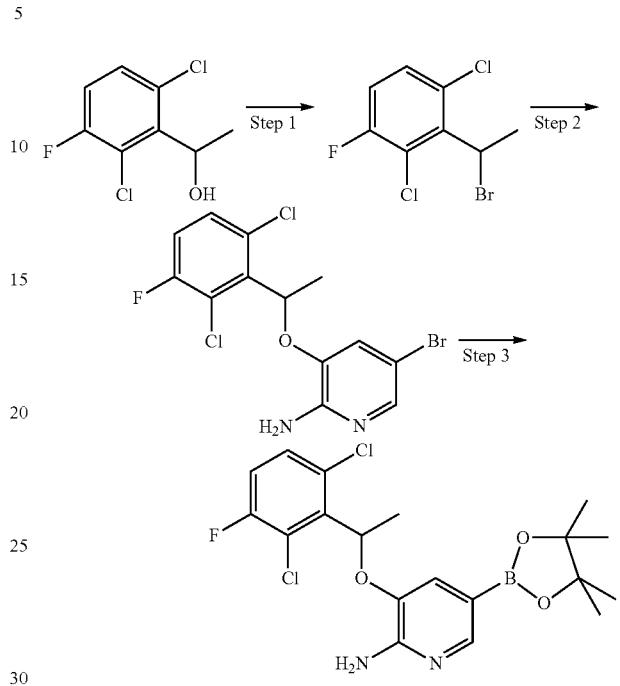

Step 1: 1,3-dichloro-2-(1-bromoethyl)-4-fluorobenzene

To a solution of triphenylphosphine (27.8 g, 0.106 mol) in CH$_2$Cl$_2$ (200 mL), liquid bromine (16.8 g, 0.105 mol) was added slowly under stirring at 0° C. Upon completion of the addition, the resultant was stirred for 10 minutes, and then to which 1-(2,6-dichloro-3-fluorophenyl)ethanol (20.9 g, 0.10 mol) was added. Upon completion of the addition, the resultant was stirred for 30 minutes. The reaction was quenched with ethanol, and the reaction liquid was poured into saturated sodium bicarbonate solution, and extracted with CH$_2$Cl$_2$. The organic phase was dried over anhydrous sodium sulfate, filtered, concentrated, and purified by silica gel column chromatography to give 1,3-dichloro-2-(1-bromoethyl)-4-fluorobenzene (25.8 g, 95% yield). $^1$H-NMR (400 MHz, CDCl$_3$): δ=7.28 (m, 1H), 7.05 (t, 1H), 5.97 (q, 1H), 2.16 (d, 3H).

Step 2: 5-bromo-3-(1-(2,6-dichloro-3-fluorophenyl)ethyoxyl)-2-aminopyridine 1,3-Dichloro-2-(1-bromoethyl)-4-fluorobenzene (25.8 g, 95 mmol), 2-amino-5-bromo-pyridin-3-ol (28.7 g, 152 mmol), and K$_2$CO$_3$ (26.2 g, 190 mmol) were added into DMF (400 mL) at room temperature. Upon completion of the addition, the resultant was reacted for 6 hours under a nitrogen atmosphere. The solution was concentrated, CH$_2$Cl$_2$ was added, and the resultant was washed with water, dried, concentrated, and purified by silica gel column chromatography to give 5-bromo-3-(1-(2,6-dichloro-3-fluorophenyl)ethyoxyl)-2-aminopyridine (15.2 g, 42% yield). MS m/z [ESI]: 380.9 [M+1].

Step 3: 3-(1-(2,6-dichloro-3-fluorophenyl)ethyoxyl)-5-(4,4,5,5-tetramethyl-1,3,2-dioxaborolan-2-yl)-2-aminopyridine 5-Bromo-3-(1-(2,6-dichloro-3-fluorophenyl)ethyoxyl)-2-aminopyridine (7.6 g, 20 mol), bis(pinacolato)diboron (7.56 g, 30 mmol), Pd(dppf)Cl$_2$ (732 mg, 1 mmol), and anhydrous potassium acetate (4.90 g, 50 mmol) were added to dry 1,4-dioxane (200 mL), and the resultant was purged with nitrogen. The resultant was reacted at 100° C. for 4 hours. After the resultant was cooled, it was concentrated and purified by silica gel column chromatography to give 3-(1-(2,6-dichloro-3-fluorophenyl)ethyoxyl)-5-(4,4,5,5-tetramethyl-1,3,2-dioxaborolan-2-yl)-2-aminopyridine (5.12 g, 60% yield). MS m/z [ESI]: 427.1 [M+1].

Intermediate 6: (R)-3-(1-(2,6-dichloro-3-fluorophenyl)ethyoxyl)-5-(4,4,5,5-tetramethyl-1,3,2-dioxaborolan-2-yl)-2-aminopyridine

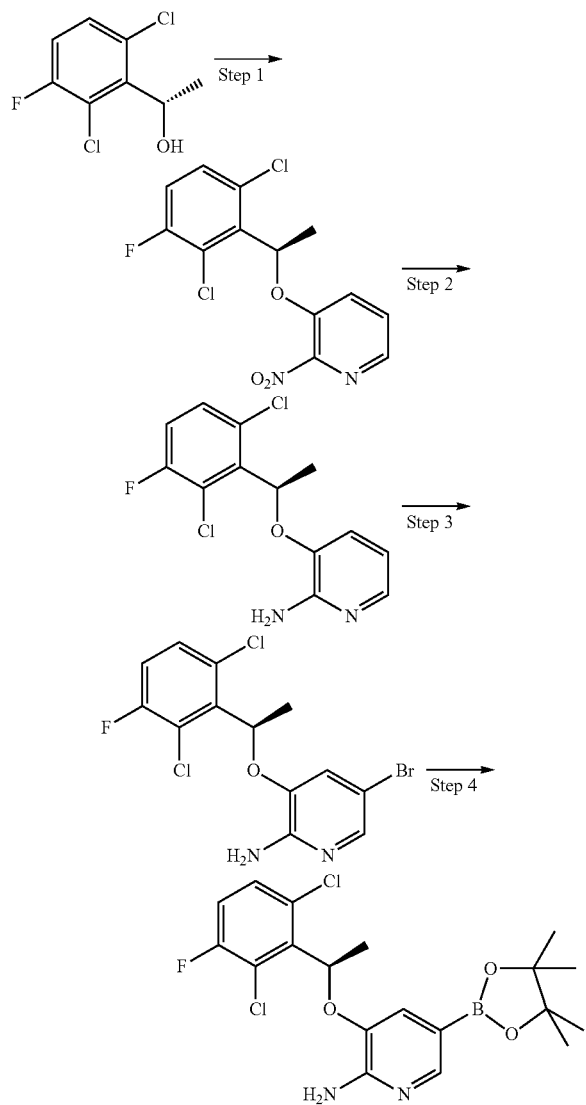

Step 1: (R)-3-(1-(2,6-dichloro-3-fluorophenyl)ethyoxyl)-2-nitropyridine (S)-3-(1-(2,6-dichloro-3-fluorophenyl)ethanol (20.9 g, 0.10 mol) was dissolved in anhydrous tetrahydrofuran (200 mL), and then 3-hydroxy-2-nitropyridine (16.0 g, 0.11 mol) and triphenylphosphine (40.0 g, 0.15 mol) were subsequently added under a nitrogen atmosphere. The reaction liquid was stirred at room temperature for 1 hour. After the reaction was cooled to 0° C., DIAD (40 mL, 0.15 mol) was added and the resultant was stirred for 12 hours. The solvent was evaporated, and the crude oil product was purified by silica gel column chromatography to give (R)-3-(1-(2,6-dichloro-3-fluorophenyl)ethyoxyl)-2-nitropyridine (20.2 g, 61% yield).

Step 2: (R)-3-(1-(2,6-dichloro-3-fluorophenyl)ethyoxyl)-2-aminopyridine

To a solution of (R)-3-(1-(2,6-dichloro-3-fluorophenyl)ethyoxyl)-2-nitropyridine (20.0 g, 60 mmol) in ethanol (300 mL), 2M HCl (15 mL) and reduced iron powder (27 g, 480 mmol) were added under stirring at 0° C. Upon completion of the addition, the reaction was heated for 12 hours. After the resultant was cooled to room temperature, it was filtered, and the filtrate was concentrated to give (R)-3-(1-(2,6-dichloro-3-fluorophenyl)ethyoxyl)-2-aminopyridine (17.0 g, 94% yield), which was directly used in the next step. MS m/z [ESI]: 301.0 [M+1].

Step 3: (R)-3-(1-(2,6-dichloro-3-fluorophenyl)ethyoxyl)-5-bromo-2-aminopyridine

To a solution of (R)-3-(1-(2,6-dichloro-3-fluorophenyl)ethyoxyl)-2-aminopyridine (15.0 g, 50 mmol) in acetonitrile (200 mL), N-bromobutanimide (10 g, 56 mmol) at was added in portions under stirring at 0° C. Upon completion of the addition, the resultant was stirred for 1 hour. The solvent was evaporated, and CH$_2$Cl$_2$ was added. The solution was washed by saturated sodium bicarbonate, dried, concentrated, and purified by silica gel column chromatography to give (R)-3-(1-(2,6-dichloro-3-fluorophenyl)ethyoxyl)-5-bromo-2-aminopyridine (9.88 g, 52% yield). MS m/z [ESI]: 380.9 [M+1].

Step 4: (R)-3-(1-(2,6-dichloro-3-fluorophenyl)ethyoxyl)-5-(4,4,5,5-tetramethyl-1,3,2-dioxaborolan-2-yl)-2-aminopyridine (R)-3-(1-(2,6-dichloro-3-fluorophenyl)ethyoxyl)-5-bromo-2-aminopyridine (7.6 g, 20 mol), bis(pinacolato)diboron (7.56 g, 30 mmol), Pd(dppf)Cl$_2$ (732 mg, 1 mmol), and anhydrous potassium acetate (4.90 g, 50 mmol) were added to dry 1,4-dioxane (200 mL), and purged with nitrogen. The resultant was stirred at 100° C. for 4 hours. After the resultant was cooled, it was concentrated and purified by silica gel column chromatography to give (R)-3-(1-(2,6-dichloro-3-fluorophenyl)ethyoxyl)-5-(4,4,5,5-tetramethyl-1,3,2-dioxaborolan-2-yl)-2-aminopyridine (5.46 g, 64% yield). MS m/z [ESI]: 427.1 [M+1].

Intermediate 7: 5-bromo-2-(4-isopropylpiperazin-1-yl)-4-methoxpyrimidine

Step 1: 2-(4-isopropylpiperazin-1-yl)-4-methoxypyrimidine

To a solution of N-isopropylpiperazine (1.27 g, 10 mmol) in anhydrous DMF (60 mL), NaH (600 mg, 60%, 15 mmol)

was added. The resultant was stirred for 10 minutes, and 2-chloro-4-methoxpyrimidine (1.44 g, 10 mmol) was added. Upon completion of the addition, the reaction was heated to 80° C. for 3 hours. The solvent was evaporated, and the crude oil product was purified by silica gel column chromatography to give 2-(4-isopropylpiperazin-1-yl)-4-methoxpyrimidine (1.75 g, 74% yield). MS m/z [ESI]: 237.2 [M+1].

Step 2: 5-bromo-2-(4-isopropylpiperazin-1-yl)-4-methoxpyrimidine

To a solution of 2-(4-isopropylpiperazin-1-yl)-4-methoxpyrimidine (1.65 g, 7 mmol) in acetonitrile (50 mL), N-bromobutanimide (1.37 g, 7.7 mmol) was added in portions under stirring at 0° C. The resultant was stirred at room temperature for 1 hour. The solvent was evaporated, and CH$_2$Cl$_2$ was added. The resultant was washed by saturated sodium bicarbonate, dried, concentrated, and purified by silica gel column chromatography to give 5-bromo-2-(4-isopropylpiperazin-1-yl)-4-methoxpyrimidine (1.58 g, 72% yield). MS m/z [ESI]: 315.1 [M+1].

Intermediate 8: 1-(5-bromo-3-methoxylpyridin-2-yl)-4-methylpiperazine

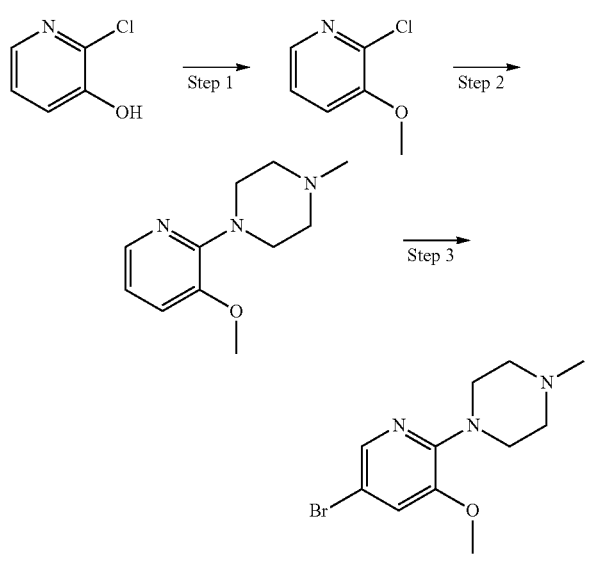

Step 1: 2-chloro-3-methoxylpyridine

2-Chloro-3-hydroxypyridine (2.59 g, 20 mmol), iodomethane (2.98 g, 21 mmol), and K$_2$CO$_3$ (5.52 g, 40 mmol) were added to DMF (50 mL), and the resultant was stirred at 60° C. for 4 hours. After the resultant was cooled, it was poured into water and extracted by ethyl acetate. The extract was dried, concentrated, and purified by silica gel column chromatography to give 2-chloro-3-methoxylpyridine (2.58 g, 90% yield). MS m/z [ESI]: 144.0 [M+1].

Step 2: 1-(3-methoxylpyridin-2-yl)-4-methylpiperazine

2-Chloro-3-methoxylpyridine (2.58 g, 18 mmol), N-methylpiperazine (2.7 g, 27 mmol), Pd$_2$(dba)$_3$ (824 mg, 0.9 mmol), BINAP (1.12 g, 1.8 mmol), and Cs$_2$CO$_3$ (14.4 g, 45 mmol) were added into dry toluene (200 mL). The resultant was refluxed for 16 hours under a nitrogen atmosphere. The reaction liquid was filtered, and the filtrate was concentrated and purified by silica gel column chromatography to give 1-(3-methoxylpyridin-2-yl)-4-methylpiperazine (1.71 g, 46% yield). MS m/z [ESI]: 208.1 [M+1].

Step 3: 1-(5-bromo-3-methoxylpyridin-2-yl)-4-methylpiperazine

To a solution of 1-(3-ethoxylpyridin-2-yl)-4-methylpiperazine (1.66 g, 8 mmol) in acetonitrile (50 mL), N-bromobutanimide (1.57 g, 8.8 mmol) was added in portions under stirring at 0° C. Upon completion of the addition, the resultant was stirred at room temperature for 2 hours. The solvent was evaporated, and CH$_2$Cl$_2$ was added. The resultant was washed by saturated sodium bicarbonate, dried, concentrated, and purified by silica gel column chromatography to give 1-(5-bromo-3-methoxylpyridin-2-yl)-4-methylpiperazine (1.58 g, 69% yield). MS m/z [ESI]: 286.1 [M+1].

Intermediate 9: 1-(5-bromo-4-methoxypyridin-2-yl)-4-methylpiperazine

Step 1: 1-(4-methoxypyridin-2-yl)-4-methylpiperazine

According to the procedure described in Step 2 of Intermediate 8, using 2-chloro-4-methoxypyridine instead of 2-chloro-3-methoxypyridine, the title compound was obtained (51% yield). MS m/z [ESI]: 208.1 [M+1].

Step 2: 1-(5-bromo-4-methoxypyridin-2-yl)-4-methylpiperazine

According to the procedure described in Step 3 of Intermediate 8, using 1-(4-methoxypyridin-2-yl)-4-methylpiperazine instead of 1-(3-methoxypyridin-2-yl)-4-methylpiperazine, the title compound was obtained (83% yield). MS m/z [ESI]: 286.1 [M+1].

Intermediate 10: (S)-1-(5-bromo-4-methoxypyridin-2-yl)-2,4-dimethylpiperazine

Step 1: (S)-1-(4-methoxypyridin-2-yl)-2,4-dimethylpiperazine

According to the procedure described in Step 2 of Intermediate 8, using 2-chloro-4-methoxypyridine instead of 2-chloro-3-methoxypyridine, and using and (S)-1,3-dimethylpiperazine instead of N-methylpiperazine, the title compound was obtained (43% yield). MS m/z [ESI]: 222.2 [M+1].

Step 2: (S)-1-(5-bromo-4-methoxypyridin-2-yl)-2,4-dimethylpiperazine

According to the procedure described in Step 3 of Intermediate 8, using (S)-1-(4-methoxypyridin-2-yl)-2,4-dimethylpiperazine instead of 1-(3-methoxypyridin-2-yl)-4-methylpiperazine the title compound was obtained (80% yield). MS m/z [ESI]: 300.1 [M+1].

Intermediate 11: (R)-1-(5-bromo-4-methoxypyridin-2-yl)-2,4-dimethylpiperazine

Step 1: (R)-1-(4-methoxypyridin-2-yl)-2,4-dimethylpiperazine

According to the procedure described in Step 2 of Intermediate 8, using 2-chloro-4-methoxypyridine instead of 2-chloro-3-methoxypyridine, and using (R)-1,3-dimethylpiperazine instead of N-methylpiperazine, the title compound was obtained (42% yield). MS m/z [ESI]: 222.2 [M+1].

Step 2: (R)-1-(5-bromo-4-methoxypyridin-2-yl)-2,4-dimethylpiperazine

According to the procedure described in Step 3 of Intermediate 8, using (R)-1-(4-methoxypyridin-2-yl)-2,4-dimethylpiperazine instead of 1-(3-methoxypyridin-2-yl)-4-methylpiperazine, the title compound was obtained (82% yield). MS m/z [ESI]: 300.1 [M+1].

Intermediate 12: (S)-1-(5-bromo-3-methoxypyridin-2-yl)-2,4-dimethylpiperazine

Step 1: (S)-1-(3-methoxypyridin-2-yl)-2,4-dimethylpiperazine

According to the procedure described in Step 2 of Intermediate 8, using (S)-1,3-dimethylpiperazine instead of N-methylpiperazine, the title compound was obtained (43% yield). MS m/z [ESI]: 222.2 [M+1].

Step 2: (S)-1-(5-bromo-3-methoxypyridin-2-yl)-2,4-dimethylpiperazine

According to the procedure described in Step 3 of Intermediate 8, using (S)-1-(3-methoxypyridin-2-yl)-2,4-dimethylpiperazine instead of 1-(3-methoxypyridin-2-yl)-4-methylpiperazine, the title compound was obtained (82% yield). MS m/z [ESI]: 300.1 [M+1].

Intermediate 13: (S)-1-(5-bromo-4-methoxypyridin-2-yl)-2-methyl-4-(1-methylpiperidin-4-yl)piperazine

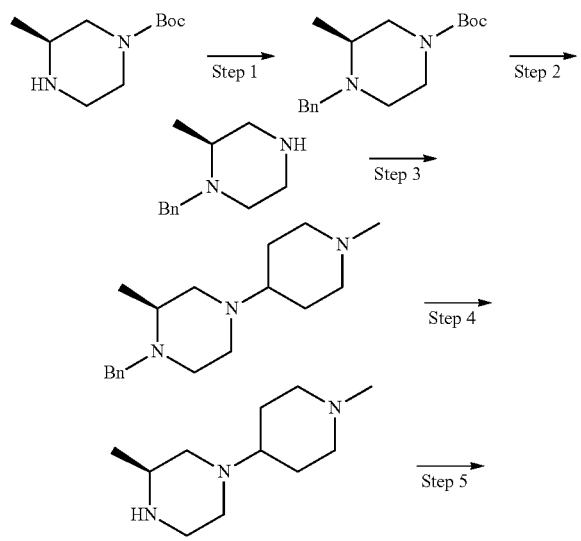

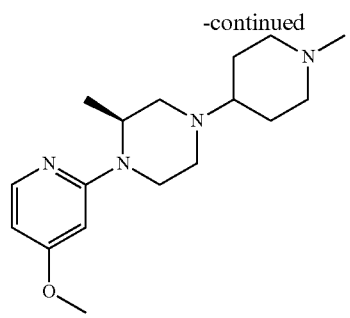

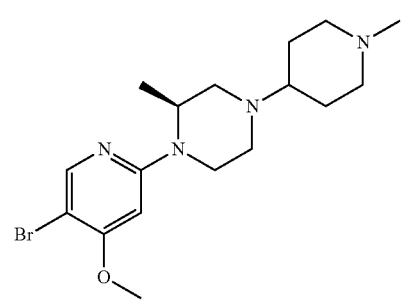

Step 1: (S)-tert-butyl 4-benzyl-3-methylpiperazine-1-carboxylate (S)-tert-butyl 3-methylpiperazine-1-carboxylate (10.0 g, 50 mmol), benzyl bromide (8.89 g, 52 mmol), and $K_2CO_3$ (13.8 g, 100 mmol) were added into acetonitrile (200 mL). The resultant was refluxed for 2 hours. The solvent was evaporated, and ethyl acetate was added. The resultant was washed by water, dried, concentrated, and purified by silica gel column chromatography to give (S)-tert-butyl 4-benzyl-3-methylpiperazine-1-carboxylate (12.2 g, 84% yield). MS m/z [ESI]: 291.2 [M+1].

Step 2: (S)-1-benzyl-2-methylpiperazine (S)-tert-butyl 4-benzyl-3-methylpiperazine-1-carboxylate (11.6 g, 40 mmol) was dissolved in $CH_2Cl_2$ (100 mL), trifluoroacetate (20 mL) was added dropwise, and the resultant was stirred for 30 minutes. Concentrated NaOH solution was added under ice-water batch to adjust the pH value to greater than 13, and then the resultant was extracted by ethyl acetate. The extract was dried and concentrated to give (S)-1-benzyl-2-methylpiperazine (6.84 g, 90% yield), which was directly used in the next step. MS m/z [ESI]: 191.2 [M+1].

Step 3: (S)-1-benzyl-2-methyl-4-(1-methylpiperidin-4-yl)piperazine (S)-1-Benzyl-2-methylpiperazine (6.84 g, 36 mmol), 1-methyl-4-piperidone (4.87 g, 43 mmol), and glacial acetic acid (4.32 g, 72 mmol) were successively added to anhydrous ethanol (100 mL). The resultant was stirred for 1 hour, and then cooled to 0° C. Sodium triacetoxyborohydride (31.6 g, 150 mmol) was added in portions. The resultant was reacted at room temperature for 6 hours. The solvent was evaporated, and the residue was dissolved by adding ethyl acetate. The resultant was washed by water, dried, concentrated, and purified by silica gel column chromatography to give (S)-1-benzyl-2-methyl-4-(1-methylpiperidin-4-yl)piperazine (7.86 g, 76% yield). MS m/z [ESI]: 288.2 [M+I].

Step 4: (S)-3-methyl-1-(1-methylpiperidin-4-yl) piperazine (S)-1-Benzyl-2-methyl-4-(1-methylpiperidin-4-yl)piperazine (7.19 g, 25 mmol) was dissolved in methanol (100 mL), Pd/C (1 g, 10%) was added, and the resultant was stirred overnight under a hydrogen atmosphere. The mixture was filtered and the filtrate was concentrated to give (S)-3-methyl-1-(1-methylpiperidin-4-yl)piperazine (4.64 g, 94% yield). MS m/z [ESI]: 198.2 [M+1].

Step 5: (S)-1-(4-methoxypyridin-2-yl)-2-methyl-4-(1-methylpiperidin-4-yl) piperazine According to the procedure described in Step 2 of Intermediate 8, using 2-chloro-4-methoxypyridine instead of 2-chloro-3-methoxypyridine, and using and (S)-2-methyl-4-(1-methylpiperidin-4-yl)piperazine instead of N-methylpiperazine, the title compound was obtained (37% yield). MS m/z [ESI]: 305.2 [M+1].

Step 6: (S)-1-(5-bromo-4-methoxypyridin-2-yl)-2-methyl-4-(1-methylpiperidin-4-yl) piperazine According to the procedure described in Step 3 of Intermediate 8, using (S)-1-(4-methoxypyridin-2-yl)-2-methyl-4-(1-methylpiperidin-4-yl)piperazine instead of 1-(3-methoxypyridin-2-yl)-4-methylpiperazine, the title compound was obtained (62% yield). MS m/z [ESI]: 383.1 [M+1].

Intermediate 14: (S)-tert-butyl 4-(5-bromo-4-methoxypyridin-2-yl)-3-methylpiperazine-1-carboxylate Step 1: (S)-tert-butyl 4-(4-methoxypyridin-2-yl)-3-methylpiperazine-1-carboxylate According to the procedure described in Step 2 of Intermediate 8, using 2-chloro-4-methoxypyridine instead of 2-chloro-3-methoxypyridine, and using (S)-tert-butyl 3-methylpiperazine-1-carboxylate instead of N-methylpiperazine, the title compound was obtained (50% yield). MS m/z [ESI]: 308.2 [M+1].

Step 2: (S)-tert-butyl 4-(5-bromo-4-methoxypyridin-2-yl)-3-methylpiperazine-1-carboxylate According to the procedure described in Step 3 of Intermediate 8, using (S)-tert-butyl 4-(4-methoxypyridin-2-yl)-3-methylpiperazine-1-carboxylate instead of 1-(3-methoxypyridin-2-yl)-4-methylpiperazine, the title compound was obtained (75% yield). MS m/z [ESI]: 386.1 [M+1]. $^1$H-NMR (400 MHz, CDCl$_3$): δ=8.104 (s, 1H), 6.030 (s, 1H), 4.60-3.85 (br, 7H), 3.20-2.90 (br, 3H), 1.135 (d, J=6.8 Hz, 3H).

Intermediate 15: 4-(5-bromo-4-methoxypyridin-2-yl)-1-(tert-butoxycarbonyl)-1,2,5,6-tetrahydropyridine

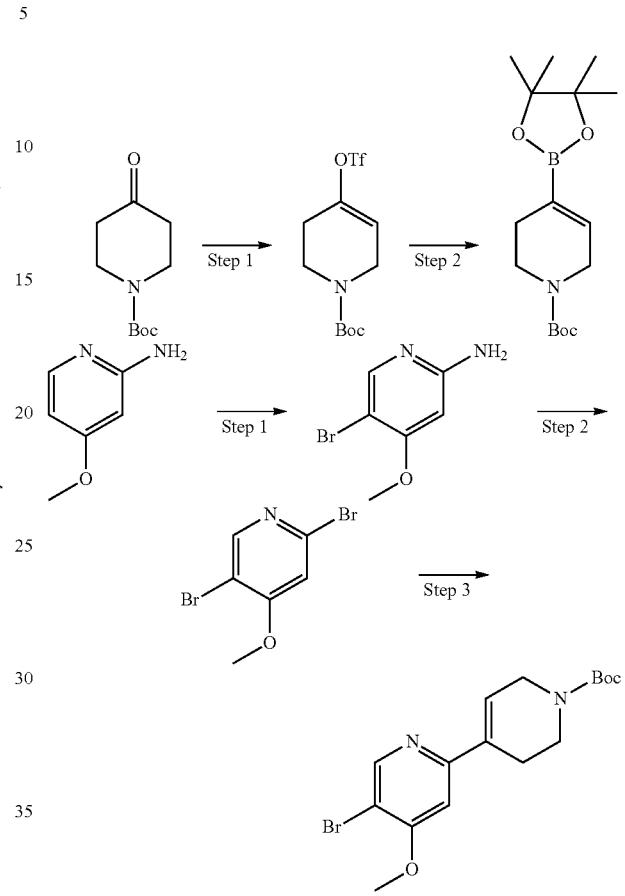

Step 1: 4-(trifluoromethanesulfonyloxy)-1-(tert-butoxycarbonyl)-1,2,5,6-tetrahydropyridine Tert-butyl 4-oxopiperidine-1-carboxylate (22.8 g, 115 mmol) was dissolved in anhydrous tetrahydrofuran (150 mL), the resultant was cooled to −78° C., and then a solution of lithium diisopropylamide (126 mmol) in tetrahydrofuran (100 mL) was added dropwise. Upon completion of the addition, the solution was stirred for 30 minutes, and a solution of bis(trifluoromethanesulfonyloxy)aniline (45.0 g) in tetrahydrofuran (126 mmol) was added dropwise. The resultant was warmed up to room temperature and stirred overnight. Tthe solvent was evaporated, and the residue was dissolved by adding ether. The solution was washed by 2 M NaOH solution, dried, concentrated, and purified by silica gel column chromatography to give 4-(trifluoromethanesulfonyloxy)-1-(tert-butoxycarbonyl)-1,2,5,6-tetrahydropyridine (23.4 g, 61% yield).

Step 2: tert-butyl 4-(4,4,5,5-tetramethyl-1,3,2-dioxaborolan-2-yl)-5,6-dihydropyridin-1(2H)-carboxylate Tert-butyl 4-(trifluoromethylsulfonyloxy)-5,6-dihydropyrid-(2H)-carboxylate (23.2 g, 70 mmol), bis(pinacolato)diboron (25.4 g, 100 mmol), Pd(dppf)Cl$_2$ (2.93 g, 4 mmol), and anhydrous potassium acetate (13.7 g, 140 mmol) were added in dry 1,4-dioxane (500 mL) and purged with nitrogen. The resultant was stirred at 100° C. for 4 hours. After the resultant was cooled, it was concentrated and purified by silica gel column chromatography to give tert-butyl 4-(4,4,5,5-tetramethyl-1,3,2-dioxaborolan-2-yl)-5,6-dihydropyridin-1(2H)-carboxylate (13.0 g, 60% yield).

Step 3: 5-bromo-4-methoxyl-2-aminopyridine

To a solution of 4-methoxyl-2-aminopyridine (12.4 g, 100 mmol) in acetonitrile (500 mL), N-bromobutanimide (17.8 g, 100 mmol) was added in portions at 0° C. under stirring. Upon completion of the addition, the mixture was stirred at room temperature for 1 hour. The solvent was evaporated and $CH_2Cl_2$ was added. The solution was washed with saturated sodium bicarbonate, dried, and concentrated to give 5-bromo-4-methoxyl-2-aminopyridine (20.3 g, 100% yield), which was directly used in the next step. MS m/z [ESI]: 203.0 [M+1].

Step 4: 2,5-dibromo-4-methoxypyridine

5-Bromo-4-methoxy-2-aminopyridine (20.3 g, 100 mmol) was dissolved in 40% HBr (60 mL) and water (40 mL) at −10° C. under stirring, and then a solution of $NaNO_2$ (17.3 g, 250 mmol) in water (25 mL) was added. The mixture was stirred at low temperature for 30 minutes. Liquid bromine (48.0 g, 300 mmol) was added, and stirring was continued for 2 hours. Concentrated NaOH was added to adjust the pH value to greater than 12, and then the resultant was extracted by ethyl acetate. The extract was dried, concentrated, and purified by silica gel column chromatography to give 2,5-dibromo-4-methoxypyridine (13.8 g, 52% yield). MS m/z [ESI]: 267.9 [M+1].

Step 5: tert-butyl 4-(5-bromo-4-methoxypyridin-2-yl)-5,6-dihydropyridin-1(2H)-carboxylate Tert-butyl 4-(4,4,5,5-tetramethyl-1,3,2-dioxaborolan-2-yl)-5,6-dihydropyridin-1(2H)-carboxylate (3.09 g, 10 mol), 2,5-dibromo-4-methoxypyridine (2.67 g, 10 mmol), $Pd(PPh_3)_4$ (578 mg, 0.5 mmol), and $K_2CO_3$ (3.34 g, 24 mmol) were added to 1,4-dioxane (50 mL) and water (10 mL) and purged with nitrogen. The resultant was stirred at 100° C. overnight. After the resultant was cooled, it was purified by silica gel column chromatography to give tert-butyl 4-(5-bromo-4-methoxypyridin-2-yl)-5,6-dihydropyridin-1(2H)-carboxylate (1.55 g, 42% yield). MS m/z [ESI]: 369.1 [M+1]. $^1$H-NMR (400 MHz, $CDCl_3$): δ=8.49 (s, 1H), 7.26 (s, 1H), 6.58 (s, 1H), 4.13 (t, 2H), 3.97 (s, 3H), 2.62 (d, 2H), 1.49 (s, 9H).

Intermediate 16:
5-bromo-2-chloro-3-methoxypyridine

Step 1: 5-bromo-2-chloro-3-aminopyridine

5-Bromo-2-chloro-3-nitropyridine (2.38 g, 10 mmol) was dissolved in methanol (50 mL), and raney nickel (0.5 g) was then added. The mixture was stirred overnight under a hydrogen atmosphere. Raney nickel was removed by filtration, and the filtrate was concentrated to give 5-bromo-2-chloro-3-aminopyridine (2.08 g, 100% yield), which was directly used in the next step. MS m/z [ESI]: 208.9 [M+1].

Step 2: 5-bromo-2-chloro-3-hydroxypyridine

5-Bromo-2-chloro-3-aminopyridine (2.08 g, 10 mmol) was dissolved in 4 M $H_2SO_4$ (50 mL) at 0° C. under stirring, and then a solution of $NaNO_2$ (760 mg, 11 mmol) in water (5 mL) was added. After stirring at 0° C. for 30 minutes, the resultant was heated to 80° C. and stirred for 2 hours. After the reluctant was cooled, concentrated NaOH was added to adjust the pH value to 7-8. The precipitated solid was filtered out, washed by water, and dried to give 5-bromo-2-chloro-3-hydroxypyridine (1.88 g, 90% yield). MS m/z[ESI]: 209.9 [M+1].

Step 3: 5-bromo-2-chloro-3-methoxypyridine

5-Bromo-2-chloro-3-hydroxypyridine (1.88 g, 9 mmol), iodomethane (1.42 g, 10 mmol), and $K_2CO_3$ (2.76 g, 20 mmol) were added to acetonitrile. The solution was stirred at 80° C. for 4 hours. The solvent was evaporated, and the residue was dissolved by adding $CH_2Cl_2$. The solution was washed by water, dried, concentrated, and purified by silica gel column chromatography to give 5-bromo-2-chloro-3-methoxypyridine (1.62 g, 81% yield). MS m/z [ESI]: 223.9 [M+1].

Intermediate 17: 1-(1-(4-methoxyl-5-(4,4,5,5-tetramethyl-1,3,2-dioxaborolan-2-yl)pyridin-2-yl) piperidin-4-yl)-4-methylpiperazine Step 1: tert-butyl 4-(4-methylpiperazin-1-yl)piperidine-1-carboxylate Tert-butyl 4-oxopiperidine-1-carboxylate (4.0 g, 20 mmol), N-methylpiperazine (2.4 g, 24 mmol), and glacial acetic acid (2.4 g, 40 mmol) were successively added to anhydrous ethanol (100 mL). The resultant was stirred for 1 hour, and then it was cooled to 0° C. Sodium triacetoxyborohydride (17.0 g, 80 mmol) was added in portions, and the resultant was reacted at room temperature for 6 hours. The solvent was evaporated. The residue was dissolved by adding ethyl acetate, washed with water, dried, concentrated, and purified by silica gel column chromatography to give tert-butyl 4-(4-methylpiperazin-1-yl)piperidine-1-carboxylate (4.25 g, 75% yield). MS m/z [ESI]: 284.2 [M+1].

Step 2: 1-methyl-4-(piperidin-4-yl)piperazine hydrochloride

Tert-butyl 4-(4-methylpiperazin-1-yl)piperidine-1-carboxylate (4.25 g, 15 mmol) was dissolved in methanol (100 mL), and then hydrogen chloride gas was introduced until saturation. The solution was stirred under reflux for 1 hour. The solvent was spin evaporated to give 1-methyl-4-(piperidin-4-yl)piperazine hydrochloride (4.39 g, 100% yield), which was directly used in the next step. MS m/z [ESI]: 184.2 [M+1].

Step 3: 1-(1-(4-methoxylpyridin-2-yl)piperidin-4-yl)-4-methylpiperazine

According to the procedure described in Step 2 of Intermediate 8, using 2-chloro-4-methoxypyridine instead of 2-chloro-3-methoxypyridine and using 1-methyl-4-(piperidin-4-yl)piperazine hydrochloride instead of N-methylpiperazine, the title compound was obtained (58% yield). MS m/z [ESI]: 291.2 [M+1].

Step 4: 1-(1-(5-bromo-4-methoxylpyridin-2-yl)piperidin-4-yl)-4-methylpiperazine

According to the procedure described in Step 3 of intermediate 8, using 1-(1-(4-methoxylpyridin-2-yl)piperidin-4- yl)-4-methylpiperazine instead of 1-(3-methoxypyridin-2-yl)-4-methylpiperazine, the title compound was obtained (62% yield). MS m/z [ESI]: 369.1 [M+1].

Step 5: 1-(1-(4-methoxyl-5-(4,4,5,5-tetramethyl-1,3,2-dioxaborolan-2-yl)pyridin-2-yl) piperidin-4-yl)-4-methylpiperazine According to the procedure described in Step 3 of Intermediate 1, using 1-(1-(5-bromo-4-methoxylpyridin-2-yl)piperidin-4-yl)-4-methylpiperazine instead of tert-butyl 4-(3-methoxyl-4-bromophenyl)piperazine-1-carboxylate, the title compound was obtained (81% yield). MS m/z [ESI]: 417.3 [M+1].

Intermediate 18: tert-butyl 4-(6-bromo-3-methoxylpyridin-2-yl)piperazine-1-carboxylate Intermediate 19: tert-butyl 4-(6-bromo-5-methoxylpyridin-2-yl)piperazine-1-carboxylate According to the procedure described in Step 2 of Intermediate 8, using 2,6-dibromo-3-methoxylpyridine instead of 2-chloro-3-methoxylpyridine and using N-methylpiperazine instead of N-tert-(butoxycarbonyl)piperazine. Intermediate 18 tert-butyl 4-(6-bromo-3-methoxylpyridin-2-yl)piperazine-1-carboxylate (21% yield) and Intermediate 19 tert-butyl 4-(6-bromo-5-methoxylpyridin-2-yl)piperazine-1-carboxylate (43% yield) were finally separated by the silica gel column chromatography. MS m/z [ESI]: 372.1 [M+1].

Intermediate 20: tert-butyl 4-(5-(4,4,5,5-tetramethyl-1,3,2-dioxaborolan-2-yl)pyridin-3-yl) piperazine-1-carboxylate Intermediate 21: 4-(5-bromo-4-methoxylpyridin-2-yl)piperazin-2-one Step 1: tert-butyl 2-(4-methoxypyridin-2-ylamino)ethylcarbamate According to the procedure described in Step 2 of Intermediate 8, using 2-chloro-4-methoxylpyridine instead of 2-chloro-3-methoxylpyridine, and using and tert-butyl 2-aminoethylcarbamate instead of N-methylpiperazine, the title compound was obtained (53% yield). MS m/z [ESI]: 268.2 [M+1].

Step 2: N-(2-aminoethyl)-4-methoxylpyridin-2-amine

Tert-butyl 2-(4-methoxypyridin-2-ylamino)ethylcarbamate (2.66 g, 10 mmol) was dissolved in $CH_2Cl_2$ (50 mL), trifluoroacetate (10 mL) was added, and the solution was stirred for 1 hour. Concentrated NaOH was used to adjust the pH value to greater than 12 under ice bath, and then the resultant was extracted by ethyl acetate. The extract was dried, concentrated, and purified by silica gel column chromatography to give N-(2-aminoethyl)-4-methoxylpyridin-2-amine (1.27 g, 76% yield). MS m/z [ESI]: 168.1 [M+1].

Step 3: 4-(4-methoxylpyridin-2-yl)piperazin-2-one

N-(2-aminoethyl)-4-methoxylpyridin-2-amine (1.17 g, 7 mmol) and anhydrous $K_2CO_3$ (2.90 g, 21 mmol) were added into anhydrous acetonitrile, cooled to 0° C., and chloroacetyl chloride (790 mg, 7 mmol) was then added dropwise. Upon completion of the addition, the reaction was stirred for 30 minutes and then refluxed for 6 hours. The mixture was filtered, and the filtrate was concentrated and purified by silica gel column chromatography to give 4-(4-methoxylpyridin-2-yl)piperazin-2-one (855 mg, 59% yield). MS m/z [ESI]: 208.1 [M+1].

Step 4: 4-(5-bromo-4-methoxylpyridin-2-yl)piperazin-2-one

According to the procedure described in Step 3 of Intermediate 8, using 4-(4-methoxylpyridin-2-yl)piperazin-2-one instead of 1-(3-methoxypyridin-2-yl)-4-methylpiperazine, the title compound was obtained (87% yield). MS m/z [ESI]: 286.0 [M+1].

Intermediate 22: tert-butyl 4-(6-chloro-4-methoxylpyridin-2-yl)piperazine-1-carboxylate According to the procedure described in Step 2 of intermediate 8, using 2,6-dichloro-4-methoxylpyridine instead of 2-chloro-3-methoxylpyridine, and using tert-butyl piperazine-1-carboxylate instead of N-methylpiperazine, the title compound was obtained (48% yield). MS m/z [ESI]: 328.1 [M+1]. $^1$H-NMR (400 MHz, $CDCl_3$): δ=6.266 (d, J=1.6 Hz, 1H), 5.944 (d, J=1.6 Hz, 1H), 3.804 (s, 3H), 3.54-3.47 (m, 8H), 1.481 (s, 9H).

Intermediate 23: tert-butyl 4-(5-bromo-4-methoxylpyridin-2-yl)piperazine-1-carboxylate According to the procedure described in Step 3 of Intermediate 8, using tert-butyl 4-(4-methoxylpyridin-2-yl)piperazine-1-carboxylate instead of 1-(3-methoxypyridin-2-yl)-4-methylpiperazine, the title compound was obtained (87% yield). MS m/z [ESI]: 372.1 [M+1].

Intermediate 24: tert-butyl 4-(4-bromo-5-methoxylpyridin-2-yl)piperazine-1-carboxylate Intermediate 25: tert-butyl 4-(2-bromo-5-methoxylpyridin-4-yl)piperazine-1-carboxylate According to the procedure described in Step 2 of Intermediate 8, using 2,4-dibromo-5-methoxylpyridine instead of 2-chloro-3-methoxylpyridine, and using tert-butyl piperazine-1-carboxylate instead of N-methylpiperazine, Intermediate 24 tert-butyl 4-(4-bromo-5-methoxylpyridin-2-yl)piperazine-1-carboxylate (37% yield) and Intermediate 25 tert-butyl 4-(2-bromo-5-methoxylpyridin-4-yl)piperazine-1-carboxylate (21% yield) were finally separated by the silica gel chromatography. MS m/z [ESI]: 372.1 [M+1].

Intermediate 26: 3-(1-(2-difluoromethyl-5-fluorophenyl)ethoxy-5-(4,4,5,5-tetramethyl-1,3,2-dioxaborolan-2-yl)-2-aminopyridine Step 1: 1-bromo-2-difluoromethyl-5-fluorobenzene 2-Bromo-4-fluorobenzaldehyde (8.04 g, 40 mmol) was added in $CH_2Cl_2$ (80 mL), cooled to 0° C., and then diethylaminosulphurtrifluoride (DAST) (7.96 mL, 60 mmol) was added dropwise. The resultant was stirred at low temperature for 30 minutes, and then refluxed overnight. The reaction was quenched with ethanol, washed with water, dried, concentrated, and purified by silica gel column chromatography to give 1-bromo-2-(difluoromethyl)-5-fluorobenzene (8.36 g, 93% yield). $^1$H-NMR (400 MHz, CDCl$_3$): δ=7.579 (m, 1H), 7.385 (m, 1H), 7.091 (m, 1H), 6.993-6.720 (t, J=54.6 Hz, 1H).

Step 2: 1-(2-(difluoromethyl)-5-fluorophenyl)ethanone

1-Bromo-2-(difluoromethyl)-5-fluorobenzene (8.36 g, 37.5 mmol) was dissolved in anhydrous ether (100 mL), cooled to −78° C., and then 2.4 M n-butyllithium (18.7 mL, 45 mmol) was added dropwise under a nitrogen atmosphere. The resultant was stirred for 1 hour. While the temperature was kept at −78° C., N-methyl-N-methoxylacetamide (7.73 g, 75 mmol) was added, and the resultant was then stirred for 2 hours. After the resultant was warmed up to room temperature, it was washed with saturated brine and extracted with ethyl acetate. The extract was dried, concentrated, and purified by silica gel column chromatography to give 1-(2-(difluoromethyl)-5-fluorophenyl)ethanone (4.2 g, 60% yield). $^1$H-NMR (400 MHz, CDCl$_3$): δ=7.45-7.40 (m, 1H), 7.31-7.27 (m, 1H), 7.20-7.12 (m, 1H), 6.78-6.50 (t, J=56 Hz, 1H), 2.42 (s, 3H).

Step 3: 1-(2-(difluoromethyl)-5-fluorophenyl)ethanol 1-(2-(Difluoromethyl)-5-fluorophenyl)ethanone (3.0 g, 16 mmol) was added in anhydrous ethanol (100 mL), cooled to 0° C., and then NaBH$_4$ (1.22 g, 32 mmol) was added in portions. The reaction was conducted at room temperature for 4 hours, then the solvent was evaporated, and the residue was dissolved by adding ethyl acetate. The resultant was washed with water, dried, concentrated, and purified by silica gel column chromatography to give 1-(2-(difluoromethyl)-5-fluorophenyl)ethanol (1.82 g, 60% yield). $^1$H-NMR (400 MHz, CDCl$_3$): δ=7.598-7.562 (m, 1H), 7.292-7.262 (m, 1H), 7.20-7.15 (m, 1H), 7.124-6.848 (t, J=45.2 Hz, 1H), 5.197 (t, J=6.4 Hz, 1H), 1.97 (s, 1H), 1.515 (d, J=6.4 Hz, 3H).

Step 4: 2-(1-bromoethyl)-1-(difluoromethyl)-4-fluorobenzene

PPh$_3$ (1.57 g, 6 mmol) was dissolved in dichloromethanol (30 mL), cooled to 0° C., Br$_2$ (1.08 g, 6 mmol) was added, and the resultant was stirred for 10 minutes. A solution of 1-(2-(difluoromethyl)-5-fluorophenyl)ethanol (950 mg, 5 mmol) in CH$_2$Cl$_2$ (5 mL) was added dropwise and stirred for 30 minutes. The resultant was washed with water, dried, concentrated, and purified by silica gel column chromatography to give 2-(1-bromoethyl)-1-(difluoromethyl)-4-fluorobenzene (1.25 g, 100% yield).

Step 5: 5-bromo-3-(1-(2-difluoromethyl-5-fluorophenyl)ethoxy)-2-amino-pyridine

According to the procedure described in Step 2 of Intermediate 5, using 2-(1-bromoethyl)-1-(difluoromethyl)-4-fluorobenzene instead of 1,3-dichloro-2-(l-bromoethyl)-4-fluorobenzene, the title compound was obtained (62% yield). MS m/z [ESI]: 361.0 [M+1].

Step 6: 3-(1-(2-difluoromethyl-5-fluorophenyl)ethoxy-5-(4,4,5,5-tetramethyl-1,3,2-dioxaborolan-2-yl)-2-aminopyridine According to the procedure described in Step 3 of Intermediate 5, using 5-bromo-3-(1-(2-difluoromethyl-5-fluorophenyl)ethoxy)-2-aminopyridine instead of 5-bromo-3-(1-(2,6-dichloro-3-fluorophenyl)ethyoxyl)-2-aminopyridine, the title compound was obtained (54% yield). MS m/z [ESI]: 409.2 [M+1].

Intermediate 27: 4-(6-bromo-3-methoxylpyridin-2-yl)-1-(tert-butoxycarbonyl)-1,2,5,6-tetrahydropyridine According to the procedure described in Step 5 of Intermediate 15, using 2,6-dibromo-3-methoxylpyridine instead of 2,5-dibromo-4-methoxylpyridine, Intermediate 27: 4-(6-bromo-3-methoxylpyridin-2-yl)-1-(tert-butoxycarbonyl)-1,2,5,6-tetrahydropyridine was finally separated by silica gel column chromatography (39% yield). MS m/z [ESI]: 369.1 [M+1].

Intermediate 28: (S)-tert-butyl 4-(6-bromo-5-methoxylpyridin-2-yl)-3-methylpiperazine-1-carboxylate According to the procedure described in Step 2 of Intermediate 8, using 2,6-dibromo-3-methoxylpyridine instead of 2-chloro-3-methoxylpyridine, and using (S)-tert-butyl 3-methylpiperazine-1-carboxylate instead of N-methylpiperazine, the title compound was finally separated by the silica gel column chromatography (38% yield). MS m/z [ESI]: 386.1 [M+1]. $^1$H-NMR (400 MHz, CDCl$_3$): δ=7.124 (d, J=2.0 Hz, 1H), 6.470 (d, J=8.4 Hz, 1H), 4.20-3.85 (br, 3H), 3.825 (s, 3H), 3.80-3.70 (br, 1H), 3.162 (d, J=10.8 Hz, 1H), 3.085 (t, J=6.8 Hz, 1H), 3.03-2.87 (br, 1H), 1.482 (s, 9H), 1.088 (d, J=6.8 Hz, 3H).

Intermediate 29: tert-butyl 4-(5-bromo-4-methoxylpyridin-3-yl)piperazine-1-carboxylate According to the procedure described in Step 2 of Intermediate 8, using 3,5-dibromo-4-methoxylpyridine instead of 2-chloro-3-methoxylpyridine, and using N-(tert-butoxycarbonyl)piperazine instead of N-methylpiperazine, the title compound was obtained (53% yield). MS m/z [ESI]: 372.1 [M+1].

Intermediate 30: 4-(5-bromo-4-methoxylpyridin-2-yl)morpholine

Step 1: 4-(4-methoxylpyridin-2-yl)morpholine

According to the procedure described in Step 2 of Intermediate 8, using 2-chloro-4-methoxylpyridine instead of 2-chloro-3-methoxylpyridine, and using and morpholine instead of N-methylpiperazine, the title compound was obtained (76% yield). MS m/z [ESI]: 195.1 [M+1].

Step 2: 4-(5-bromo-4-methoxylpyridin-2-yl)morpholine

According to the procedure described in Step 3 of Intermediate 8, using 4-(4-methoxylpyridin-2-yl)morpholine instead of 1-(3-methoxypyridin-2-yl)-4-methylpiperazine, the title compound was obtained (91% yield). MS m/z [ESI]: 273.0 [M+1]. $^1$H-NMR (400 MHz, CDCl$_3$): δ=8.119 (s, 1H), 6.080 (s, 1H), 3.905 (s, 3H), 3.816 (t, J=4.8 Hz, 4H), 3.478 (t, J=5.0 Hz, 4H).

Intermediate 31: (S)-tert-butyl 4-(6-bromo-3-methoxylpyridin-2-yl)-3-methylpiperazine-1-carboxylate (S)-tert-butyl 4-(6-bromo-3-methoxylpyridin-2-yl)-3-methylpiperazine-1-carboxylate was isolated by silica gel column chromatography as an isomer of Intermediate 28 in the preparation of Intermediate 28. MS m/z [ESI]: 386.1 [M+1].

Intermediate 33: tert-butyl 5-methyl-4-(4,4,5,5-tetramethyl-1,3,2-dioxaborolan-2-yl)-5,6-dihydropyridin-1(2H)-carboxylate

Intermediate 34: 5-bromo-2-chloro-3-(2-hydroxyethoxy)-pyridine

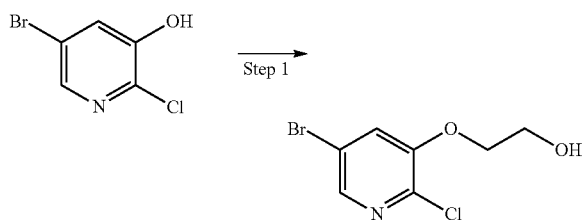

According to the procedure described in Step 3 of Intermediate 16, using 2-bromoethanol instead of iodomethane, 5-bromo-2-chloro-3-(2-hydroxyethoxy)-pyridine was obtained (50% yield). MS m/z [ESI]: 253.9 [M+1]. $^1$H-NMR (400 MHz, CDCl$_3$): δ=8.094 (d, J=2.0 Hz, 1H), 7.378 (d, J=2.0 Hz, 1H), 4.176-4.154 (t, J=4.4 Hz, 2H), 4.056-4.018 (m, 2H), 2.055-2.023 (t, J=4.4 Hz, 1H).

Intermediate 35: (S)-tert-butyl 4-(5-bromo-4-ethoxylpyridin-2-yl)-3-methylpiperazine-1-carboxylate

Step 1: (S)-tert-butyl 4-(4-ethoxylpyridin-2-yl)-3-methylpiperazine-1-carboxylate According to the procedure described in Step 2 of Intermediate 8, using (S)-tert-butyl 3-methylpiperazine-1-carboxylate instead of N-methylpiperazine, and using 2-chloro-4-ethoxylpyridine instead of 2-chloro-3-methoxylpyridine, the title compound was obtained (76% yield). MS m/z [ESI]: 322.2 [M+1].

Step 2: (S)-tert-butyl 4-(5-bromo-4-ethoxylpyridin-2-yl)-3-methylpiperazine-1-carboxylate According to the procedure described in Step 3 of Intermediate 8, using (S)-tert-butyl 4-(4-ethoxylpyridin-2-yl)-3-methylpiperazine-1-carboxylate instead of 1-(3-methoxypyridin-2-yl)-4-methylpiperazine, the title compound was obtained (91% yield). MS m/z [ESI]: 400.1 [M+1].

Intermediate 36: 4-(2-((5-bromo-2-morpholinopyridin-3-yl)oxy)ethyl)morpholine

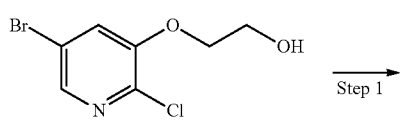

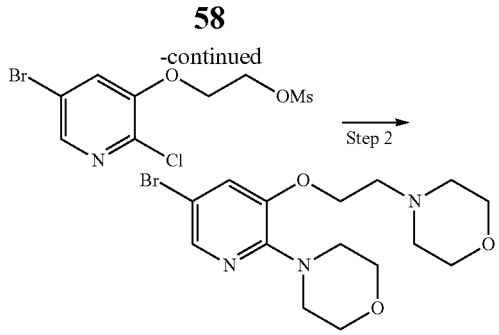

Step 1: 2-((5-bromo-2-chloropyridin-3-yl)oxy)ethylmethanesulfonate

Intermediate 34: 5-Bromo-2-chloro-3-(2-hydroxyethoxy) pyridine and triethylamine (487 mg, 4.82 mmol) were added to CH$_2$Cl$_2$ (10 mL), cooled to 0° C., methanesulfonyl chloride (387 mg, 3.38 mmol) was then added, and the resultant was stirred for 2 hours. The resultant was washed with water, dried, and concentrated after finished to give 2-((5-bromo-2-chloropyridin-3-yl)oxy)ethyl methanesulfonate (796 mg, 100% yield), which was directly used in the next step. MS m/z [ESI]: 331.9 [M+1].

Step 2: 4-(2-((5-bromo-2-morpholinopyridin-3-yl)oxy)ethyl)morpholine 2-((5-Bromo-2-chloropyridin-3-yl)oxy)ethylmethanesulfonate (796 mg, 2.41 mmol) and Na$_2$CO$_3$ (511 mg, 4.82 mmol) were added to morpholine (10 mL). The resultant was stirred at 100° C. overnight. The reaction was concentrated and purified by silica gel column chromatography (CH$_2$Cl$_2$/CH$_3$OH, 80:1) to give 4-(2-((5-bromo-2-morpholinopyridin-3-yl)oxy)ethyl)morpholine (820 mg, 92% yield). MS m/z [ESI]: 372.1 [M+1].

Intermediate 37: (S)-tert-butyl 4-(5-bromo-4-(2-morpholinoethoxy)pyridin-2-yl)-3-methylpiperazine-1-carboxylate

Step 1: 2-chloro-4-(2-morpholinoethoxy)pyridine

N-(2-Hydroxyethyl)morpholine (3.15 g, 24 mmol) was dissolved in dry DMF, NaH (891 mg, 26 mmol) was added in portions, and the resultant was stirred for 30 minutes. Then 2-chloro-4-nitropyridine (3.17 g, 20 mmol) was added and the resultant was stirred at room temperature for 3 hours. The solvent was spin evaporated, the residue was dissolved by adding ethyl acetate and purified by silica gel column chromatography, to give 2-chloro-4-(2-morpholinoethoxy) pyridine (1.60 g, 33% yield). MS m/z [ESI]: 243.1 [M+1].

Step 2: (S)-tert-butyl 3-methyl-4-(4-(2-morpholinoethoxy)pyridin-2-yl)piperazine-1-carboxylate According to the procedure described in Step 2 of Intermediate 8, using (S)-tert-butyl 3-methylpiperazine-1-carboxylate instead of N-methylpiperazine, and using 2-chloro-4-(2-morpholinoethoxy) pyridine instead of 2-chloro-3-methoxylpyridine, the title compound was obtained (36% yield). MS m/z [ESI]: 407.3 [M+1].

Step 3: (S)-tert-butyl 4-(5-bromo-4-(2-morpholinoethoxy)pyridin-2-yl)-3-methylpiperazine-1-carboxylate According to the procedure described in Step 3 of Intermediate 8, using (S)-tert-butyl 3-methyl-4-(4-(2-morpholinoethoxy)pyridin-2-yl)piperazine-1-carboxylate instead of 1-(3-methoxypyridin-2-yl)-4-methylpiperazine, the title compound was obtained (71% yield). MS m/z [ESI]: 487.2 [M+1].

Intermediate 38: 2-chloro-4-((1-(4-chloro-3-fluorobenzyl)-1H-imidazol-5-yl)ethynyl) pyridine

Step 1: 4-(bromomethyl)-1-chloro-2-fluorobenzene

To a solution of triphenylphosphine (27.8 g, 0.103 mol) in $CH_2Cl_2$ (200 mL), bromine (16.5 g, 0.103 mol) was added dropwise at 0° C. under stirring. Upon completion of the addition, the resultant was stirred for 10 minutes. (4-Chloro-3-fluorophenyl)methanol (15.8 g, 0.098 mol) was then added. The resultant was stirred for 30 minutes. The reaction was quenched with ethanol, poured into saturated sodium bicarbonate solution, and extracted with $CH_2Cl_2$. The organic phase was dried over anhydrous sodium sulfate, filtered, concentrated, and purified by silica gel column chromatography to give 4-(bromomethyl)-1-chloro-2-fluorobenzene (18.6 g, 85% yield). $^1$H-NMR (400 MHz, $CDCl_3$): δ=7.27 (t, J=7.9 Hz, 1H), 7.10 (dd, J=7.9 Hz, 2.1 Hz, 1H), 7.04-6.99 (m, 1H), 4.32 (s, 2H).

Step 2: 1-(4-chloro-3-fluorobenzyl)-1H-pyrazole 4-(Bromomethyl)-1-chloro-2-fluorobenzene (16.0 G, 72 mmol), pyrazole (5.35 g, 79 mmol), and $K_2CO_3$ (20.0 g, 145 mmol) were added into dry DMF. The resultant was stirred at room temperature overnight. The solvent was spin evaporated, the residue was dissolved by adding ethyl acetate and purified by silica gel column chromatography to give 1-(4-chloro-3-fluorobenzyl)-1H-pyrazole (13.7 g, 91% yield). MS m/z [ESI]: 211.0 [M+1].

Step 3: 1-(4-chloro-3-fluorobenzyl)-1H-pyrazole-2-oxide 1-(4-Chloro-3-fluorobenzyl)-1H-pyrazole (9.7 g, 46 mmol) and urea hydrogen peroxide (9.1 g, 97 mmol) were added to $CH_2Cl_2$ (200 mL) and cooled to 0° C. Trifluoroaceticanhydride (19.4 g, 92 mmol) was added, and the solution was stirred at room temperature for 5 hours. The reaction was washed with sodium sulfite solution and extracted. The organic layer was spin evaporated and purified by silica gel column chromatography to give 1-(4-chloro-3-fluorobenzyl)-1H-pyrazole-2-oxide (7.30 g, 70% yield). MS m/z [ESI]: 227.0 [M+1].

Step 4: 5-bromo-1-(4-chloro-3-fluorobenzyl)-1H-pyrazole-2-oxide 1-(4-Chloro-3-fluorobenzyl)-1H-pyrazole-2-oxide (5.44 g, 24 mmol) and $K_2CO_3$ (5.96 g, 43 mmol) were added into $CH_2Cl_2$ (100 mL), cooled to −80° C., and a solution of liquid bromine (4.0 g, 25 mmol) in $CH_2Cl_2$ (10 mL) pre-cooled to −80° C. was added dropwise within 2 minutes. Stirring was continued at this temperature for 15 minutes. The temperature was risen up to 0° C., and stirring was continued for 30 minutes. The resultant was washed with sodium sulfite and extracted. The organic layer was spin evaporated and purified by silica gel column chromatography to give 5-bromo-1-(4-chloro-3-fluorobenzyl)-1H-pyrazole-2-oxide (6.67 g, 91% yield). MS m/z[ESI]: 306.9[M+1].

Step 5: 5-bromo-1-(4-chloro-3-fluorobenzyl)-1H-pyrazole

5-Bromo-1-(4-chloro-3-fluorobenzyl)-1H-pyrazole-2-oxide (3.84 g, 12.6 mmol) was added into $CH_2Cl_2$ (50 mL), cooled to 0° C., and then a solution of $PCl_3$ (3.97 g, 28.9 mmol) in $CH_2Cl_2$ (10 mL) was added dropwise. The resultant was stirred at this temperature for 1 hour, and then heated up to 50° C. and then stirred for 3 hours. A solution of sodium acetate in methanol (1.21 M, 170 mL) was added. The mixture was spin evaporated and purified by silica gel column chromatography to give 5-bromo-1-(4-chloro-3-fluorobenzyl)-1H-pyrazole (3.10 g, 85% yield). MS m/z [ESI]: 290.9 [M+1].

Step 6: 1-(4-chloro-3-fluorobenzyl)-5-((trimethylsilyl)ethynyl)-1H-pyrazole 5-Bromo-1-(4-chloro-3-fluorobenzyl)-1H-pyrazole (2.0 g, 6.9 mmol), ethynyl-trimethylsilane (1.0 g, 10.4 mmol), $Pd(OAc)_2$ (155 mg, 0.69 mmol), X-phos (657 mg, 1.38 mmol), $Cs_2CO_3$ (3.4 g, 10 mmol), and 1,4-dioxane (20 mL) were added into a microwave reaction tube. The mixture was reacted at 150° C. for 3 hours under a nitrogen atmosphere. The solvent was spin evaporated, and the residue was purified by silica gel column chromatography to give 1-(4-chloro-3-fluorobenzyl)-5-((trimethylsilyl)ethynyl)-1H-pyrazole (510 mg, 24% yield). MS m/z [ESI]: 307.1 [M+1].

Step 7: 1-(4-chloro-3-fluorobenzyl)-5-ethynyl-1H-pyrazole 1-(4-Chloro-3-fluorobenzyl)-5-((trimethylsilyl)ethynyl)-1H-pyrazole (510 mg, 1.66 mmol) and $K_2CO_3$ (460 mg, 3.33 mmol) were added into methanol (30 mL) and stirred at room temperature for 2 hours. The solid was removed by filtration, and the filtrate was spin evaporated and purified by silica gel column chromatography to give 1-(4-chloro-3-fluorobenzyl)-5-ethynyl-1H-pyrazole (350 mg, 90% yield). MS m/z [ESI]: 235.0 [M+1].

Step 8: 2-chloro-4-((1-(4-chloro-3-fluorobenzyl)-1H-pyrazol-5-yl)ethynyl)pyridine 1-(4-Chloro-3-fluorobenzyl)-5-ethynyl-1H-pyrazole (348 mg, 1.48 mmol), 2-chloropyridin-4-yl-trifluoromethanesulfonate (1.78 mmol), $[(C_6H_5)_3P]_2PdCl_2$ (0.148 mmol), CuI (562 mg, 2.96 mmol), and triethylamine (300 mg, 2.96 mmol) were added into DMF (20 mL). The resultant was reacted at 70° C. overnight under a nitrogen atmosphere. The solvent was spin evaporated, and the residue was purified by silica gel column chromatography to give 2-chloro-4-((1-(4-chloro-3-fluorobenzyl)-1H-pyrazol-5-yl)ethynyl)pyridine (360 mg, 70% yield). MS m/z [ESI]: 346.0 [M+1].

Intermediate 39: 5-bromo-3-(1-(2-(dimethylphosphoryl)-5-fluorophenyl)ethoxyl)-2-aminopyridine

Step 1: 3-(1-(2-(dimethylphosphoryl)-5-fluorophenyl)ethoxyl)-2-nitropyridine 3-(1-(2-Bromo-5-fluorophenyl)ethoxyl)-2-nitropyridine (371 mg, 1.1 mmol), dimethylphosphine oxide

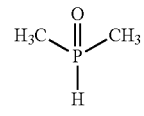

(94 mg, 1.2 mmol), Pd(OAc)$_2$ ((22 mg, 0.1 mmol), X-phos (95 mg, 0.2 mmol), and K$_3$PO$_4$ (244 mg, 1.1 mmol) were dissolved in DMF (10 mL) and purged with nitrogen. The mixture was reacted at 130° C. for 1 hour. After the resultant was cooled, the solvent was spin evaporated, and the residue was purified by silica gel column chromatography to give the title compound (35% yield). MS m/z [ESI]: 339.1 [M+1].

Step 2: 3-(1-(2-(dimethylphosphoryl)-5-fluorophenyl)ethoxyl)-2-aminopyridine

According to the procedure described in Step 2 of Intermediate 6, using 3-(1-(2-(dimethylphosphoryl)-5-fluorophenyl)ethoxyl)-2-nitropyridine instead of (R)-3-(1-(2,6-dichloro-3-fluorophenyl)ethyoxyl)-2-nitropyridine, the title compound was obtained (73% yield). MS m/z [ESI]: 309.1 [M+1].

Step 3: 5-bromo-3-(1-(2-(dimethylphosphoryl)-5-fluorophenyl)ethoxyl)-2-aminopyridine According to the procedure described in Step 3 of Intermediate 6, using 3-(1-(2-(dimethylphosphoryl)-5-fluorophenyl)ethoxyl)-2-aminopyridine instead of (R)-3-(1-(2,6-dichloro-3-fluorophenyl)ethyoxyl)-2-aminopyridine, the title compound was obtained (75% yield). MS m/z [ESI]: 387.0 [M+1].

Intermediate 40: 5-bromo-3-(1-(4-chloro-2-(dimethylamino)-5-fluorophenyl)ethoxy)-2-aminopyridine Step 1: 2-bromo-5-chloro-4-fluoroaniline To a solution of 3-chloro-4-fluoroaniline (5.82 g, 0.04 mol) in CH$_2$Cl$_2$ (150 mL), N-bromosuccinimide (7.12 g, 0.04 mol) was added in portions at 0° C. under stirring. Upon completion of the addition, the resultant was stirred for 30 minutes and filtered. The filtrate was concentrated and purified by silica gel column chromatography to give 2-bromo-5-chloro-4-fluoroaniline (6.16 g, 69% yield). $^1$H-NMR (400 MHz, CDCl$_3$): δ=7.234 (d, J=8.4 Hz, 1H), 6.788 (d, J=6.4 Hz, 1H), 3.982 (br, 2H). MS m/z [ESI]: 225.9 [M+1].

Step 2: 2-bromo-5-chloro-4-fluoro-N,N-dimethylaniline

2-Bromo-5-chloro-4-fluoroaniline (2.25 g, 0.01 mol), 40% formaldehyde solution (10 mL, 0.133 mol), and formic acid (4.6 g, 0.1 mol) were reacted at 100° C. for 3 hours. NaOH was added to adjust it to strongly alkaline, and then the resultant was extracted with CH$_2$Cl$_2$. The extract was dried, spin evaporated, and purified by silica gel column chromatography to give 2-bromo-5-chloro-4-fluoro-N,N-dimethylaniline (2.46 g, 97% yield). $^1$H-NMR (400 MHz, CDCl$_3$): δ=7.368 (d, J=8.4 Hz, 1H), 7.079 (d, J=6.8 Hz, 1H), 2.748 (s, 6H). MS m/z [ESI]: 253.9 [M+1].

Step 3: 2-(dimethylamino)-4-chloro-5-(fluorophenyl)ethanone

To a solution of 2-bromo-5-chloro-4-fluoro-N,N-dimethylaniline (2.46 g, 9.7 mmol) in dry THF (50 mL) cooled to −78° C., 2.5 M n-butyllithium (4.1 mL, 10.2 mmol) was added under a nitrogen atmosphere and stirred at −78° C. for 2 hours.

N-methyl-N-methoxylacetamide (1.00 g, 9.7 mmol) was added, and the solution was stirred at −78° C. for 2 hours. The reaction was warmed up to room temperature, stirred for 2 hours. The solvent was spin evaporated, and the residue was purified by silica gel column chromatography to give 2-(dimethylamino)-4-chloro-5-(fluorophenyl)ethanone (0.66 g, 32% yield). $^1$H-NMR (400 MHz, CDCl$_3$): δ=7.234 (d, J=9.2 Hz, 1H), 7.032 (d, J=6.0 Hz, 1H), 2.760 (s, 6H), 2.597 (s, 3H). MS m/z [ESI]: 216.0 [M+1].

Step 4: 1-(2-(dimethylamino)-4-chloro-5-fluorophenyl)ethanol 2-(Dimethylamino)-4-chloro-5-(fluorophenyl)ethanone (646 mg, 3 mmol) was dissolved in ethanol (10 mL), and NaBH$_4$ (342 mg, 9 mmol) was added in portions under ice-bath. The resultant was stirred at room temperature for 2 hours. The solvent was evaporated, and the residue was purified by silica gel column chromatography to give 1-(2-(dimethylamino)-4-chloro-5-fluorophenyl)ethanol (458 mg, 70% yield). $^1$H-NMR (400 MHz, CDCl$_3$): δ=7.25 (d, J=6.6 Hz, 1H), 7.03 (d, J=10.0 Hz, 1H), 5.77 (brs, 1H), 5.06 (q, J=6.5 Hz, 1H), 2.68 (s, 6H), 1.51 (d, J=6.5 Hz, 3H). MS m/z [ESI]: 218.1 [M+1].

Step 5: 2-(1-bromoethyl)-5-chloro-4-fluoro-N,N-dimethylaniline

According to the procedure described in Step 1 of Intermediate 5, using 1-(2-(dimethylamino)-4-chloro-5-fluorophenyl)ethanol instead of 1-(2,6-dichloro-3-fluorophenyl)ethanol, the title compound was obtained (31% yield). MS m/z [ESI]: 282.0 [M+1].

Step 6: 5-bromo-3-(1-(4-chloro-2-(dimethylamino)-5-fluorophenyl)ethoxy)-2-aminopyridine According to the procedure described in Step 2 of Intermediate 5, using 2-(1-bromoethyl)-5-chloro-4-fluoro-N,N-dimethylaniline instead of 1,3-dichloro-2-(1-bromoethyl)-4-fluorobenzene, the title compound was obtained (22% yield). MS m/z [ESI]: 390.0 [M+1].

Intermediate 41: 4-(2-((5-bromo-2-chloropyridin-3-yl)oxy)ethyl)morpholine

According to the procedure described in Step 3 of Intermediate 16, using 4-(2-chloroethyl)morpholine hydrochloride instead of iodomethane, the title compound was obtained (67% yield). MS m/z [ESI]: 323.0 [M+1].

Example 1: 4-(1-(3-chloro-4-fluorophenyl)-1H-pyrazol-5-yl)-5-(2-methoxy-4-(piperazin-1-yl)phenyl)pyridin-2-amine General Synthetic Methods:

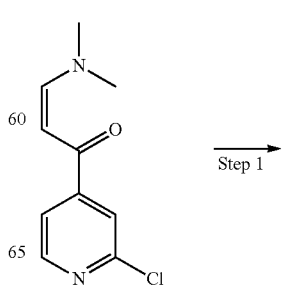

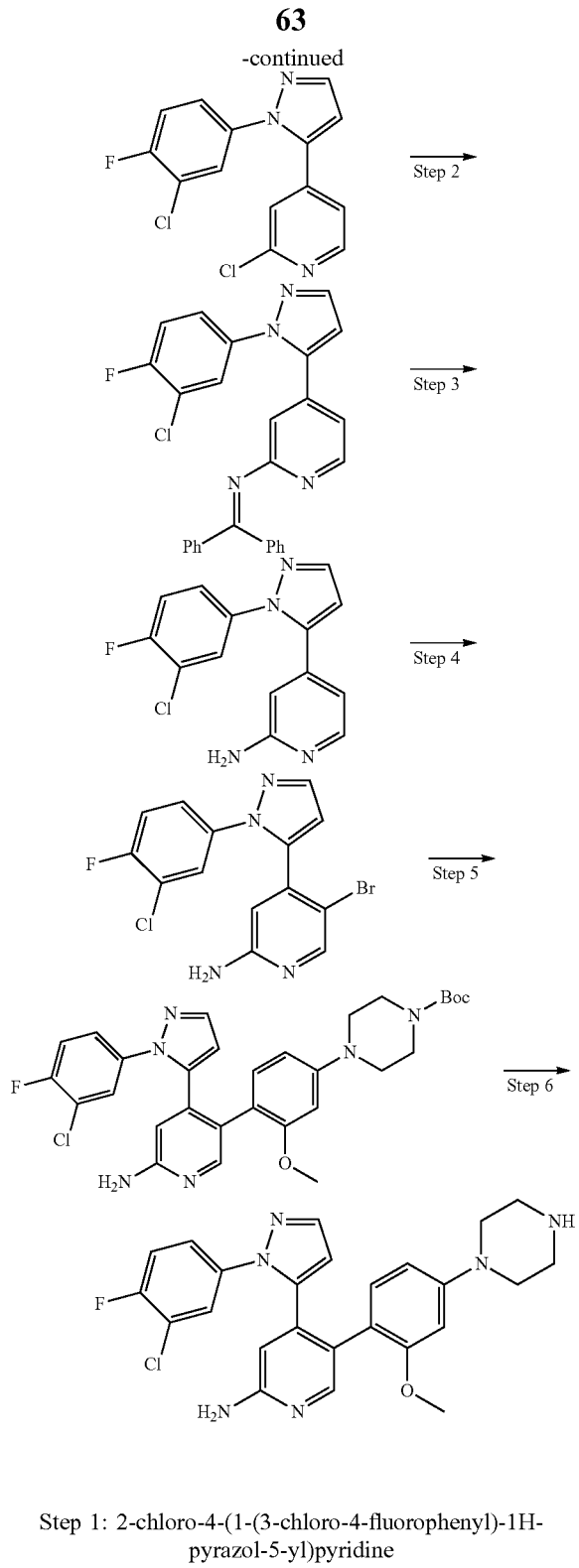

Step 1: 2-chloro-4-(1-(3-chloro-4-fluorophenyl)-1H-pyrazol-5-yl)pyridine 1-(2-Chloropyridin-4-yl)-3-(dimethylamino)prop-2-en-1-one (2.11 g, 10 mmol), 3-chloro-4-fluorophenylhydrazine (1.61 g, 10 mmol), a few drops of glacial acetic acid, and water (1 mL) were added into ethanol (50 mL). The resultant was refluxed for 1.5 hours. The solvent was spin evaporated. The residue was dissolved by adding ethyl acetate and washed with water. The organic layer was dried and purified by silica gel column chromatography to give 2-chloro-4-(1- (3-chloro-4-fluorophenyl)-1H-pyrazol-5-yl)pyridine (2.50 g, 81% yield). MS m/z [ESI]: 308.0 [M+1].

Step 2: 4-(1-(3-chloro-4-fluorophenyl)-1H-pyrazol-5-yl)-N-(diphenylmethylene)pyridin-2-amine 2-Chloro-4-(1-(3-chloro-4-fluorophenyl)-1H-pyrazol-5-yl)pyridine (2.0 g, 6.5 mmol), benzophenone imine (1.4 g, 7.7 mmol), $Pd_2(dba)_3$ (297 mg, 0.325 mmol), BINAP (0.42 g, 0.65 mmol), sodium tert-butoxide (0.94 g, 9.75 mmol), and toluene (30 mL) were added into a sealed tube and purged with nitrogen. The mixture was stirred at 120° C. for 3 hours. The solvent was spin evaporated, and ethyl acetate and water were added. The organic layer was dried and purified by silica gel column chromatography to give 4-(1-(3-chloro-4-fluorophenyl)-1H-pyrazol-5-yl)-N-(diphenylmethylene)pyridin-2-amine (1.4 g, 48% yield). $^1$H-NMR (400 MHz, $CDCl_3$): δ=8.235 (t, 1.8 Hz, 1H), 7.803 (d, J=7.2 Hz, 2H), 7.679 (d, J=1.6 Hz, 1H), 7.502 (d, J=7.6 Hz, 1H), 7.44-7.26 (m, 6H), 7.155 (d, J=6.8 Hz, 2H), 7.052 (t, J=8.3 Hz, 1H), 6.92-6.88 (m, 1H), 6.551-6.536 (q, 2H), 6.389 (d, J=1.6 Hz, 1H). MSm/z [ESI]: 453.1 [M+1].

Step 3: 4-(1-(3-chloro-4-fluorophenyl)-1H-pyrazol-5-yl)pyridin-2-amine 4-(1-(3-Chloro-4-fluorophenyl)-1H-pyrazol-5-yl)-N-(diphenylmethylene)pyridin-2-amine was added into 2 N HCl (50 mL), and the resultant was stirred overnight. After the reaction was extracted with ethyl acetate to remove benzophenone, the aqueous phase was adjusted to a pH value of greater than 12 by adding concentrated NaOH and then extracted by ethyl acetate. The organic layer was dried and spin evaporated to give 4-(1-(3-chloro-4-fluorophenyl)-1H-pyrazol-5-yl)pyridin-2-amine (0.77 g, 87% yield), which was directly used in the next step. MS m/z [ESI]: 289.1 [M+1].

Step 4: 5-bromo-4-(1-(3-chloro-4-fluorophenyl)-1H-pyrazol-5-yl)pyridin-2-amine

To a solution of 4-(1-(3-chloro-4-fluorophenyl)-1H-pyrazol-5-yl)pyridin-2-amine (0.72 g, 2.5 mmol) in $CH_2Cl_2$ (25 mL), liquid bromine (400 mg, 2.5 mmol) was added under stirring in ice bath. The resultant was stirred for 1 hour, washed with $Na_2CO_3$ solution, and extracted with $CH_2Cl_2$. The organic layer was dried over anhydrous sodium sulfate, concentrated, and purified by silica gel column chromatography ($CH_2Cl_2$: methanol=50:1) to give 5-bromo-4-(1-(3-chloro-4-fluorophenyl)-1H-pyrazol-5-yl)pyridin-2-amine (588 mg, 64% yield). $^1$H-NMR (400 MHz, $CDCl_3$): δ=8.49 (s, 1H), 7.746 (d, J=2.0 Hz, 1H), 7.523 (dd, J=7.2 Hz, 2.0 Hz, 1H), 7.066-7.048 (m, 2H), 6.517 (d, J=2.0 Hz, 1H), 6.424 (s, 1H), 4.622 (s, 2H). MS m/z [ESI]: 369.0 [M+1].

Step 5: tert-butyl 4-(4-(6-amino-4-(1-(3-chloro-4-fluorophenyl)-1H-pyrazol-5-yl)pyridin-3-yl)-3-methoxyphenyl)piperazine-1-carboxylate 5-Bromo-4-(1-(3-chloro-4-fluorophenyl)-1H-pyrazol-5-yl)pyridin-2-amine (237 mg, 0.644 mmol), tert-butyl 4-(3-methoxyl-4-(4,4,5,5-tetramethyl-1,3,2-dioxaborolan-2-yl) phenyl) piperazine-1-carboxylate (297 mg, 0.709 mmol), $Pd(PPh_3)_4$ (75 mg, 0.064 mmol), and $Cs_2CO_3$ (419 mg, 1.29 mmol) were added to 1,4-dioxane (10 mL) and water (1.5 mL), purged with nitrogen, and stirred at 100° C. overnight. After the solution was cooled, it was purified by silica gel column chromatography to give tert-butyl 4-(4-(6-amino-4-(1-(3-chloro-4-fluorophenyl)-1H-pyrazol-5-yl)pyridin-3-yl)-3-methoxyphenyl)piperazine-1-carboxylate (112 mg, 30% yield). MS m/z [ESI]: 579.2 [M+1].

Step 6: 4-(1-(3-chloro-4-fluorophenyl)-1H-pyrazol-5-yl)-5-(2-methoxy-4-(piperazin-1-yl)phenyl)pyridin-2-amine To a solution of tert-butyl 4-(4-(6-amino-4-(1-(3-chloro-4-fluorophenyl)-1H-pyrazol-5-yl)pyridin-3-yl)-3-methoxyphenyl)piperazine-1-carboxylate (110 mg, 0.19 mmol) in $CH_2Cl_2$ (10 mL), trifluoroacetate (1 mL) was added under stirring, and the mixture was stirred for 1 hour. NaOH solution was used to adjust the pH value of the aqueous phase to greater than 13, and the resultant was extracted by $CH_2Cl_2$. The organic layer was dried over anhydrous sodium sulfate, and filtered. The filtrate was concentrated, and purified by silica gel column chromatography ($CH_2Cl_2$: methanol (v/v)=8:1) to give 4-(1-(3-chloro-4-fluorophenyl)-1H-pyrazol-5-yl)-5-(2-methoxy-4-(piperazin-1-yl)phenyl)pyridin-2-amine (64 mg, 70% yield). $^1$H-NMR (400 MHz, $CDCl_3$): δ=7.650-7.631 (m, 2H), 7.079-7.035 (m, 2H), 6.872-6.850 (m, 1H), 6.812 (m, 1H), 6.589 (d, J=1.6 Hz, 1H), 6.355 (d, J=9.2 Hz, 1H), 6.295 (d, J=7.2 Hz, 2H), 3.416-3.364 (m, 4H), 3.341 (s, 3H), 3.297-3.273 (m, 4H). MS m/z [ESI]: 479.2 [M+1].

Example 2: 4-(1-(4-fluorophenyl)-1H-pyrazol-5-yl)-5-(2-methoxy-4-(piperazin-1-yl) phenyl)pyridin-2-amine hydrochloride Step 1: 2-chloro-4-(1-(4-fluorophenyl)-1H-pyrazol-5-yl)pyridine According to the procedure described in Step 1 of Example 1, using 4-fluorophenylhydrazine instead of 3-chloro-4-fluorophenylhydrazine, the title compound was obtained (86% yield). MS m/z [ESI]: 274.0 [M+1].

Step 2: 4-(1-(4-fluorophenyl)-1H-pyrazol-5-yl)-N-(diphenylmethylene)pyridin-2-amine

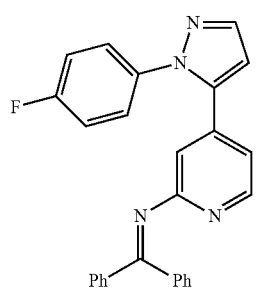 [SMILES: Fc1ccc(-n2nccc2-c2ccnc(N=C(c3ccccc3)c3ccccc3)c2)cc1]

According to the procedure described in Step 2 of Example 1, using 2-chloro-4-(1-(4-fluorophenyl)-1H-pyrazol-5-yl)pyridine instead of 2-chloro-4-(1-(3-chloro-4-fluorophenyl)-1H-pyrazol-5-yl)pyridine, the title compound was obtained (56% yield). MS m/z [ESI]: 419.2 [M+1].

Step 3: 4-(1-(4-fluorophenyl)-1H-pyrazol-5-yl)pyridin-2-amine

According to the procedure described in Step 3 of Example 1, using 4-(1-(4-fluorophenyl)-1H-pyrazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (77% yield). MS m/z [ESI]: 255.1 [M+1].

Step 4: 5-bromo-4-(1-(4-fluorophenyl)-1H-pyrazol-5-yl)pyridin-2-amine

According to the procedure described in Step 4 of Example 1, using 4-(1-(4-fluorophenyl)-1H-pyrazol-5-yl)pyridin-2-amine instead of 4-(1-(3-chloro-4-fluorophenyl)-1H-pyrazol-5-yl)pyridin-2-amine, the title compound was obtained (52% yield). MS m/z [ESI]: 333.0 [M+1]. $^1$H-NMR (400 MHz, $CDCl_3$): δ=8.176 (s, 1H), 7.742 (d, J=2.0 Hz, 1H), 7.291-7.256 (m, 2H), 7.022 (t, J=8.6 Hz, 2H), 6.521 (d, J=2.0 Hz, 1H), 6.394 (s, 1H), 4.502 (s, 2H).

Step 5: 4-(1-(4-fluorophenyl)-1H-pyrazol-5-yl)-5-(2-methoxy-4-(4-tert-butoxycarbonylpiperazin-1-yl)phenyl)pyridin-2-amine According to the procedure described in Step 5 of Example 1, using 5-bromo-4-(1-(4-fluorophenyl)-1H-pyrazol-5-yl)pyridin-2-amine instead of 5-bromo-4-(1-(3-chloro-4-fluorophenyl)-1H-pyrazol-5-yl)pyridin-2-amine, the title compound was obtained (35% yield). MS m/z [ESI]: 545.3 [M+1].

Step 6: 4-(1-(4-fluorophenyl)-1H-pyrazol-5-yl)-5-(2-methoxy-4-(piperazin-1-yl)phenyl) pyridin-2-amine hydrochloride 4-(1-(4-Fluorophenyl)-1H-pyrazol-5-yl)-5-(2-methoxy-4-(4-tert-butoxycarbonylpiperazin-1-yl)phenyl)pyridin-2-amine (54 mg, 0.1 mmol) was dissolved in methanol (20 mL), and then hydrogen chloride gas was supplied until saturation. Stirring was kept for 1 hour. The solvent was spin evaporated, and the residue was washed with ether and dried to give 4-(1-(4-fluorophenyl)-1H-pyrazol-5-yl)-5-(2-methoxy-4-(piperazin-1-yl)phenyl) pyridin-2-amine hydrochloride (46 mg). MS m/z[ESI]: 445.2[M+1].

Example 3: 4-(1-(3-fluorophenyl)-1H-pyrazol-5-yl)-5-(2-methoxy-4-(piperazin-1-yl)phenyl)pyridin-2-amine hydrochloride

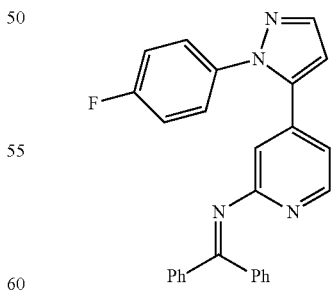

Step 1: 2-chloro-4-(1-(3-fluorophenyl)-1H-pyrazol-5-yl)pyridine

According to the procedure described in Step 1 of Example 1, using 3-fluorophenylhydrazine instead of 3-chloro-4-fluorophenylhydrazine, the title compound was obtained (79% yield). MS m/z [ESI]: 274.0 [M+1].

Step 2: 4-(1-(3-fluorophenyl)-1H-pyrazol-5-yl)-N-(diphenylmethylene)pyridin-2-amine

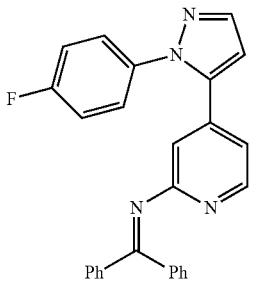 [SMILES: Fc1ccc(-n2nccc2-c2ccnc(N=C(c3ccccc3)c3ccccc3)c2)cc1]

According to the procedure described in Step 2 of Example 1, using 2-chloro-4-(1-(3-fluorophenyl)-1H-pyrazol-5-yl)pyridine instead of 2-chloro-4-(1-(3-chloro-4-fluorophenyl)-1H-pyrazol-5-yl)pyridine, the title compound was obtained (69% yield). MS m/z [ESI]: 419.2 [M+1].

Step 3: 4-(1-(3-fluorophenyl)-1H-pyrazol-5-yl)pyridin-2-amine

According to the procedure described in Step 3 of Example 1, using 4-(1-(3-fluorophenyl)-1H-pyrazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (80% yield). MS m/z [ESI]: 255.1 [M+1].

Step 4: 5-bromo-4-(1-(3-fluorophenyl)-1H-pyrazol-5-yl)pyridin-2-amine

According to the procedure described in Step 4 of Example 1, using 4-(1-(3-fluorophenyl)-1H-pyrazol-5-yl)pyridin-2-amine instead of 4-(1-(3-chloro-4-fluorophenyl)-1H-pyrazol-5-yl)pyridin-2-amine, the title compound was obtained (58% yield). MS m/z [ESI]: 333.0 [M+1].

Step 5: 4-(1-(3-fluorophenyl)-1H-pyrazol-5-yl)-5-(2-methoxy-4-(4-tert-butoxycarbonylpiperazin-1-yl)phenyl)pyridin-2-amine According to the procedure described in Step 5 of Example 1, using 5-bromo-4-(1-(3-fluorophenyl)-1H-pyrazol-5-yl)pyridin-2-amine instead of 5-bromo-4-(1-(3-chloro-4-fluorophenyl)-1H-pyrazol-5-yl)pyridin-2-amine, the title compound was obtained (30% yield). MS m/z [ESI]: 545.3 [M+1].

Step 6: 4-(1-(3-fluorophenyl)-1H-pyrazol-5-yl)-5-(2-methoxy-4-(piperazin-1-yl)phenyl) pyridin-2-amine hydrochloride According to the procedure described in Step 6 of Example 2, using 4-(1-(3-fluorophenyl)-1H-pyrazol-5-yl)-5-(2-methoxy-4-(4-tert-butoxycarbonylpiperazin-1-yl)phenyl)pyridin-2-amine instead of 4-(1-(4-fluorophenyl)-1H-pyrazol-5-yl)-5-(2-methoxy-4-(4-tert-butoxycarbonylpiperazin-1-yl)phenyl)pyridin-2-amine, the title compound was obtained (38 mg, 77% yield). MS m/z [ESI]: 445.2 [M+1]. $^1$H-NMR (400 MHz, DMSO-$d_6$): δ=9.362 (br, 2H), 8.233 (br, 2H), 7.833 (s, 1H), 7.769 (d, J=2.0 Hz, 1H), 7.384-7.327 (m, 1H), 7.189-7.142 (m, 1H), 6.986 (s, 1H), 6.849-6.779 (m, 2H), 6.508-6.467 (m, 2H), 6.343 (d, J=6.8 Hz, 2H), 3.451-3.356 (m, 4H), 3.327 (s, 3H), 3.185 (m, 4H).

Example 4: 4-(1-(4-chloro-3-fluorophenyl)-1H-pyrazol-5-yl)-5-(2-methoxy-4-(piperazin-1-yl)phenyl)pyridin-2-amine Step 1: 2-chloro-4-(1-(4-chloro-3-fluorophenyl)-1H-pyrazol-5-yl)pyridine According to the procedure described in Step 1 of Example 1, using 4-chloro-3-fluorophenylhydrazine instead of 3-chloro-4-fluorophenylhydrazine, the title compound was obtained (79% yield). MS m/z [ESI]: 308.0 [M+1].

Step 2: 4-(1-(4-chloro-3-fluorophenyl)-1H-pyrazol-5-yl)-N-(diphenylmethylene)pyridin-2-amine

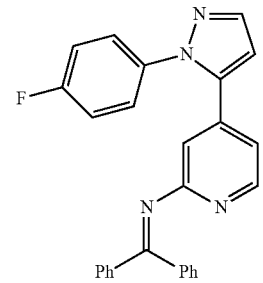 [SMILES: Fc1ccc(-n2nccc2-c2ccnc(N=C(c3ccccc3)c3ccccc3)c2)cc1]

According to the procedure described in Step 2 of Example 1, using 2-chloro-4-(1-(4-chloro-3-fluorophenyl)-1H-pyrazol-5-yl)pyridine instead of 2-chloro-4-(1-(3-chloro-4-fluorophenyl)-1H-pyrazol-5-yl)pyridine, the title compound was obtained (69% yield). MS m/z [ESI]: 453.1 [M+1].

Step 3: 4-(1-(4-chloro-3-fluorophenyl)-1H-pyrazol-5-yl)pyridin-2-amine

According to the procedure described in Step 3 of Example 1, using 4-(1-(4-chloro-3-fluorophenyl)-1H-pyrazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (80% yield). MS m/z [ESI]: 289.1 [M+1].

Step 4: 5-bromo-4-(1-(4-chloro-3-fluorophenyl)-1H-pyrazol-5-yl)pyridin-2-amine

According to the procedure described in Step 4 of Example 1, using 4-(1-(4-chloro-3-fluorophenyl)-1H-pyrazol-5-yl)pyridin-2-amine instead of 4-(1-(3-chloro-4-fluorophenyl)-1H-pyrazol-5-yl)pyridin-2-amine, the title compound was obtained (58% yield). MS m/z [ESI]: 369.0 [M+1].

Step 5: 4-(1-(4-chloro-3-fluorophenyl)-1H-pyrazol-5-yl)-5-(2-methoxy-4-(4-tert-butoxycarbonylpiperazin-1-yl)phenyl)pyridin-2-amine According to the procedure described in Step 5 of Example 1, using 5-bromo-4-(1-(4-chloro-3-fluorophenyl)-

1H-pyrazol-5-yl)pyridin-2-amine instead of 5-bromo-4-(1-(3-chloro-4-fluorophenyl)-1H-pyrazol-5-yl)pyridin-2-amine, the title compound was obtained (30% yield). MS m/z [ESI]: 579.2 [M+1].

Step 6: 4-(1-(4-chloro-3-fluorophenyl)-1H-pyrazol-5-yl)-5-(2-methoxy-4-(piperazin-1-yl)phenyl)pyridin-2-amine According to the procedure described in Step 6 of Example 2, using 4-(1-(4-chloro-3-fluorophenyl)-1H-pyrazol-5-yl)-5-(2-methoxy-4-(4-tert-butoxycarbonylpiperazin-1-yl)phenyl)pyridin-2-amine instead of 4-(1-(4-fluorophenyl)-1H-pyrazol-5-yl)-5-(2-methoxy-4-(4-tert-butoxycarbonylpiperazin-1-yl)phenyl)pyridin-2-amine, the title compound was obtained (56 mg, 77% yield). MS m/z [ESI]: 479.2 [M+1]. $^1$H-NMR (400 MHz, CDCl3): δ=8.049 (s, 1H), 7.598 (d, J=1.6 Hz, 1H), 7.157 (t, J=8.0 Hz, 1H), 6.873-6.842 (dd, J=10.0 Hz, 2.4 Hz, 1H), 6.756 (d, J=8.8 Hz, 1H), 6.502 (m, 2H), 6.315-6.281 (m, 2H), 6.168 (d, J=2.0 Hz, 1H), 4.491 (s, 2H), 3.359 (s, 3H), 3.138-3.114 (m, 4H), 3.052-3.028 (m, 4H).

Example 5: 4-(1-(3-trifluoromethylphenyl)-1H-pyrazol-5-yl)-5-(2-methoxy-4-(piperazin-1-yl)phenyl)pyridin-2-amine Step 1: 2-chloro-4-(1-(3-trifluoromethylphenyl)-1H-pyrazol-5-yl)pyridine According to the procedure described in Step 1 of Example 1, using 3-trifluoromethylphenyhydrazine instead of 3-chloro-4-fluorophenylhydrazine, the title compound was obtained (40% yield). MS m/z [ESI]: 324.0 [M+1]. $^1$H-NMR (400 MHz, CDCl$_3$): δ=8.331 (d, J=8.8 Hz, 1H), 7.806 (s, 1H), 7.713 (s, 1H), 7.665 (d, J=7.6 Hz, 1H), 7.526 (t, J=7.6 Hz, 1H), 7.393 (d, J=8.0 Hz, 1H), 7.272-7.249 (m, 1H), 6.971-6.956 (m, 1H), 6.964 (s, 1H).

Step 2: 4-(1-(3-trifluoromethylphenyl)-1H-pyrazol-5-yl)-N-(diphenylmethylene)pyridin-2-amine

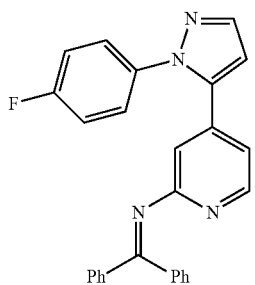 [SMILES: Fc1ccc(-n2nccc2-c2ccnc(N=C(c3ccccc3)c3ccccc3)c2)cc1]

According to the procedure described in Step 2 of Example 1, using 2-chloro-4-(1-(3-trifluoromethylphenyl)-1H-pyrazol-5-yl)pyridine instead of 2-chloro-4-(1-(3-chloro-4-fluorophenyl)-1H-pyrazol-5-yl)pyridine, the title compound was obtained (66% yield). MS m/z [ESI]: 469.2 [M+1].

Step 3: 4-(1-(3-trifluoromethylphenyl)-1H-pyrazol-5-yl)pyridin-2-amine

According to the procedure described in Step 3 of Example 1, using 4-(1-(3-trifluoromethylphenyl)-1H-pyrazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (79% yield). MS m/z [ESI]: 305.1 [M+1].

Step 4: 5-bromo-4-(1-(3-trifluoromethylphenyl)-1H-pyrazol-5-yl)pyridin-2-amine

According to the procedure described in Step 4 of Example 1, using 4-(1-(3-trifluoromethylphenyl)-1H-pyrazol-5-yl)pyridin-2-amine instead of 4-(1-(3-chloro-4-fluorophenyl)-1H-pyrazol-5-yl)pyridin-2-amine, the title compound was obtained (57% yield). MS m/z [ESI]: 383.0 [M+1].

Step 5: 4-(1-(3-trifluoromethylphenyl)-1H-pyrazol-5-yl)-5-(2-methoxy-4-(4-tert-butoxycarbonylpiperazin-1-yl)phenyl)pyridin-2-amine According to the procedure described in Step 5 of Example 1, using 5-bromo-4-(1-(3-trifluoromethylphenyl)-1H-pyrazol-5-yl)pyridin-2-amine instead of 5-bromo-4-(1-(3-chloro-4-fluorophenyl)-1H-pyrazol-5-yl)pyridin-2-amine, the title compound was obtained (42% yield). MS m/z[ESI]: 595.3[M+1].

Step 6: 4-(1-(3-trifluoromethylphenyl)-1H-pyrazol-5-yl)-5-(2-methoxy-4-(piperazin-1-yl)phenyl)pyridin-2-amine According to the procedure described in Step 6 of Example 2, using 4-(1-(3-trifluoromethylphenyl)-1H-pyrazol-5-yl)-5-(2-methoxy-4-(4-tert-butoxycarbonylpiperazin-1-yl)phenyl)pyridin-2-amine instead of 4-(1-(4-fluorophenyl)-1H-pyrazol-5-yl)-5-(2-methoxy-4-(4-tert-butoxycarbonylpiperazin-1-yl)phenyl)pyridin-2-amine, 4-(1-(3-trifluoromethylphenyl)-1H-pyrazol-5-yl)-5-(2-methoxy-4-(piperazin-1-yl)phenyl)pyridin-2-amine was obtained (65 mg, 83% yield). MS m/z [ESI]: 495.2 [M+1]. $^1$H-NMR (400 MHz, CDCl3): δ=7.82 (s, 1H), 7.76 (d, J=2.0 Hz, 1H), 7.67 (d, J=7.6 Hz, 1H), 7.57 (t, J=7.6 Hz, 1H), 7.33-7.30 (m, 2H), 6.48 (s, 1H), 6.43-6.40 (m, 2H), 6.28-6.27 (m, 2H), 6.12 (s, 2H), 3.31 (s, 3H), 3.16-3.14 (m, 4H), 2.98-2.96 (m, 4H).

Example 6: 4-(1-(4-fluorobenzyl)-1H-pyrazol-5-yl)-5-(2-methoxy-4-(4-methylpiperazin-1-yl)phenyl)pyridin-2-amine Step 1: 2-chloro-4-(1-(4-fluorobenzyl)-1H-pyrazol-5-yl)pyridine According to the procedure described in Step 1 of Example 1, using 4-fluorobenzylhydrazine instead of 3-chloro-4-fluorophenylhydrazine, the title compound was obtained (56% yield). MS m/z [ESI]: 288.1 [M+1].

Step 2: 4-(1-(4-fluorobenzyl)-1H-pyrazol-5-yl)-N-(diphenylmethylene)pyridin-2-amine

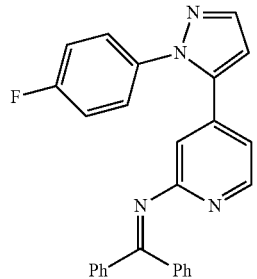 [SMILES: Fc1ccc(-n2nccc2-c2ccnc(N=C(c3ccccc3)c3ccccc3)c2)cc1]

According to the procedure described in Step 2 of Example 1, using 2-chloro-4-(1-(4-fluorobenzyl)-1H-pyrazol-5-yl)pyridine instead of 2-chloro-4-(1-(3-chloro-4-fluorophenyl)-1H-pyrazol-5-yl)pyridine, the title compound was obtained (65% yield). MS m/z [ESI]: 433.2 [M+1].

Step 3: 4-(1-(4-fluorobenzyl)-1H-pyrazol-5-yl)pyridin-2-amine

According to the procedure described in Step 3 of Example 1, using 4-(1-(4-fluorobenzyl)-1H-pyrazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (90% yield). MS m/z [ESI]: 269.1 [M+1].

Step 4: 5-bromo-4-(1-(4-fluorobenzyl)-1H-pyrazol-5-yl)pyridin-2-amine

According to the procedure described in Step 4 of Example 1, using 4-(1-(4-fluorobenzyl)-H-pyrazol-5-yl)pyridin-2-amine instead of 4-(1-(3-chloro-4-fluorophenyl)-1H-pyrazol-5-yl)pyridin-2-amine, the title compound was obtained (97% yield). MS m/z [ESI]: 347.0 [M+1].

Step 5: 4-(1-(4-fluorobenzyl)-1H-pyrazol-5-yl)-5-(2-methoxy-4-(4-methylpiperazin-1-yl)phenyl)pyridin-2-amine According to the procedure described in Step 5 of Example 1, using 5-bromo-4-(1-(4-fluorobenzyl)-1H-pyrazol-5-yl)pyridin-2-amine instead of 5-bromo-4-(1-(3-chloro-4-fluorophenyl)-1H-pyrazol-5-yl)pyridin-2-amine, and using 1-(3-methoxyl-4-(4,4,5,5-tetramethyl-1,3,2-dioxaborolan-2-yl)phenyl)-4-methylpiperazine instead of tert-butyl 4-(3-methoxyl-4-(4,4,5,5-tetramethyl-1,3,2-dioxaborolan-2-yl)phenyl) piperazine-1-carboxylate, the title compound was obtained (42% yield). MS m/z [ESI]: 473.2 [M+1]. $^1$H-NMR (400 MHz, CDCl$_3$): δ=8.065 (s, 1H), 7.798 (m, 1H), 7.696-7.552 (m, 3H), 7.428 (d, J=1.6 Hz, 1H), 6.82 (d, J=8.0 Hz, 1H), 6.396 (dd, J=8.0 Hz, 2.0 Hz, 1H), 6.310 (d, J=3.6 Hz, 2H), 6.065 (d, J=1.6 Hz, 1H), 4.936 (s, 2H), 4.762 (brs, 2H), 3.969 (s, 3H), 3.50 (m, 4H), 3.14 (m, 4H), 2.757 (s, 3H).

Example 7: 4-(1-(3-fluorophenyl-1H-imidazol-5-yl)-5-(2-methoxy-4-(4-methylpiperazin-1-yl)phenyl) pyridin-2-amine General Synthetic Methods:

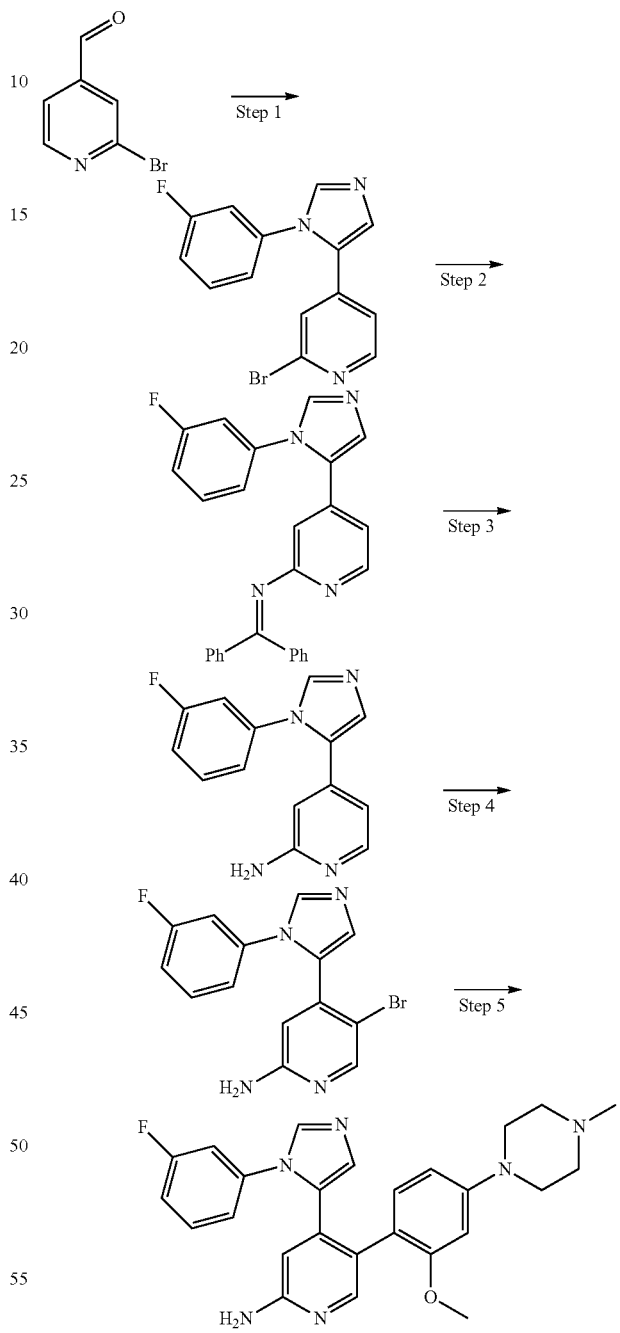

Step 1: 2-bromo-4-(1-(3-fluorophenyl)-1H-imidazol-5-yl)pyridine

2-Bromo-4-pyridinecarboxaldehyde (1.96 g, 10 mmol), 3-fluoroaniline (1.11 g, 10 mmol), and 4-methylbenzenesulfonic acid (50 mg) were added in toluene (50 mL). The resultant was refluxed for 12 hours with a water trap to remove the water generated during the reaction. The solvent was spin evaporated, and then tosylmethylisocyanidethe (1.95 g, 10 mmol), Na₂CO₃ (9.66 g, 91 mmol), and ethanol (50 mL) were added. The mixture was refluxed for 6 hours. The solvent was spin evaporated, and ethyl acetate and water were added. The organic layer was dried and purified by silica gel column chromatography to give 2-bromo-4-(1-(3-fluorophenyl)-H-imidazol-5-yl)pyridine (1.39 g, 44% yield). MS m/z [ESI]: 318.0 [M+1].

Step 2: 4-(1-(3-fluorophenyl)-1H-imidazol-5-yl)-N-(diphenylmethylene)pyridin-2-amine

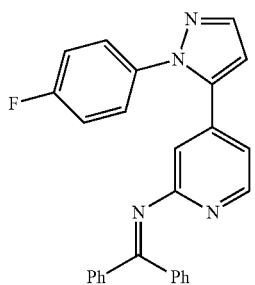 [SMILES: Fc1ccc(-n2nccc2-c2ccnc(N=C(c3ccccc3)c3ccccc3)c2)cc1]

According to the procedure described in Step 2 of Example 1, using 2-bromo-4-(1-(3-fluorophenyl)-1H-imidazol-5-yl)pyridine instead of 2-chloro-4-(1-(3-chloro-4-fluorophenyl)-1H-pyrazol-5-yl)pyridine, the title compound was obtained (70% yield). ¹H-NMR (400 MHz, CDCl₃): δ=8.235 (t, 1.8 Hz, 1H), 7.803 (d, J=7.2 Hz, 2H), 7.679 (d, J=1.6 Hz, 1H), 7.502 (d, J=7.6 Hz, 1H), 7.44-7.26 (m, 6H), 7.155 (d, J=6.8 Hz, 2H), 7.052 (t, J=8.3 Hz, 1H), 6.92-6.88 (m, 2H), 6.551-6.536 (q, 2H), 6.389 (d, J=1.6 Hz, 1H). MS m/z [ESI]: 419.2 [M+1].

Step 3: 4-(1-(3-fluorophenyl)-1H-imidazol-5-yl)pyridin-2-amine

According to the procedure described in Step 3 of Example 1, using 4-(1-(3-fluorophenyl)-1H-imidazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (87% yield). MS m/z [ESI]: 255.1 [M+1].

Step 4: 5-bromo-4-(1-(3-fluorophenyl)-1H-imidazol-5-yl)pyridin-2-amine

According to the procedure described in Step 4 of Example 1, using 4-(1-(3-fluorophenyl)-1H-imidazol-5-yl)pyridin-2-amine instead of 4-(1-(3-chloro-4-fluorophenyl)-1H-pyrazol-5-yl)pyridin-2-amine, the title compound was obtained (64% yield). MS m/z [ESI]: 333.0 [M+1].

Step 5: 4-(1-(3-fluorophenyl)-1H-imidazol-5-yl)-5-(2-methoxy-4-(4-methylpiperazin-1-yl)phenyl)pyridin-2-amine According to the procedure described in Step 5 of Example 1, using 5-bromo-4-(1-(3-fluorophenyl)-1H-imidazol-5-yl)pyridin-2-amine instead of 5-bromo-4-(1-(3-chloro-4-fluorophenyl)-1H-pyrazol-5-yl)pyridin-2-amine, and using 1-(3-methoxyl-4-(4,4,5,5-tetramethyl-1,3,2-dioxaborolan-2-yl)phenyl)-4-methylpiperazine instead of tert-butyl 4-(3-methoxyl-4-(4,4,5,5-tetramethyl-1,3,2-dioxaborolan-2-yl)phenyl) piperazine-1-carboxylate, the title compound was obtained (33% yield). MS m/z [ESI]: 459.2 [M+1]. ¹H-NMR (400 MHz, CDCl₃): δ=7.969 (s, 1H), 7.501 (d, J=1.2 Hz, 1H), 7.159-7.118 (m, 1H), 7.09 (s, 1H), 6.954-6.927 (m, 1H), 6.593 (d, J=8.0 Hz, 1H), 6.504-6.429 (m, 3H), 6.284-6.258 (dd, J=8.2 Hz, 2.2 Hz, 1H), 4.483 (s, 2H), 3.373 (s, 3H), 3.254 (m, 4H), 2.68 (m, 4H), 2.436 (s, 3H).

Example 8: 4-(1-(4-methylsulfonylphenyl)-1H-pyrazol-5-yl)-5-(2-methoxy-4-(4-methylpiperazin-1-yl)phenyl)pyridin-2-amine Step 1: 2-chloro-4-(1-(4-methylsulfonylphenyl)-1H-pyrazol-5-yl)pyridine According to the procedure described in Step 1 of Example 1, using 4-methylsulfonylphenylhydrazine instead of 3-chloro-4-fluorophenylhydrazine, the title compound was obtained (40% yield). MS m/z [ESI]: 334.0 [M+1].

Step 2: 4-(1-(4-methylsulfonylphenyl)-1H-pyrazol-5-yl)-N-(diphenylmethylene)pyridin-2-amine

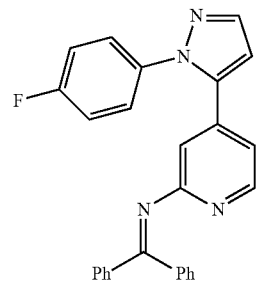 [SMILES: Fc1ccc(-n2nccc2-c2ccnc(N=C(c3ccccc3)c3ccccc3)c2)cc1]

According to the procedure described in Step 2 of Example 1, using 2-chloro-4-(1-(4-methylsulfonylphenyl)-1H-pyrazol-5-yl)pyridine instead of 2-chloro-4-(1-(3-chloro-4-fluorophenyl)-1H-pyrazol-5-yl)pyridine, the title compound was obtained (70% yield). MSm/z [ESI]: 315.1 [M+1].

Step 3: 4-(1-(4-methylsulfonylphenyl)-1H-pyrazol-5-yl)pyridin-2-amine

According to the procedure described in Step 3 of Example 1, using 4-(1-(4-methylsulfonylphenyl)-1H-pyrazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (87% yield). MS m/z [ESI]: 315.1 [M+1].

Step 4: 5-bromo-4-(1-(4-methylsulfonylphenyl)-1H-pyrazol-5-yl)pyridin-2-amine

According to the procedure described in Step 4 of Example 1, using 4-(1-(4-methylsulfonylphenyl)-1H-pyrazol-5-yl)pyridin-2-amine instead of 4-(1-(3-chloro-4-fluorophenyl)-1H-pyrazol-5-yl)pyridin-2-amine, the title compound was obtained (64% yield). MS m/z [ESI]: 395.0 [M+1].

Step 5: 4-(1-(4-4-methylsulfonylphenyl)-1H-pyrazol-5-yl)-5-(2-methoxy-4-(4-methylpiperazin-1-yl)phenyl)pyridin-2-amine According to the procedure described in Step 5 of Example 1, using 5-bromo-4-(1-(4-methylsulfonylphenyl)-1H-pyrazol-5-yl)pyridin-2-amine instead of 5-bromo-4-(1-(3-chloro-4-fluorophenyl)-1H-pyrazol-5-yl)pyridin-2-amine, and using 1-(3-methoxyl-4-(4,4,5,5-tetramethyl-1,3,2-dioxaborolan-2-yl)phenyl)-4-methylpiperazine instead of tert-butyl 4-(3-methoxyl-4-(4,4,5,5-tetramethyl-1,3,2-dioxaborolan-2-yl)phenyl) piperazine-1-carboxylate, the title compound was obtained (33% yield). MS m/z [ESI]: 519.2 [M+1]. $^1$H-NMR (400 MHz, CDCl$_3$): δ=7.99 (d, J=8.8 Hz, 2H), 7.88 (s, 1H), 7.80 (d, J=5.6 Hz, 1H), 7.58 (d, J=8.8 Hz, 2H), 7.00 (d, J=8.4 Hz, 1H), 7.59 (d, J=2.0 Hz, 1H), 6.53 (dd, J=8.4 Hz, 2.0 Hz, 1H), 6.33 (s, 1H), 6.29 (d, J=5.6 Hz, 1H), 3.61 (s, 3H), 3.30-3.33 (m, 4H), 3.17 (s, 3H), 2.79-2.87 (m, 4H), 2.52 (s, 3H).

Example 9: 3-(5-(2-amino-5-(2-methoxy-4-(4-methylpiperazin-1-yl)phenyl)pyridin-4-yl)-1H-pyrazol-1-yl)benzoic acid General Synthetic Methods:

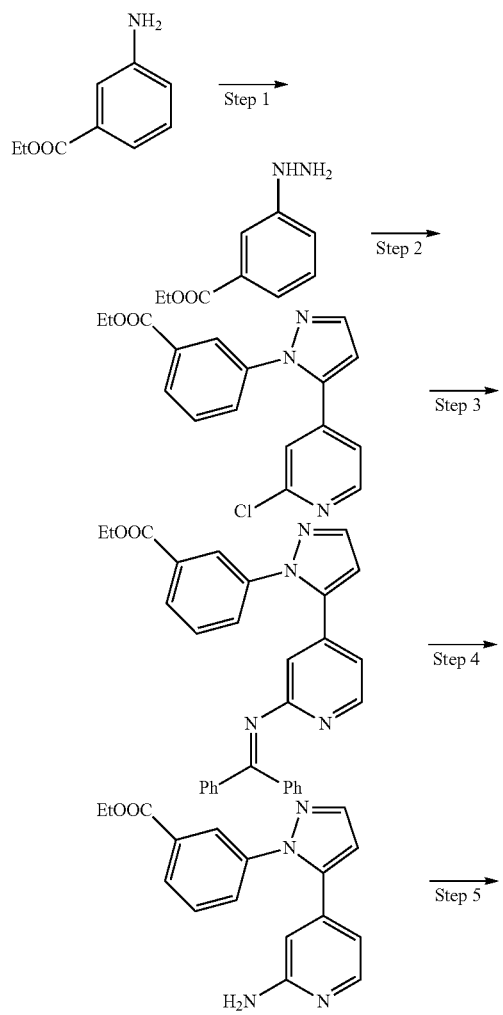

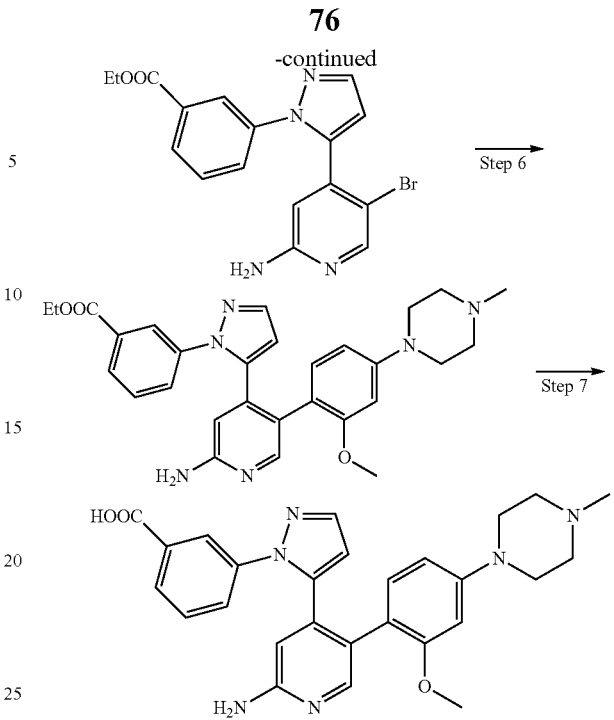

Step 1: ethyl 3-hydrazinylbenzoate

Ethyl 3-aminobenzoate (5.0 g, 30 mmol) was dissolved in concentrated hydrochloric acid (25 mL), the resultant was cooled to 0° C., and then a solution of NaNO$_2$ (2.09 g, 30 mmol) in water (10 mL) was added dropwise. After the resultant was stirred at 0° C. for 30 minutes, SnCl$_4$ (12.86 g, 57 mmol) was added. The resultant was warmed up to room temperature and stirred for 1 hour. Concentrated NaOH solution was used to adjust the solution to strongly alkaline, and then it was extracted by ether. The extract was dried, concentrated, and purified by silica gel column chromatography to give ethyl 3-hydrazinylbenzoate (3.9 g, 72% yield). MS m/z [ESI]: 181.1 [M+1].

Step 2: ethyl 3-(5-(2-chloropyridin-4-yl)-1H-pyrazol-1-yl)benzoate

According to the procedure described in Step 1 of Example 1, using ethyl 3-hydrazinylbenzoate instead of 3-chloro-4-fluorophenylhydrazine, the title compound was obtained (49% yield). MS m/z [ESI]: 328.1 [M+1].

Step 3: ethyl 3-(5-(2-((diphenylmethylene)amino)pyridin-4-yl)-1H-pyrazol-1-yl)benzoate According to the procedure described in Step 2 of Example 1, using ethyl 3-(5-(2-chloropyridin-4-yl)-1H-pyrazol-1-yl)benzoate instead of 2-chloro-4-(1-(3-chloro-4-fluorophenyl)-1H-pyrazol-5-yl)pyridine, the title compound was obtained (50% yield). MS m/z [ESI]: 473.2 [M+1].

Step 4: ethyl 3-(5-(3-aminophenyl)-1H-pyrazol-1-yl)benzoate

According to the procedure described in Step 3 of Example 1, using ethyl 3-(5-(2-((diphenylmethylene)amino)pyridin-4-yl)-1H-pyrazol-1-yl)benzoate instead of 4-(1-(3-chloro-4-fluorophenyl)-1H-pyrazol-5-yl)-N-(diphenylmethylene)pyridin-2-amine, the title compound was obtained (70% yield). MS m/z [ESI]: 309.1 [M+1].

Step 5: ethyl 3-(5-(5-amino-2-bromophenyl)-1H-pyrazol-1-yl)benzoate

According to the procedure described in Step 4 of Example 1, using ethyl 3-(5-(3-aminophenyl)-1H-pyrazol-1-yl)benzoate instead of 4-(1-(3-chloro-4-fluorophenyl)-1H-pyrazol-5-yl)pyridin-2-amine, the title compound was obtained (90% yield). $^1$H-NMR (400 MHz, CDCl$_3$): δ=8.60-8.24 (brs, 2H), 8.17 (s, 1H), 8.03 (t, J=1.7 Hz, 1H), 7.97 (dt, J=7.6, 1.4 Hz, 1H), 7.78 (d, J=1.8 Hz, 1H), 7.47 (ddd, J=8.0, 2.2, 1.3 Hz, 1H), 7.40 (t, J=7.8 Hz, 1H), 6.54 (s, 1H), 6.47-6.42 (m, 1H), 4.34 (q, J=7.1 Hz, 2H), 1.36 (t, J=7.1 Hz, 3H). MS m/z [ESI]: 387.0 [M+1].

Step 6: ethyl 3-(5-(2-amino-5-(2-methoxy-4-(4-methylpiperazin-1-yl)phenyl)pyridin-4-yl)-1H-pyrazol-1-yl)benzoate According to the procedure described in Step 5 of Example 1, using ethyl 3-(5-(5-amino-2-bromophenyl)-1H-pyrazol-1-yl)benzoate instead of 5-bromo-4-(1-(3-chloro-4-fluorophenyl)-1H-pyrazol-5-yl)pyridin-2-amine, and using 1-(3-methoxyl-4-(4,4,5,5-tetramethyl-1,3,2-dioxaborolan-2-yl)phenyl)-4-methylpiperazine instead of tert-butyl 4-(3-methoxyl-4-(4,4,5,5-tetramethyl-1,3,2-dioxaborolan-2-yl)phenyl) piperazine-1-carboxylate, the title compound was obtained (30% yield). MS m/z [ESI]: 513.3 [M+1].

Step 7: 3-(5-(2-amino-5-(2-methoxy-4-(4-methyl-piperazin-1-yl)phenyl)pyridin-4-yl)-1H-pyrazol-1-yl)benzoic acid Ethyl 3-(5-(2-amino-5-(2-methoxy-4-(4-methylpiperazin-1-yl)phenyl)pyridin-4-yl)-1H-pyrazol-1-yl)benzoate (103 mg, 0.2 mmol) was dissolved in methanol (10 mL), saturated sodium hydroxide solution (5 mL) was added, and then the solution was stirred at room temperature for 3 hours. Hydrochloric acid was used to neutralize the resultant, and the solvent was spin evaporated. The residue was purified by silica gel column chromatography to give 3-(5-(2-amino-5-(2-methoxy-4-(4-methylpiperazin-1-yl)phenyl)pyridin-4-yl)-1H-pyrazol-1-yl)benzoic acid (63 mg, 65% yield). MS m/z[ESI]: 485.2[M+1]. $^1$H-NMR (400 MHz, CDCl$_3$): δ=8.54 (s, 1H), 7.89 (s, 1H), 7.78-7.83 (m, 2H), 7.57 (s, 1H), 7.27 (t, J=6.8 Hz, 1H), 6.14 (d, J=6.8 Hz, 1H), 6.77 (d, J=8.0 Hz, 1H), 6.38-6.42 (m, 2H), 6.14 (s, 1H), 6.03 (s, 1H), 5.91 (s, 2H), 3.41 (s, 3H), 3.12-3.24 (m, 4H), 2.44-2.51 (m, 4H), 2.26 (s, 3H).

Example 10: 3-(5-(2-amino-5-(2-methoxy-4-(4-methylpiperazin-1-yl)phenyl)pyridin-4-yl)-1H-pyrazol-1-yl)benzyl alcohol The product of Step 6 in Example 9, that is, Ethyl 3-(5-(2-amino-5-(2-methoxy-4-(4-methylpiperazin-1-yl)phenyl)pyridin-4-yl)-1H-pyrazol-1-yl)benzoate (51 mg, 0.1 mmol), was dissolved in dry THF (10 mL). Lithium aluminum hydride (23 mg, 0.6 mmol) was added, and the resultant was stirred at room temperature for 4 hours. The reaction was quenched by several drops of methanol, and the solvent was spin evaporated. The residue was purified by silica gel column chromatography to give 3-(5-(2-amino-5-(2-methoxy-4-(4-methylpiperazin-1-yl)phenyl)pyridin-4-yl)-1H-pyrazol-1-yl)benzyl alcohol (23 mg, 49% yield). MS m/z[ESI]: 471.2[M+1]. $^1$H-NMR (400 MHz, DMSO-d$_6$): δ=7.793 (s, 1H), 7.636 (s, 1H), 7.251 (s, 2H), 7.122 (s, 1H), 6.923 (s, 1H), 6.578 (d, J=8.8 Hz, 1H), 6.354 (d, J=8.0 Hz, 3H), 6.228 (s, 1H), 6.013 (s, 2H), 5.29 (s, 1H), 4.496 (s, 2H), 3.36 (br, 4H), 3.23 (s, 3H), 2.886 (br, 4H), 2.56 (s, 3H).

Example 11: 2-((2-amino-5-(2-methoxy-4-(piperazin-1-yl)phenyl)pyridin-4-yl)amino)-N-isopropylbenzenesulfonamide hydrochloride General Synthetic Methods:

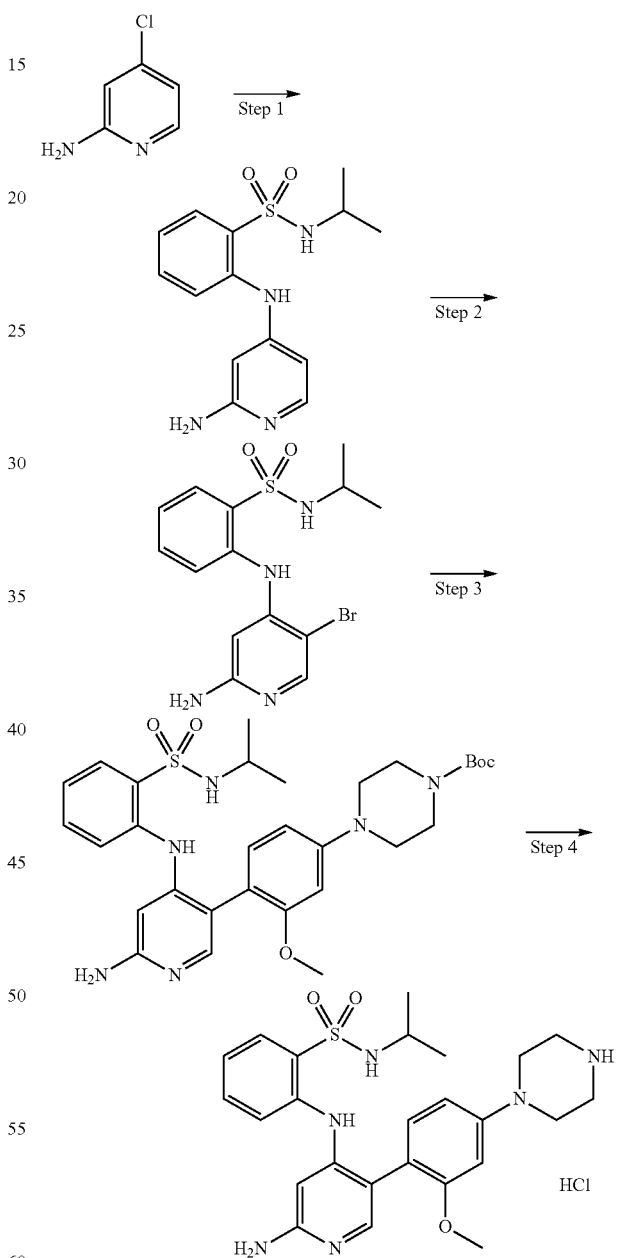

Step 1: 2-(2-aminopyridin-4-yl-amino)-N-isopropyl-benzenesulfonamide

4-Chloro-2-aminopyridine (1.28 g, 10 mmol), 2-amino-N-isopropylbenzenesulfonamide (2.35 g, 11 mmol), Pd$_2$ (dba)$_3$ (915 mg, 1 mmol), BINAP (1.31 g, 2 mmol), Cs$_2$CO$_3$ (6.50 g, 20 mmol), and dry toluene (80 mL) were added into a sealed tube and purged with nitrogen. The resultant was stirred at 130° C. overnight. After the resultant was cooled, it was purified by silica gel column chromatography to give 2-(2-aminopyridin-4-yl-amino)-N-isopropylbenzenesulfonamide (740 mg, 24% yield). MS m/z [ESI]: 307.1 [M+1].

Step 2: 2-(2-amino-5-bromo-pyridin-4-yl-amino)-N-isopropylbenzenesulfonamide

According to the procedure described in Step 4 of Example 1, using 2-(2-aminopyridin-4-yl-amino)-N-isopropylbenzenesulfonamide instead of 4-(1-(3-chloro-4-fluorophenyl)-1H-pyrazol-5-yl)pyridin-2-amine, the title compound was obtained (36% yield). MS m/z [ESI]: 387.0 [M+1].

Step 3: 2-(2-amino-5-(2-methoxy-4-(4-(tert-butoxycarbonyl)piperazin-1-yl)phenyl) pyridin-4-yl-amino)-N-isopropylbenzenesulfonamide According to the procedure described in Step 5 of Example 1, using 2-(2-amino-5-bromo-pyridin-4-yl-amino)-N-isopropylbenzenesulfonamide instead of 5-bromo-4-(1-(3-chloro-4-fluorophenyl)-1H-pyrazol-5-yl) pyridin-2-amine, the title compound was obtained (21% yield). MS m/z [ESI]: 597.3 [M+1].

Step 4: 2-(2-amino-5-(2-methoxy-4-(piperazin-1-yl) phenyl)pyridin-4-yl-amino)-N-isopropylbenzenesulfonamide hydrochloride According to the procedure described in Step 6 of Example 2, using 2-(2-amino-5-(2-methoxy-4-(4-(tert-butoxycarbonyl)piperazin-1-yl)phenyl) pyridin-4-yl-amino)-N-isopropylbenzenesulfonamide instead of 4-(1-(4-fluorophenyl)-1H-pyrazol-5-yl)-5-(2-methoxy-4-(4-tert-butoxycarbonylpiperazin-1-yl)phenyl)pyridin-2-amine, the title compound was obtained (75% yield). MS m/z [ESI]: 497.2 [M+1]. $^1$H-NMR (400 MHz, DMSO-d$_6$): δ=13.02 (s, 1H), 9.49 (s, 2H), 7.81 (d, J=7.2 Hz, 1H), 7.80 (s, 1H), 7.63-7.67 (m, 2H), 7.61 (d, J=7.2 Hz, 1H), 7.53 (s, 1H), 7.50 (d, J=8.0 Hz, 1H), 7.34 (td, J=8.0 Hz, 1.6 Hz, 1H), 7.17 (d, J=8.4 Hz, 1H), 6.69 (s, 1H), 6.65 (dd, J=8.0 Hz, 1.6 Hz, 1H), 6.48 (s, 1H), 3.72 (s, 3H), 3.46-3.49 (m, 4H), 3.14-3.19 (m, 5H), 0.89 (d, J=6.0 Hz, 6H).

Example 12: 4-((1-(4-chloro-3-fluorobenzyl)-1H-pyrazol-5-yl)ethynyl)-5-(2-methoxy-4-(4-methylpiperazin-1-yl)phenyl)pyridin-2-amine Step 1: 4-((1-(4-chloro-3-fluorobenzyl)-1H-pyrazol-5-yl)ethynyl)-N-(diphenylmethylene)pyridin-2-amine

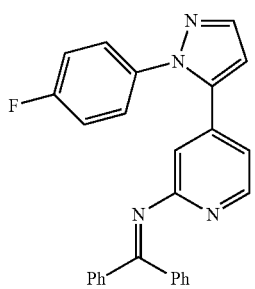 [SMILES: Fc1ccc(-n2nccc2-c2ccnc(N=C(c3ccccc3)c3ccccc3)c2)cc1]

According to the procedure described in Step 2 of Example 1, using 2-chloro-4-((1-(4-chloro-3-fluorobenzyl)-1H-pyrazol-5-yl)ethynyl)pyridine instead of 2-chloro-4-(1-(3-chloro-4-fluorophenyl)-1H-pyrazol-5-yl)pyridine, the title compound was obtained (35% yield). MS m/z [ESI]: 491.1 [M+1].

Step 2: 4-((1-(4-chloro-3-fluorobenzyl)-1H-pyrazol-5-yl)ethynyl)pyridin-2-amine

According to the procedure described in Step 3 of Example 1, using 4-((1-(4-chloro-3-fluorobenzyl)-1H-pyrazol-5-yl)ethynyl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (67% yield). MS m/z [ESI]: 327.1 [M+1].

Step 3: 5-bromo-4-((1-(4-chloro-3-fluorobenzyl)-1H-pyrazol-5-yl)ethynyl) pyridin-2-amine According to the procedure described in Step 4 of Example 1, using 4-((1-(4-chloro-3-fluorobenzyl)-1H-pyrazol-5-yl)ethynyl)pyridin-2-amine instead of 4-(1-(3-chloro-4-fluorophenyl)-1H-pyrazol-5-yl)pyridin-2-amine, the title compound was obtained (76% yield). MS m/z [ESI]: 407.0 [M+1].

Step 4: 4-((1-(4-chloro-3-fluorobenzyl)-1H-pyrazol-5-yl)ethynyl)-5-(2-methoxy-4-(4-methylpiperazin-1-yl)phenyl)pyridin-2-amine According to the procedure described in Step 5 of Example 1, using 5-bromo-4-((1-(4-chloro-3-fluorobenzyl)-1H-pyrazol-5-yl)ethynyl)pyridin-2-amine instead of 5-bromo-4-(1-(3-chloro-4-fluorophenyl)-1H-pyrazol-5-yl) pyridin-2-amine, and using 1-(3-methoxyl-4-(4,4,5,5-tetramethyl-1,3,2-dioxaborolan-2-yl)phenyl)-4-methylpiperazine instead of tert-butyl 4-(3-methoxyl-4-(4,4,5,5-tetramethyl-1,3,2-dioxaborolan-2-yl)phenyl) piperazine-1-carboxylate, the title compound was obtained (49% yield). MS m/z [ESI]: 531.2 [M+1].

Example 13: 4-(1-(4-fluorophenyl)-1H-pyrazol-5-yl)-5-(1-(piperidin-4-yl)-1H-pyrazol-4-yl)pyridin-2-amine hydrochloride

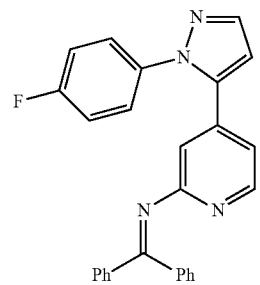 [SMILES: Fc1ccc(-n2nccc2-c2ccnc(N=C(c3ccccc3)c3ccccc3)c2)cc1]

Step 1: tert-butyl 4-(4-(6-amino-4-(1-(4-fluorophenyl)-1H-pyrazol-5-yl)pyridin-3-yl)-1H-pyrazol-1-yl) piperidine-1-carboxylate According to the procedure described in Step 5 of Example 1, using 5-bromo-4-(1-(4-fluorophenyl)-1H-pyrazol-5-yl)pyridin-2-amine instead of 5-bromo-4-(1-(3-chloro-4-fluorophenyl)-1H-pyrazol-5-yl)pyridin-2-amine, and using tert-butyl 4-(4,4,5,5-tetramethyl-1,3,2-dioxaborolan-2-yl)pyridin-1-carboxylate instead of tert-butyl 4-(3-methoxyl-4-(4,4,5,5-tetramethyl-1,3,2-dioxaborolan-2-yl) phenyl) piperazine-1-carboxylate, the title compound was obtained (76% yield). MS m/z [ESI]: 504.2 [M+1].

Step 2: 4-(1-(4-fluorophenyl)-1H-pyrazol-5-yl)-5-(1-(piperidin-4-yl)-1H-pyrazol-4-yl) pyridin-2-amine hydrochloride According to the procedure described in Step 6 of Example 2, using tert-butyl 4-(4-(6-amino-4-(1-(4-fluorophenyl)-1H-pyrazol-5-yl)pyridin-3-yl)-1H-pyrazol-1-yl) piperidine-1-carboxylate instead of 4-(1-(4-fluorophenyl)-1H-pyrazol-5-yl)-5-(2-methoxy-4-(4-tert-butoxycarbonylpiperazin-1-yl)phenyl)pyridin-2-amine, the title compound was obtained (49% yield). MS m/z [ESI]: 404.2 [M+1]. $^1$H-NMR (400 MHz, DMSO-$d_6$): δ=9.06-9.17 (1H, brs), 8.81-8.98 (1H, brs), 8.13-8.24 (2H, brs), 7.92 (1H, s), 7.87 (1H, d, J=1.6 Hz), 7.17 (1H, s), 7.05-7.10 (2H, m), 7.00 (1H, s), 6.90-6.94 (2H, m), 6.83 (1H, d, J=1.6 Hz), 6.64 (1H, s), 4.23-4.34 (1H, m), 3.33 (2H, d, J=12.8 Hz), 2.95-3.05 (2H, m), 1.92-2.08 (4H, m).

Example 14: 4-(1-(3-(dimethylphosphoryl)phenyl)-1H-pyrazol-5-yl)-5-(2-methoxy-4-(4-methylpiperazin-1-yl)phenyl)pyridin-2-amine Step 1: 2-chloro-4-(1-(3-bromophenyl)-1H-pyrazol-5-yl)pyridine According to the procedure described in Step 1 of Example 1, using 3-bromophenylhydrazine instead of 3-chloro-4-fluorophenylhydrazine, the title compound was obtained (77% yield). MS m/z [ESI]: 336.0 [M+1].

Step 2: 2-chloro-4-(1-(3-(dimethylphosphoryl)phenyl)-1H-pyrazol-5-yl)pyridine

2-Chloro-4-(1-(3-bromophenyl)-1H-pyrazol-5-yl)pyridine (335 mg, 1 mmol), dimethyl phosphine oxide (94 mg, 1.2 mmol), Pd(OAc)$_2$ (22 mg, 0.1 mmol), X-phos (95 mg, 0.2 mmol), and K$_3$PO$_4$ (244 Mg, 1.1 mmol) were added in DMF (10 mL) and purged with nitrogen. The resultant was reacted at 150° C. for 2 hours. After the resultant was cooled, the solvent was spin evaporated, and the residue was purified by silica gel column chromatography to give the title compound (36% yield). MS m/z[ESI]: 332.1 [M+1].

Step 3: 4-(1-(3-(dimethylphosphoryl)phenyl)-1H-pyrazol-5-yl)-N-(diphenylmethylene)pyridin-2-amine According to the procedure described in Step 2 of Example 1, using 2-chloro-4-(1-(3-(dimethylphosphoryl) phenyl)-1H-pyrazol-5-yl)pyridine instead of 2-chloro-4-(1-(3-chloro-4-fluorophenyl)-1H-pyrazol-5-yl)pyridine, the title compound was obtained (65% yield). MS m/z [ESI]: 477.2 [M+1].

Step 4: 4-(1-(3-(dimethylphosphoryl)phenyl)-1H-pyrazol-5-yl)pyridin-2-amine

According to the procedure described in Step 3 of Example 1, using 4-(1-(3-(dimethylphosphoryl)phenyl)-1H-pyrazol-5-yl)-N-(diphenylmethylene)pyridin-2-amine instead of 4-(1-(3-chloro-4-fluorophenyl)-1H-pyrazol-5-yl)-N-(diphenylmethylene)pyridin-2-amine, the title compound was obtained (90% yield). MS m/z [ESI]: 313.1 [M+1].

Step 5: 5-bromo-4-(1-(3-(dimethylphosphoryl)phenyl)-1H-pyrazol-5-yl) pyridin-2-amine According to the procedure described in Step 4 of Example 1, using 4-(1-(3-(dimethylphosphoryl)phenyl)-1H-pyrazol-5-yl)pyridin-2-amine instead of 4-(1-(3-chloro-4-fluorophenyl)-1H-pyrazol-5-yl)pyridin-2-amine, the title compound was obtained (89% yield). MS m/z [ESI]: 391.0 [M+1].

Step 6: 4-(1-(3-(dimethylphosphoryl)phenyl)-1H-pyrazol-5-yl)-5-(2-methoxy-4-(4-methylpiperazin-1-yl)phenyl)pyridin-2-amine According to the procedure described in Step 5 of Example 1, using 5-bromo-4-(1-(3-(dimethylphosphoryl) phenyl)-1H-pyrazol-5-yl)pyridin-2-amine instead of 5-bromo-4-(1-(3-chloro-4-fluorophenyl)-1H-pyrazol-5-yl) pyridin-2-amine, and using 1-(3-methoxyl-4-(4,4,5,5-tetramethyl-1,3,2-dioxaborolan-2-yl)phenyl)-4-methylpiperazine instead of tert-butyl 4-(3-methoxyl-4-(4,4,5,5-tetramethyl-1,3,2-dioxaborolan-2-yl)phenyl) piperazine-1-carboxylate, the title compound was obtained (42% yield). MS m/z [ESI]: 517.2 [M+1]. $^1$H-NMR (400 MHz, CDCl$_3$): δ=8.24 (1H, s), 8.18 (1H, d, J=12.4 Hz), 7.95 (1H, d, J=8.0 Hz), 7.66-7.76 (3H, m), 7.61 (1H, s), 7.17 (1H, d, J=8.0 Hz), 6.70 (1H, d, J=8.0 Hz), 6.63 (1H, s), 6.98 (1H, d, J=1.6 Hz), 3.93-3.96 (2H, m), 3.59-3.62 (2H, m), 3.50 (3H, s), 3.10-3.26 (4H, m), 2.97 (3H, s), 1.84 (6H, d, J=13.2 Hz).

Example 15: 2-(2-amino-5-(2-methoxy-4-(piperazin-1-yl)phenyl)pyridin-3-yl)-N-isopropylbenzenesulfonamide General Synthetic Methods:

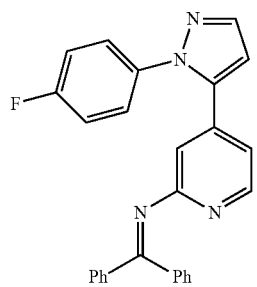 [SMILES: Fc1ccc(-n2nccc2-c2ccnc(N=C(c3ccccc3)c3ccccc3)c2)cc1]

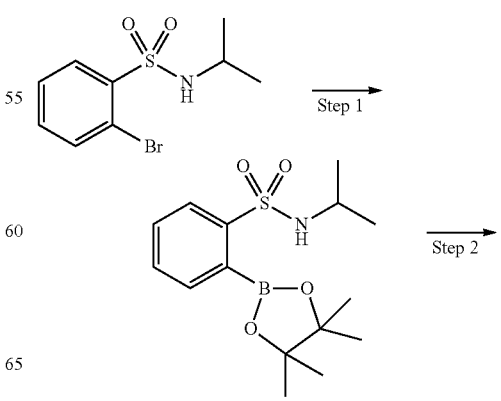

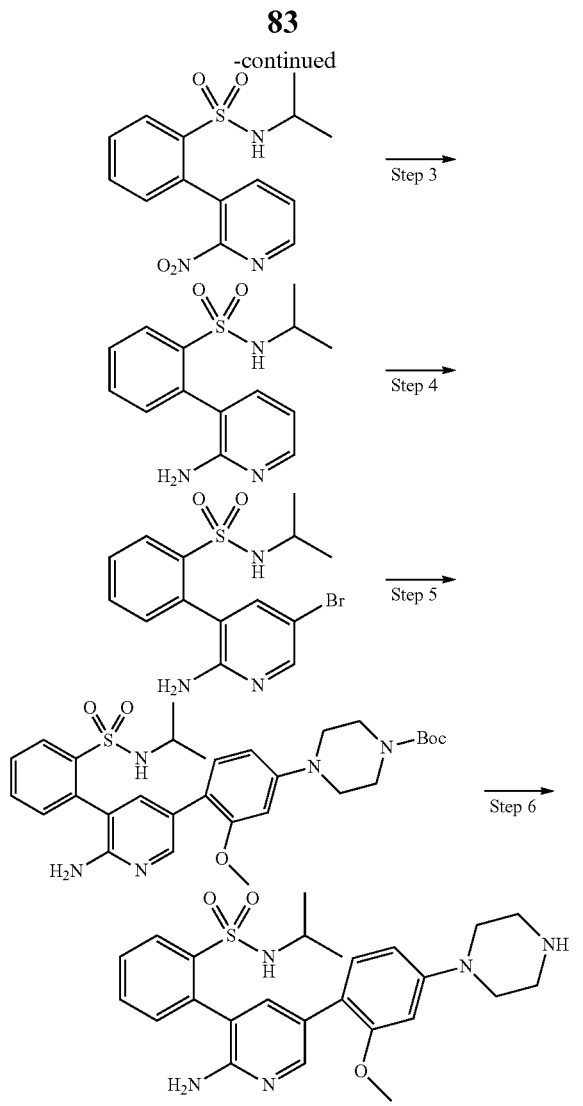

Step 1: 2-(4,4,5,5-tetramethyl-1,3,2-dioxaborolan-2-yl)-N-isopropylbenzenesulfonamide 2-Bromo-N-isopropylbenzenesulfonamide (2.4 g, 8.6 mmol), bis(pinacolato)diboron (3.3 g, 12.9 mmol), Pd(dppf)Cl$_2$ (630 mg, 0.86 mmol), and anhydrous potassium acetate (1.7 g, 17.2 mmol) were added in dry 1,4-dioxane (100 mL) and then purged with nitrogen. The resultant was stirred at 110° C. for 2 days. The resultant was filtered. The filtrate was spin evaporated and purified by silica gel column chromatography to give the title compound (37% yield).

Step 2: 2-(2-nitropyridin-3-yl)-N-isopropylbenzenesulfonamide 2-(4,4,5,5-Tetramethyl-1,3,2-dioxaborolan-2-yl)-N-isopropylbenzenesulfonamide (390 mg, 1.2 mmol), 2-nitro-3-(trifluoromethylsulfonyloxy)pyridine (272 mg, 1 mmol), Pd(PPh$_3$)$_4$ (58 mg, 0.05 mmol), and Cs$_2$CO$_3$ (650 mg, 2 mmol) were added in 1,4-dioxane (20 mL), purged with nitrogen, and the resultant was stirred at 120° C. for 2 hours under microwave. The solution was filtered, and the solvent was spin evaporated. The residue was purified by silica gel column chromatography to give the title compound (47% yield). MS m/z [ESI]: 322.1 [M+1].

Step 3: 2-(2-aminopyridin-3-yl)-N-isopropylbenzenesulfonamide 2-(2-Nitropyridin-3-yl)-N-isopropylbenzenesulfonamide (150 mg, 0.47 mmol) was dissolved in ethanol (15 mL), and then 2M HCl (0.5 mL) and reduced iron powder (185 mg, 3.29 mmol) were added. The resultant was refluxed for 2 hours and then filtered. The filtrate was spin evaporated and purified by silica gel column chromatography to give the title compound (80% yield). MS m/z[ESI]: 292.1[M+1].

Step 4: 2-(2-amino-5-bromopyridin-3-yl)-N-isopropylbenzenesulfonamide

According to the procedure described in Step 4 of Example 1, using 2-(2-aminopyridin-3-yl)-N-isopropylbenzenesulfonamide instead of 4-(1-(3-chloro-4-fluorophenyl)-1H-pyrazol-5-yl)pyridin-2-amine, the title compound was obtained (58% yield). MS m/z [ESI]: 372.0 [M+1].

Step 5: 2-(2-amino-5-(2-methoxy-4-(4-(tert-butoxycarbonyl)piperazin-1-yl)phenyl) pyridin-3-yl-amino)-N-isopropylbenzenesulfonamide According to the procedure described in Step 5 of Example 1, using 2-(2-amino-5-bromopyridin-3-yl)-N-isopropylbenzenesulfonamide instead of 5-bromo-4-(1-(3-chloro-4-fluorophenyl)-1H-pyrazol-5-yl)pyridin-2-amine, the title compound was obtained (30% yield). MS m/z [ESI]: 582.3 [M+1].

Step 6: 2-(2-amino-5-(2-methoxy-4-(piperazin-1-yl)phenyl)pyridin-3-yl)-N-isopropylbenzenesulfonamide According to the procedure described in Step 6 of Example 1, using 2-(2-amino-5-(2-methoxy-4-(4-(tert-butoxycarbonyl)piperazin-1-yl)phenyl) pyridin-3-yl-amino)-N-isopropylbenzenesulfonamide instead of 4-(1-(3-chloro-4-fluorophenyl)-1H-pyraol-5-yl)-5-(2-methoxy-4-(4-tert-butoxycarbonylpiperazin-1-yl)phenyl)pyridin-2-amine, the title compound was obtained (77% yield). MS m/z [ESI]: 482.2 [M+1]. $^1$H-NMR (400 MHz, CDCl$_3$): δ=8.15 (d, J=8.0 Hz, 1H), 8.07 (d, J=1.6 Hz, 1H), 7.95 (d, J=2.0 Hz, 1H), 7.70-7.80 (m, 2H), 7.49 (d, J=7.2 Hz, 1H), 7.33 (d, J=8.4 Hz, 1H), 6.73 (d, J=1.6 Hz, 1H), 6.69 (dd, J=8.8 Hz, 2.4 Hz, 1H), 3.87 (s, 3H), 3.30-3.60 (m, 9H), 1.09 (d, J=6.4 Hz, 6H).

Example 16: 3-((3-fluorophenoxy)methyl)-5-(1-(piperidin-4-yl)-1H-pyrazol-4-yl) pyridin-2-amine hydrochloride General Synthetic Methods:

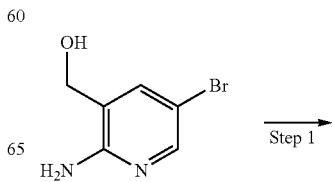

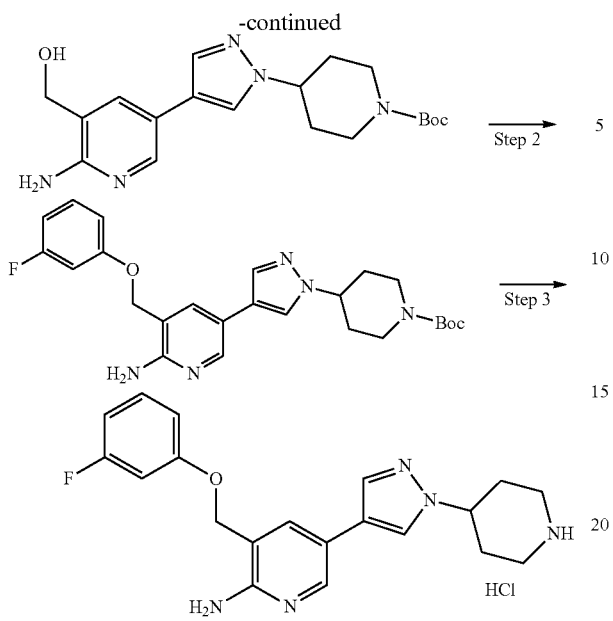

Step 1: 3-hydroxymethyl-5-(1-(1-(tert-butoxycarbonyl)piperidin-4-yl)-H-pyrazol-4-yl) pyridin-2-amine According to the procedure described in Step 5 of Example 1, using 3-hydroxymethyl-5-bromo-pyridin-2-amine instead of 5-bromo-4-(1-(3-chloro-4-fluorophenyl)-1H-pyrazol-5-yl)pyridin-2-amine, and using tert-butyl 4-(4,4,5,5-tetramethyl-1,3,2-dioxaborolan-2-yl)pyridin-1-carboxylate instead of tert-butyl 4-(3-methoxyl-4-(4,4,5,5-tetramethyl-1,3,2-dioxaborolan-2-yl)phenyl) piperazine-1-carboxylate, the title compound was obtained (37% yield). MS m/z [ESI]: 374.2 [M+1].

Step 2: 3-((3-fluorophenoxy)methyl)-5-(1-(1-(tert-butoxycarbonyl)piperidin-4-yl)-1H-pyrazol-4-yl) pyridin-2-amine 3-Hydroxymethyl-5-(1-(1-(tert-butoxycarbonyl)piperidin-4-yl)-1H-pyrazol-4-yl) pyridin-2-amine, 3-fluorophenol (61.6 mg, 0.55 mmol), and PPh$_3$ (200 mg, 0.75 mmol) were added in dry THF (20 mL), purged with nitrogen, and the resultant was stirred for 1 hour. After the resultant was cooled to 0° C., DIAD (152 mg, 0.75 mmol) was added dropwise, and the resultant was stirred at room temperature overnight. The solvent was spin evaporated, and the residue was purified by silica gel column chromatography to give the title compound (50 mg, 21% yield). MS m/z[ESI]: 468.2[M+1].

Step 3: 3-((3-fluorophenoxy)methyl)-5-(1-(piperidin-4-yl)-1H-pyrazol-4-yl) pyridin-2-amine hydrochloride According to the procedure described in Step 6 of Example 2, using 3-((3-fluorophenoxy)methyl)-5-(1-(1-(tert-butoxycarbonyl)piperidin-4-yl)-1H-pyrazol-4-yl)pyridin-2-amine instead of 4-(1-(4-fluorophenyl)-1H-pyrazol-5-yl)-5-(2-methoxy-4-(4-tert-butoxycarbonylpiperazin-1-yl) phenyl)pyridin-2-amine, the title compound was obtained (68% yield). MS m/z [ESI]: 368.2 [M+1]. $^1$H-NMR (400 MHz, DMSO-d$_6$): δ=8.93 (1H, brs), 8.75 (1H, brs), 8.421 (1H, s), 8.343 (1H, s), 8.301 (1H, s), 8.016 (1H, s), 7.95 (2H, brs), 7.417-7.358 (1H, m), 7.012 (1H, dd, J=11.2 Hz, 2.4 Hz), 6.947 (1H, dd, J=8.4H, 2.4 Hz), 6.852 (1H, m), 5.085 (2H, s), 4.508 (1H, m), 3.384 (4H, m), 2.17 (4H, m).

Example 17: 3-(1-(2,6-dichloro-3-fluorophenyl) ethoxy)-5-(2-(4-isopropylpiperazin-1-yl)-4-methoxy-pyrimidin-5-yl)pyridin-2-amine General Synthetic Methods:

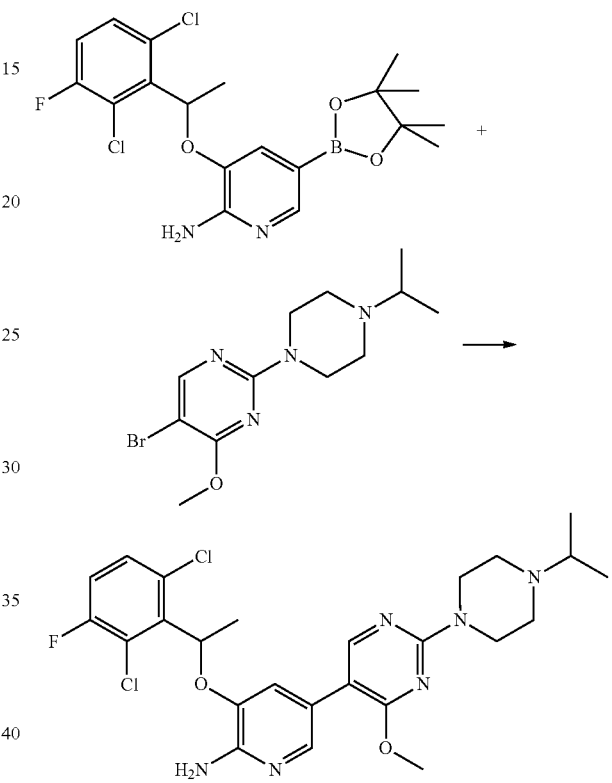

According to the procedure described in Step 5 of Example 1, 5-bromo-2-(4-isopropylpiperazin-1-yl)-4-methoxypyrimidin (158 Mg, 0.5 mmol), 3-(1-(2,6-dichloro-3-fluorophenyl)ethoxy)-5-(4,4,5,5-tetramethyl-1,3,2-dioxaborolan-2-yl)pyridin-2-amine (235 mg, 0.55 mmol), Pd(PPh$_3$)$_4$ (58 mg, 0.05 mmol), and Cs$_2$CO$_3$ (325 mg, 1 mmol) were dissolved in 1,4-dioxane (10 mL) and water (1.5 mL), purged with nitrogen, and the resultant was stirred at 100° C. overnight. After the resultant was cooled, it was purified by silica gel column chromatography to give the title compound (58% yield). MS m/z[ESI]: 535.2[M+1]. $^1$H-NMR (400 MHz, CDCl$_3$): δ=8.00 (s, 1H), 7.69 (d, J=1.6 Hz, 1H), 7.31-7.27 (m, 1H), 7.05 (t, J=8.2 Hz, 1H), 6.94 (s, 1H), 6.04 (q, J=6.5 Hz, 1H), 4.79 (s, 2H), 3.85 (s, 3H), 3.84-3.79 (m, 4H), 2.73 (dt, J=12.9, 6.4 Hz, 1H), 2.58 (dd, J=9.9, 4.9 Hz, 4H), 1.83 (d, J=6.7 Hz, 3H), 1.08 (d, J=6.5 Hz, 6H).

Example 18: 5-(1-(2,6-dichloro-3-fluorophenyl) ethoxy)-5'-methoxy-6'-(4-methylpiperazin-1-yl)-[3,3'-bipyridin]-6-amine According to the procedure described in Example 17, using 5-bromo-2-(4-methylpiperazin-1-yl)-3-methoxypyridine instead of 5-bromo-2-(4-isopropylpiperazin-1-yl)-4-methoxypyrimidine, the title compound was obtained (55% yield). MS m/z [ESI]: 506.1 [M+1]. ¹H-NMR (400 MHz, CDCl₃): δ=7.71 (s, 1H), 7.63 (s, 1H), 7.37 (dd, J=8.8 Hz, 4.8 Hz, 1H), 7.15 (t, J=9.2 Hz, 1H), 7.06 (s, 1H), 6.84 (s, 1H), 6.11 (q, J=6.4 Hz, 1H), 3.81 (s, 3H), 3.37-3.52 (m, 4H), 2.87-2.97 (m, 4H), 2.56 (s, 3H), 1.79 (d, J=6.8 Hz, 3H).

Example 19: 5-(1-(2,6-dichloro-3-fluorophenyl)ethoxy)-4'-methoxy-6'-(4-methylpiperazin-1-yl)-[3,3'-bipyridin]-6-amine According to the procedure described in Example 17, using 5-bromo-2-(4-methylpiperazin-1-yl)-4-methoxypyridine instead of 5-bromo-2-(4-isopropylpiperazin-1-yl)-4-methoxypyrimidine, the title compound was obtained (64% yield). MS m/z [ESI]: 506.1 [M+1]. ¹H-NMR (400 MHz, CDCl₃): δ=7.91 (1H, s), 7.69 (1H, s), 7.28-7.31 (1H, m), 7.06 (1H, t, J=8.0 Hz), 6.95 (1H, s), 6.12 (1H, s), 6.04 (1H, q, J=6.8 Hz), 4.96 (2H, s), 3.75 (3H, s), 3.67-3.72 (4H, m), 2.66-2.75 (4H, m), 2.47 (3H, s), 1.83 (3H, d, J=6.8 Hz).

Example 20: 3-(1-(2-(dimethylphosphoryl)-5-fluorophenyl)ethoxy)-5-(2-methoxy-4-(4-methylpiperazin-1-yl)phenyl)pyridin-2-amine According to the procedure described in Example 17, using 5-bromo-3-(1-(2-(dimethylphosphoryl)-5-fluorophenyl)ethoxy)pyridin-2-amine instead of 5-bromo-2-(4-isopropylpiperazin-1-yl)-4-methoxypyrimidine, and using 1-(3-methoxy-4-(4,4,5,5-tetramethyl-1,3,2-dioxaborolan-2-yl)phenyl)-4-methylpiperazine instead of 3-(1-(2,6-dichloro-3-fluorophenyl)ethoxy)-5-(4,4,5,5-tetramethyl-1,3,2-dioxaborolan-2-yl)pyridin-2-amine, the title compound was obtained (64% yield). MS m/z [ESI]: 513.2 [M+1]. ¹H-NMR (400 MHz, DMSO-d6): δ=7.78-7.69 (m, 2H), 7.65 (d, J=10.5 Hz, 1H), 7.58 (s, 1H), 7.29 (dd, J=15.6, 6.8 Hz, 1H), 7.20 (d, J=8.4 Hz, 1H), 7.09 (q, J=5.3 Hz, 1H), 6.64 (s, 1H), 6.61 (q, J=6.5 Hz, 1H), 3.67 (s, 3H), 3.37-2.93 (m, 8H), 2.86 (s, 3H), 1.74 (dd, J=13.3, 5.6 Hz, 6H), 1.67 (d, J=6.3 Hz, 3H).

Example 21: 3-(1-(4-chloro-2-(dimethylamino)-5-fluorophenyl)ethoxy)-5-(2-methoxy-4-(4-methylpiperazin-1-yl)phenyl)pyridin-2-amine According to the procedure described in Example 17, using 5-bromo-3-(1-(2-(dimethylamino)-4-chloro-5-fluorophenyl)ethoxy)pyridin-2-amine instead of 5-bromo-2-(4-isopropylpiperazin-1-yl)-4-methoxypyrimidine, and using 1-(3-methoxy-4-(4,4,5,5-tetramethyl-1,3,2-dioxaborolan-2-yl)phenyl)-4-methylpiperazine instead of 3-(1-(2,6-dichloro-3-fluorophenyl)ethoxy)-5-(4,4,5,5-tetramethyl-1,3,2-dioxaborolan-2-yl)pyridin-2-amine, the title compound was obtained (64% yield). MS m/z [ESI]: 513.2 [M+1]. ¹H-NMR (400 MHz, CDCl₃): δ=8.035 (1H, s), 7.534 (1H, s), 7.105 (1H, s), 6.987 (1H, d, J=8.4 Hz), 6.546 (1H, s), 6.460-6.422 (2H, m), 6.385 (1H, s), 5.564 (1H, q), 3.612 (3H, s), 3.453 (4H, m), 2.983 (4H, m), 2.815 (6H, s), 2.620 (3H, s), 1.64 (3H, d, J=6.4 Hz).

Example 22: 5-(1-(2,6-dichloro-3-fluorophenyl)ethoxy)-6'-((S)-2,4-dimethylpiperazin-1-yl)-4'-methoxy-[3,3'-bipyridin]-6-amine According to the procedure described in Example 17, using (S)-1-(5-bromo-4-methoxypyridin-2-yl)-2,4-dimethylpiperazine instead of 5-bromo-2-(4-isopropylpiperazin-1-yl)-4-methoxypyrimidine, the title compound was obtained (64% yield). MS m/z [ESI]: 520.2 [M+1]. ¹H-NMR (400 MHz, CDCl₃): δ=7.90 (1H, s), 7.63 (1H, s), 7.27-7.30 (1H, m), 7.05 (1H, t, J=8.0 Hz), 6.95 (1H, s), 6.05 (1H, s), 6.02 (1H, q, J=6.8 Hz), 5.29 (2H, s), 4.40-4.50 (1H, m), 3.87-4.15 (1H, m), 3.74 (3H, s), 3.12 (1H, t, J=12.4 Hz), 2.93 (1H, d, J=11.2 Hz), 2.77 (1H, d, J=11.2 Hz), 2.32 (3H, s), 2.30 (1H, m), 2.07-2.14 (1H, m), 1.82 (3H, d, J=6.8 Hz), 1.28 (3H, d, J=6.8 Hz).

Example 23: 5-(1-(2,6-dichloro-3-fluorophenyl)ethoxy)-6'-((R)-2,4-dimethylpiperazin-1-yl)-4'-methoxy-[3,3'-bipyridin]-6-amine According to the procedure described in Example 17, using (R)-1-(5-bromo-4-methoxypyridin-2-yl)-2,4-dimethylpiperazine instead of 5-bromo-2-(4-isopropylpiperazin-1-yl)-4-methoxypyrimidine, the title compound was obtained (64% yield). MS m/z [ESI]: 520.2 [M+1]. ¹H-NMR (400 MHz, CDCl₃): δ=7.91 (s, 1H), 7.69 (s, 1H), 7.31-7.28 (m, 1H), 7.05 (t, J=8.4 Hz, 1H), 6.96 (s, 1H), 6.06 (s, 1H), 6.03 (q, J=6.5 Hz, 1H), 4.98 (s, 2H), 4.54 (m, 1H), 3.99 (d, J=12.4 Hz, 1H), 3.74 (s, 3H), 3.28 (t, J=13.8 Hz, 1H), 2.99 (d, J=10.8 Hz, 1H), 2.83 (d, J=11.2 Hz, 1H), 2.37 (s, 3H), 2.32 (m, 1H), 2.23-2.11 (m, 1H), 1.83 (d, J=6.6 Hz, 3H), 1.31 (d, J=6.4 Hz, 3H).

Example 24: 5-((R)-1-(2,6-dichloro-3-fluorophenyl)ethoxy)-6'-((S)-2,4-dimethylpiperazin-1-yl)-4'-methoxy-[3,3'-bipyridin]-6-amine According to the procedure described in Example 17, using (S)-1-(5-bromo-4-methoxypyridin-2-yl)-2,4-dimethylpiperazine instead of 5-bromo-2-(4-isopropylpiperazin-1-yl)-4-methoxypyrimidine, and using (R)-3-(1-(2,6-dichloro-3-fluorophenyl)ethoxy)-5-(4,4,5,5-tetramethyl-1,3,2-dioxaborolan-2-yl)pyridin-2-amine instead of 3-(1-(2,6-dichloro-3-fluorophenyl)ethoxy)-5-(4,4,5,5-tetramethyl-1,3,2-dioxaborolan-2-yl)pyridin-2-amine, the title compound was obtained (64% yield). MS m/z[ESI]: 520.2[M+1]. ¹H-NMR (400 MHz, CDCl₃): δ=7.91 (1H, s), 7.65 (1H, s), 7.27-7.30 (1H, m), 7.05 (1H, t, J=8.4 Hz), 6.96 (1H, s), 6.02-6.10 (2H, m), 5.25 (2H, s), 4.43-4.50 (1H, m), 3.97 (1H, d, J=12.8 Hz), 3.74 (3H, s), 3.23 (1H, td, J=12.8 Hz, 3.2 Hz), 2.94 (1H, d, J=11.2 Hz), 2.78 (1H, d, J=11.2 Hz), 2.29-2.32 (4H, m), 2.07-2.14 (1H, m), 1.82 (3H, d, J=6.8 Hz), 1.28 (3H, d, J=6.4 Hz).

Example 25: 5-((R)-1-(2,6-dichloro-3-fluorophenyl)ethoxy)-6'-((R)-2,4-dimethylpiperazin-1-yl)-4'-methoxy-[3,3'-bipyridin]-6-amine According to the procedure described in Example 17, using (R)-1-(5-bromo-4-methoxypyridin-2-yl)-2,4-dimethylpiperazine instead of 5-bromo-2-(4-isopropylpiperazin-1-yl)-4-methoxypyrimidine, and using (R)-3-(1-(2,6-dichloro-3-fluorophenyl)ethoxy)-5-(4,4,5,5-tetramethyl-1,3,2-dioxaborolan-2-yl)pyridin-2-amine instead of 3-(1-(2,6-dichloro-3-fluorophenyl)ethoxy)-5-(4,4,5,5-tetramethyl-1,3,2-dioxaborolan-2-yl)pyridin-2-amine, the title compound was obtained (64% yield). MS m/z [ESI]: 520.2 [M+1]. ¹H-NMR (400 MHz, CDCl₃): δ=7.93 (1H, s), 7.70 (1H, s), 7.28-7.31 (1H, m), 7.07 (1H, t, J=8.0 Hz), 6.97 (1H, s), 6.04-6.13 (2H, m), 4.98 (2H, s), 4.43-4.52 (1H, m), 3.98 (1H, d, J=12.4 Hz), 3.76 (3H, s), 3.24 (1H, td, J=12.4 Hz, 2.8

Hz), 2.93 (1H, d, J=10.8 Hz), 2.78 (1H, d, J=10.4 Hz), 2.29-2.34 (4H, m), 2.09-2.14 (1H, m), 1.84 (3H, d, J=6.8 Hz), 1.29 (3H, d, J=6.8 Hz).

Example 26: 5-((R)-1-(2,6-dichloro-3-fluorophenyl) ethoxy)-6'-((S)-2,4-dimethylpiperazin-1-yl)-5'-methoxy-[3,3'-bipyridin]-6-amine According to the procedure described in Example 17, using (S)-1-(5-bromo-3-methoxypyridin-2-yl)-2,4-dimethylpiperazine instead of 5-bromo-2-(4-isopropylpiperazin-1-yl)-4-methoxypyrimidine, and using and (R)-3-(1-(2,6-dichloro-3-fluorophenyl)ethoxy)-5-(4,4,5,5-tetramethyl-1,3,2-dioxaborolan-2-yl)pyridin-2-amine instead of 3-(1-(2,6-dichloro-3-fluorophenyl)ethoxy)-5-(4,4,5,5-tetramethyl-1,3,2-dioxaborolan-2-yl)pyridin-2-amine, the title compound was obtained (64% yield). MS m/z [ESI]: 520.2 [M+1]. $^1$H-NMR (400 MHz, CDCl$_3$): δ=7.89 (s, 1H), 7.78 (s, 1H), 7.33 (dd, J=8.8, 4.8 Hz, 1H), 7.09 (t, J=8.4 Hz, 1H), 7.01 (s, 1H), 6.95 (s, 1H), 6.13 (q, J=6.6 Hz, 1H), 5.50 (s, 2H), 4.47 (m, 1H), 3.88 (s, 3H), 3.85 (t, J=4.2 Hz, 1H), 3.79 (d, J=11.8 Hz, 1H), 3.40 (m, 1H), 3.25 (m, 2H), 3.12 (m, 1H), 2.85 (s, 3H), 1.89 (d, J=6.6 Hz, 3H), 1.26 (d, J=6.5 Hz, 3H).

Example 27: 5-((R)-1-(2,6-dichloro-3-fluorophenyl) ethoxy)-4'-methoxy-6'-((S)-2-methylpiperazin-1-yl)-[3,3'-bipyridin]-6-amine General Synthetic Methods:

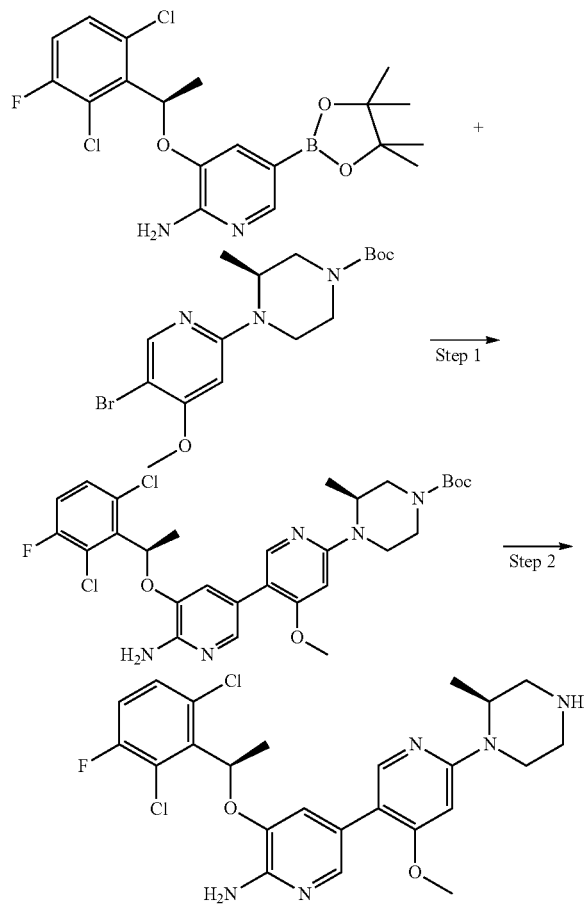

Step 1: (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate (S)-tert-butyl 4-(5-bromo-4-methoxypyridin-2-yl)-3-methylpiperazine-1-carboxylate (106 mg, 0.275 mmol), (R)-3-(1-(2,6-dichloro-3-fluorophenyl)ethoxy)-5-(4,4,5,5-tetramethyl-1,3,2-dioxaborolan-2-yl)pyridin-2-am ine (140 mg, 0.33 mmol), Pd(PPh$_3$)$_4$ (32 mg, 0.0275 mmol), and Cs$_2$CO$_3$ (179 mg, 0.55 mmol) were dissolved in 1,4-dioxane (10 mL) and water (1.5 mL), purged with nitrogen, and the resultant was stirred at 100° C. overnight. After the resultant was cooled, it was purified by silica gel column chromatography to give (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate (70 mg, 42% yield). MS m/z [ESI]: 606.2 [M+1].

Step 2: 5-((R)-1-(2,6-dichloro-3-fluorophenyl) ethoxy)-4'-methoxy-6'-((S)-2-methylpiperazin-1-yl)-[3,3'-bipyridin]-6-amine To a stirred solution of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate (67 mg, 0.11 mmol) in CH$_2$Cl$_2$ (10 mL), trifluoroacetate (1 mL) was added, and the mixture was then stirred for 1 hour. Concentrated NaOH was added to adjust the pH value to greater than 13, and the resultant was extracted by CH$_2$Cl$_2$. The extract was dried over anhydrous sodium sulphate, filtered, concentrated, and purified by silica gel column chromatography (CH$_2$Cl$_2$: methanol=8:1) to give 5-((R)-1-(2,6-dichloro-3-fluorophenyl)ethoxy)-4'-methoxy-6'-((S)-2-methylpiperazin-1-yl)-[3,3'-bipyridin]-6-amine (55% yield). MS m/z[ESI]: 506.1 [M+1]. $^1$H-NMR (400 MHz, CDCl$_3$): δ=7.94 (1H, s), 7.71 (1H, s), 7.28-7.32 (1H, m), 7.07 (1H, t, J=8.4 Hz), 6.97 (1H, s), 6.04-6.13 (2H, m), 4.86 (2H, s), 4.57-4.59 (1H, m), 4.03 (1H, d, J=14 Hz), 3.76 (3H, s), 3.07-3.33 (4H, m), 2.88-3.00 (1H, m), 1.84 (3H, d, J=6.8 Hz), 1.34 (3H, d, J=6.8 Hz).

Example 28: 5-((R)-1-(2,6-dichloro-3-fluorophenyl) ethoxy)-4'-methoxy-6'-((S)-2-methyl-4-(1-methylpiperidin-4-yl)piperazin-1-yl)-[3,3'-bipyridin]-6-amine According to the procedure described in Example 17, using (S)-1-(5-bromo-4-methoxypyridin-2-yl)-2-methyl-4-(1-methylpiperidin-4-yl)piperazine instead of 5-bromo-2-(4-isopropylpiperazin-1-yl)-4-methoxypyrimidine, and using and (R)-3-(1-(2,6-dichloro-3-fluorophenyl)ethoxy)-5-(4,4,5,5-tetramethyl-1,3,2-dioxaborolan-2-yl)pyridin-2-amine instead of 3-(1-(2,6-dichloro-3-fluorophenyl) ethoxy)-5-(4,4,5,5-tetramethyl-1,3,2-dioxaborolan-2-yl) pyridin-2-amine, the title compound was obtained (27% yield). MS m/z [ESI]: 603.2 [M+1]. $^1$H-NMR (400 MHz, CDCl$_3$): δ=7.88 (1H, s), 7.66 (1H, s), 7.26-7.28 (1H, m), 7.03 (1H, t, J=8.0 Hz), 6.93 (1H, s), 5.99-6.02 (2H, m), 4.83 (2H, s), 4.43-4.46 (1H, m), 3.98 (1H, d, J=12.4 Hz), 3.72 (3H, s), 3.21-3.30 (2H, m), 3.12 (1H, t, J=11.6 Hz), 2.92 (1H, J=9.6 Hz), 2.79 (1H, d, J=10.8 Hz), 2.64-2.80 (4H, m), 2.44-2.47 (3H, m), 2.29-2.34 (1H, m), 2.06-2.14 (4H, m), 1.79 (3H, d, J=6.8 Hz), 1.21 (3H, d, J=6.4 Hz).

Example 29: (R)-5-(1-(2,6-dichloro-3-fluorophenyl)ethoxy)-4'-methoxy-1",2",3",6"-tetrahydro-[3,3':6',4"-terpyridin]-6-amine

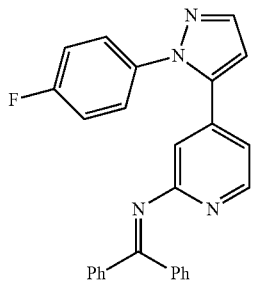 [SMILES: Fc1ccc(-n2nccc2-c2ccnc(N=C(c3ccccc3)c3ccccc3)c2)cc1]

Step 1: (R)-tert-butyl 6-amino-5-(1-(2,6-dichloro-3-fluorophenyl)ethoxy)-4'-methoxy-5",6"-dihydro-[3,3':6',4"-terpyridine]-1"(2"H)-carboxylate According to the procedure described in Step 1 of Example 27, using tert-butyl 4-(5-bromo-4-methoxypyridin-2-yl)-5,6-dihydropyridin-(2H)-carboxylate instead of (S)-tert-butyl 4-(5-bromo-4-methoxypyridin-2-yl)-3-methylpiperazine-1-carboxylate, the title compound was obtained (20% yield). MS m/z [ESI]: 589.2 [M+1].

Step 2: (R)-5-(1-(2,6-dichloro-3-fluorophenyl)ethoxy)-4'-methoxy-1",2",3",6"-tetrahydro-[3,3':6',4"-terpyridin]-6-amine According to the procedure described in Step 2 of Example 27, using (R)-tert-butyl 6-amino-5-(1-(2,6-dichloro-3-fluorophenyl)ethoxy)-4'-methoxy-5",6"-dihydro-[3,3':6',4"-terpyridine]-1"(2"H)-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (41% yield). MS m/z [ESI]: 489.1 [M+1]. $^1$H-NMR (400 MHz, CDCl$_3$): δ=8.21 (1H, s), 7.60 (1H, s), 7.26-7.29 (1H, m), 7.04 (1H, t, J=8.0 Hz), 6.96 (1H, s), 6.87 (1H, s), 6.49 (1H, s), 6.01 (1H, q, J=6.8 Hz), 5.33 (2H, s), 3.94 (2H, s), 3.74 (3H, s), 3.49 (2H, t, J=4.2 Hz), 3.00 (2H, dt, J=4.2 Hz), 1.81 (3H, d, J=6.8 Hz).

Example 30: (R)-5-(1-(2,6-dichloro-3-fluorophenyl)ethoxy)-5'-methoxy-1",2",3",6"-tetrahydro-[3,3':6',4"-terpyridin]-6-amine General Synthetic Methods:

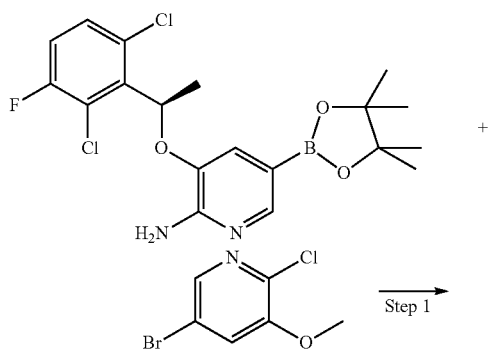

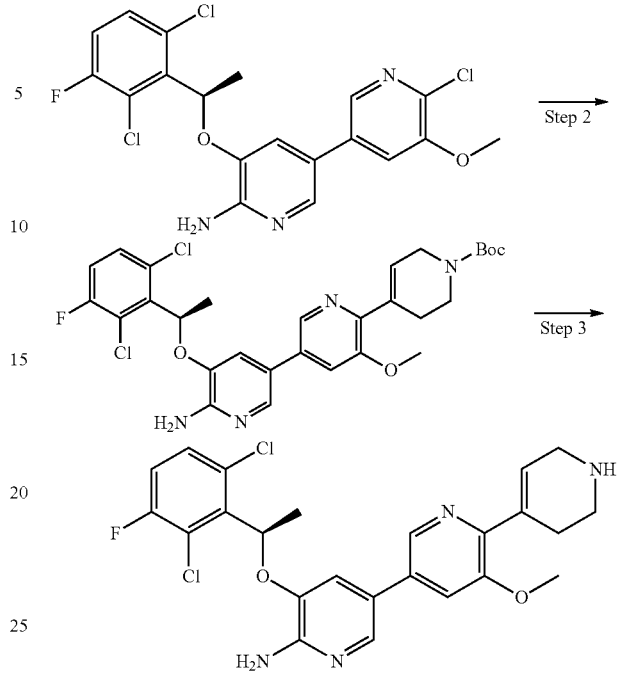

Step 1: (R)-6'-chloro-5-(1-(2,6-dichloro-3-fluorophenyl)ethoxy)-5'-methoxy-[3,3'-bipyridin]-6-amine 5-Bromo-2-chloro-3-methoxypyridine (244 mg, 1.1 mmol), (R)-3-(1-(2,6-dichloro-3-fluorophenyl)ethoxy)-5-(4,4,5,5-tetramethyl-1,3,2-dioxaborolan-2-yl)pyridin-2-amine (427 mg, 1.0 mmol), Pd(PPh$_3$)$_4$ (116 mg, 0.1 mmol), and Cs$_2$CO$_3$ (652 mg, 2.0 mmol) were dissolved in 1,4-dioxane (10 mL) and water (1.5 mL), purged with nitrogen, and the resultant was stirred at 100° C. overnight. After the resultant was cooled, it was purified by silica gel column chromatography to give (R)-6'-chloro-5-(1-(2,6-dichloro-3-fluorophenyl)ethoxy)-5'-methoxy-[3,3'-bipyridin]-6-amine (252 mg, 57% yield). MS m/z[ESI]: 442.0[M+1].

Step 2: (R)-tert-butyl 6-amino-5-(1-(2,6-dichloro-3-fluorophenyl)ethoxy)-5'-methoxy-5",6"-dihydro-[3,3':6',4"-terpyridine]-1"(2"H)-carboxylate (R)-6'-chloro-5-(1-(2,6-dichloro-3-fluorophenyl)ethoxy)-5'-methoxy-[3,3'-bipyridin]-6-amine (243 mg, 0.55 mmol), tert-butyl 4-(4,4,5,5-tetramethyl-1,3,2-dioxaborolan-2-yl)-1-carboxylate-1,2,5,6-tetrahydro-pyridine (204 mg, 0.66 mmol), Pd(PPh$_3$)$_4$ (64 mg, 0.055 mmol) and Cs$_2$CO$_3$ (359 mg, 1.1 mmol) were dissolved in 1,4-dioxane (6 mL) and water (1.5 mL), purged with nitrogen, and the resultant was reacted at 100° C. overnight. After the resultant was cooled, it was purified by silica gel column chromatography to give (R)-tert-butyl 6-amino-5-(1-(2,6-dichloro-3-fluorophenyl)ethoxy)-5'-methoxy-5",6"-dihydro-[3,3':6',4"-terpyridine]-1"(2"H)-carboxylate (65 mg, 20% yield). MS m/z [ESI]: 589.2 [M+1].

Step 3: (R)-5-(1-(2,6-dichloro-3-fluorophenyl)ethoxy)-5'-methoxy-1",2",3",6"-tetrahydro-[3,3':6',4"-terpyridin]-6-amine According to the procedure described in Step 2 of Example 27, using (R)-tert-butyl 6-amino-5-(1-(2,6-dichloro-3-fluorophenyl)ethoxy)-5'-methoxy-5'',6''-dihydro-[3,3':6',4''-terpyridine]-1''(2''H)-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (41% yield). MS m/z [ESI]: 489.1 [M+1]. $^1$H-NMR (400 MHz, CDCl$_3$): δ=8.21 (1H, s), 7.84 (1H, s), 7.28-7.32 (1H, m), 7.04-7.08 (2H, m), 6.93 (1H, s), 6.52 (1H, s), 6.10 (1H, q, J=6.4 Hz), 5.21 (2H, s), 3.86 (3H, s), 3.74 (2H, s), 3.28 (2H, t, J=4.2 Hz), 2.77 (2H, t, J=4.2 Hz), 1.87 (3H, d, J=6.8 Hz).

Example 31: 5-(1-(2-(1,1-difluoroethyl)-5-fluorophenyl)ethoxy)-4'-methoxy-6'-(4-(4-methylpiperazin-1-yl)piperidin-1-yl)-[3,3'-bipyridin]-6-amine General Synthetic Methods:

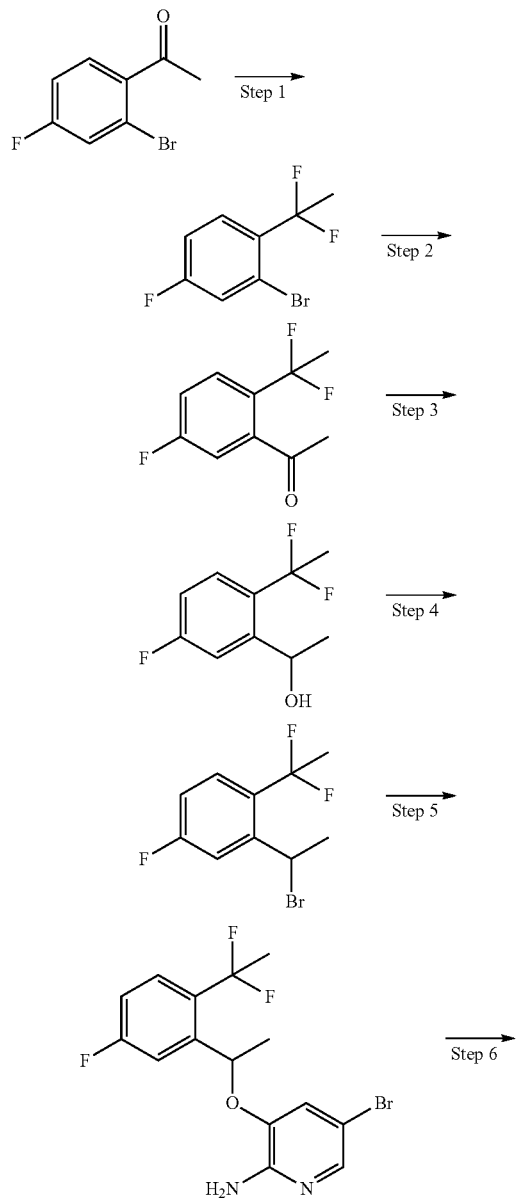

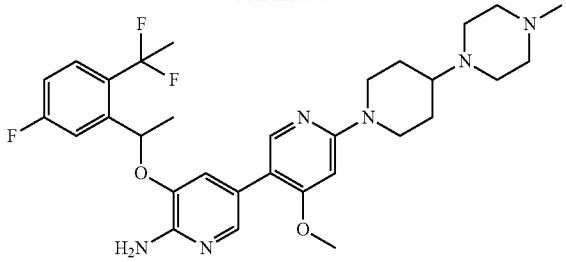

Step 1: 2-bromo-1-(1,1-difluoroethyl)-4-fluorobenzene 1-(2-Bromo-4-fluorophenyl)ethanone (3.5 g, 16 mmol) and DAST (20 mL) were added into a sealed tube, and the mixture was reacted at 60° C. overnight. After the resultant was cooled, it was carefully poured onto crushed ice and extracted by n-pentane. The extract was dried and purified by silica gel column chromatography to give the title compound (2.3 g, 60% yield).

Step 2: 1-(2-(1,1-difluoroethyl)-5-fluorophenyl)ethanone

2-Bromo-1-(1,1-difluoroethyl)-4-fluorobenzene (717 mg, 3 mmol), n-Butyl vinyl ether (3.0 g, 30 mmol), Pd(OAc)$_2$ (67 mg, 0.3 mmol), 1,3-bis(diphenylphosphino)propane (DPPP) (248 mg, 0.6 mmol), triethylamine (909 mg, 9 mmol), and DMF (10 mL) were added into a sealed tube, purged with nitrogen, and the mixture was reacted at 120° C. overnight. After the resultant was cooled, it was poured into 10% hydrochloric acid, stirred for 1 hour, neutralized by saturated NaHCO$_3$, and extracted with CH$_2$Cl$_2$. The extract was separated by silica gel column chromatography to give the title compound (33% yield).

Step 3: 1-(2-(1,1-difluoroethyl)-5-fluorophenyl)ethanol

According to the procedure described in Step 4 of Intermediate 40, using 1-(2-(1,1-difluoroethyl)-5-fluorophenyl)ethanone instead of 2-(dimethylamino)-4-chloro-5-(fluorophenyl)ethanone, the title compound was obtained (30% yield).

Step 4: 2-(1-bromoethyl)-1-(1,1-difluoroethyl)-4-fluorobenzene

According to the procedure described in Step 5 of Intermediate 40, using 1-(2-(1,1-difluoroethyl)-5-fluorophenyl)ethanol instead of 2-(dimethylamino)-4-chloro-5-(fluorophenyl)ethanol, the title compound was obtained (50% yield).

Step 5: 5-bromo-3-(1-(2-(1,1-difluoroethyl)-5-fluorophenyl)ethoxy)pyridin-2-amine According to the procedure described in Step 6 of Intermediate 40, using 2-(1-bromoethyl)-1-(1,1-difluoroethyl)-4-fluorobenzene instead of 2-(1-bromoethyl)-5-chloro-4-fluoro-N,N-dimethylaniline, the title compound was obtained (41% yield). MS m/z [ESI]: 375.0 [M+1].

Step 6: 5-(1-(2-(1,1-difluoroethyl)-5-fluorophenyl)ethoxy)-4'-methoxy-6'-(4-(4-methylpiperazin-1-yl)piperidin-1-yl)-[3,3'-bipyridin]-6-amine According to the procedure described in Step 1 of Example 27, using 5-bromo-3-(1-(2-(1,1-difluoroethyl)-5-fluorophenyl)ethoxy)pyridin-2-amine instead of (S)-tert-butyl 4-(5-bromo-4-methoxypyridin-2-yl)-3-methylpiperazine-1-carboxylate, using 1-(1-(4-methoxyl-5-(4,4,5,5-tetramethyl-1,3,2-dioxaborolan-2-yl)pyridin-2-yl)piperidin-4-yl)-4-methylpiperazine instead of (R)-3-(1-(2,6-dichloro-3-fluorophenyl)ethoxy)-5-(4,4,5,5-tetramethyl-1,3,2-dioxaborolan-2-yl)pyridin-2-amine, the title compound was obtained (32% yield). MS m/z [ESI]: 585.3 [M+1]. ¹H-NMR (400 MHz, CDCl₃): δ=7.59-7.65 (2H, m), 7.12-7.18 (2H, m), 6.98 (1H, d, J=7.6 Hz), 6.47 (1H, d, J=6.4 Hz), 6.42 (1H, s), 5.86 (2H, s), 5.36 (1H, q, J=6.8 Hz), 3.72-3.79 (2H, m), 3.64 (3H, s), 2.95-3.08 (4H, m), 2.75 (2H, t, J=12.4 Hz), 2.56-2.68 (4H, m), 2.22 (1H, m), 2.07 (3H, s), 2.027 (3H, t, J=18.8 Hz), 1.93-1.83 (4H, m), 1.67 (3H, d, J=6.0 Hz).

Example 32: (R)-5'-(1-(2,6-dichloro-3-fluorophenyl)ethoxy)-5-methoxy-6-(piperazin-1-yl)-[2,3'-bipyridin]-6'-amine Step 1: (R)-tert-butyl 4-(6'-amino-5'-(1-(2,6-dichloro-3-fluorophenyl)ethoxy)-5-methoxy-[2,3'-bipyridin]-6-yl)piperazine-1-carboxylate According to the procedure described in Step 1 of Example 27, using tert-butyl 4-(6-bromo-3-methoxypyridin-2-yl)piperazine-1-carboxylate instead of (S)-tert-butyl 4-(5-bromo-4-methoxypyridin-2-yl)-3-methylpiperazine-1-carboxylate, the title compound was obtained (53% yield). MS m/z [ESI]: 592.2 [M+1].

Step 2: (R)-5'-(1-(2,6-dichloro-3-fluorophenyl)ethoxy)-5-methoxy-6-(piperazin-1-yl)-[2,3'-bipyridin]-6'-amine According to the procedure described in Step 2 of Example 27, using (R)-tert-butyl 4-(6'-amino-5'-(1-(2,6-dichloro-3-fluorophenyl)ethoxy)-5-methoxy-[2,3'-bipyridin]-6-yl) piperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (65% yield). MS m/z [ESI]: 492.1 [M+1]. ¹H-NMR (400 MHz, CDCl₃): δ=8.09 (1H, s), 7.57-7.62 (1H, m), 7.43 (1H, t, J=8.0 Hz), 7.22-7.30 (2H, m), 7.16 (1H, s), 6.01 (1H, q, J=6.4 Hz), 5.90 (2H, s), 3.78 (3H, s), 3.40-3.42 (4H, m), 3.05-3.17 (4H, m), 1.77 (3H, d, J=6.4 Hz).

Example 33: 5-(1-(2-chloro-5-fluorophenyl)-2,2,2-trifluoroethoxy)-5'-(piperazin-1-yl)-[3,3'-bipyridin]-6-amine General Synthetic Methods:

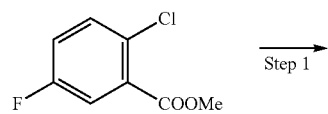

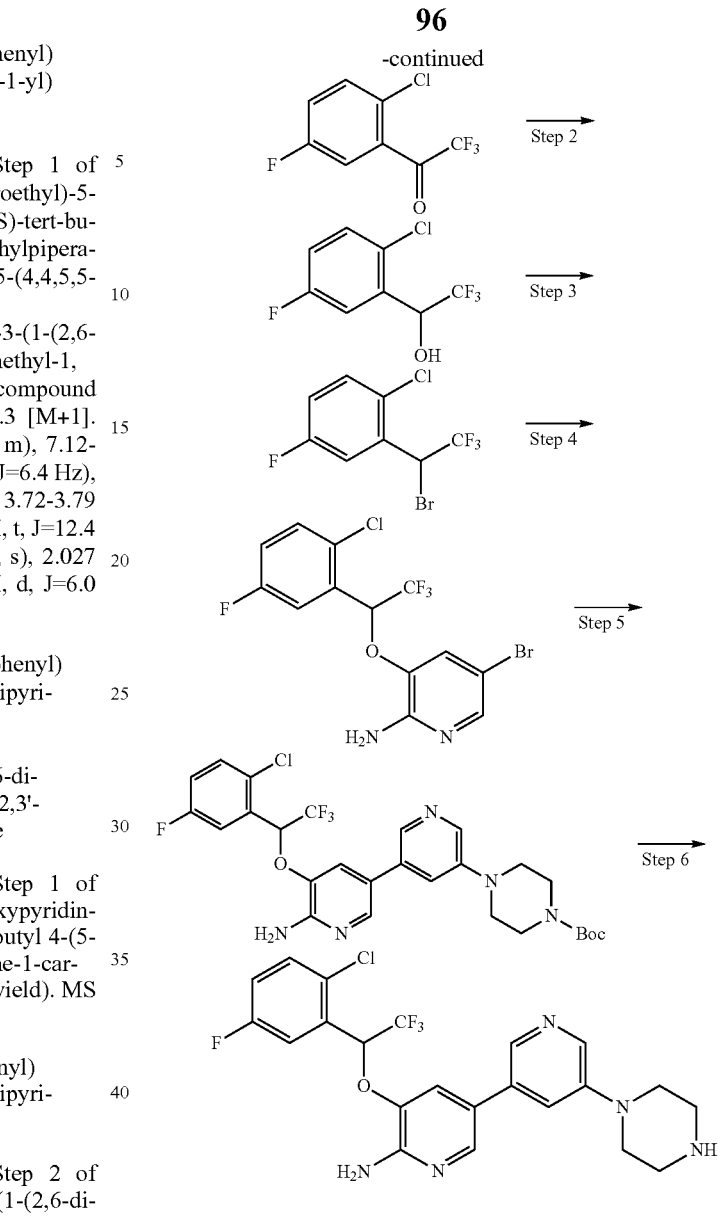

Step 1: 1-(2-chloro-5-fluorophenyl)-2,2,2-trifluoroethanone

A mixture of methyl 2-chloro-5-fluorobenzoate (18.8 g, 0.1 mol), (trifluoromethyl)trimethylsilane (15.6 g, 0.11 mol), and CsF (2.0 g, 0.013 mmol) was stirred at room temperature for 30 minutes under a nitrogen atmosphere. 5 M hydrochloric acid (50 mL) was then added and the resultant was stirred overnight. Dimethoxyethane (50 mL) was added and the resultant was stirred at 120° C. overnight. After the resultant was cooled, it was neutralized by NaOH and extracted with CH₂Cl₂. The extract was dried and purified by silica gel column chromatography to give the title compound (3.5 g, 15% yield).

Step 2: 1-(2-chloro-5-fluorophenyl)-2,2,2-trifluoroethanol

According to the procedure described in Step 4 of Intermediate 40, using 1-(2-chloro-5-fluorophenyl)-2,2,2-trifluoroethanone instead of 2-(dimethylamino)-4-chloro-5-(fluorophenyl)ethanone, the title compound was obtained (85% yield).

Step 3: 2-(1-bromo-2,2,2-trifluoroethyl)-1-chloro-4-fluorobenzene 1-(2-Chloro-5-fluorophenyl)-2,2,2-trifluoroethanol (2.0 g, 8.75 mmol) and PBr$_5$ (5.0 g, 11.6 mmol) were added into a sealed tube, and the mixture was reacted at 140° C. overnight. After crushed ice was added, the mixture was neutralized by NaOH and extracted with CH$_2$Cl$_2$. The extract was dried and purified by silica gel column chromatography to give the title compound (33% yield).

Step 4: 5-bromo-3-(1-(2-chloro-5-fluorophenyl)-2,2,2-trifluoroethoxy)pyridin-2-amine According to the procedure described in Step 6 of Intermediate 40, using 2-(1-bromo-2,2,2-trifluoroethyl)-1-chloro-4-fluorobenzene instead of 2-(1-bromoethyl)-5-chloro-4-fluoro-N,N-dimethylaniline, the title compound was obtained (27% yield). MS m/z [ESI]: 400.9[M+1].

Step 5: tert-butyl 4-(6'-amino-5'-(1-(2-chloro-5-fluorophenyl)-2,2,2-trifluoroethoxy)-[3,3'-bipyridin]-5-yl)piperazine-1-carboxylate According to the procedure described in Step 2 Example 27, using 5-bromo-3-(1-(2-chloro-5-fluorophenyl)-2,2,2-trifluoroethoxy)pyridin-2-amine instead of (S)-tert-butyl 4-(5-bromo-4-methoxypyridin-2-yl)-3-methylpiperazine-1-carboxylate, and using tert-butyl 4-(5-(4,4,5,5-tetramethyl-1,3,2-dioxaborolan-2-yl)pyridin-3-yl) piperazine-1-carboxylate instead of (R)-3-(1-(2,6-dichloro-3-fluorophenyl)ethoxy)-5-(4,4,5,5-tetramethyl-1,3,2-dioxaborolan-2-yl)pyridin-2-amine, the title compound was obtained (41% yield). MS m/z [ESI]: 582.2 [M+1].

Step 6: 5-(1-(2-chloro-5-fluorophenyl)-2,2,2-trifluoroethoxy)-5'-(piperazin-1-yl)-[3,3'-bipyridin]-6-amine According to the procedure described in Step 2 of Example 27, using tert-butyl 4-(6'-amino-5'-(1-(2-chloro-5-fluorophenyl)-2,2,2-trifluoroethoxy)-[3,3'-bipyridin]-5-yl) piperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (32% yield). MS m/z [ESI]: 482.1 [M+1]. $^1$H-NMR (400 MHz, CDCl$_3$): δ=8.07 (1H, s), 7.97 (1H, s), 7.80 (1H, s), 7.40-7.50 (2H, m), 7.27 (1H, s), 7.15 (1H, s) 7.07 (1H, s), 6.43 (1H, m), 3.20 (4H, m), 3.06 (4H, m).

Example 34: (R)-5'-(1-(2,6-dichloro-3-fluorophenyl)ethoxy)-3-methoxy-6-(piperazin-1-yl)-[2,3'-bipyridin]-6'-amine

Step 1: (R)-tert-butyl 4-(6'-amino-5'-(1-(2,6-dichloro-3-fluorophenyl)ethoxy)-3-methoxy-[2,3'-bipyridin]-6-yl)piperazine-1-carboxylate According to the procedure described in Step 1 of Example 27, using tert-butyl 4-(6-bromo-5-methoxypyridin-2-yl)piperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 592.2 [M+1].

Step 2: (R)-5'-(1-(2,6-dichloro-3-fluorophenyl)ethoxy)-3-methoxy-6-(piperazin-1-yl)-[2,3'-bipyridin]-6'-amine According to the procedure described in Step 2 of Example 27, using (R)-tert-butyl 4-(6'-amino-5'-(1-(2,6-dichloro-3-fluorophenyl)ethoxy)-3-methoxy-[2,3'-bipyridin]-6-yl) piperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 492.1 [M+1]. $^1$H-NMR (400 MHz, CDCl$_3$): δ=8.20 (1H, s), 7.54-7.58 (1H, m), 7.45 (1H, t, J=8.8 Hz), 7.41 (1H, d, J=9.2 Hz), 7.22 (1H, s), 6.77 (1H, d, J=9.2 Hz), 6.04 (2H, s), 5.98 (1H, q, J=6.6 Hz), 3.66 (3H, s), 3.53-3.58 (4H, m), 3.14-3.17 (4H, m), 1.76 (3H, d, J=6.4 Hz).

Example 35: (R)-4-(6'-amino-5'-(1-(2,6-dichloro-3-fluorophenyl)ethoxy)-4-methoxy-[3,3'-bipyridin]-6-yl)piperazin-2-one According to the procedure described in Step 1 of Example 27, using 4-(5-bromo-4-methoxypyridin-2-yl)piperazin-2-one instead of (S)-tert-butyl 4-(5-bromo-4-methoxypyridin-2-yl)-3-methylpiperazine-1-carboxylate, the title compound was obtained (46% yield). MS m/z [ESI]: 506.1 [M+1]. $^1$H-NMR (400 MHz, CDCl$_3$): δ=7.16 (1H, s), 7.59 (1H, s), 7.46 (1H, dd, J=9.2 Hz, 4.8 Hz), 7.26 (1H, t, J=8.4 Hz), 6.93 (1H, s), 6.32 (1H, s), 6.10 (1H, q, J=6.8 Hz), 4.14 (2H, s), 3.81 (2H, t, J=5.2 Hz), 3.77 (3H, s), 3.45 (2H, t, J=5.6 Hz), 1.85 (3H, d, J=6.4 Hz).

Example 36: (R)-5'-(1-(2,6-dichloro-3-fluorophenyl)ethoxy)-4-methoxy-6-(piperazin-1-yl)-[2,3'-bipyridin]-6'-amine

Step 1: (R)-tert-butyl 4-(6'-amino-5'-(1-(2,6-dichloro-3-fluorophenyl)ethoxy)-4-methoxy-[2,3'-bipyridin]-6-yl)piperazine-1-carboxylate According to the procedure described in Step 1 of Example 27, using tert-butyl 4-(6-chloro-4-methoxypyridin-2-yl)piperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 592.2 [M+1].

Step 2: (R)-5'-(1-(2,6-dichloro-3-fluorophenyl)ethoxy)-4-methoxy-6-(piperazin-1-yl)-[2,3'-bipyridin]-6'-amine According to the procedure described in Step 2 of Example 27, using (R)-tert-butyl 4-(6'-amino-5'-(1-(2,6-dichloro-3-fluorophenyl)ethoxy)-4-methoxy-[2,3'-bipyridin]-6-yl) piperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 492.1 [M+1]. $^1$H-NMR (400 MHz, CDCl$_3$): δ=8.15 (s, 1H), 7.87 (s, 1H), 7.46 (dd, J=9.4, 4.6 Hz, 1H), 7.25 (t, J=8.5 Hz, 1H), 6.62 (d, J=1.6 Hz, 1H), 6.29

(d, J=1.6 Hz, 1H), 6.17 (q, J=6.3 Hz, 1H), 3.86 (s, 3H), 3.82 (m, 4H), 3.29 (m, 4H), 1.88 (d, J=6.6 Hz, 3H).

Example 37: (R)-5-(1-(2,6-dichloro-3-fluorophenyl) ethoxy)-4'-methoxy-6'-(piperazin-1-yl)-[3,3'-bipyridin]-6-amine Step 1: (R)-tert-butyl 4-(6'-amino-5'-(1-(2,6-dichloro-3-fluorophenyl)ethoxy)-4-methoxy-[3,3'-bipyridin]-6-yl)piperazine-1-carboxylate According to the procedure described in Step 1 of Example 27, using tert-butyl 4-(5-bromo-4-methoxypyridin-2-yl)piperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 592.2 [M+1].

Step 2: (R)-5'-(1-(2,6-dichloro-3-fluorophenyl) ethoxy)-4-methoxy-6-(piperazin-1-yl)-[2,3'-bipyridin]-6'-amine According to the procedure described in Step 2 of Example 27, using (R)-tert-butyl 4-(6'-amino-5'-(1-(2,6-dichloro-3-fluorophenyl)ethoxy)-4-methoxy-[3,3'-bipyridin]-6-yl) piperazine-1-carboxylate instead of (S)-tert-butyl 4-(6'-amino-5'-((R)-1-(2,6-dichloro-3-fluorophenyl) ethoxy)-4-methoxy-[3,3'-bipyridin]-6-yl)-3-methylpiperazine-1-carboxylate, the title compound was obtained (67% yield). MS m/z [ESI]: 492.1 [M+1]. $^1$H-NMR (400 MHz, CDCl$_3$): δ=7.91 (1H, s), 7.68 (1H, s), 7.26-7.30 (1H, m), 7.05 (1H, t, J=8.4 Hz), 6.94 (1H, s), 6.12 (1H, s), 6.04 (1H, q, J=6.8 Hz), 4.9 (2H, s), 3.66-3.75 (7H, m), 3.11-3.18 (4H, m), 1.83 (3H, d, J=6.8 Hz).

Example 38: (R)-5-(1-(2,6-dichloro-3-fluorophenyl) ethoxy)-5'-methoxy-2'-(piperazin-1-yl)-[3,4'-bipyridin]-6-amine Step 1: (R)-tert-butyl 4-(6-amino-5-(1-(2,6-dichloro-3-fluorophenyl)ethoxy)-5'-methoxy-[3,4'-bipyridin]-2'-yl)piperazine-1-carboxylate According to the procedure described in Step 1 of Example 27, using tert-butyl 4-(4-bromo-5-methoxypyridin-2-yl)piperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 592.2 [M+1].

Step 2: (R)-5-(1-(2,6-dichloro-3-fluorophenyl) ethoxy)-5'-methoxy-2'-(piperazin-1-yl)-[3,4'-bipyridin]-6-amine According to the procedure described in Step 2 of Example 27, using (R)-tert-butyl 4-(6-amino-5-(1-(2,6-dichloro-3-fluorophenyl)ethoxy)-5'-methoxy-[3,4'-bipyridin]-2'-yl) piperazine-1-carboxylate instead of (S)-tert-butyl 4-(6'-amino-5'-((R)-1-(2,6-dichloro-3-fluorophenyl) ethoxy)-4-methoxy-[3,3'-bipyridin]-6-yl)-3-methylpiperazine-1-carboxylate, the title compound was obtained (67% yield). MS m/z [ESI]: 492.1 [M+1]. $^1$H-NMR (400 MHz, CDCl$_3$): δ=7.89 (1H, s), 7.85 (1H, s), 7.30 (1H, dd, J=8.8 Hz, 4.8 Hz), 7.08 (1H, t, J=8.0 Hz), 7.01 (1H, s), 6.51 (1H, s), 6.05 (1H, q, J=6.8 Hz), 5.13 (2H, s), 3.72-3.80 (4H, m), 3.70 (3H, s), 3.25-3.31 (4H, m), 1.84 (3H, d, J=6.4 Hz).

Example 39: (R)-5'-(1-(2,6-dichloro-3-fluorophenyl) ethoxy)-5-methoxy-4-(piperazin-1-yl)-[2,3'-bipyridin]-6'-amine Step 1: (R)-tert-butyl 4-(6'-amino-5'-(1-(2,6-dichloro-3-fluorophenyl)ethoxy)-5-methoxy-[2,3'-bipyridin]-4-yl)piperazine-1-carboxylate According to the procedure described in Step 1 of Example 27, using tert-butyl 4-(2-bromo-5-methoxypyridin-4-yl)piperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 592.2 [M+1].

Step 2: (R)-5'-(1-(2,6-dichloro-3-fluorophenyl) ethoxy)-5-methoxy-4-(piperazin-1-yl)-[2,3'-bipyridin]-6'-amine According to the procedure described in Step 2 of Example 27, using (R)-tert-butyl 4-(6'-amino-5'-(1-(2,6-dichloro-3-fluorophenyl)ethoxy)-5-methoxy-[2,3'-bipyridin]-4-yl) piperazine-1-carboxylate instead of (S)-tert-butyl 4-(6'-amino-5'-((R)-1-(2,6-dichloro-3-fluorophenyl) ethoxy)-4-methoxy-[3,3'-bipyridin]-6-yl)-3-methylpiperazine-1-carboxylate, the title compound was obtained (67% yield). MS m/z [ESI]: 492.1 [M+1]. $^1$H-NMR (400 MHz, CDCl$_3$): δ=8.18 (1H, s), 8.11 (1H, s), 7.35 (1H, s), 7.30-7.32 (1H, m), 7.06 (1H, t, J=8.4 Hz), 6.88 (1H, s), 6.15 (1H, q, J=6.8 Hz), 5.04-5.20 (2H, brs), 3.93 (3H, s), 3.41-3.48 (4H, m), 3.28-3.32 (4H, m), 1.85 (3H, d, J=6.4 Hz).

Example 40: 3-(1-(2-(difluoromethyl)-5-fluorophenyl)ethoxy)-5-(2-methoxy-4-(piperazin-1-yl)phenyl) pyridin-2-amine Step 1: tert-butyl 4-(4-(6-amino-5-(1-(2-(difluoromethyl)-5-fluorophenyl)ethoxy)pyridin-3-yl)-3-methoxyphenyl)piperazine-1-carboxylate According to the procedure described in Step 1 of Example 27, using tert-butyl 4-(3-methoxy-4-(4,4,5,5-tetramethyl-1,3,2-dioxaborolan-2-yl)phenyl) piperazine-1-carboxylate instead of (R)-3-(1-(2,6-dichloro-3-fluorophenyl)ethoxy)-5-(4,4,5,5-tetramethyl-1,3,2-dioxaborolan-2-yl)pyridin-2-amine, and using 5-bromo-3-(1-(2-(difluoromethyl)-5-fluorophenyl)ethoxy)pyridin-2-amine instead of (S)-tert-butyl 4-(5-bromo-4-methoxypyridin-2-yl)-3-methylpiperazine-1-carboxylate, the title compound was obtained (46% yield). MS m/z [ESI]: 573.3 [M+1].

Step 2: 3-(1-(2-(difluoromethyl)-5-fluorophenyl) ethoxy)-5-(2-methoxy-4-(piperazin-1-yl)phenyl) pyridin-2-amine According to the procedure described in Step 2 of Example 27, using tert-butyl 4-(4-(6-amino-5-(1-(2-(difluoromethyl)-5-fluorophenyl)ethoxy)pyridin-3-yl)-3-methoxyphenyl)piperazine-1-carboxylate instead of (S)-tert-butyl 4-(6'-amino-5'-((R)-1-(2,6-dichloro-3-fluorophenyl) ethoxy)-4-methoxy-[3,3'-bipyridin]-6-yl)-3-methylpiperazine-1-carboxylate, the title compound was obtained (67% yield). MS m/z [ESI]: 473.2 [M+1]. $^1$H-NMR (400 MHz, CDCl$_3$): δ=7.68 (1H, s), 7.56 (1H, dd, J=8.8 Hz, 5.2 Hz), 7.21-7.23 (1H, m), 7.16 (1H, t, J=9.6 Hz), 7.03 (1H, d, J=8.0 Hz), 6.99 (1H, s), 6.81 (1H, t, J=54.8 Hz), 6.48 (1H, dd, J=8.4 Hz, 1.6 HZ), 6.42 (1H, d, J=2.0 Hz), 5.64 (1H, q, J=6.4

Hz), 5.08 (2H, s), 3.61 (3H, s), 3.43-3.46 (4H, m), 3.32-3.35 (4H, m), 1.67 (3H, d, J=6.4 Hz).

Example 41: 5-(5-chloro-2-methoxy-4-(piperazin-1-yl)phenyl)-3-(1-(2-(difluoromethyl)-5-fluorophenyl)ethoxy)pyridin-2-amine According to the procedure described in Example 40, column chromatography separation resulted the title compound 41 (7% yield). MS m/z [ESI]: 507.2 [M+1]. $^1$H-NMR (400 MHz, CDCl$_3$): δ=7.72 (1H, s), 7.60 (1H, dd, J=8.4 Hz, 5.6 Hz), 7.26 (1H, d, J=8.8 Hz), 7.20 (1H, t, J=8.4 Hz), 7.17 (1H, s), 6.98 (1H, s), 6.84 (1H, t, J=52.0 Hz), 6.59 (1H, s), 5.68 (1H, q, J=6.4 Hz), 5.08 (2H, s), 3.65 (3H, s), 3.30-3.50 (8H, m), 1.72 (3H, d, J=6.4 Hz).

Example 42: (R)-5-(1-(2,6-dichloro-3-fluorophenyl)ethoxy)-5'-methoxy-6'-(piperidin-4-yl)-[3,3'-bipyridin]-6-amine The product of example 30, that is, (R)-5-(1-(2,6-dichloro-3-fluorophenyl)ethoxy)-5'-methoxy-1",2",3",6"-tetrahydro-[3,3':6',4"-terpyridin]-6-amine (98 mg, 0.2 mmol) and Pd/C (10 mg) were added in methanol (20 mL), and the mixture was reacted for 6 hours under a hydrogen atmosphere and then filtered. The filtrate was concentrated and purified by silica gel column chromatography to give the title compound (12 mg, 12% yield). MS m/z [ESI]: 491.1 [M+1]. $^1$H-NMR (400 MHz, CDCl$_3$): δ=8.00 (d, J=1.8 Hz, 1H), 7.70 (d, J=1.7 Hz, 1H), 7.37 (dd, J=9.0, 4.9 Hz, 1H), 7.18 (s, 1H), 7.14 (d, J=8.5 Hz, 1H), 6.90 (d, J=1.7 Hz, 1H), 6.14 (q, J=6.5 Hz, 1H), 4.46 (m, 1H), 3.83 (s, 3H), 3.41 (m, 2H), 3.11-2.99 (m, 2H), 1.95 (dd, J=9.6, 3.6 Hz, 4H), 1.81 (d, J=6.7 Hz, 3H).

Example 43: (R)-5-(1-(2,6-dichloro-3-fluorophenyl)ethoxy)-5'-methoxy-1",2",3",6"-tetrahydro-[3,2':6',4"-terpyridin]-6-amine Step 1: (R)-tert-butyl 6-amino-5-(1-(2,6-dichloro-3-fluorophenyl)ethoxy)-5'-methoxy-5",6"-dihydro-[3,2':6',4"-terpyridine]-1"(2"H)-carboxylate According to the procedure described in Step 1 of Example 27, using tert-butyl 4-(6-bromo-3-methoxypyridin-2-yl)-5,6-dihydropyridin-1 (2H)-carboxylate instead of (S)-tert-butyl 4-(5-bromo-4-methoxypyridin-2-yl)-3-methylpiperazine-1-carboxylate, the title compound was obtained (46% yield). MS m/z [ESI]: 589.2 [M+1].

Step 2: (R)-5-(1-(2,6-dichloro-3-fluorophenyl)ethoxy)-5'-methoxy-1",2",3",6"-tetrahydro-[3,2':6',4"-terpyridin]-6-amine According to the procedure described in Step 2 of Example 27, using (R)-tert-butyl 6-amino-5-(1-(2,6-dichloro-3-fluorophenyl)ethoxy)-5'-methoxy-5",6"-dihydro-[3,2':6',4"-terpyridine]-1"(2"H)-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 489.1 [M+1]. $^1$H-NMR (400 MHz, CDCl$_3$): δ=8.09 (1H, s), 7.40-7.42 (2H, m), 7.28-7.30 (1H, s), 7.13 (1H, d, J=8.8 Hz), 7.00 (1H, t, J=8.8 Hz), 6.73 (1H, s), 6.10 (1H, q, J=6.8 Hz), 5.16 (2H, s), 3.99 (2H, t, J=5.6 Hz), 3.84 (2H, m), 3.52 (2H, t, J=5.6 Hz), 3.49 (3H, s), 1.83 (3H, d, J=6.8 Hz)/

Example 44: 5'-((R)-1-(2,6-dichloro-3-fluorophenyl)ethoxy)-3-methoxy-6-((S)-2-methylpiperazin-1-yl)-[2,3'-bipyridin]-6'-amine Step 1: (S)-tert-butyl 4-(6'-amino-5'-((R)-1-(2,6-dichloro-3-fluorophenyl)ethoxy)-3-methoxy-[2,3'-bipyridin]-6-yl)-3-methylpiperazine-1-carboxylate According to the procedure described in Step 1 of Example 27, using (S)-tert-butyl 4-(6-bromo-5-methoxypyridin-2-yl)-3-methylpiperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 606.2 [M+1].

Step 2: 5'-((R)-1-(2,6-dichloro-3-fluorophenyl)ethoxy)-3-methoxy-6-((S)-2-methylpiperazin-1-yl)-[2,3'-bipyridin]-6'-amine According to the procedure described in Step 2 of Example 27, using (S)-tert-butyl 4-(6'-amino-5'-((R)-1-(2,6-dichloro-3-fluorophenyl)ethoxy)-3-methoxy-[2,3'-bipyridin]-6-yl)-3-methylpiperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 506.1 [M+1]. $^1$H-NMR (400 MHz, CDCl$_3$): δ=8.38 (d, J=1.4 Hz, 1H), 7.45 (d, J=1.5 Hz, 1H), 7.30 (dd, J=8.9, 4.8 Hz, 1H), 7.21 (d, J=9.0 Hz, 1H), 7.11-7.01 (m, 1H), 6.53 (d, J=9.0 Hz, 1H), 6.08 (d, J=6.7 Hz, 1H), 5.23 (s, 2H), 4.62 (m, 1H), 4.03 (d, J=14.0 Hz, 1H), 3.73 (s, 3H), 3.59 (d, J=12.3 Hz, 1H), 3.45-3.29 (m, 3H), 3.11 (m, 1H), 1.82 (d, J=6.7 Hz, 3H), 1.38 (d, J=6.9 Hz, 3H).

Example 45: (R)-5-(1-(2,6-dichloro-3-fluorophenyl)ethoxy)-4'-methoxy-5'-(piperazin-1-yl)-[3,3'-bipyridin]-6-amine Step 1: (R)-tert-butyl 4-(6'-amino-5'-(1-(2,6-dichloro-3-fluorophenyl)ethoxy)-4-methoxy-[3,3'-bipyridin]-5-yl)piperazine-1-carboxylate According to the procedure described in Step 1 of Example 27, using tert-butyl 4-(5-bromo-4-methoxypyridin-3-yl)piperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 592.2 [M+1].

Step 2: (R)-5-(1-(2,6-dichloro-3-fluorophenyl)ethoxy)-4'-methoxy-5'-(piperazin-1-yl)-[3,3'-bipyridin]-6-amine According to the procedure described in Step 2 of Example 27, using (R)-tert-butyl 4-(6'-amino-5'-(1-(2,6-dichloro-3-fluorophenyl)ethoxy)-4-methoxy-[3,3'-bipyridin]-5-yl) piperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 492.1 [M+1]. $^1$H-NMR (400 MHz, CDCl$_3$): δ=8.13 (s, 1H), 8.10 (s, 1H), 7.75 (s, 1H), 7.29 (d, J=5.0 Hz, 1H), 7.07 (t, J=8.4 Hz, 1H), 6.96 (s, 1H), 6.04 (q, J=6.8 Hz, 1H), 4.89 (s, 2H), 3.43 (s, 3H), 3.21 (d, J=7.3 Hz, 2H), 3.07 (m, 6H), 1.85 (d, J=6.7 Hz, 3H).

Example 46: 3-(1-(2-(1,1-difluoroethyl)-5-fluorophenyl)ethoxy)-5-(2-methoxy-4-(piperazin-1-yl)phenyl)pyridin-2-amine

Step 1: tert-butyl 4-(4-(6-amino-5-(1-(2-(1,1-difluoroethyl)-5-fluorophenyl)ethoxy)pyridin-3-yl)-3-methoxyphenyl)piperazine-1-carboxylate According to the procedure described in Step 1 of Example 27, using 5-bromo-3-(1-(2-(difluoroethyl)-5-fluorophenyl)ethoxy)pyridin-2-amine instead of (S)-tert-butyl 4-(5-bromo-4-methoxypyridin-2-yl)-3-methylpiperazine-1-carboxylate, and using tert-butyl 4-(3-methoxy-4-(4,4,5,5-tetramethyl-1,3,2-dioxaborolan-2-yl)phenyl) piperazine-1-carboxylate instead of (R)-3-(1-(2,6-dichloro-3-fluorophenyl)ethoxy)-5-(4,4,5,5-tetramethyl-1,3,2-dioxaborolan-2-yl)pyridin-2-amine, the title compound was obtained (46% yield). MS m/z [ESI]: 587.3 [M+1].

Step 2: 3-(1-(2-(1,1-difluoroethyl)-5-fluorophenyl)ethoxy)-5-(2-methoxy-4-(piperazin-1-yl)phenyl)pyridin-2-amine According to the procedure described in Step 2 of Example 27, using tert-butyl 4-(4-(6-amino-5-(1-(2-(1,1-difluoroethyl)-5-fluorophenyl)ethoxy)pyridin-3-yl)-3-methoxyphenyl)piperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 487.2 [M+1]. $^1$H-NMR (400 MHz, CDCl$_3$): δ=7.63 (t, J=9.0 Hz, 2H), 7.54 (s, 1H), 7.23 (t, J=8.2 Hz, 1H), 6.99 (d, J=4.3 Hz, 2H), 6.57 (s, 1H), 6.52 (d, J=8.4 Hz, 1H), 5.86 (s, 2H), 5.81 (d, J=5.7 Hz, 1H), 3.60 (s, 3H), 3.17 (s, 4H), 3.12 (s, 4H), 2.08 (t, J=19.6 Hz, 3H), 1.61 (d, J=6.1 Hz, 3H).

Example 47: (R)-5-(1-(2,6-dichloro-3-fluorophenyl)ethoxy)-4'-methoxy-6'-morpholino-[3,3'-bipyridin]-6-amine According to the procedure described in Step 1 of Example 27, using 4-(5-bromo-4-methoxypyridin-2-yl)morpholino instead of (S)-tert-butyl 4-(5-bromo-4-methoxypyridin-2-yl)-3-methylpiperazine-1-carboxylate, the title compound was obtained (46% yield). MS m/z [ESI]: 493.1 [M+1]. $^1$H-NMR (400 MHz, CDCl$_3$): δ=7.93 (s, 1H), 7.70 (s, 1H), 7.31-7.26 (m, 1H), 7.05 (t, J=8.4 Hz, 1H), 6.95 (s, 1H), 6.10 (s, 1H), 6.04 (q, J=6.7 Hz, 1H), 4.94 (s, 2H), 3.86-3.81 (m, 4H), 3.75 (s, 3H), 3.56-3.50 (m, 4H), 1.83 (d, J=6.7 Hz, 3H).

Example 48: 5'-((R)-1-(2,6-dichloro-3-fluorophenyl)ethoxy)-5-methoxy-6-((S)-2-methylpiperazin-1-yl)-[2,3'-bipyridin]-6'-amine

Step 1: (S)-tert-butyl 4-(6'-amino-5'-((R)-1-(2,6-dichloro-3-fluorophenyl)ethoxy)-5-methoxy-[2,3'-bipyridin]-6-yl)-3-methylpiperazine-1-carboxylate According to the procedure described in Step 1 of Example 27, using (S)-tert-butyl 4-(6-bromo-3-methoxypyridin-2-yl)-3-methylpiperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 606.2 [M+1].

Step 2: 5'-((R)-1-(2,6-dichloro-3-fluorophenyl)ethoxy)-5-methoxy-6-((S)-2-methylpiperazin-1-yl)-[2,3'-bipyridin]-6'-amine According to the procedure described in Step 2 of Example 27, using (S)-tert-butyl 4-(6'-amino-5'-((R)-1-(2,6-dichloro-3-fluorophenyl)ethoxy)-5-methoxy-[2,3'-bipyridin]-6-yl)-3-methylpiperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 506.1 [M+1]. $^1$H-NMR (400 MHz, CDCl$_3$): δ=8.13 (1H, s), 7.73 (1H, m), 7.55 (1H, m), 7.32 (1H, s), 7.20-7.09 (2H, m), 6.12 (1H, d, J=6.6 Hz), 5.21 (2H, s), 4.54 (1H, m), 3.86 (3H, s), 3.77 (1H, m), 3.67 (1H, m), 3.51 (2H, m), 3.43 (1H, d, J=9.3 Hz), 3.24 (3H, d, J=11.9 Hz), 1.87 (3H, d, J=6.6 Hz), 1.38 (3H, d, J=6.9 Hz).

Example 49: 5-(5-chloro-2-methoxy-4-(piperazin-1-yl)phenyl)-3-(1-(2-(1,1-difluoroethyl)-5-fluorophenyl)ethoxy)pyridin-2-amine According to the procedure described in Example 46, purification and separation by silica gel column chromatography resulted the title compound 49 (67% yield). MS m/z [ESI]: 521.2 [M+1]. $^1$H-NMR (400 MHz, CDCl$_3$): δ=7.65 (d, J=10.7 Hz, 2H), 7.59 (d, J=13.4 Hz, 1H), 7.24 (s, 1H), 7.13 (s, 1H), 6.99 (s, 1H), 6.71 (s, 1H), 6.01 (s, 2H), 5.83 (d, J=5.8 Hz, 1H), 3.64 (s, 3H), 3.17 (s, 4H), 3.11 (s, 4H), 2.09 (t, J=19.6 Hz, 3H), 1.62 (d, J=6.1 Hz, 3H).

Example 50: (R)-5-(1-(2,6-dichloro-3-fluorophenyl)ethoxy)-5'-ethoxy-1",2",3",6"-tetrahydro-[3,3':6',4"-terpyridin]-6-amine

Step 1: (R)-6'-chloro-5-(1-(2,6-dichloro-3-fluorophenyl)ethoxy)-5'-ethoxy-[3,3'-bipyridin]-6-amine According to the procedure described in Step 1 of Example 30, using 5-bromo-2-chloro-3-ethoxypyridine instead of 5-bromo-2-chloro-3-methoxypyridine, the title compound was obtained (46% yield). MS m/z [ESI]: 456.0 [M+1].

Step 2: (R)-tert-butyl 6-amino-5-(1-(2,6-dichloro-3-fluorophenyl)ethoxy)-5'-ethoxy-5",6"-dihydro-[3,3':6',4"-terpyridine]-1"(2"H)-carboxylate According to the procedure described in Step 2 of Example 30, using (R)-6'-chloro-5-(1-(2,6-dichloro-3-fluorophenyl)ethoxy)-5'-ethoxy-[3,3'-bipyridin]-6-amine instead of (R)-6'-chloro-5-(1-(2,6-dichloro-3-fluorophenyl)ethoxy)-5'-methoxy-[3,3'-bipyridin]-6-amine, the title compound was obtained (46% yield). MS m/z [ESI]: 603.2 [M+1].

Step 3: (R)-5-(1-(2,6-dichloro-3-fluorophenyl)ethoxy)-5'-ethoxy-1",2",3",6"-tetrahydro-[3,3':6',4"-terpyridin]-6-amine According to the procedure described in Step 3 of Example 30, using (R)-tert-butyl 6-amino-5-(1-(2,6-dichloro-3-fluorophenyl)ethoxy)-5'-ethoxy-5",6"-dihydro-[3,3':6',4"-terpyridine]-1"(2"H)-carboxylate instead of (R)-tertbutyl 6-amino-5-(1-(2,6-dichloro-3-fluorophenyl)ethoxy)-5'-methoxy-5",6"-dihydro-[3,3':6',4"-terpyridine]-1"(2"H)-carboxylate, the title compound was obtained (67% yield). MS m/z [ESI]: 503.1 [M+1]. ¹H-NMR (400 MHz, CD₃OD): δ=8.06 (s, 1H), 7.73 (s, 1H), 7.36 (dd, J=9.0, 4.9 Hz, 1H), 7.23 (s, 1H), 7.16 (t, J=8.6 Hz, 1H), 6.90 (s, 1H), 6.48 (s, 1H), 6.13 (d, J=6.7 Hz, 1H), 4.08 (q, J=6.8 Hz, 2H), 3.79 (d, J=2.7 Hz, 2H), 3.34 (t, J=6.1 Hz, 2H), 2.82 (s, 2H), 1.80 (d, J=6.6 Hz, 3H), 1.38 (t, J=6.9 Hz, 3H).

Example 51: 5-((R)-1-(2,6-dichloro-3-fluorophenyl)ethoxy)-5'-methoxy-3"-methyl-1",2",3",6"-tetrahydro-[3,3':6',4"-terpyridin]-6-amine

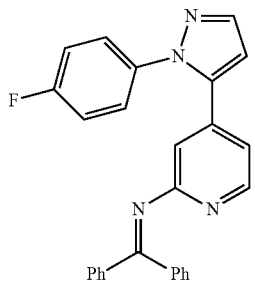

Step 1: tert-butyl 6-amino-5-((R)-1-(2,6-dichloro-3-fluorophenyl)ethoxy)-5'-methoxy-5"-methyl-5",6"-dihydro-[3,3':6',4"-terpyridine]-1"(2"H)-carboxylate

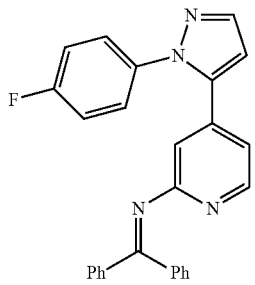 [SMILES: Fc1ccc(-n2nccc2-c2ccnc(N=C(c3ccccc3)c3ccccc3)c2)cc1]

According to the procedure described in Step 2 of Example 30, using tert-butyl 5-methyl-4-(4,4,5,5-tetramethyl-1,3,2-dioxaborolan-2-yl)-5,6-dihydropyridin-1(2H)-carboxylate instead of tert-butyl 4-(4,4,5,5-tetramethyl-1,3,2-dioxaborolan-2-yl)-1-carboxylate-1,2,5,6-tetrahydropyridine, the title compound was obtained (46% yield). MS m/z[ESI]: 603.2[M+1].

Step 2: 5-((R)-1-(2,6-dichloro-3-fluorophenyl)ethoxy)-5'-methoxy-1",2",3",6"-tetrahydro-[3,3':6',4"-terpyridin]-6-amine According to the procedure described in Step 3 of Example 30, using tert-butyl 6-amino-5-((R)-1-(2,6-dichloro-3-fluorophenyl)ethoxy)-5'-methoxy-5"-methyl-5",6"-dihydro-[3,3':6',4"-terpyridine]-1"(2"H)-carboxylate instead of (R)-tert-butyl 6-amino-5-(1-(2,6-dichloro-3-fluorophenyl)ethoxy)-5'-methoxy-5",6"-dihydro-[3,3': 6',4"-terpyridine]-1"(2"H)-carboxylate, the title compound was obtained (67% yield). MS m/z [ESI]: 503.1 [M+1]. ¹H-NMR (400 MHz, CD₃OD): δ=8.16 (dd, J=4.4, 1.7 Hz, 1H), 7.86 (s, 1H), 7.46 (d, J=2.3 Hz, 1H), 7.38 (s, 1H), 7.25 (m, 1H), 7.03 (s, 1H), 6.25 (q, J=6.5 Hz, 1H), 6.12 (s, 1H), 3.92 (s, 3H), 3.84 (dd, J=5.9, 3.0 Hz, 2H), 3.54 (dd, J=12.3, 5.4 Hz, 1H), 3.48 (s, 1H), 3.10 (dd, J=12.3, 7.6 Hz, 1H), 1.91 (d, J=6.7 Hz, 3H), 0.96 (d, J=7.0 Hz, 3H).

Example 52: (R)-2-((6-amino-5-(1-(2,6-dichloro-3-fluorophenyl)ethoxy)-1",2",3",6"-tetrahydro-[3,3':6',4"-terpyridin]-5'-yl)oxy)ethanol Step 1: (R)-2-((6'-amino-6-chloro-5'-(1-(2,6-dichloro-3-fluorophenyl)ethoxy)-[3,3'-bipyridin]-5-yl)oxy)ethanol According to the procedure described in Step 1 of Example 30, using 5-bromo-2-chloro-3-(2-hydroxyethoxy)pyridine instead of 5-bromo-2-chloro-3-methoxypyridine, the title compound was obtained (46% yield). MS m/z [ESI]: 472.0 [M+1].

Step 2: (R)-tert-butyl 6-amino-5-(1-(2,6-dichloro-3-fluorophenyl)ethoxy)-5'-(2-hydroxyethoxy)-5",6"-dihydro-[3,3': 6',4"-terpyridine]-1"(2")-carboxylate According to the procedure described in Step 2 of Example 30, using (R)-2-((6'-amino-6-chloro-5'-(1-(2,6-dichloro-3-fluorophenyl)ethoxy)-[3,3'-bipyridin]-5-yl)oxy)ethanol instead of (R)-6'-chloro-5-(1-(2,6-dichloro-3-fluorophenyl)ethoxy)-5'-methoxy-[3,3'-bipyridin]-6-amine, the title compound was obtained (46% yield). MS m/z [ESI]: 619.2 [M+1].

Step 3: (R)-2-((6-amino-5-(1-(2,6-dichloro-3-fluorophenyl)ethoxy)-1",2",3",6"-tetrahydro-[3,3':6',4"-terpyridin]-5'-yl)oxy)ethanol According to the procedure described in Step 3 of Example 30, using (R)-tert-butyl 6-amino-5-(1-(2,6-dichloro-3-fluorophenyl)ethoxy)-5'-(2-hydroxyethoxy)-5",6"-dihydro-[3,3':6',4"-terpyridine]-1"(2"H)-carboxylate instead of (R)-tert-butyl 6-amino-5-(1-(2,6-dichloro-3-fluorophenyl)ethoxy)-5'-methoxy-5",6"-dihydro-[3,3':6',4"-terpyridine]-1"(2"H)-carboxylate, the title compound was obtained (67% yield). MS m/z [ESI]: 519.1 [M+1]. ¹H-NMR (400 MHz, CDCl₃): δ=8.23 (s, 1H), 7.87 (d, J=1.1 Hz, 1H), 7.31 (dd, J=8.9, 4.7 Hz, 1H), 7.11 (s, 1H), 7.07 (t, J=8.4 Hz, 1H), 6.94 (s, 1H), 6.41 (s, 1H), 6.11 (q, J=6.6 Hz, 1H), 4.96 (s, 2H), 4.18-4.04 (m, 2H), 4.01 (d, J=4.3 Hz, 2H), 3.64 (d, J=2.6 Hz, 2H), 3.16 (t, J=5.7 Hz, 2H), 2.68 (s, 2H), 1.88 (d, J=6.7 Hz, 3H).

Example 53: 5-((R)-1-(2,6-dichloro-3-fluorophenyl)ethoxy)-4'-ethoxy-6'-((S)-2-methylpiperazin-1-yl)-[3,3'-bipyridin]-6-amine Step 1: (S)-tert-butyl 4-(6'-amino-5'-((R)-1-(2,6-dichloro-3-fluorophenyl)ethoxy)-4-ethoxy-[3,3'-bipyridin]-6-yl)-3-methylpiperazine-1-carboxylate According to the procedure described in Step 1 of Example 27, using (S)-tert-butyl 4-(5-bromo-4-ethoxypyridin-2-yl)-3-methylpiperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 620.2 [M+1].

Step 2: 5-((R)-1-(2,6-dichloro-3-fluorophenyl) ethoxy)-4'-ethoxy-6'-((S)-2-methylpiperazin-1-yl)- [3,3'-bipyridin]-6-amine According to the procedure described in Step 2 of Example 27, using (S)-tert-butyl 4-(6'-amino-5'-((R)-1-(2,6-dichloro-3-fluorophenyl)ethoxy)-4-ethoxy-[3,3'-bipyridin]-6-yl)-3-methylpiperazine-1-carboxylate instead of (S)-tert-butyl 4-(6'-amino-5'-((R)-1-(2,6-dichloro-3-fluorophenyl) ethoxy)-4-methoxy-[3,3'-bipyridin]-6-yl)-3-methylpiperazine-1-carboxylate, the title compound was obtained (67% yield). MS m/z [ESI]: 520.2 [M+1]. $^1$H-NMR (400 MHz, CDCl$_3$): δ=7.91 (s, 1H), 7.78 (d, J=1.0 Hz, 1H), 7.31-7.26 (m, 1H), 7.03 (dd, J=17.1, 8.9 Hz, 2H), 6.05 (m, 2H), 4.77 (s, 2H), 4.41 (m, 1H), 4.05 (q, J=6.8 Hz, 2H), 3.99-3.85 (m, 1H), 3.20-3.02 (m, 3H), 2.98-2.77 (m, 2H), 1.82 (d, J=6.7 Hz, 3H), 1.36 (t, J=7.0 Hz, 3H), 1.23 (s, 3H).

Example 54: (R)-5-(1-(2,6-dichloro-3-fluorophenyl) ethoxy)-6'-morpholino-5'-(2-morpholinoethoxy)-[3, 3'-bipyridin]-6-amine According to the procedure described in Step 1 of Example 27, using 4-(2-(5-bromo-2-morpholinopyridin-3-yl-oxy)ethyl)morpholine instead of (S)-tert-butyl 4-(5-bromo-4-methoxypyridin-2-yl)-3-methylpiperazine-1-carboxylate, the title compound was obtained (46% yield). MS m/z [ESI]: 592.2 [M+1]. $^1$H-NMR (400 MHz, CDCl$_3$): δ=7.93 (d, J=1.8 Hz, 1H), 7.81 (d, J=1.4 Hz, 1H), 7.31 (dd, J=8.9, 4.8 Hz, 1H), 7.11-7.03 (m, 1H), 6.99 (d, J=1.6 Hz, 1H), 6.91 (s, 1H), 6.10 (q, J=6.7 Hz, 1H), 4.91 (s, 2H), 4.19-4.06 (m, 2H), 3.88-3.83 (m, 4H), 3.74-3.69 (m, 4H), 3.48-3.38 (m, 4H), 2.85 (t, J=5.6 Hz, 2H), 2.60 (d, J=4.3 Hz, 4H), 1.87 (d, J=6.7 Hz, 3H).

Example 55: (R)-5-(1-(2,6-dichloro-3-fluorophenyl) ethoxy)-5'-(2-morpholinoethoxy)-1",2",3",6"-tetrahydro-[3,3':6',4"-terpyridin]-6-amine

Step 1: (R)-6'-chloro-5-(1-(2,6-dichloro-3-fluorophenyl)ethoxy)-5'-(2-morpholinoethoxy)-[3,3'-bipyridin]-6-amine According to the procedure described in Step 1 of Example 30, using 4-(2-(5-bromo-2-chloropyridin-3-yl-oxy)ethyl)morpholine instead of 5-bromo-2-chloro-3-methoxypyridine, the title compound was obtained (46% yield). MS m/z[ESI]: 543.1[M+1].

Step 2: (R)-tert-butyl 6-amino-5-(1-(2,6-dichloro-3-fluorophenyl)ethoxy)-5'-(2-morpholinoethoxy)-5", 6"-dihydro-[3,3':6',4"-terpyridine]-1"(2"H)-carboxylate According to the procedure described in Step 2 of Example 30, using (R)-6'-chloro-5-(1-(2,6-dichloro-3-fluorophenyl)ethoxy)-5'-(2-morpholinoethoxy)-[3,3'-bipyridin]-6-amine instead of (R)-6'-chloro-5-(1-(2,6-dichloro-3-fluorophenyl)ethoxy)-5'-methoxy-[3,3'-bipyridin]-6-amine, the title compound was obtained (46% yield). MS m/z [ESI]: 688.2 [M+1].

Step 3: (R)-5-(1-(2,6-dichloro-3-fluorophenyl) ethoxy)-5'-(2-morpholinoethoxy)-1",2",3",6"-tetrahydro-[3,3':6',4"-terpyridin]-6-amine According to the procedure described in Step 3 of Example 30, using (R)-tert-butyl 6-amino-5-(1-(2,6-dichloro-3-fluorophenyl)ethoxy)-5'-(2-morpholinoethoxy)-5", 6"-dihydro-[3,3':6',4"-terpyridine]-1"(2"H)-carboxylate instead of (R)-tert-butyl 6-amino-5-(1-(2,6-dichloro-3-fluorophenyl)ethoxy)-5'-methoxy-5",6"-dihydro-[3,3':6',4"-terpyridine]-1"(2"H)-carboxylate, the title compound was obtained (67% yield). MS m/z [ESI]: 588.2 [M+1]. $^1$H-NMR (400 MHz, CDCl$_3$): δ=8.20 (s, 1H), 7.85 (s, 1H), 7.30 (dd, J=8.9, 4.8 Hz, 1H), 7.12-7.00 (m, 2H), 6.93 (s, 1H), 6.55 (s, 1H), 6.09 (d, J=6.7 Hz, 1H), 4.95 (s, 2H), 4.11 (dd, J=14.4, 5.8 Hz, 2H), 3.76-3.66 (m, 4H), 3.59 (d, J=2.6 Hz, 2H), 3.11 (t, J=5.6 Hz, 2H), 2.83 (t, J=5.7 Hz, 2H), 2.65-2.51 (m, 6H), 1.86 (d, J=6.7 Hz, 3H).

Example 56: 5-((R)-1-(2,6-dichloro-3-fluorophenyl) ethoxy)-6'-((S)-2-methylpiperazin-1-yl)-4'-(2-morpholinoethoxy)-[3,3'-bipyridin]-6-amine

Step 1: (S)-tert-butyl 4-(6'-amino-5'-((R)-1-(2,6-dichloro-3-fluorophenyl)ethoxy)-4-(2-morpholinoethoxy)-[3,3'-bipyridin]-6-yl)-3-methylpiperazine-1-carboxylate According to the procedure described in Step 1 of Example 27, using (S)-tert-butyl 4-(5-bromo-4-(2-morpholinoethoxypyridin-2-yl)-3-methylpiperazine-1-carboxylate instead of (S)-tert-butyl 4-(5-bromo-4-methoxypyridin-2-yl)-3-methylpiperazine-1-carboxylate, the title compound was obtained (46% yield). MS m/z [ESI]: 705.3 [M+1].

Step 2: 5-((R)-1-(2,6-dichloro-3-fluorophenyl) ethoxy)-6'-((S)-2-methylpiperazin-1-yl)-4'-(2-morpholinoethoxy)-[3,3'-bipyridin]-6-amine According to the procedure described in Step 2 of Example 27, using (S)-tert-butyl 4-(6'-amino-5'-((R)-1-(2,6-dichloro-3-fluorophenyl)ethoxy)-4-(2-morpholinoethoxy)-[3,3'-bipyridin]-6-yl)-3-methylpiperazine-1-carboxylate instead of (S)-tert-butyl 4-(6'-amino-5'-((R)-1-(2,6-dichloro-3-fluorophenyl)ethoxy)-4-methoxy-[3,3'-bipyridin]-6-yl)-3-methylpiperazine-1-carboxylate, the title compound was obtained (67% yield). MS m/z [ESI]: 605.2 [M+1]. $^1$H-NMR (400 MHz, CDCl$_3$): δ=7.89 (s, 1H), 7.76 (d, J=1.5 Hz, 1H), 7.32-7.27 (m, 1H), 7.08-7.01 (m, 1H), 6.93 (d, J=1.5 Hz, 1H), 6.07 (s, 1H), 6.05 (d, J=6.7 Hz, 1H), 4.82 (s, 2H), 4.45-4.36 (m, 1H), 4.10 (dd, J=10.3, 6.1 Hz, 2H), 3.99-3.89 (m, 1H), 3.68-3.64 (m, 4H), 3.08 (dd, J=10.8, 7.5 Hz, 3H), 2.94 (d, J=12.1 Hz, 1H), 2.85 (dd, J=13.5, 10.0 Hz, 1H), 2.72 (dd, J=10.1, 6.1 Hz, 2H), 2.49-2.44 (m, 4H), 1.82 (d, J=6.7 Hz, 3H), 1.24 (d, J=6.7 Hz, 3H).

ALK Kinase Inhibition Activity Assay

The following method was used to determine ALK kinase inhibitory activity of the compounds of the present invention. The inhibitory activity is indicated by IC$_{50}$, which means the concentration of the compound when ALK kinase activity is inhibited by 50%. The present patent established and optimized ALK (purchased from Millipore) kinase activity assay platform using the method of homogeneous time-resolved fluorescence (HTRF, Cisbio) for measuring the activity of the compounds.

Materials and Methods:
Materials:
a. White 384 Orifice plate (Perkin Elmer, Catalog No. 607290/99)
b. HEPES buffer: 50 ml of 0.05M HEPES buffer is formulated with 1M HEPES buffer (Invitrogen, Catalog No. 15630-080), by taking 2.5 ml of 1 M HEPES buffer, adding appropriate amount of distilled water (ddH$_2$O), adjusting pH to 7.0 with NaOH, and finally adding ddH$_2$O (double distilled water) to 50 ml.
- c. ALK kinase (Millipore).
- d. 0.1M Na$_3$VO$_4$
- e. 1 M MgCl$_2$
- f. 0.2 M DTT
- g. 10% BAS
- h. DMSO
- i. ddH$_2$O
- j. Test compounds: Example Compounds The test was carried out according to the following procedure:

1. preparing ALK enzyme reaction buffer: 50 mM HEPES (pH=7.0), 0.1 mM Na$_3$VO$_4$, 0.01% BAS, 5 mM MgCl$_2$, 1 mM DTT, placing on ice as preserve;

2. using 100% DMSO to make a 3-fold serial dilution of the compound from 1 mM, adding 4 µl of each concentration to 96 µl of reaction buffer, then taking 2.5 µl and adding it to 384 well plate (OptiPlate-384, PerkinElmer), followed by adding 5 µl of kinase, uniformly mixing by centrifugation, then adding 2.5 µl of the mixed liquid of ATP and TK peptide (ATP final concentration is Km value) to initiate the reaction.

3. placing the 384 well plate in an incubator at 23° C. for 120 minutes.

4. Adding 5 µl of TK Antibody-Cryptate antibody, 5 µl of streptavidin-labeled XL-665 to stop the reaction.

5. Incubating in the incubator (22-23° C.) for 1 hour;

6. Using a microplate reader Envision (PerkinElmer) to read the fluorescent signal of the reaction: 320 nm excitation, reading 665 nm wavelength emission spectra;

7. Generating IC$_{50}$ of the compounds against ALK: calculating IC$_{50}$ of the compounds using GraFit6.

TABLE 1

ALK inhibition activity of Example compounds

| Example | Structure | IC$_{50}$ (nM) |
|---|---|---|
| 1 | 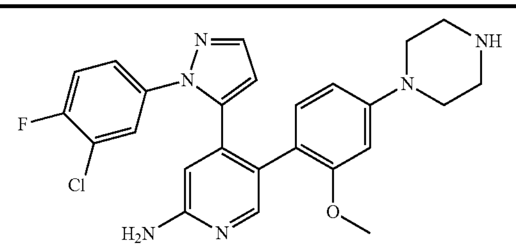 | 536 |
| 2 | 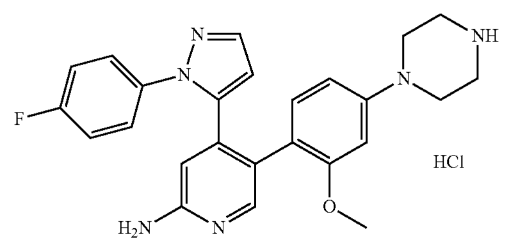 [SMILES: COc1cc(N2CCNCC2)ccc1-c1cnc(N)cc1-c1ccnn1-c1ccc(F)cc1 ; Cl] | 136 |
| 12 | 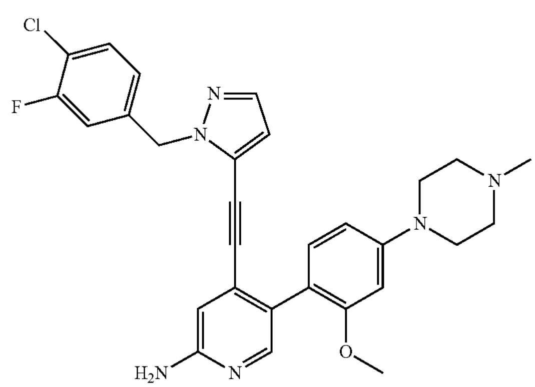 [SMILES: COc1cc(N2CCN(C)CC2)ccc1-c1cnc(N)cc1C#Cc1ccnn1Cc1ccc(Cl)c(F)c1] | 1000 |
| 16 | 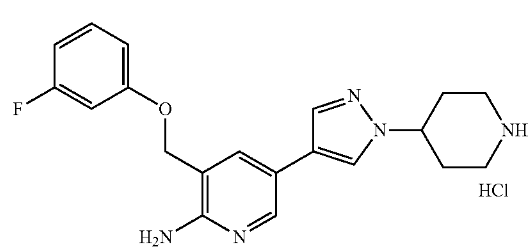 [SMILES: Nc1ncc(-c2cnn(C3CCNCC3)c2)cc1COc1cccc(F)c1 ; Cl] | 1000 |

TABLE 1-continued
ALK inhibition activity of Example compounds
| Example | Structure | IC$_{50}$ (nM) |
|---|---|---|
| 17 | 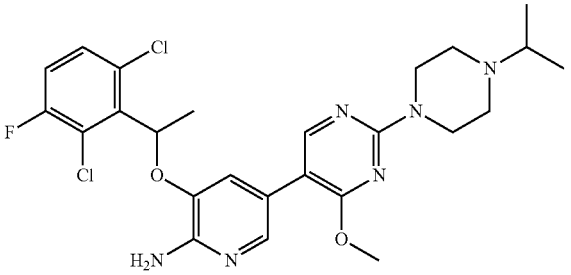 [SMILES: COc1nc(N2CCN(C(C)C)CC2)ncc1-c1cnc(N)c(OC(C)c2c(Cl)ccc(F)c2Cl)c1] | 396 |
| 18 | 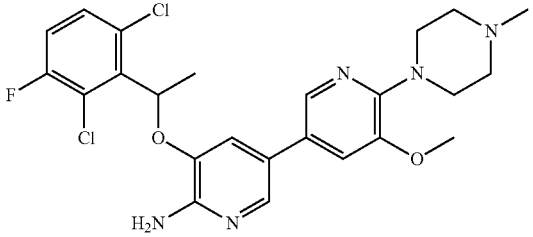 [SMILES: COc1cc(-c2cnc(N)c(OC(C)c3c(Cl)ccc(F)c3Cl)c2)cnc1N1CCN(C)CC1] | 89.4 |
| 19 | 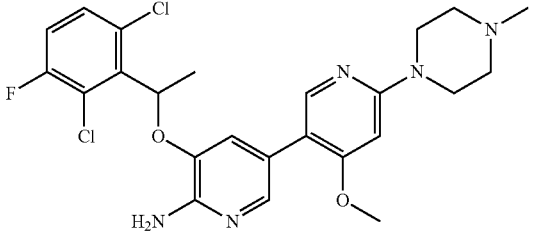 [SMILES: COc1cc(N2CCN(C)CC2)ncc1-c1cnc(N)c(OC(C)c2c(Cl)ccc(F)c2Cl)c1] | 80.2 |
| 22 | 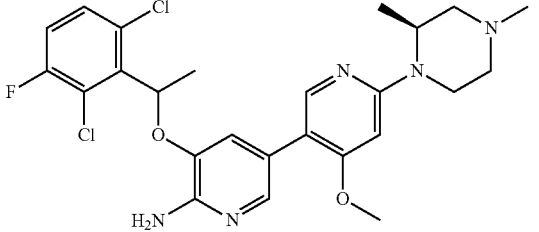 [SMILES: COc1cc(N2CCN(C)C[C@@H]2C)ncc1-c1cnc(N)c(OC(C)c2c(Cl)ccc(F)c2Cl)c1] | 38.1 |
| 23 | 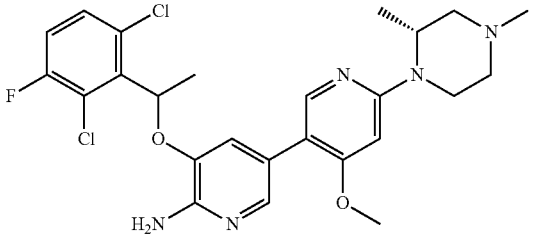 [SMILES: COc1cc(N2CCN(C)C[C@H]2C)ncc1-c1cnc(N)c(OC(C)c2c(Cl)ccc(F)c2Cl)c1] | 75.7 |
| 24 | 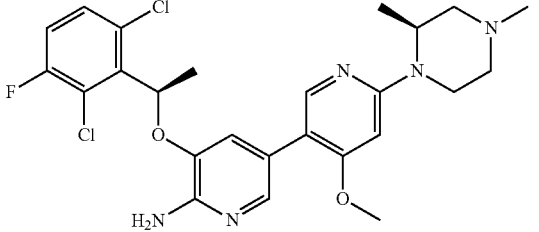 [SMILES: COc1cc(N2CCN(C)C[C@@H]2C)ncc1-c1cnc(N)c(O[C@H](C)c2c(Cl)ccc(F)c2Cl)c1] | 22.4 |

TABLE 1-continued

ALK inhibition activity of Example compounds

| Example | Structure | IC$_{50}$ (nM) |
|---|---|---|
| 25 | 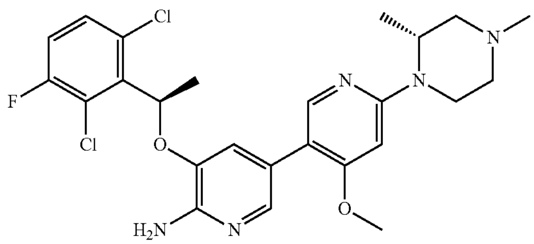 [SMILES: COc1cc(N2CCN(C)C[C@H]2C)ncc1-c1cnc(N)c(O[C@H](C)c2c(Cl)ccc(F)c2Cl)c1] | 55.1 |
| 26 | 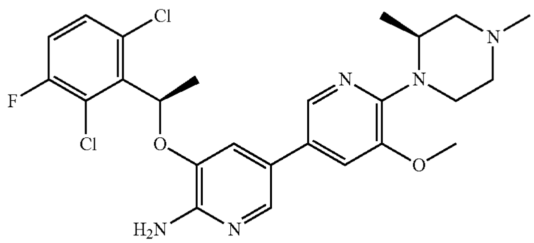 [SMILES: COc1cc(-c2cnc(N)c(O[C@H](C)c3c(Cl)ccc(F)c3Cl)c2)cnc1N1CCN(C)C[C@@H]1C] | 42.0 |
| 27 | 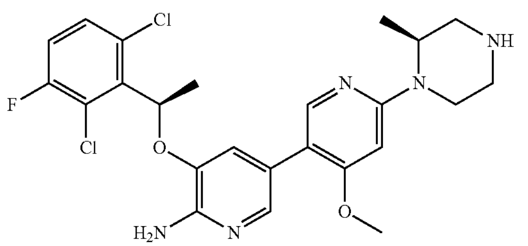 [SMILES: COc1cc(N2CCNC[C@@H]2C)ncc1-c1cnc(N)c(O[C@H](C)c2c(Cl)ccc(F)c2Cl)c1] | 1.96 |
| 28 | 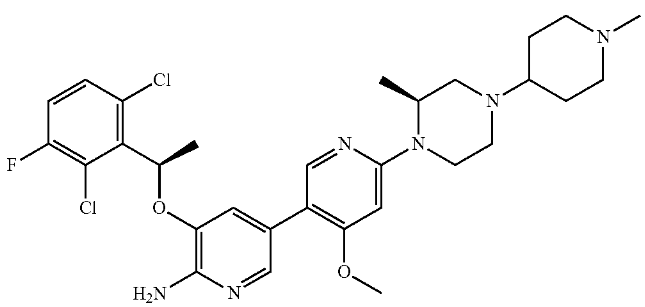 [SMILES: COc1cc(N2CCN(C3CCN(C)CC3)C[C@@H]2C)ncc1-c1cnc(N)c(O[C@H](C)c2c(Cl)ccc(F)c2Cl)c1] | 9.1 |
| 29 | 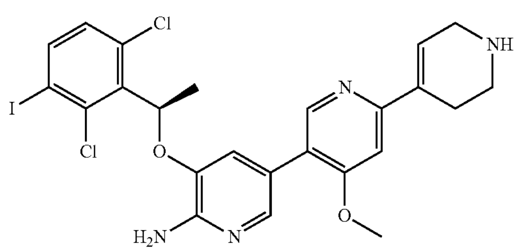 [SMILES: COc1cc(C2=CCNCC2)ncc1-c1cnc(N)c(O[C@H](C)c2c(Cl)ccc(I)c2Cl)c1] | 19.2 |
| 30 | 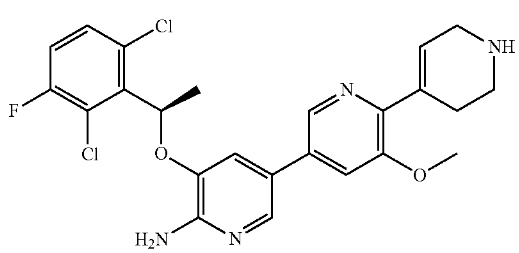 [SMILES: COc1cc(-c2cnc(N)c(O[C@H](C)c3c(Cl)ccc(F)c3Cl)c2)cnc1C1=CCNCC1] | 9.8 |

TABLE 1-continued

ALK inhibition activity of Example compounds

| Example | Structure | IC$_{50}$ (nM) |
|---|---|---|
| 31 | 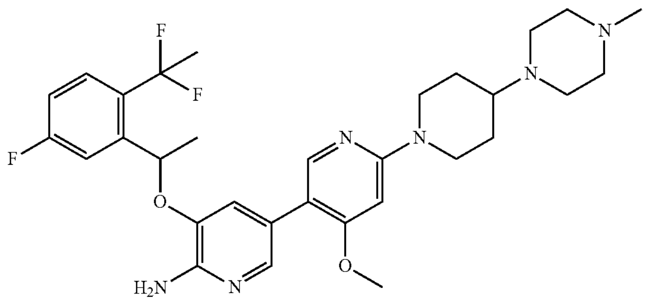 [SMILES: COc1cc(N2CCC(N3CCN(C)CC3)CC2)ncc1-c1cnc(N)c(OC(C)c2cc(F)ccc2C(C)(F)F)c1] | 20.8 |
| 32 | 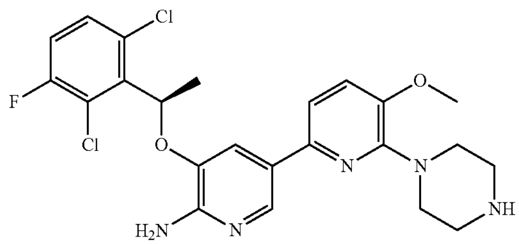 [SMILES: COc1ccc(-c2cnc(N)c(O[C@H](C)c3c(Cl)ccc(F)c3Cl)c2)nc1N1CCNCC1] | 27.8 |
| 34 | 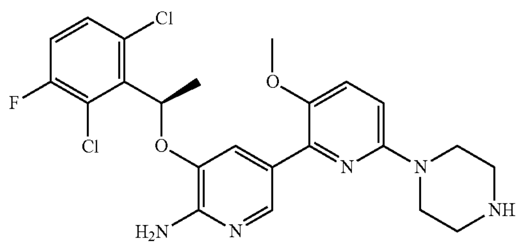 [SMILES: COc1ccc(N2CCNCC2)nc1-c1cnc(N)c(O[C@H](C)c2c(Cl)ccc(F)c2Cl)c1] | 19.0 |
| 35 | 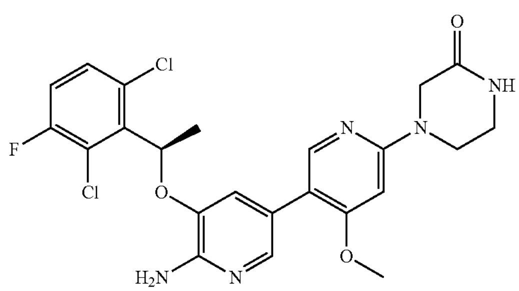 [SMILES: COc1cc(N2CCNC(=O)C2)ncc1-c1cnc(N)c(O[C@H](C)c2c(Cl)ccc(F)c2Cl)c1] | 250 |
| 36 | 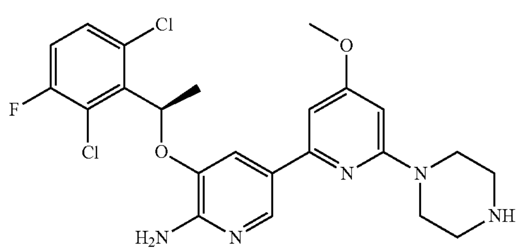 [SMILES: COc1cc(-c2cnc(N)c(O[C@H](C)c3c(Cl)ccc(F)c3Cl)c2)nc(N2CCNCC2)c1] | 160 |

TABLE 1-continued

ALK inhibition activity of Example compounds

| Example | Structure | IC$_{50}$ (nM) |
|---|---|---|
| 37 | 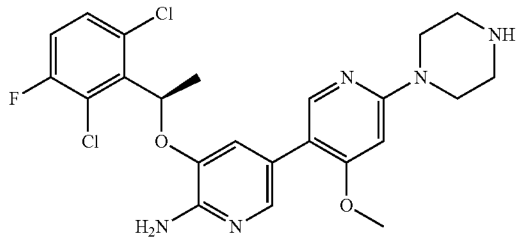 [SMILES: COc1cc(N2CCNCC2)ncc1-c1cnc(N)c(O[C@H](C)c2c(Cl)ccc(F)c2Cl)c1] | 8.0 |
| 38 | 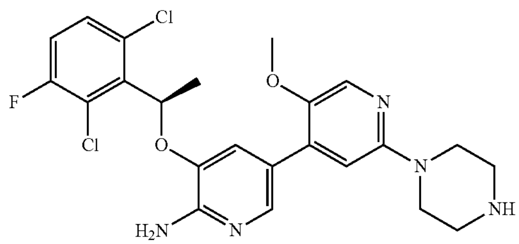 [SMILES: COc1cnc(N2CCNCC2)cc1-c1cnc(N)c(O[C@H](C)c2c(Cl)ccc(F)c2Cl)c1] | 20.0 |
| 39 | 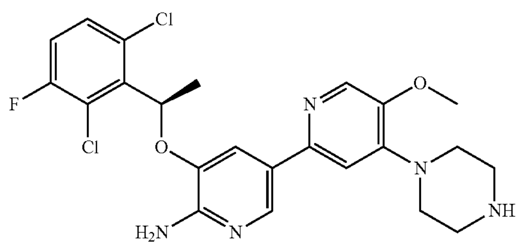 [SMILES: COc1cnc(-c2cnc(N)c(O[C@H](C)c3c(Cl)ccc(F)c3Cl)c2)cc1N1CCNCC1] | 130 |
| 40 | 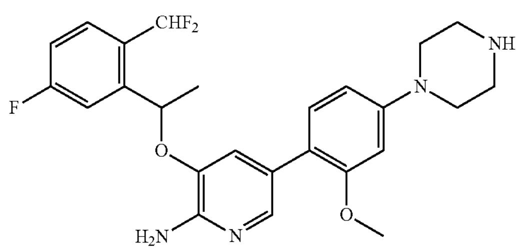 | 227 |
| 41 | 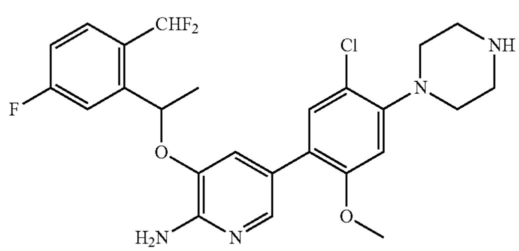 [SMILES: COc1cc(N2CCNCC2)c(Cl)cc1-c1cnc(N)c(OC(C)c2cc(F)ccc2C(F)F)c1] | 664 |
| 42 | 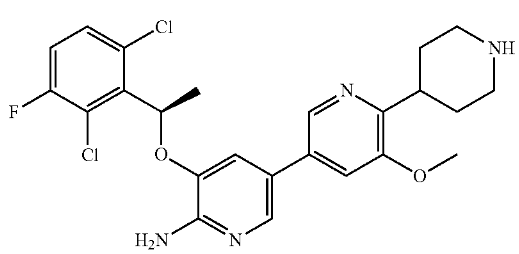 [SMILES: COc1cc(-c2cnc(N)c(O[C@H](C)c3c(Cl)ccc(F)c3Cl)c2)cnc1C1CCNCC1] | 29.4 |

TABLE 1-continued

ALK inhibition activity of Example compounds

| Example | Structure | IC$_{50}$ (nM) |
| --- | --- | --- |
| 43 | 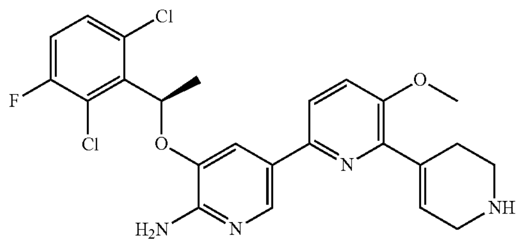 [SMILES: COc1ccc(-c2cnc(N)c(O[C@H](C)c3c(Cl)ccc(F)c3Cl)c2)nc1C1=CCNCC1] | 64.4 |
| 44 | 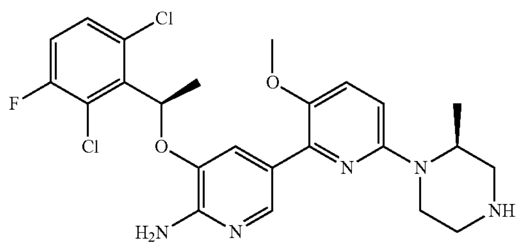 [SMILES: COc1ccc(N2CCNC[C@@H]2C)nc1-c1cnc(N)c(O[C@H](C)c2c(Cl)ccc(F)c2Cl)c1] | 60.5 |
| 45 | 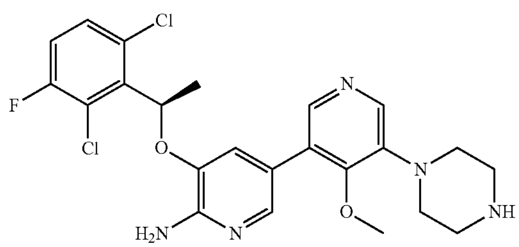 [SMILES: COc1c(-c2cnc(N)c(O[C@H](C)c3c(Cl)ccc(F)c3Cl)c2)cncc1N1CCNCC1] | 105 |
| 46 | 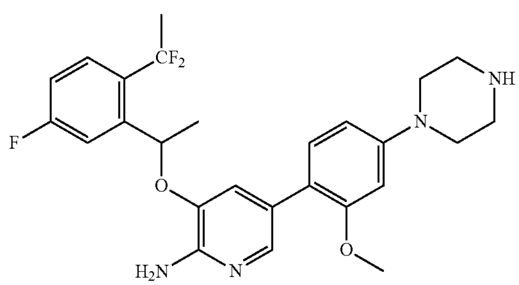 [SMILES: COc1cc(N2CCNCC2)ccc1-c1cnc(N)c(OC(C)c2cc(F)ccc2C(C)(F)F)c1] | 44.8 |
| 47 | 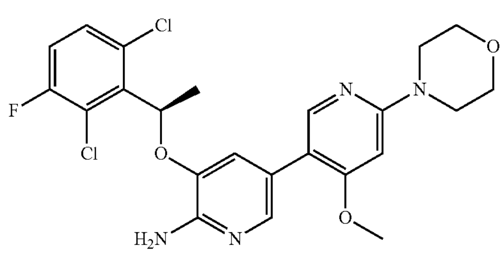 [SMILES: COc1cc(N2CCOCC2)ncc1-c1cnc(N)c(O[C@H](C)c2c(Cl)ccc(F)c2Cl)c1] | 175 |
| 48 | 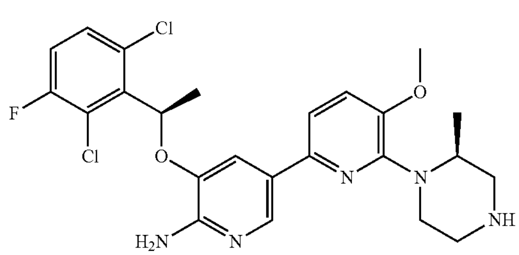 [SMILES: COc1ccc(-c2cnc(N)c(O[C@H](C)c3c(Cl)ccc(F)c3Cl)c2)nc1N1CCNC[C@@H]1C] | 258.6 |

TABLE 1-continued

ALK inhibition activity of Example compounds

| Example | Structure | IC$_{50}$ (nM) |
|---|---|---|
| 49 | 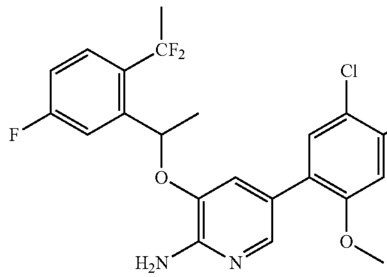 | 106.3 |
| 50 | 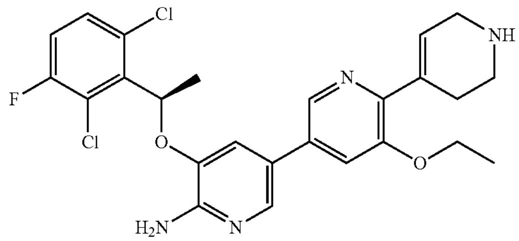 [SMILES: CCOc1cc(-c2cnc(N)c(O[C@H](C)c3c(Cl)ccc(F)c3Cl)c2)cnc1C1=CCNCC1] | 78 |
| 51 | 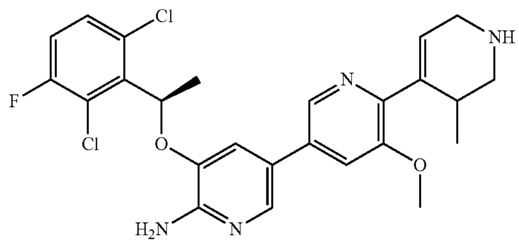 [SMILES: COc1cc(-c2cnc(N)c(O[C@H](C)c3c(Cl)ccc(F)c3Cl)c2)cnc1C1=CCNCC1C] | 46.8 |
| 52 | 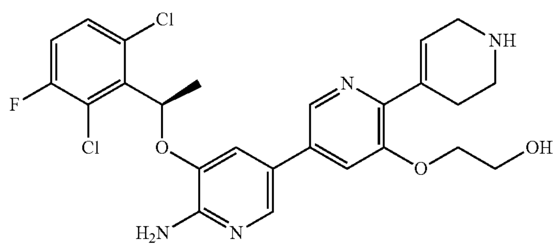 [SMILES: C[C@@H](Oc1cc(-c2cnc(C3=CCNCC3)c(OCCO)c2)cnc1N)c1c(Cl)ccc(F)c1Cl] | 6.9 |
| 53 | 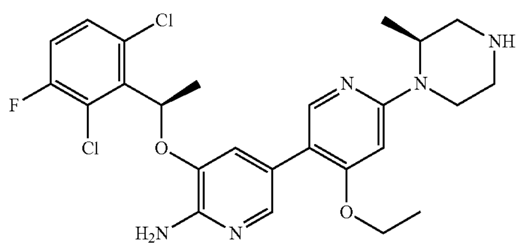 [SMILES: CCOc1cc(N2CCNC[C@@H]2C)ncc1-c1cnc(N)c(O[C@H](C)c2c(Cl)ccc(F)c2Cl)c1] | 13.9 |
| 54 | 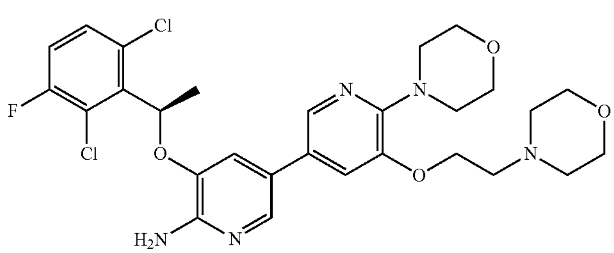 [SMILES: C[C@@H](Oc1cc(-c2cnc(N3CCOCC3)c(OCCN3CCOCC3)c2)cnc1N)c1c(Cl)ccc(F)c1Cl] | 90.0 |

TABLE 1-continued

ALK inhibition activity of Example compounds

| Example | Structure | IC$_{50}$ (nM) |
|---|---|---|
| 55 | 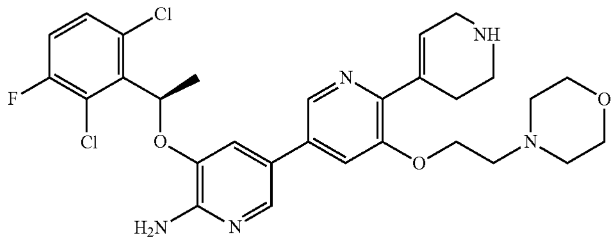 [SMILES: C[C@@H](Oc1cc(-c2cnc(C3=CCNCC3)c(OCCN3CCOCC3)c2)cnc1N)c1c(Cl)ccc(F)c1Cl] | 13.1 |
| 56 | 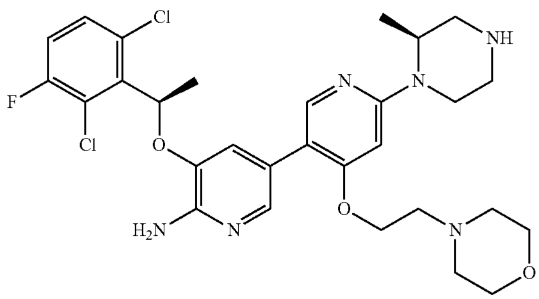 [SMILES: C[C@@H](Oc1cc(-c2cnc(N3CCNC[C@@H]3C)cc2OCCN2CCOCC2)cnc1N)c1c(Cl)ccc(F)c1Cl] | 92.9 |

Test data in Table 1 indicate that compounds provided by the present invention have high ALK inhibitory activities.

Table 2 lists inhibitory activities of the Example compounds 27, 30, and 53 against mutated ALK kinase. Among them, F1174L, L1196M, G1269S, and R1275Q mutated ALK kinases can be obtained from commercial sources.

TABLE 2

Inhibitory activities of Example compounds against four mutated ALK kinase

| Example compounds | Inhibitory activity IC$_{50}$ (nM) against mutated ALK kinase | | | |
|---|---|---|---|---|
| | F1174L | L1196M | G1269S | R1275Q |
| 27 | | 35.1 ± 5.3 | 61.3 ± 7.9 | |
| 30 | 2.6 ± 0.3 | 18.8 ± 1.7 | 93.3 ± 16 | 3.2 ± 0.6 |
| 53 | 3.1 ± 0.1 | 32.1 ± 3.5 | 115 ± 15 | 4.4 ± 0.4 |

Compounds provided by the present invention have very good in vivo metabolism. Table 3 lists in vivo pharmacokinetic data for Example compounds 27, 30, and 53 of the present invention in SD rats.

TABLE 3

Pharmacokinetic parameters of Example compounds

| Parameter | Unit | PK values (20% aqueous sulfobutyl-β-cycludextrin, oral 5 mg/kg) | | |
|---|---|---|---|---|
| | | 27 | 30 | 53 |
| T$_{1/2}$ | hr | 5.45 | 4.43 | 4.75 |
| T$_{max}$ | hr | 3.67 | 3.00 | 3.33 |
| C$_{max}$ | ng/mL | 69.7 | 112.8 | 62.57 |
| AUC$_{0-inf}$ | hr · ng/mL | 600.66 | 1266.2 | 830.29 |

CYP-3A4 is an important human metabolic enzyme CYP-3A. Inhibition of this enzyme may lead to adverse effect on the metabolism of other drugs in combination therapy. As shown in Table 4, Example compounds 27 and 30 show no significant inhibition against CYP-3A4, and thereby reduce or avoid impact on the metabolism of other drugs in combination therapy.

TABLE 4

Inhibition of Example Compounds 27 and 30 to CYP-3A4

| | Positive control* | 27 | 30 |
|---|---|---|---|
| 3A4_Midazolam | 0.083 μM | >10 μM | >10 μM |

*Ketoconazole

Table 5 lists the therapeutic effect of the final target compound of Example 27 against human non-small cell lung carcinoma NCI-H2228 in nude mice. The used experimental method was as follows. Nude mice was inoculated subcutaneously with human non-small cell lung carcinoma NCI-H2228 cells, upon the tumor grew to 80-200 mm$^3$, the mice were randomly grouped (D0) and administered. Administration dose and administration regimen are listed in Table 5. Twice a week the tumor volume was measured, the mice was weighed, and data were recorded. Tumor volume (V) is calculated as:

$V = \frac{1}{2} \times a \times b^2$, wherein a and b represent length and width respectively.

$T/C(\%) = (T-T_0)/(C-C_0) \times 100$, wherein T, C respectively represents the tumor volume at the end of the experiment; $T_0$, $C_0$ respectively represents the tumor volume at the start of the experiment.

When tumor regression was observed, $T/C(\%) = (T-T_0)/T_0 \times 100$, wherein T is the tumor volume at the end of the experiment; $T_0$ is the tumor volume at the start of the experiment.

Inhibition rate(%)=100−T/C(%), partial regression indicates that the tumor diminishes but doesn't disappear, complete regression indicates that the tumor disappears.

TABLE 5

Therapeutic effect on human non-small cell lung carcinoma NCI-H2228 xenografts in nude mice

| Group | Administration | Route | Average tumor volume (mm³) D0 | SD | Average tumor volume (mm³) D21 | SD | % T/C D21 | % Inhibition rate D21 | P values D21 | Partial Regression (n) | Complete Regression (n) | The number of animals per group |
|---|---|---|---|---|---|---|---|---|---|---|---|---|
| Solvent | D0-20 | PO | 139.6 | ±11.5 | 1319.8 | ±322.6 | — | — | — | 0 | 0 | 12 |
| Example 27 12.5 mg/kg | D0-13 | PO | 134.3 | ±14.8 | 394.8 | ±315.6 | 22 | 78 | 0.000 | 1 | 0 | 6 |
| Example 27 25 mg/kg | D0-13 | PO | 131.0 | ±7.2 | 21.7 | ±35.4 | −83 | 183 | 0.000 | 2 | 4 | 6 |

In the table: the solvent group is a control group, compounds of the treatment groups are formulated with distilled water containing 0.1% Tween-80.

D0-20 represents administrating once a day from day 0 (D0), and continuously administrating for 21 days; D0-13 represents administrating once a day from day 0 (D0), and continuously administrating for 14 days.

P values are obtained from the student's t test over the control.

n is the number of mice, for the control group, the number of test mice n is 12, and n is always 6 for the treatment group.

The invention claimed is:

1. A compound of Formula (I)

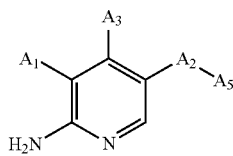

(I)

wherein
$A_1$ is selected from the group consisting of hydrogen, —O—(CHR$^1$)-A$_4$, —CH$_2$OR$^2$, and aryl substituted by one or more R$^3$(s);
$R^1$ is selected from the group consisting of methyl and methyl substituted by one to three halogen(s);
$A_4$ is selected from the group consisting of aryl optionally substituted by one or more R$^4$(s);
$R^2$ is selected from the group consisting of aryl optionally substituted by one or more R$^3$(s);
$R^3$ is selected from the group consisting of halogen, —SO$_2$(C$_{1-6}$ alkyl), —SO$_2$NR$^6$R$^7$, —NR$^6$R$^7$, —NHSO$_2$(C$_{1-6}$ alkyl), and —P(O)R$^6$R$^7$;
$R^4$ is selected from the group consisting of halogen, C$_{1-6}$ alkyl, —NR$^6$R$^7$, and —P(O)R$^6$R$^7$;
$R^6$ and $R^7$ are each independently selected from the group consisting of hydrogen and C$_{1-6}$ alkyl, or $R^6$ and $R^7$ link to form a 3-12 membered heteroalicyclyl with the atom to which they are attached to;
$A_2$ is selected from the group consisting of phenyl, pyridinyl, pyrimidinyl, and pyrazolyl, all of which are optionally substituted by one or more substituent(s) selected from the group consisting of halogen and —OC$_{1-6}$ alkyl in which each hydrogen of the C$_{1-6}$ alkyl moiety is optionally substituted by hydroxy, carboxyl, or 3-12 membered heteroalicyclyl;

$A_5$ is a 3-12 membered heteroalicyclyl, which is optionally substituted by one or more substituent(s) selected from the group consisting of
=O,
unsubstituted C$_{1-6}$ alkyl, and
C$_{1-6}$ alkyl substituted by one or more substituent(s) independently selected from the group consisting of hydroxy, carboxyl, and 3-12 membered heteroalicyclyl, and
3-12 membered heteroalicyclyl;
$A_3$ is selected from the group consisting of hydrogen, —NH-aryl, heteroaryl substituted by aryl, heteroaryl substituted by heteroaryl, heteroaryl substituted by arylalkyl, heteroaryl substituted by heteroarylalkyl, heteroarylethynyl substituted by arylalkyl, and heteroarylethynyl substituted by heteroarylalkyl, wherein each of the aryl and heteroaryl is optionally substituted by one or more substituent(s) selected from the group consisting of
halogen,
C$_{1-6}$ alkyl optionally substituted by halogen, hydroxy or 3-12 membered heteroalicyclyl, and
—OH, —OC$_{1-6}$ alkyl, —CN, —COOH, —C$_{1-6}$-alkyl-NH$_2$, —C$_{1-6}$-alkyl-NH(C$_{1-6}$ alkyl), —C$_{1-6}$-alkyl-N(C$_{1-6}$ alkyl)$_2$, —COO—C$_{1-6}$ alkyl, —SO$_2$(C$_{1-6}$ alkyl), —SO$_2$N(C$_{1-6}$ alkyl)$_2$, —SO$_2$NH(C$_{1-6}$ alkyl), —NR$^6$R$^7$, —NHSO$_2$(C$_{1-6}$ alkyl), and —P(O)R$^6$R$^7$;
with the proviso that
$A_1$ and $A_3$ are not both hydrogen, and one of $A_1$ and $A_3$ must be hydrogen; and
when $A_1$ is —O—(CHR$^1$)-A$_4$ and R$^1$ is methyl, $A_2$ is substituted by at least one —OC$_{1-6}$ alkyl; and
when $A_1$ is aryl substituted by one or more R$^3$(s) and R$^3$ is —NR$^6$R$^7$, R$^6$ and R$^7$ are each independently selected from the group consisting of C$_{1-6}$ alkyl, or R$^6$ and R$^7$ link to form a 3-12 membered heteroalicyclyl with the atom to which they are attached to;

and the pharmaceutically acceptable salts, stereoisomers, and enantiomers thereof, and mixtures thereof.

2. The compound of claim 1, wherein
$A_3$ is selected from the group consisting of —NH-phenyl, heteroaryl substituted by phenyl, heteroaryl substituted by heteroaryl, heteroaryl substituted by phenylmethyl, heteroaryl substituted by heteroarylmethyl, heteroarylethynyl substituted by phenylmethyl, and heteroarylethynyl substituted by heteroarylmethyl, wherein each of the phenyl and heteroaryl is optionally substituted by one or more substituent(s) selected from the group consisting of
halogen,
$C_{1-6}$ alkyl optionally substituted by halogen, hydroxy, or 3-12 membered heteroalicyclyl, and
—OH, —OC$_{1-6}$ alkyl, —CN, —COOH, —C$_{1-6}$-alkyl-NH$_2$, —C$_{1-6}$-alkyl-NH(C$_{1-6}$ alkyl), —C$_{1-6}$-alkyl-N(C$_{1-6}$ alkyl)$_2$, —COOC$_{1-6}$ alkyl, —SO$_2$(C$_{1-6}$ alkyl), —SO$_2$N(C$_{1-6}$ alkyl)$_2$, —SO$_2$NH(C$_{1-6}$ alkyl), —NR$^6$R$^7$, —NHSO$_2$(C$_{1-6}$ alkyl), and —P(O)R$^6$R$^7$; or preferably, $A_3$ is selected from the group consisting of —NH-phenyl, heteroaryl substituted by phenyl, heteroaryl substituted by heteroaryl, heteroaryl substituted by phenylmethyl, heteroaryl substituted by heteroarylmethyl, heteroarylethynyl substituted by phenylmethyl, and heteroarylethynyl substituted by heteroarylmethyl, wherein each of the phenyl and heteroaryl is optionally substituted by one or more substituent(s) selected from the group consisting of
halogen,
$C_{1-4}$ alkyl optionally substituted by halogen, hydroxy or 5 or 6 membered heteroalicyclyl, and
—OH, —OC$_{1-4}$alkyl, —CN, —COOH, —C$_{1-4}$-alkyl-NH$_2$, —C$_{1-4}$-alkyl-NH(C$_{1-4}$ alkyl), —C$_{1-4}$-alkyl-N(C$_{1-4}$ alkyl)$_2$, —COOC$_{1-4}$ alkyl, —SO$_2$(C$_{1-4}$ alkyl), —SO$_2$N(C$_{1-4}$ alkyl)$_2$, —SO$_2$NH(C$_{1-4}$ alkyl), —NH$_2$, —NH(C$_{1-4}$ alkyl), —N(C$_{1-4}$ alkyl)$_2$, —NHSO$_2$(C$_{1-4}$ alkyl), and —P(O)(C$_{1-4}$ alkyl)$_2$; or more preferably, $A_3$ is selected from the group consisting of —NH-phenyl, pyrazolyl substituted by phenyl, pyrazolyl substituted by phenylmethyl, and pyrazolylethynyl substituted by phenylmethyl, wherein phenyl is optionally substituted by one or more substituent(s) selected from the group consisting of
halogen,
$C_{1-4}$ alkyl substituted by halogen or hydroxy, and
—OH, —OC$_{1-4}$ alkyl, —CN, —COOH, —C$_{1-4}$ alkyl NH$_2$, —C$_{1-4}$ alkyl NH(C$_{1-4}$ alkyl), —C$_{1-4}$ alkyl N(C$_{1-4}$ alkyl)$_2$, —COOC$_{1-4}$ alkyl, —SO$_2$(C$_{1-4}$ alkyl), —NH$_2$, —NH(C$_{1-4}$ alkyl), —N(C$_{1-4}$ alkyl)$_2$, —NHSO$_2$(C$_{1-4}$ alkyl), —SO$_2$N(C$_{1-4}$ alkyl)$_2$, —SO$_2$NH(C$_{1-4}$ alkyl), and —P(O)(C$_{1-4}$ alkyl)$_2$; or most preferably, $A_3$ is selected from the group consisting of —NH-phenyl, pyrazolyl substituted by phenyl, pyrazolyl substituted by phenylmethyl, and pyrazolylethynyl substituted by phenylmethyl, wherein phenyl is optionally substituted by one or more substituent(s) selected from the group consisting of F, Cl, trifluoromethyl, —COOH, —CH$_2$OH, —OCH$_3$, —OC$_2$H$_5$, —CN, —SO$_2$NHCH(CH$_3$)$_2$, —COOCH$_3$, —SO$_2$CH$_3$, —NH$_2$, and —P(O)(CH$_3$)$_2$.

3. The compound of claim 1, wherein $A_3$ is hydrogen.
4. The compound of claim 3, wherein
$R^2$ is selected from the group consisting of phenyl optionally substituted by one or more $R^3$(s); or preferably,
$R^2$ is selected from the group consisting of phenyl optionally substituted by one or more $R^3$(s) selected from the group consisting of halogen, —SO$_2$(C$_{1-6}$alkyl), —SO$_2$N(C$_{1-6}$alkyl)$_2$, —SO$_2$NH(C$_{1-6}$alkyl), —NH(C$_{1-6}$alkyl), —N(C$_{1-6}$alkyl)$_2$, —NHSO$_2$(C$_{1-6}$alkyl), and —P(O)(C$_{1-6}$alkyl)$_2$; or more preferably,
$R^2$ is selected from the group consisting of phenyl substituted by one or more $R^3$(s) selected from the group consisting of F, Cl, —SO$_2$CH$_3$, —SO$_2$N(CH$_3$)C$_2$H$_5$, —SO$_2$NHCH(CH$_3$)$_2$, —NHCH$_3$, —N(CH$_3$)C$_2$H$_5$, —NHSO$_2$CH$_3$, and —P(O)(CH$_3$)$_2$.

5. The compound of claim 3, wherein
$A_4$ is selected from the group consisting of phenyl substituted by one or more $R^4$(s); or preferably,
$A_4$ is selected from the group consisting of phenyl substituted by one or more $R^4$(s) selected from the group consisting of halogen, $C_{1-6}$ alkyl substituted by halogen, —NR$_6$R$_7$, and —P(O)R$_6$R$_7$, wherein $R^6$ and $R^7$ are each independently selected from the group consisting of $C_{1-6}$ alkyl; or more preferably,
$A_4$ is selected from the group consisting of phenyl substituted by one or more $R^4$(s) selected from the group consisting of F, Cl, methyl substituted by halogen, ethyl substituted by halogen, —N(CH$_3$)$_2$, and —P(O)(CH$_3$)$_2$; or more preferably,
$A_4$ is selected from the group consisting of phenyl substituted by one or more $R^4$(s) selected from the group consisting of F, Cl, —CHF$_2$, —CF$_3$, —CF$_2$CH$_3$, —N(CH$_3$)$_2$, and —P(O)(CH$_3$)$_2$, and $A_4$ is substituted by at least one F atom.

6. A compound of Formula (III),

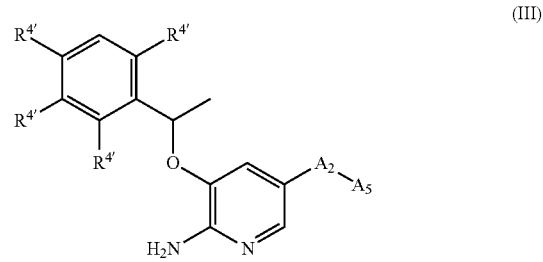

wherein
$R^{4'}$ is each independently selected from the group consisting of hydrogen, halogen, $C_{1-6}$ alkyl, —NR$^6$R$^7$, and —P(O)R$^6$R$^7$;
$R^6$ and $R^7$ are each independently selected from the group consisting of hydrogen, $C_{1-6}$ alkyl, or $R^6$ and $R^7$ link to form a 3-12 membered heteroalicyclyl with the atom to which they are attached to;
$A_2$ is selected from the group consisting of phenyl, pyridinyl, and pyrimidinyl, all of which are optionally substituted by 1, 2, 3 or 4 substituent(s) independently selected from the group consisting of halogen and —OC$_{1-6}$ alkyl in which each hydrogen of the $C_{1-6}$ alkyl moiety is optionally substituted by hydroxy, carboxyl, or 3-12 membered heteroalicyclyl;
$A_5$ is a 3-12 membered heteroalicyclyl, which is optionally substituted by one or more substituents selected from the group consisting of
=O,
unsubstituted $C_{1-6}$ alkyl,
3-12 membered heteroalicyclyl, and
$C_{1-6}$ alkyl substituted by one or more substituent(s) independently selected from the group consisting of hydroxy, carboxyl, and 3-12 membered heteroalicyclyl;
with the proviso that
$A_2$ is substituted by at least one —OC$_{1-6}$ alkyl,
and
pharmaceutically acceptable salts, stereoisomers, and enantiomers thereof, and mixtures thereof.

7. The compound of claim 6, wherein
each $R^{4\prime}$ is the same or different, with the proviso that at least one $R^{4\prime}$ is not hydrogen; or preferably,
the $R^{4\prime}$ substituent on 3-position is halogen; or further preferably,
the $R^{4\prime}$ substituent on 3-position is F, and the other $R^{4\prime}$ substituents are each independently selected from the group consisting of hydrogen, halogen, $C_{1-6}$ alkyl substituted by halogen, —$NR^6R^7$, and —$P(O)R^6R^7$, wherein $R^6$ and $R^7$ are each independently selected from the group consisting of $C_{1-6}$ alkyl; or more preferably,
the $R^{4\prime}$ substituent on 3-position is F, and the other $R^{4\prime}$ substituents are each independently selected from the group consisting of hydrogen, halogen, methyl substituted by halogen, ethyl substituted by halogen, —$N(CH_3)_2$, and —$P(O)(CH_3)_2$; or further more preferably,
the $R^{4\prime}$ substituent on 3-position is F, and the other $R^{4\prime}$ substituents are each independently selected from the group consisting of hydrogen, F, Cl, —$CHF_2$, —$CF_2CH_3$, —$N(CH_3)_2$, and —$P(O)(CH_3)_2$; or more preferably,
the $R^{4\prime}$ substituent on 3-position is F, the $R^{4\prime}$ substituents on 2-position and 6-position are Cl, and the $R^{4\prime}$ substituent on 4-position is hydrogen.

8. The compound of claim 1, wherein $A_2$ is optionally substituted by one or more substituents selected from the group consisting of halogen and —$OC_{1-6}$ alkyl, wherein the $C_{1-6}$ alkyl is optionally substituted by hydroxy, carboxyl, morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, dihydrothienyl; preferably, $A_2$ is optionally substituted by one or more substituents selected from the group consisting of halogen and —$OC_{1-6}$ alkyl, wherein the $C_{1-6}$ alkyl is optionally substituted by hydroxy, carboxyl, morpholinyl; more preferably, $A_2$ is optionally substituted by one or more substituents selected from the group consisting of F, Cl, methoxy, ethoxy, —$OCH_2CH_2OH$,

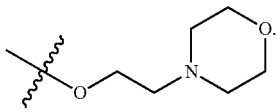 [SMILES: *OCCN1CCOCC1]

9. The compound of claim 1, wherein
$A_5$ is a 5 or 6 membered heteroalicyclyl; or preferably,
$A_5$ is morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, or dihydrothienyl; or more preferably,
$A_5$ is morpholinyl, 1,2,3,4-tetrahydropyridyl, 1,2,3,6-tetrahydropyridyl, 2,3,4,5-tetrahydropyridyl, piperazinyl, piperazin-2-one-yl, or piperidinyl; or more preferably,
$A_5$ is piperazin-1-yl, piperazin-2-yl, piperazin-3-yl, piperidin-4-yl, piperidin-1-yl, piperidin-2-yl, piperidin-3-yl, morpholin-4-yl, morpholin-2-yl, morpholin-3-yl, 1,2,3,4-tetrahydropyridin-4-yl, 1,2,3,6-tetrahydropyridin-4-yl, 2,3,4,5-tetrahydropyridin-4-yl, or piperazin-2-one-yl; or most preferably, $A_5$ is

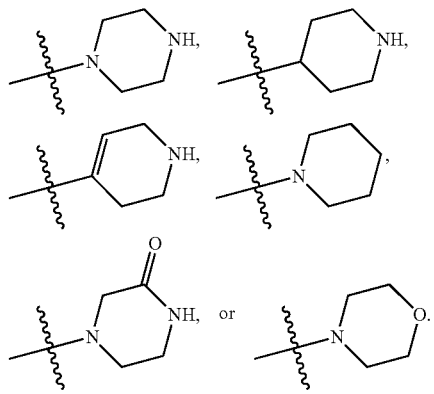

10. The compound of claim 9, wherein
$A_5$ is optionally substituted by one or more substituent(s) selected from the group consisting of
=O,
unsubstituted $C_{1-6}$ alkyl,
3-12 membered heteroalicyclyl,
$C_{1-6}$ alkyl substituted by one or more substituent(s) independently selected from the group consisting of hydroxy, carboxyl, and 3-12 membered heteroalicyclyl, wherein the 3-12 membered heteroalicyclyl is further optionally substituted by substituent(s) selected from the group consisting of $C_{1-6}$ alkyl, =O, —OH, —COOH, —CN, halogen, —NH($C_{1-6}$ alkyl), and —N($C_{1-6}$ alkyl)$_2$;
or preferably,
$A_5$ is optionally substituted by one or more substituent(s) selected from the group consisting of =O, methyl, ethyl, n-propyl, isopropyl, and 5 or 6 membered heteroalicyclyl, wherein each of methyl, ethyl, n-propyl, and isopropyl is optionally substituted by one or more substituent(s) independently selected from the group consisting of —OH, —COOH, and 5 or 6 membered heteroalicyclyl, wherein the 5 or 6 membered heteroalicyclyl is further optionally substituted by substituent(s) selected from the group consisting of: methyl, ethyl, n-propyl, isopropyl, =O, —OH, —COOH, —CN, halogen, —NH($C_{1-3}$ alkyl), and —N($C_{1-3}$ alkyl)$_2$;
or more preferably,
$A_5$ is optionally substituted by one or more substituent(s) selected from the group consisting of: methyl, ethyl, n-propyl, isopropyl, =O, piperidinyl, and piperazinyl, wherein piperidinyl or piperazinyl is optionally substituted by methyl.

11. The compound of claim 1, which is selected from the group consisting of

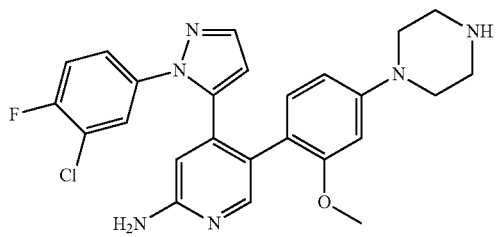

131
-continued
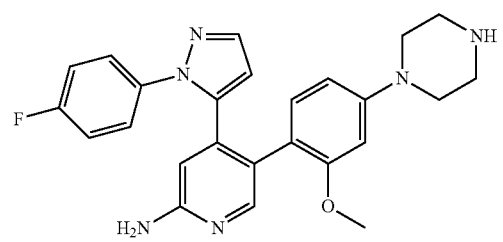
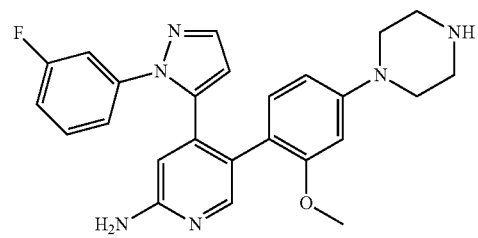
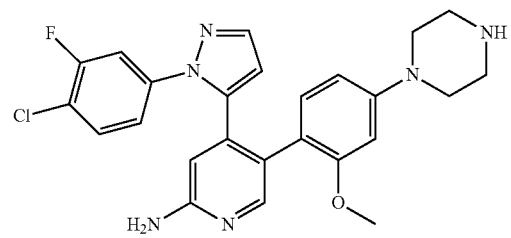
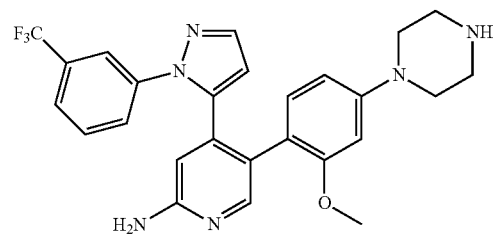
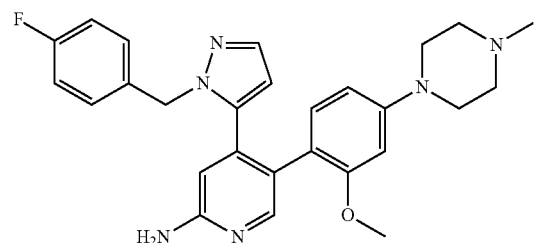
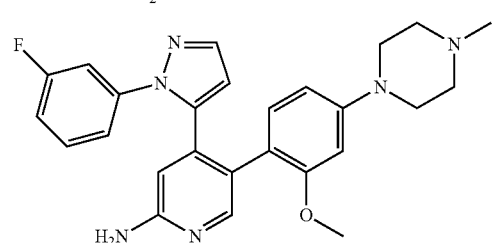
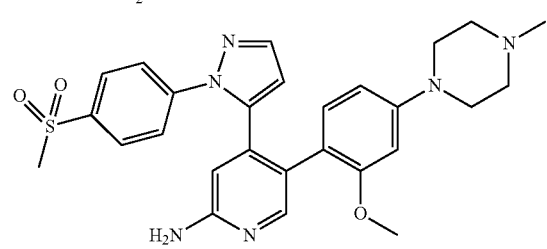
132
-continued
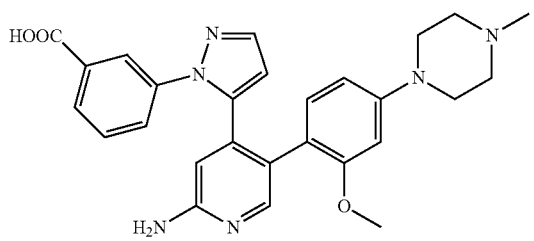
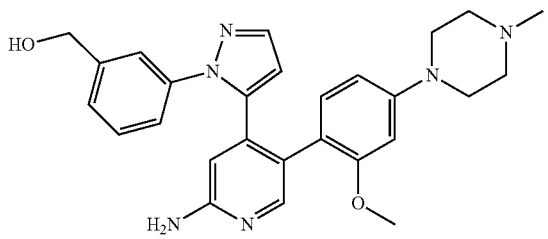
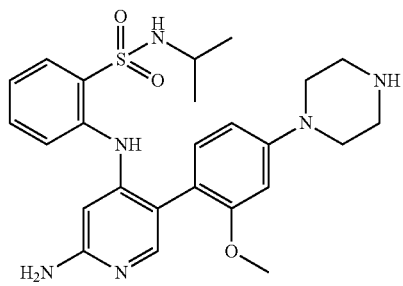
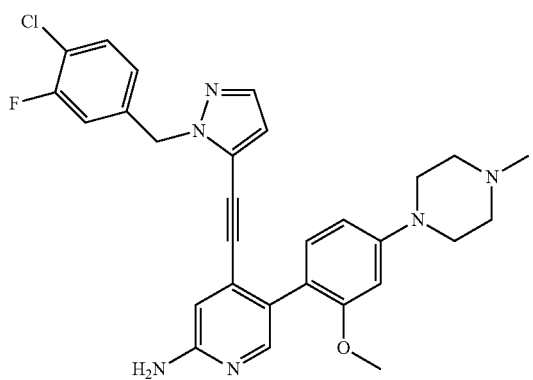
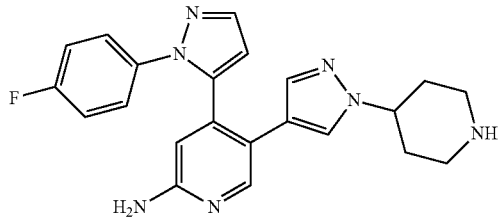
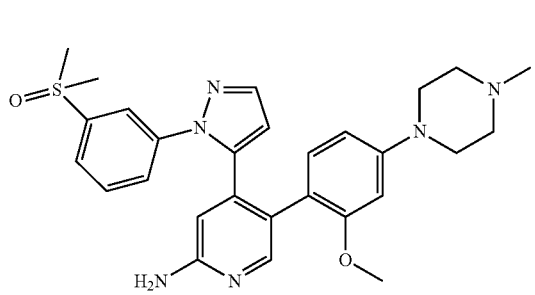

133
-continued
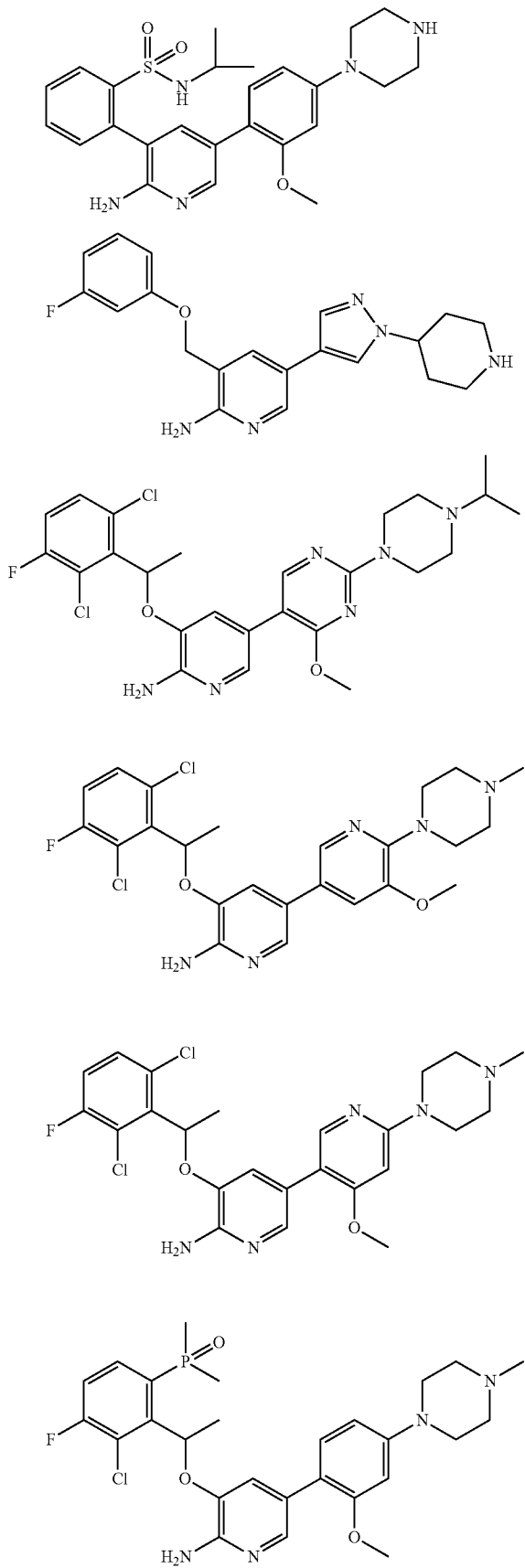
134
-continued
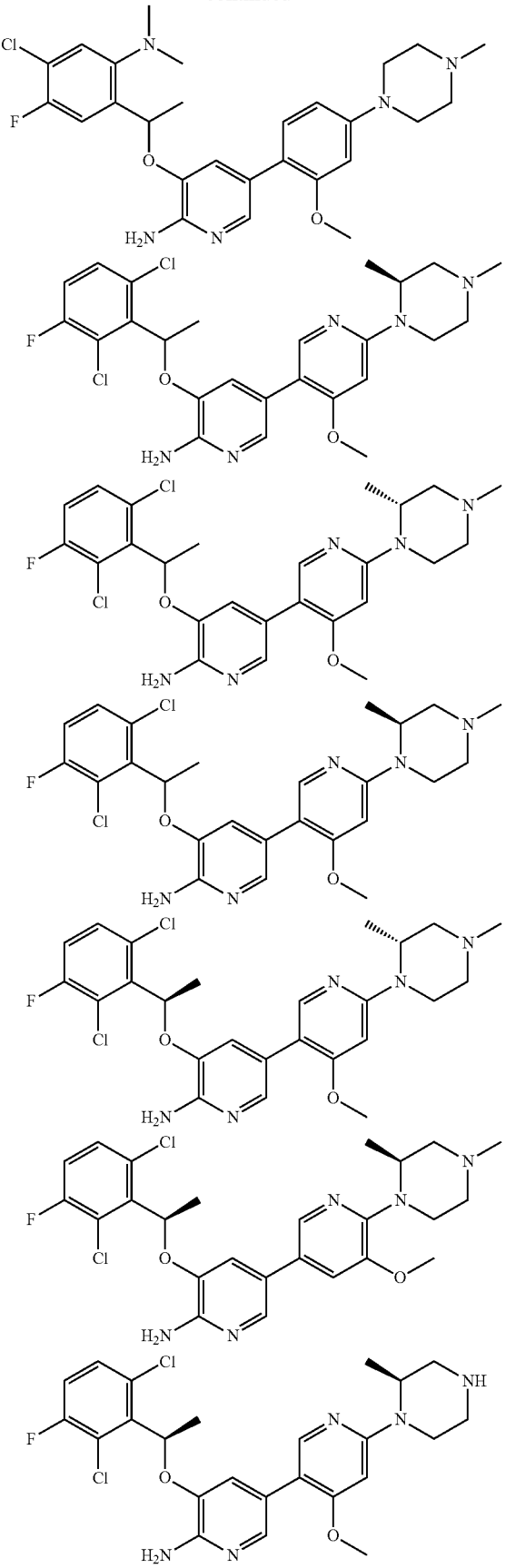

135
-continued
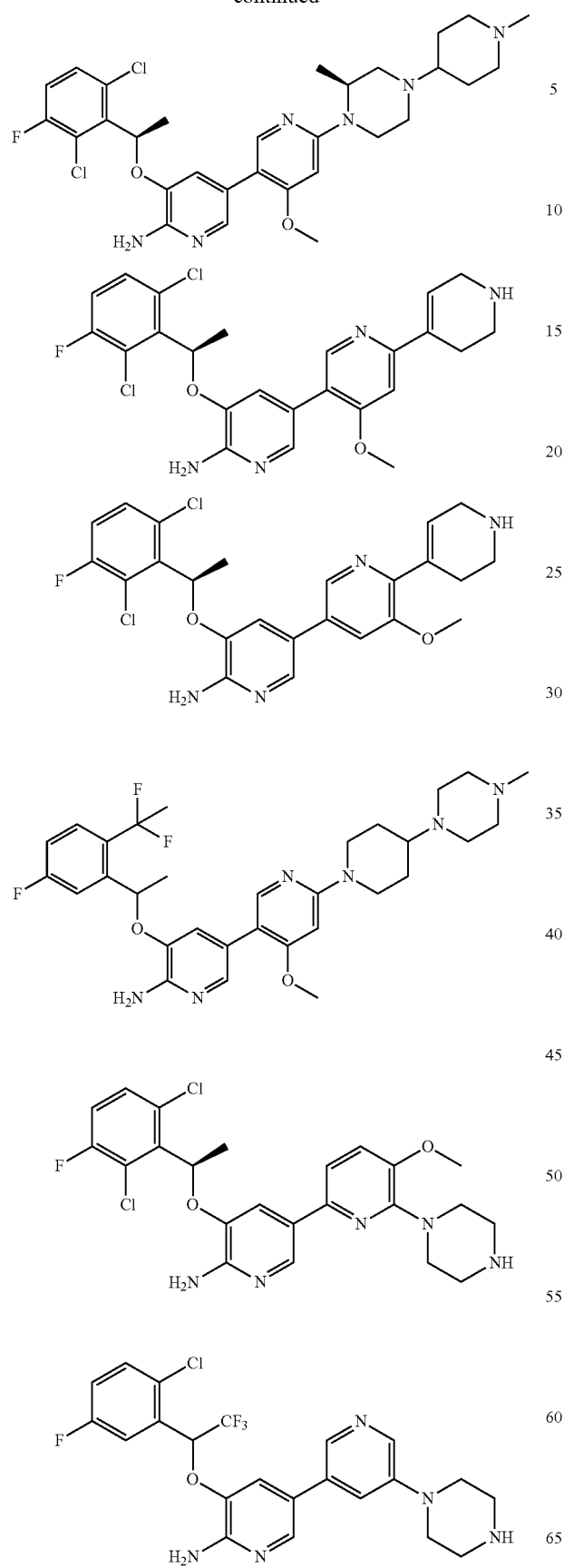
136
-continued
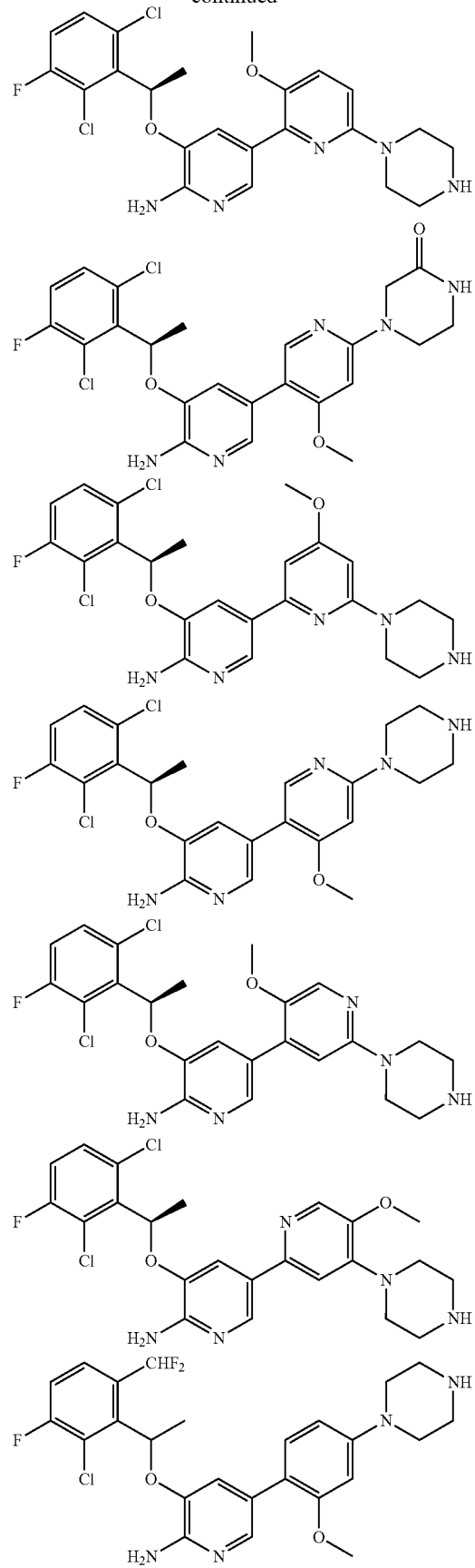

137
-continued
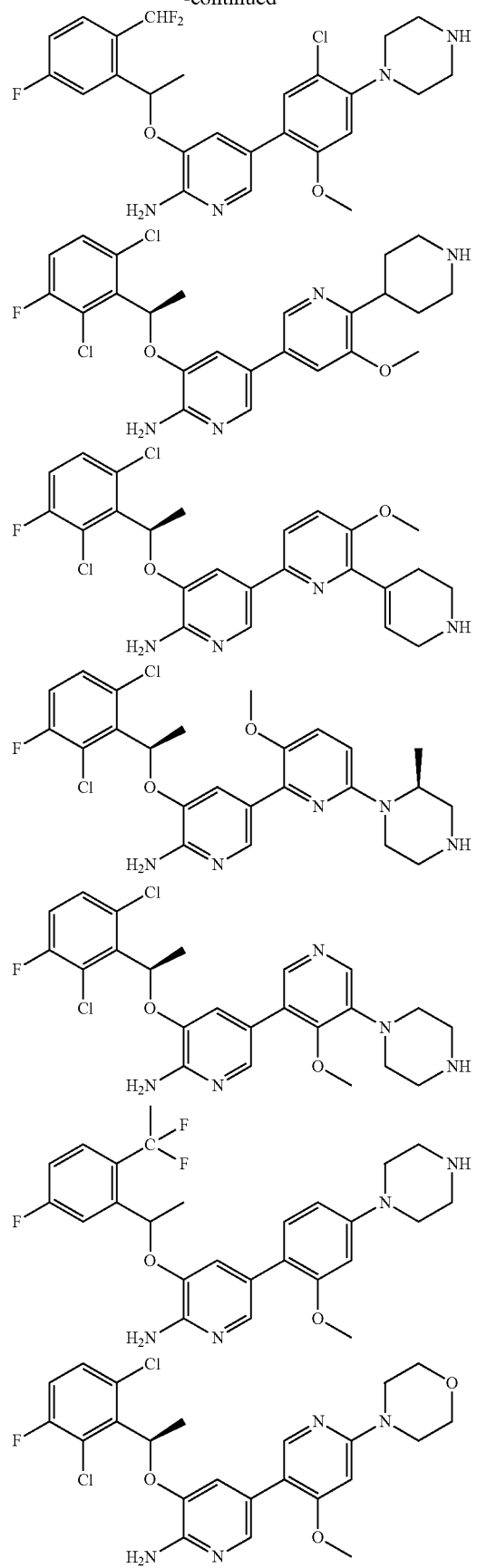
138
-continued
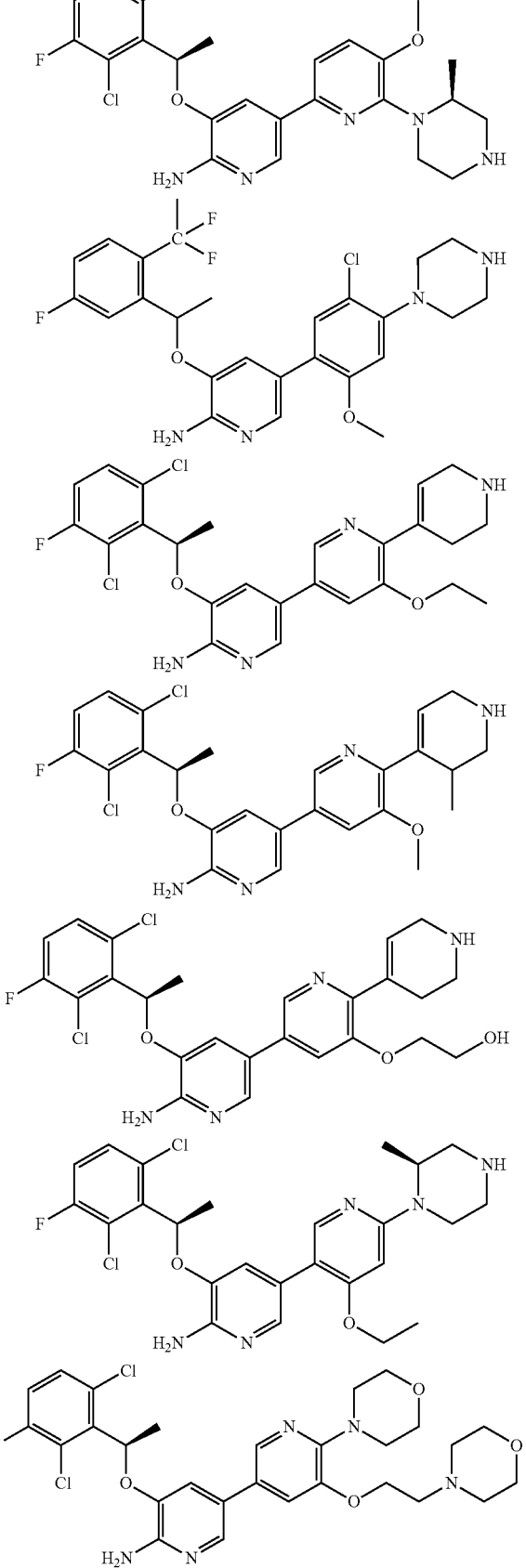

-continued

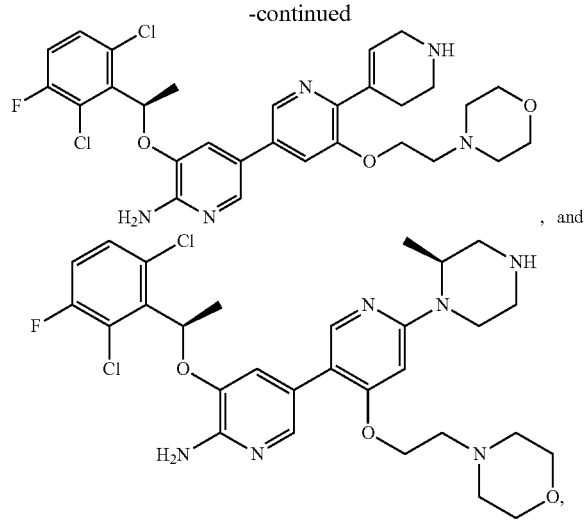

, and and
pharmaceutically acceptable salts, stereoisomers, and enantiomers thereof, and mixtures thereof.

12. A pharmaceutical composition comprising the compound according to claim 1, together with one or more pharmaceutically acceptable carrier(s).

13. A method for therapeutically treating a disease mediated by anaplastic lymphoma kinase (ALK), comprising administering to a mammal in need thereof an effective amount of the compound of claim 1, wherein the disease mediated by ALK is ALK-positive non-small cell lung carcinoma, anaplastic large cell lymphoma, inflammatory myofibroblastic tumor, diffuse large B-cell lymphoma, or neuroblastoma.

14. The compound of claim 6, wherein $A_2$ is optionally substituted by one or more substituents selected from the group consisting of halogen and —$OC_{1-6}$ alkyl, wherein the $C_{1-6}$ alkyl is optionally substituted by hydroxy, carboxyl, morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, dihydrothienyl; preferably, $A_2$ is optionally substituted by one or more substituents selected from the group consisting of halogen and —$OC_{1-6}$ alkyl, wherein the $C_{1-6}$ alkyl is optionally substituted by hydroxy, carboxyl, morpholinyl; more preferably, $A_2$ is optionally substituted by one or more substituents selected from the group consisting of F, Cl, methoxy, ethoxy, —$OCH_2CH_2OH$,

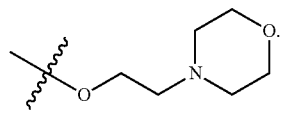 [SMILES: *OCCN1CCOCC1]

15. The compound of claim 6, wherein
$A_5$ is a 5 or 6 membered heteroalicyclyl; or preferably,
$A_5$ is morpholinyl, tetrahydrofuryl, piperidinyl, piperazinyl, tetrahydropyridyl, dihydropyridyl, tetrahydrothienyl, pyrrolidinyl, oxazolidinyl, thiazolidinyl, imidazolidinyl, isoxazolidinyl, isothiazolidinyl, pyrazolidinyl, thiomorpholinyl, piperazin-2-one-yl, pyrrolinyl, dihydrofuryl, or dihydrothienyl; or more preferably, $A_5$ is morpholinyl, 1,2,3,4-tetrahydropyridyl, 1,2,3,6-tetrahydropyridyl, 2,3,4,5-tetrahydropyridyl, piperazinyl, piperazin-2-one-yl, or piperidinyl; or more preferably,
$A_5$ is piperazin-1-yl, piperazin-2-yl, piperazin-3-yl, piperidin-4-yl, piperidin-1-yl, piperidin-2-yl, piperidin-3-yl, morpholin-4-yl, morpholin-2-yl, morpholin-3-yl, 1,2,3,4-tetrahydropyridin-4-yl, 1,2,3,6-tetrahydropyridin-4-yl, 2,3,4,5-tetrahydropyridin-4-yl, or piperazin-2-one-yl; or most preferably,
$A_5$ is

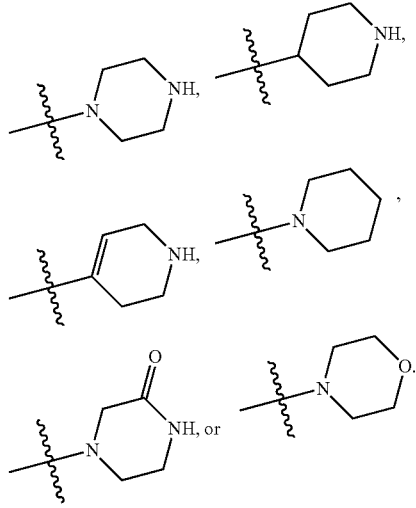

16. The compound of claim 15, wherein
$A_5$ is optionally substituted by one or more substituent(s) selected from the group consisting of
=O,
unsubstituted $C_{1-6}$ alkyl,
3-12 membered heteroalicyclyl,
$C_{1-6}$ alkyl substituted by one or more substituent(s) independently selected from the group consisting of hydroxy, carboxyl, and 3-12 membered heteroalicyclyl, wherein the 3-12 membered heteroalicyclyl is further optionally substituted by substituent(s) selected from the group consisting of $C_{1-6}$ alkyl, =O, —OH, —COOH, —CN, halogen, —NH($C_{1-6}$ alkyl), and —N($C_{1-6}$ alkyl)$_2$;
or preferably,
$A_5$ is optionally substituted by one or more substituent(s) selected from the group consisting of =O, methyl, ethyl, n-propyl, isopropyl, and 5 or 6 membered heteroalicyclyl, wherein each of methyl, ethyl, n-propyl, and isopropyl is optionally substituted by one or more substituent(s) independently selected from the group consisting of —OH, —COOH, and 5 or 6 membered heteroalicyclyl, wherein the 5 or 6 membered heteroalicyclyl is further optionally substituted by substituent(s) selected from the group consisting of: methyl, ethyl, n-propyl, isopropyl, =O, —OH, —COOH, —CN, halogen, —NH($C_{1-3}$ alkyl), and —N($C_{1-3}$ alkyl)$_2$;
or more preferably,
$A_5$ is optionally substituted by one or more substituent(s) selected from the group consisting of: methyl, ethyl, n-propyl, isopropyl, =O, piperidinyl, and piperazinyl, wherein piperidinyl or piperazinyl is optionally substituted by methyl.

17. A method for therapeutically treating a disease mediated by ALK, comprising administering to a mammal in need thereof an effective amount of the compound of claim 6, wherein the disease mediated by ALK is ALK-positive non-small cell lung carcinoma, anaplastic large cell lymphoma, inflammatory myofibroblastic tumor diffuse large B-cell lymphoma, or neuroblastoma.

* * * * *